US008957280B2

(12) United States Patent
Damude et al.

(10) Patent No.: US 8,957,280 B2
(45) Date of Patent: Feb. 17, 2015

(54) DELTA-5 DESATURASES AND THEIR USE IN MAKING POLYUNSATURATED FATTY ACIDS

(75) Inventors: Howard Glenn Damude, Hockessin, DE (US); Quinn Qun Zhu, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1460 days.

(21) Appl. No.: 12/111,228

(22) Filed: Apr. 29, 2008

(65) Prior Publication Data

US 2008/0274259 A1 Nov. 6, 2008

Related U.S. Application Data

(60) Provisional application No. 60/915,733, filed on May 3, 2007.

(51) Int. Cl.

| | |
|---|---|
| ***C12N 15/82*** | (2006.01) |
| ***A01H 5/00*** | (2006.01) |
| ***C07H 21/04*** | (2006.01) |
| ***A23D 9/00*** | (2006.01) |
| ***A23D 9/02*** | (2006.01) |
| ***A23K 1/16*** | (2006.01) |
| ***A23L 1/30*** | (2006.01) |
| ***C12N 9/02*** | (2006.01) |

(52) U.S. Cl.

CPC .............. *C12N 15/8247* (2013.01); *A23D 9/00* (2013.01); *A23D 9/02* (2013.01); *A23K 1/164* (2013.01); *A23L 1/3006* (2013.01); *C12N 9/0083* (2013.01)

USPC ........... 800/281; 800/298; 536/23.2; 435/419

(58) Field of Classification Search

None

See application file for complete search history.

(56) References Cited

U.S. PATENT DOCUMENTS

| | | | |
|---|---|---|---|
| 5,972,664 | A | 10/1999 | Knutzon et al. |
| 6,075,183 | A | 6/2000 | Knutzon et al. |
| 6,635,451 | B2 | 10/2003 | Mukerji et al. |
| 7,087,432 | B2 | 8/2006 | Qiu et al. |
| 7,125,672 | B2 | 10/2006 | Picataggio et al. |
| 7,238,482 | B2 | 7/2007 | Picataggio et al. |
| 7,335,476 | B2 | 2/2008 | Picataggio et al. |
| 2005/0136519 | A1 | 6/2005 | Picataggio et al. |
| 2006/0035351 | A1 | 2/2006 | Zhu et al. |
| 2006/0094092 | A1 | 5/2006 | Damude et al. |
| 2006/0110806 | A1 | 5/2006 | Damude et al. |
| 2006/0115881 | A1 | 6/2006 | Damude et al. |
| 2007/0207528 | A1 | 9/2007 | Picataggio et al. |
| 2007/0271632 | A1 | 11/2007 | Damude et al. |
| 2007/0277266 | A1 | 11/2007 | Damude et al. |
| 2007/0292924 | A1 | 12/2007 | Damude et al. |
| 2008/0194685 | A1 | 8/2008 | Damude et al. |
| 2008/0254191 | A1 | 10/2008 | Damude et al. |
| 2008/0274521 | A1 | 11/2008 | Damude et al. |
| 2009/0093543 | A1 | 4/2009 | Xue et al. |
| 2009/0117253 | A1 | 5/2009 | Hong et al. |
| 2010/0189868 | A1 | 7/2010 | Damude et al. |

FOREIGN PATENT DOCUMENTS

| | | |
|---|---|---|
| WO | 98/46764 | 10/1998 |
| WO | WO02/081668 | 10/2002 |
| WO | WO2004/071467 | 8/2004 |
| WO | WO2004/101753 | 11/2004 |
| WO | WO2004/101757 | 11/2004 |
| WO | 2005/080578 | 9/2005 |
| WO | 2005/118814 | 12/2005 |
| WO | 2006/012325 | 2/2006 |
| WO | WO2006/052870 | 5/2006 |
| WO | WO2006/055322 | 5/2006 |
| WO | 2007/136877 | 11/2007 |
| WO | WO 2007/136876 A2 | 11/2007 |

OTHER PUBLICATIONS

National Center for Biotechnology Information General Identifier No. 6842049, Accession No. AF199596, Jun. 21, 2000, H. P. Cho et al., Cloning, expression and fatty acid regulation of the human delta-5 desaturase.

National Center for Biotechnology Information General Identifier No. 7861969, Accession No. AF226273, May 17, 2000, A. E. Leonard et al., cDNA cloning and characterization of human delta-5 desaturase involved in the biosynthesis of arachidonic acid.

National Center for Biotechnology Information General Identifier No. 11386008, Accession No. AF320509, Aug. 13, 2001, R. Zolfaghari et al., Fatty acid delta(5)-desaturase mRNA is regulated by dietary vitamin A and exogenous retinoic acid in liver of adult rats.

National Center for Biotechnology Information General Identifier No. 16151828, Accession No. AB072976, Oct. 16, 2001, T. Matsuzaka et al., Dual gene of mouse delta-5 and -6 desaturases by SREBP-1 and PPAR alpha.

National Center for Biotechnology Information General Identifier No. 20069122, Accession No. AF489588, Apr. 8, 2002, X. Qiu et al., Identification of a delta-4 fatty acid desaturase from *thraustochytrium* sp. involved in the biosynthesis of the docosahexanoic acid by heterologous expression in *Saccaromyces cerevisiae* and *Brassica juncea.*

National Center for Biotechnology Information General Identifier No. 23894017, Accession No. AJ510244, Apr. 15, 2005, E. Hornung et al., Specific formation of arachidonic acid by a front-end delta5-desaturase from *Phytophthora megasperma.*

National Center for Biotechnology Information General Identifier No. 16033739, Accession No. AF419297, Mar. 24, 2005, H. Hong et al., Isolation and characterization of a delta-5 FA desaturase from pythium irregulare by heterologous expression in *Saccharomyces cerevisiae* and oilseed crops.

National Center for Biotechnology Information General Identifier No. 4003522, Accession No. AF078796, Dec. 11, 1998, L. V. Michaelson et al., Functional identification of a fatty acid delta-5 desaturase gene from *Caenorhabditis elegans.*

(Continued)

*Primary Examiner* — Elizabeth McElwain

(57) ABSTRACT

Isolated nucleic acid fragments and recombinant constructs comprising such fragments encoding delta-5 desaturases along with a method of making long-chain polyunsaturated fatty acids (PUFAs) using these delta-5 desaturases in plants are disclosed.

21 Claims, 13 Drawing Sheets

(56) References Cited

OTHER PUBLICATIONS

National Center for Biotechnology Information General Identifier No. 3859487, Accession No. AF067654, Nov. 11, 1998, D. S. Knutzon et al., Identification of delta5-desaturase from *Mortierella alpina* by heterologous expression in bakers' yeast and canola.
National Center for Biotechnology Information General Identifier No. 4150955, Accession No. AB022097, Apr. 17, 2003, T. Saito et al., A second functional delta-5 fatty acid desaturase in the cellular slime mould *Dictyostelium discoideum*.
National Center for Biotechnology Information General Identifier No. 60172920, Accession No. AAX14502, Jul. 16, 2005, T. Tonon et al., Fatty acid desaturases from the microalga *Thalassiosira pseudonana*.
Tonon et al., FEBS Journal, Fatty acid desaturases from the microalga *Thalassiosira pseudonana,* vol. 272, pp. 3401-3412 (2005).
National Center for Biotechnology Information General Identifier No. 19879687, Accession No. AAL92562, Aug. 23, 2002, F. Domergue et al., Cloning and functional characterization of *Phaeodactylum tricornutum* front-end desaturases involved in eicosapentaenoic acid biosynthesis.
Domergue et al., Eur. J. Biochem., Cloning and functional characterization of *Phaeodactylum tricornutum* front-end desaturases involved in eicosapentaenoic acid biosynthesis, vol. 269, pp. 4105-4113 (2002).
U.S. Appl. No. 60/801,119, filed May 17, 2006, E. I. du Pont de Nemours and Company.
U.S. Appl. No. 60/801,172, filed May 17, 2006, E. I. du Pont de Nemours and Company.
U.S. Appl. No. 11/264,737, filed Nov. 1, 2005, E. I. du Pont de Nemours and Company.
U.S. Appl. No. 11/264,784, filed Nov. 1, 2005, E. I. du Pont de Nemours and Company.
U.S. Appl. No. 11/265,761, filed Nov. 2, 2005, E. I. du Pont de Nemours and Company.
U.S. Appl. No. 11/737,772, filed Apr. 20, 2007, E. I. du Pont de Nemours and Company.
U.S. Appl. No. 11/876,115, filed Oct. 22, 2007, E. I. du Pont de Nemours and Company.

FIG. 6

| | | Fatty acid composition (wt.%) | | | | | | | | | | | | | | | | | | % | Ave. % | Ratio | Ratio |
|---|---|---|---|---|---|---|---|---|---|---|---|---|---|---|---|---|---|---|---|---|---|---|---|
| Clone | Fatty Acid | 16:0 | 16:1 | 18:0 | 18:1 | LA | GLA | ALA | STA | EDA | SCI | DGLA | ARA | ERA | JUP | ETA | EPA | DPA | DHA | desat | desat | n-6/n-3 | Prod/By-Prod |
| pY169-1 | None | 13.0 | 9.1 | 1.9 | 25.0 | 50.5 | 0.0 | 0.2 | 0.0 | 0.2 | 0.0 | 0.0 | 0.0 | 0.0 | 0.0 | 0.0 | 0.0 | 0.0 | 0.1 | 0.0 | 0.0 | | |
| pY169-2 | None | 12.8 | 9.4 | 1.7 | 23.7 | 51.9 | 0.0 | 0.2 | 0.0 | 0.2 | 0.0 | 0.0 | 0.0 | 0.0 | 0.0 | 0.0 | 0.0 | 0.0 | 0.2 | 0.0 | | | |
| pY169-3 | None | 13.1 | 9.2 | 1.7 | 23.2 | 52.2 | 0.0 | 0.1 | 0.0 | 0.2 | 0.0 | 0.0 | 0.0 | 0.0 | 0.0 | 0.0 | 0.0 | 0.0 | 0.2 | 0.0 | | | |
| pY169-1 | ALA | 11.1 | 7.6 | 1.0 | 32.4 | 27.4 | 0.0 | 19.3 | 0.0 | 0.1 | 0.0 | 0.0 | 0.0 | 0.5 | 0.0 | 0.0 | 0.0 | 0.0 | 0.5 | 0.0 | 0.0 | | |
| pY169-2 | ALA | 11.4 | 7.0 | 0.9 | 30.4 | 25.1 | 0.0 | 24.2 | 0.0 | 0.1 | 0.0 | 0.0 | 0.0 | 0.6 | 0.0 | 0.0 | 0.0 | 0.0 | 0.3 | 0.0 | | | |
| pY169-3 | ALA | 11.6 | 7.3 | 1.1 | 31.8 | 27.0 | 0.0 | 20.1 | 0.0 | 0.1 | 0.0 | 0.0 | 0.0 | 0.5 | 0.0 | 0.0 | 0.0 | 0.0 | 0.4 | 0.0 | | | |
| pY169-1 | EDA | 13.0 | 8.3 | 1.9 | 26.5 | 47.8 | 0.0 | 0.1 | 0.0 | 1.8 | 0.3 | 0.0 | 0.0 | 0.0 | 0.0 | 0.1 | 0.0 | 0.0 | 0.2 | 16.2 | 15.4 | 1.7 | |
| pY169-2 | EDA | 12.8 | 8.4 | 1.9 | 24.4 | 49.4 | 0.0 | 0.1 | 0.0 | 2.4 | 0.4 | 0.0 | 0.0 | 0.0 | 0.0 | 0.0 | 0.0 | 0.0 | 0.2 | 15.0 | | | |
| pY169-3 | EDA | 13.0 | 8.3 | 2.0 | 26.4 | 47.7 | 0.0 | 0.1 | 0.0 | 1.9 | 0.3 | 0.0 | 0.0 | 0.0 | 0.0 | 0.0 | 0.0 | 0.0 | 0.2 | 15.1 | | | |
| pY169-1 | ERA | 12.2 | 7.6 | 1.8 | 25.4 | 43.3 | 0.0 | 5.6 | 0.0 | 0.2 | 0.0 | 0.0 | 0.0 | 3.1 | 0.3 | 0.0 | 0.0 | 0.0 | 0.3 | 9.6 | 8.8 | | |
| pY169-2 | ERA | 11.5 | 8.0 | 1.3 | 24.5 | 43.7 | 0.0 | 5.9 | 0.0 | 0.2 | 0.0 | 0.0 | 0.0 | 4.2 | 0.4 | 0.0 | 0.0 | 0.0 | 0.3 | 8.5 | | | |
| pY169-3 | ERA | 11.8 | 7.8 | 1.5 | 24.8 | 43.8 | 0.0 | 5.6 | 0.0 | 0.2 | 0.0 | 0.0 | 0.0 | 3.7 | 0.3 | 0.0 | 0.0 | 0.0 | 0.2 | 8.4 | | | |
| pY169-1 | DGLA | 12.7 | 8.3 | 1.2 | 25.3 | 46.6 | 0.4 | 0.1 | 0.0 | 0.2 | 0.0 | 2.3 | 2.7 | 0.0 | 0.0 | 0.0 | 0.0 | 0.0 | 0.2 | 53.3 | 51.5 | 1.5 | 3.3 |
| pY169-2 | DGLA | 13.3 | 7.9 | 1.1 | 25.9 | 44.8 | 0.4 | 0.1 | 0.0 | 0.2 | 0.0 | 3.2 | 3.0 | 0.0 | 0.0 | 0.0 | 0.0 | 0.0 | 0.2 | 49.0 | | | |
| pY169-3 | DGLA | 12.7 | 8.1 | 1.3 | 25.6 | 46.2 | 0.3 | 0.1 | 0.0 | 0.2 | 0.0 | 2.5 | 2.7 | 0.0 | 0.0 | 0.0 | 0.0 | 0.0 | 0.2 | 52.1 | | | |
| pY169-1 | ETA | 11.4 | 8.2 | 1.3 | 37.9 | 27.2 | 0.0 | 0.0 | 0.6 | 0.1 | 0.0 | 0.0 | 0.0 | 0.0 | 0.0 | 8.3 | 4.8 | 0.0 | 0.3 | 36.9 | 34.7 | | 3.9 |
| pY169-2 | ETA | 11.6 | 8.0 | 1.1 | 38.5 | 24.6 | 0.0 | 0.0 | 0.6 | 0.1 | 0.0 | 0.0 | 0.0 | 0.0 | 0.0 | 10.5 | 4.8 | 0.0 | 0.2 | 31.5 | | | |
| pY169-3 | ETA | 11.4 | 8.2 | 1.3 | 38.3 | 26.7 | 0.0 | 0.0 | 0.5 | 0.1 | 0.0 | 0.0 | 0.0 | 0.0 | 0.0 | 8.5 | 4.7 | 0.0 | 0.1 | 35.6 | | | |
| pY169-1 | DPA | 13.2 | 7.0 | 1.7 | 24.9 | 47.8 | 0.0 | 0.1 | 0.2 | 0.3 | 0.0 | 0.0 | 0.0 | 0.0 | 0.0 | 0.0 | 1.2 | 3.6 | 0.0 | 0.0 | 0.0 | | |
| pY169-2 | DPA | 13.0 | 7.3 | 1.5 | 24.7 | 47.2 | 0.0 | 0.1 | 0.2 | 0.3 | 0.0 | 0.0 | 0.0 | 0.0 | 0.0 | 0.0 | 1.4 | 4.4 | 0.0 | 0.0 | | | |
| pY169-3 | DPA | 13.2 | 7.1 | 1.6 | 27.1 | 45.7 | 0.0 | 0.1 | 0.2 | 0.2 | 0.0 | 0.0 | 0.0 | 0.0 | 0.0 | 0.0 | 1.2 | 3.6 | 0.0 | 0.0 | | | |

FIG. 8A

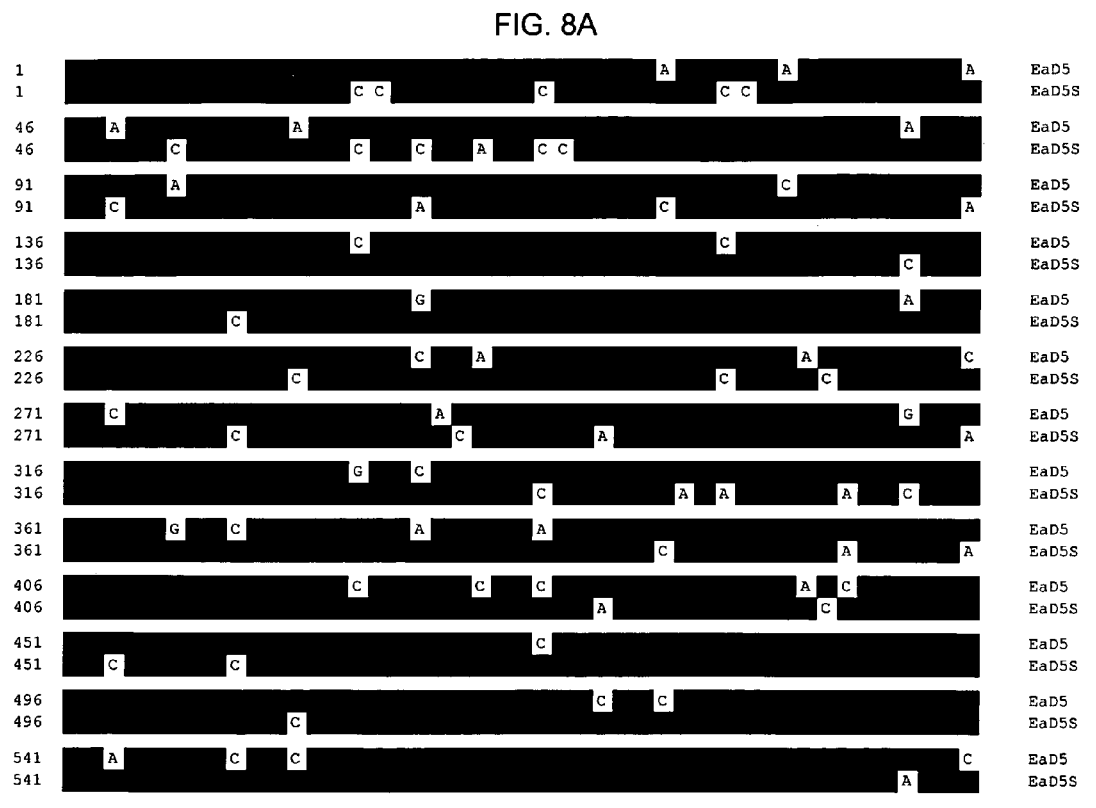

1 A A A EaD5
1 C C C C C EaD5S
46 A A A EaD5
46 C C C A C C EaD5S
91 A C EaD5
91 C A C A EaD5S
136 C C EaD5
136 C EaD5S
181 G A EaD5
181 C EaD5S
226 C A A C EaD5
226 C C C EaD5S
271 C A G EaD5
271 C C A A EaD5S
316 G C EaD5
316 C A A A C EaD5S
361 G C A A EaD5
361 C A A EaD5S
406 C C C A C EaD5
406 A C EaD5S
451 C EaD5
451 C C EaD5S
496 C C EaD5
496 C EaD5S
541 A C C C EaD5
541 A EaD5S

EaD5 (same as EaD5Des1) (SEQ ID NO:12)
EaD5S (SEQ ID NO:45)

FIG. 11

| Event | Average Fatty acid composition (wt.%) | | | | | | | | | | | | | % delta-5 |
|---|---|---|---|---|---|---|---|---|---|---|---|---|---|---|
| | 16:0 | 18:0 | 18:1 | LA | ALA | EDA | SCI | DGLA | ARA | ERA | JUP | ETA | EPA | desat |
| 2140-6-15-1 | 17.4 | 5.2 | 11.1 | 26.8 | 9.5 | 9.5 | 3.1 | 0.3 | 10.4 | 1.5 | 0.7 | 0.1 | 4.3 | 97.3 |
| 2140-6-8-1 | 17.1 | 3.3 | 9.7 | 29.7 | 9.3 | 9.1 | 1.2 | 0.2 | 0.6 | 2.0 | 2.4 | 0.2 | 15.1 | 97.1 |
| 2140-3-7-1 | 17.3 | 4.2 | 13.1 | 31.4 | 10.3 | 8.8 | 2.7 | 0.3 | 7.2 | 1.2 | 0.5 | 0.0 | 3.0 | 97.0 |
| 2140-3-14-1 | 20.3 | 3.6 | 11.0 | 30.8 | 21.3 | 3.2 | 0.3 | 0.1 | 0.0 | 1.8 | 2.1 | 0.1 | 5.4 | 96.6 |
| 2140-4-3-1 | 17.4 | 3.6 | 11.5 | 29.0 | 11.0 | 9.3 | 3.4 | 0.3 | 2.2 | 1.5 | 2.5 | 0.1 | 8.2 | 96.6 |
| 2140-6-14-1 | 17.4 | 4.1 | 13.9 | 30.7 | 12.1 | 6.4 | 4.8 | 0.3 | 4.9 | 1.1 | 1.6 | 0.1 | 2.6 | 95.8 |
| 2140-5-5-1 | 16.0 | 3.2 | 14.1 | 26.8 | 7.5 | 10.7 | 0.4 | 0.0 | 0.0 | 7.5 | 9.2 | 0.4 | 4.3 | 90.4 |
| 2140-6-1-1 | 17.1 | 4.4 | 9.2 | 33.1 | 16.7 | 9.0 | 1.1 | 0.2 | 2.2 | 3.8 | 0.6 | 0.3 | 2.3 | 89.9 |
| 2140-3-12-1 | 18.7 | 4.0 | 11.7 | 29.0 | 15.3 | 6.6 | 1.2 | 1.1 | 7.4 | 1.3 | 0.3 | 0.4 | 3.0 | 87.2 |
| 2140-3-6-1 | 17.6 | 4.3 | 15.5 | 31.0 | 10.2 | 8.5 | 0.2 | 0.1 | 0.0 | 5.7 | 1.4 | 0.7 | 4.8 | 86.4 |

DELTA-5 DESATURASES AND THEIR USE IN MAKING POLYUNSATURATED FATTY ACIDS

This application claims the benefit of U.S. Provisional Application No. 60/915,733, filed May 3, 2007, the entire content of which is herein incorporated by reference.

FIELD OF THE INVENTION

This invention is in the field of biotechnology, in particular, this pertains to polynucleotide sequences encoding delta-5 desaturases and the use of these desaturases in making long-chain polyunsaturated fatty acids (PUFAs).

BACKGROUND OF THE INVENTION

The importance of PUFAs is undisputed. For example, certain PUFAs are important biological components of healthy cells and are recognized as: "essential" fatty acids that cannot be synthesized de novo in mammals and instead must be obtained either in the diet or derived by further elongation and desaturation of linoleic acid (LA; 18:2 ω-6) or α-linolenic acid (ALA; 18:3 ω-3); constituents of plasma membranes of cells, where they may be found in such forms as phospholipids or triacylglycerols; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of long-chain ω-3 PUFAs produces cardiovascular protective effects (Dyerberg et al., *Amer. J. Clin. Nutr.* 28:958-966 (1975); Dyerberg et al., *Lancet.* 2(8081):117-119 (1978); Shimokawa, H., *World Rev. Nutr. Diet* 88:100-108 (2001); von Schacky et al., *World Rev. Nutr. Diet* 88:90-99 (2001)). Numerous other studies document wide-ranging health benefits conferred by administration of omega-3 and/or omega-6 PUFAs against a variety of symptoms and diseases (e.g., asthma, psoriasis, eczema, diabetes, cancer).

Today, a variety of different hosts including plants, algae, fungi and yeast are being investigated as means for commercial PUFA production via numerous divergent efforts. Although the natural PUFA-producing abilities of the host organisms are sometimes essential to a given methodology, genetic engineering has also proven that the natural abilities of some hosts (even those natively limited to LA and ALA fatty acid production) can be substantially altered to result in high-level production of various long-chain omega-3/omega-6 PUFAs. Whether this effect is the result of natural abilities or recombinant technology, production of arachidonic acid (ARA; 20:4 ω-6), eicosapentaenoic acid (EPA; 20:5 ω-3) and docosahexaenoic acid (DHA; 22:6 ω-3) all require expression of either the delta-9 elongase/delta-8 desaturase pathway (which operates in some organisms, such as euglenoid species and which is characterized by the production of eicosadienoic acid (EDA; 20:2 ω-6) and/or eicosatrienoic acid (ETrA; 20:3 ω-3)) or the delta-6 desaturase/delta-6 elongase pathway (which is predominantly found in algae, mosses, fungi, nematodes and humans and which is characterized by the production of γ-linoleic acid (GLA; 18:3 ω-6) and/or stearidonic acid (STA; 18:4 ω-3) (FIG. 1). A delta-6 elongase is also known as a $C_{18/20}$ elongase.

The delta-8 desaturase enzymes identified thus far have the ability to convert both EDA to dihomo-γ-linolenic acid (DGLA; 20:3) and ETrA to eicosatetraenoic acid (ETA; 20:4) (wherein ARA are EPA are subsequently synthesized from DGLA and ETA, respectively, following reaction with a delta-5 desaturase, while DHA synthesis requires subsequent expression of an additional $C_{20/22}$ elongase and a delta-4 desaturase).

Based on the role delta-8 desaturase enzymes play in the synthesis of e.g., ARA, EPA and DHA, there has been effort to identify and characterize these enzymes. Initial efforts on the isolation and characterization of delta-8 desaturases from *Euglena gracilis*; and, several sequence variations within the *Euglena gracilis* delta-8 desaturase have been reported (see, e.g., Wallis et al., *Arch. Biochem. and Biophys.* 365(2):307-316 (1999); PCT Publication No. WO 2000/34439; U.S. Pat. No. 6,825,017; PCT Publication No. WO 2004/057001). Also, Applicants' Assignee's co-pending applications having U.S. application Ser. Nos. 11/166,003 and 11/166,993 filed Jun. 24, 2005, respectively (PCT Publication Nos. WO 2006/012325 and WO 2006/012326; both published Feb. 2, 2006)) discloses amino acid and nucleic acid sequences for a *Euglena gracilis* delta-8 desaturase.

More recently, PCT Publication No. WO 2005/103253 (published Apr. 22, 2005) discloses amino acid and nucleic acid sequences for a delta-8 desaturase enzyme from *Pavlova salina* (see also U.S. Publication No. 2005/0273885). Sayanova et al. (*FEBS Lett.* 580:1946-1952 (2006)) describes the isolation and characterization of a cDNA from the free living soil amoeba *Acanthamoeba castellanii* that, when expressed in *Arabidopsis*, encodes a $C_{20}$ delta-8 desaturase. Also, Applicants' Assignee's co-pending application having U.S. patent application Ser. No. 11/737,772 (filed Apr. 20, 2007) discloses amino acid and nucleic acid sequences for a delta-8 desaturase enzyme from *Pavlova lutheri* (CCMP459). U.S. patent application Ser. No. 11/876,115 (filed Oct. 22, 2007; discloses amino acid and nucleic acid sequences for a delta-8 desaturase enzyme from *Tetruetreptia pomquetensis* CCMP1491, *Eutreptiella* sp. CCMP389 and *Eutreptiella* cf_*gymnastica* CCMP1594.

Based on the utility of expressing delta-8 desaturases in conjunction with delta-9 elongases, there has also been effort to identify and characterize delta-9 elongases from various sources. Most delta-9 elongase enzymes identified so far have the ability to convert both LA to EDA and ALA to ETrA (wherein DGLA and ETA are subsequently synthesized from EDA and ETrA, respectively, following reaction with a Δ8 desaturase; ARA and EPA are subsequently synthesized from DGLA and ETA, respectively, following reaction with a Δ5 desaturase; and, DHA synthesis requires subsequent expression of an additional $C_{20/22}$ elongase and a Δ4 desaturase). A delta-9 elongase from *Isochrysis galbana* has been publicly available (described in GenBank Accession No. AAL37626, as well as PCT Publication No. WO 02/077213). Applicants' Assignee's co-pending application having U.S. application Ser. No. 11/601,563 (filed Nov. 16, 2006, which published May 24, 2007; discloses a delta-9 elongase from *Euglena gracilis*. Applicants' Assignee's co-pending application having U.S. application Ser. No. 11/601,564 filed Nov. 16, 2006, discloses a delta-9 elongase from *Eutreptiella* sp. CCMP389.

Most delta-5 desaturase enzymes identified so far have the primary ability to convert dihomo-gamma-linolenic acid [20:3, DGLA] to ARA, with secondary activity in converting eicosatetraenoic acid [20:4, ETA] to EPA (where DHA is subsequently synthesized from EPA following reaction with an additional $C_{20/22}$ elongase and a delta-4 desaturase). The delta-5 desaturase has a role in both the delta-6 desaturase/delta-6 elongase pathway (which is predominantly found in algae, mosses, fungi, nematodes and humans and which is characterized by the production of gamma-linoleic acid ["GLA"; 18:3 ω-6] and/or stearidonic acid ["STA"; 18:4

ω-3]) and the delta-9 elongase/delta-8 desaturase pathway (which operates in some organisms, such as euglenoid species and which is characterized by the production of eicosadienoic acid ["EDA"; 20:2 ω-6] and/or eicosatrienoic acid ["ETrA"; 20:3 ω-3]) (FIG. 1).

Furthermore, based on the role delta-5 desaturase enzymes play in the synthesis of e.g., ARA, EPA and DHA, there has also been an effort to identify and characterize these enzymes from various sources. As such, delta-5 desaturases have been disclosed in both the open literature (e.g., GenBank Accession Nos. AF199596, AF226273, AF320509, AB072976, AF489588, AJ510244, AF419297, AF07879, AF067654 and AB022097) and the patent literature (e.g., U.S. Pat. No. 5,972,664 and U.S. Pat. No. 6,075,183).

Applicants' Assignee has a number of patent applications concerning the production of PUFAs in oleaginous yeasts (i.e., *Yarrowia lipolytica*), including: PCT Publication Nos. WO 2004/101757 and WO 2004/101753 (both published Nov. 25, 2004); U.S. application Ser. No. 11/265,761 (filed Nov. 2, 2005); U.S. application Ser. No. 11/264,784 (filed Nov. 1, 2005); and U.S. application Ser. No. 11/264,737 (filed Nov. 1, 2005).

Relatedly, PCT Publication No. WO 2004/071467 (published Aug. 26, 2004) concerns the production of PUFAs in plants, while PCT Publication No. WO 2004/071178 (published Aug. 26, 2004) concerns annexin promoters and their use in expression of transgenes in plants; both are Applicants' Assignee's copending applications.

SUMMARY OF THE INVENTION

The present invention concerns an isolated polynucleotide comprising:

(a) a nucleotide sequence encoding a polypeptide having delta-5 desaturase activity, wherein the polypeptide has at least 80% amino acid identity, based on the Clustal V method of alignment, when compared to an amino acid sequence as set forth in SEQ ID NO:13;

(b) a nucleotide sequence encoding a polypeptide having delta-5 desaturase activity, wherein the nucleotide sequence has at least 80% sequence identity, based on the BLASTN method of alignment, when compared to a nucleotide sequence as set forth in SEQ ID NO:12;

(c) a nucleotide sequence encoding a polypeptide having delta-5 desaturase activity, wherein the nucleotide sequence hybridizes under stringent conditions to a nucleotide sequence as set forth in SEQ ID NO:12; or (d) a complement of the nucleotide sequence of (a), (b) or (c), wherein the complement and the nucleotide sequence consist of the same number of nucleotides and are 100% complementary.

In a second embodiment, the invention concerns a recombinant DNA construct comprising any of the isolated polynucleotides of the invention operably linked to at least one regulatory sequence.

In a third embodiment, the invention concerns a plant cell comprising in its genome the recombinant DNA construct of the invention.

In a fourth embodiment, the invention concerns a method for transforming a plant cell, comprising transforming a plant cell with a recombinant construct of the invention or an isolated polynucleotide of the invention and selecting those plant cells transformed with the recombinant construct or the isolated polynucleotide.

In a fifth embodiment, the invention concerns transgenic seed comprising in its genome the recombinant construct of the invention or a transgenic seed obtained from a plant made by a method of the invention. Also of interest is oil or by-products obtained from such transgenic seeds.

In a sixth embodiment, the invention concerns a method for making long-chain polyunsaturated fatty acids in a plant cell comprising:

(a) transforming a plant cell with the recombinant construct of the invention; and (b) selecting those transformed plant cells that make long-chain polyunsaturated fatty acids.

In a seventh embodiment, the invention concerns a method for producing at least one polyunsaturated fatty acid in an oilseed plant cell comprising:

(a) transforming an oilseed plant cell with a first recombinant DNA construct comprising an isolated polynucleotide encoding at least one delta-5 desaturase polypeptide, operably linked to at least one regulatory sequence and at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase;

(b) regenerating an oilseed plant from the transformed cell of step (a); and (c) selecting those seeds obtained from the plants of step (b) having an altered level of polyunsaturated fatty acids when compared to the level in seeds obtained from a nontransformed oilseed plant.

In an eighth embodiment, the invention concerns an oilseed plant comprising in its genome the recombinant construct of the invention. Suitable oilseed plants include, but are not limited to, soybean, *Brassica* species, sunflower, maize, cotton, flax and safflower.

In a ninth embodiment, the invention concerns an oilseed plant comprising:

(a) a first recombinant DNA construct comprising an isolated polynucleotide encoding at least one delta-5 desaturase polypeptide, operably linked to at least one regulatory sequence; and (b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase.

Also of interest are transgenic seeds obtained from such oilseed plants as well as oil or by-products obtained from these transgenic seeds. A preferred by-product is lecithin.

In a tenth embodiment, the invention concerns food or feed incorporating an oil or seed of the invention or food or feed comprising an ingredient derived from the processing of the seeds.

In an eleventh embodiment, the invention concerns progeny plants obtained from obtained from a plant made by the method of the invention or an oilseed plant of the invention.

BIOLOGICAL DEPOSITS

The following plasmid has been deposited with the American Type Culture Collection (ATCC), 10801 University Boulevard, Manassas, Va. 20110-2209, and bears the following designation, Accession Number and date of deposit (Table 1).

TABLE 1

| ATCC Deposit | | |
|---|---|---|
| Plasmid | Accession Number | Date of Deposit |
| pKR72 | PTA-6019 | May 28, 2004 |

BRIEF DESCRIPTION OF THE DRAWINGS AND SEQUENCE LISTINGS

The invention can be more fully understood from the following detailed description and the accompanying drawings and Sequence Listing, which form a part of this application.

FIG. 6 are the fatty acid profiles for *Yarrowia lipolytica* expressing pY169.

FIGS. 8A, 8B and 8C shows a comparison of the nucleotide sequences of EaD5 (same as EaD5Des1) (SEQ ID NO:12) and EaD5S (SEQ ID NO:45).

Figure 1:
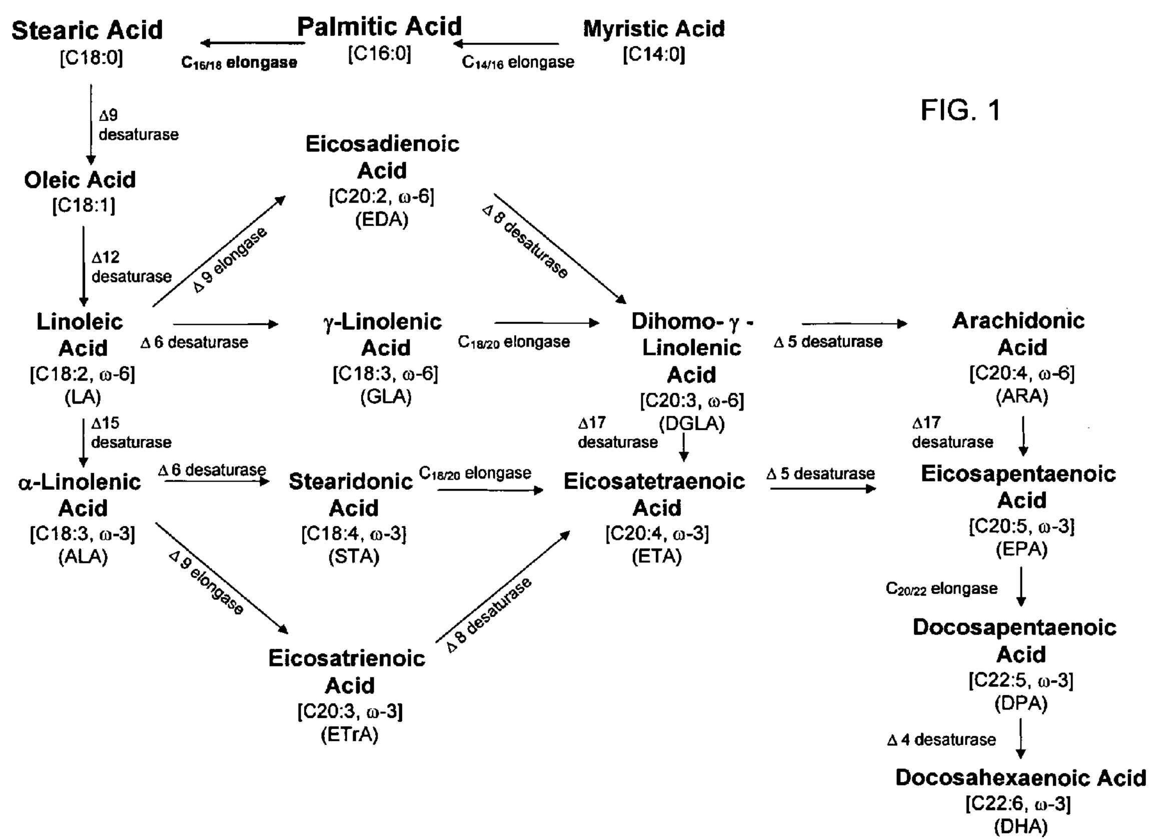
FIG. 1 is a representative omega-3 and omega-6 fatty acid pathway providing for the conversion of myristic acid through various intermediates to DHA.

FIG. 11 shows ten events having the highest average correct delta-5 desaturase activities (average of the 5 somatic soybean embryos analyzed) from approximately 30 events transformed with pKR1153 (Experiment MSE2140). Fatty acids are identified as 16:0 (palmitate), 18:0 (stearic acid), 18:1 (oleic acid), LA, ALA, EDA, SCI, DGLA, ARA, ERA, JUP, ETA and EPA. Fatty acid compositions for an individual embryo were expressed as the weight percent (wt. %) of total fatty acids and the average fatty acid composition is an average of six individual embryos for each event. The activity of the delta-5 desaturase is expressed as percent delta-desaturation ("% delta-5 desat"), calculated according to the following formula: ([product]/[substrate+product])*100. More specifically, the percent delta-5 desaturation was determined as: ([ARA+EPA]/[DGLA+ETA+ARA+EPA])*100.

The sequence descriptions summarize the Sequences Listing attached hereto. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219(2):345-373 (1984).

SEQ ID NO:1 is the cDNA sequence of the *Euglena anabaena* delta-5 desaturase 1 (EaD5Des1).

SEQ ID NO:2 is the nucleotide sequence of the *Euglena gracilis* delta-5 desaturase coding sequence (EgD5).

SEQ ID NO:3 is the nucleotide sequence of the *Euglena gracilis* delta-5 desaturase oligonucleotide YL794.

SEQ ID NO:4 is the nucleotide sequence of the *Euglena gracilis* delta-5 desaturase oligonucleotide YL797.

SEQ ID NO:5 is the nucleotide sequence of the *Euglena gracilis* delta-5 desaturase oligonucleotide YL796.

SEQ ID NO:6 is the nucleotide sequence of the *Euglena gracilis* delta-5 desaturase oligonucleotide YL795.

SEQ ID NO:7 is the nucleotide sequence of plasmid pZUF17.

SEQ ID NO:8 is the nucleotide sequence of plasmid pDMW367.

SEQ ID NO:9 is the nucleotide sequence of the M13F universal primer.

SEQ ID NO:10 is the nucleotide sequence of M13-28Rev.

SEQ ID NO:11 is the nucleotide sequence of plasmid pLF119.

SEQ ID NO:12 is the nucleotide sequence of the *Euglena anabaena* delta-5 desaturase 1 coding sequence (EaD5Des1).

SEQ ID NO:13 is the amino acid sequence of the *Euglena anabaena* delta-5 desaturase 1 (EaD5Des1).

SEQ ID NO:14 is the amino acid sequence of the *Thalassiosira pseudonana* delta-8 fatty acid desaturase.

SEQ ID NO:15 is the amino acid sequence of the *Phaeodactylum tricornutum* delta-5 fatty acid desaturase.

SEQ ID NO:16 is the amino acid sequence of the *Euglena gracilis* delta-5 desaturase (EgD5).

SEQ ID NO:17 is the nucleotide sequence of plasmid pDMW263.

SEQ ID NO:18 is the nucleotide sequence of plasmid pDMW237.

SEQ ID NO:19 is the nucleotide sequence of plasmid pY115.

SEQ ID NO:20 is the nucleotide sequence of oligonucleotide oYFBA1.

SEQ ID NO:21 is the nucleotide sequence of oligonucleotide oYFBA1-6.

SEQ ID NO:22 is the nucleotide sequence of plasmid pY158.

SEQ ID NO:23 is the nucleotide sequence of plasmid pY159.

SEQ ID NO:24 is the nucleotide sequence of plasmid pY169.

SEQ ID NO:25 is the nucleotide sequence of the *Euglena gracilis* delta-9 elongase (EgD9e).

SEQ ID NO:26 is the nucleotide sequence of the *Euglena gracilis* delta-8 desaturase (EgD8).

SEQ ID NO:27 is the nucleotide sequence of the *Euglena gracilis* elongase sense oligonucleotide oEugEL1-1.

SEQ ID NO:28 is the nucleotide sequence of the *Euglena gracilis* elongase anti-sense oligonucleotide oEugEL1-2.

SEQ ID NO:29 is the nucleotide sequence of plasmid pKR906.

SEQ ID NO:30 is the nucleotide sequence of plasmid pKR72.

SEQ ID NO:31 is the nucleotide sequence of plasmid KS102.

SEQ ID NO:32 is the nucleotide sequence of plasmid pKR197.

SEQ ID NO:33 is the nucleotide sequence of plasmid pKR911.

SEQ ID NO:34 is the nucleotide sequence of plasmid pKR680.

SEQ ID NO:35 is the nucleotide sequence of plasmid pKR913.

SEQ ID NO:36 is the nucleotide sequence of oligonucleotide oEAd5-1-1.

SEQ ID NO:37 is the nucleotide sequence of oligonucleotide oEAd5-1-2.

SEQ ID NO:38 is the nucleotide sequence of plasmid pKR1136.

SEQ ID NO:39 is the nucleotide sequence of plasmid pKR767.

SEQ ID NO:40 is the nucleotide sequence of the *Mortierella alpina* delta-5 desaturase coding sequence (MaD5).

SEQ ID NO:41 is the nucleotide sequence of plasmid pKR974.

SEQ ID NO:42 is the nucleotide sequence of the *Saprolegnia diclina* delta-5 desaturase coding sequence (SdD5).

SEQ ID NO:43 is the nucleotide sequence of plasmid pKR1139.

SEQ ID NO:44 is the nucleotide sequence of plasmid pKR1153.

SEQ ID NO:45 is the nucleotide sequence of the codon-optimized *Euglena anabaena* delta-5 desaturase gene (EaD5S).

SEQ ID NO:46 is the nucleotide sequence of plasmid pEaD5S.

DETAILED DESCRIPTION OF THE INVENTION

The disclosure of each reference set forth herein is hereby incorporated by reference in its entirety.

As used herein and in the appended claims, the singular forms “a”, “an”, and “the” include plural reference unless the context clearly dictates otherwise. Thus, for example, reference to “a plant” includes a plurality of such plants, reference to “a cell” includes one or more cells and equivalents thereof known to those skilled in the art, and so forth.

The present invention relates to delta-5 desaturase enzymes and nucleic acid for encoding the same isolated from *Euglena anabaena*. These are useful for, inter alia, for the manipulation of biochemical pathways for the production of PUFAs. Thus, the subject invention finds many applications.

PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Supplementation of humans or animals with PUFAs produced by recombinant means can result in increased levels of the added PUFAs, as well as their metabolic progeny. For example, treatment with EPA can result not only in increased levels of EPA, but also downstream products of EPA such as eicosanoids (i.e., prostaglandins, leukotrienes, thromboxanes). Complex regulatory mechanisms can make it desirable to combine various PUFAs, or add different conjugates of PUFAs, in order to prevent, control or overcome such mechanisms to achieve the desired levels of specific PUFAs in an individual.

In the context of this disclosure, a number of terms and abbreviations are used. The following definitions are provided.

“Open reading frame” is abbreviated ORF.

“Polymerase chain reaction” is abbreviated PCR.

“American Type Culture Collection” is abbreviated ATCC.

“Polyunsaturated fatty acid(s)” is abbreviated PUFA(s).

“Triacylglycerols” are abbreviated TAGs.

The term “fatty acids” refers to long-chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. Additional details concerning the differentiation between “saturated fatty acids” versus “unsaturated fatty acids”, “monounsaturated fatty acids” versus “polyunsaturated fatty acids” (or “PUFAs”), and “omega-6 fatty acids” (ω-6 or n-6) versus “omega-3 fatty acids” (ω-3 or n-3) are provided in PCT Publication No. WO 2004/101757.

Fatty acids are described herein by a simple notation system of “X:Y”, wherein X is number of carbon (C) atoms in the particular fatty acid and Y is the number of double bonds. The number following the fatty acid designation indicates the position of the double bond from the carboxyl end of the fatty acid with the “c” affix for the cis-configuration of the double bond (e.g., palmitic acid (16:0), stearic acid (18:0), oleic acid (18:1, 9c), petroselinic acid (18:1, 6c), LA (18:2, 9c, 12c), GLA (18:3, 6c, 9c, 12c) and ALA (18:3, 9c, 12c, 15c)). Unless otherwise specified, 18:1, 18:2 and 18:3 refer to oleic, LA and ALA fatty acids, respectively. If not specifically written as otherwise, double bonds are assumed to be of the cis configuration. For instance, the double bonds in 18:2 (9,12) would be assumed to be in the cis configuration.

Nomenclature used to describe PUFAs in the present disclosure is shown below in Table 2. In the column titled “Shorthand Notation”, the omega-reference system is used to indicate the number of carbons, the number of double bonds and the position of the double bond closest to the omega carbon, counting from the omega carbon (which is numbered 1 for this purpose). The remainder of the table summarizes the common names of omega-3 and omega-6 fatty acids and their precursors, the abbreviations that will be used throughout the remainder of the specification, and each compounds’ chemical name.

TABLE 2

Nomenclature of Polyunsaturated Fatty Acids and Precursors

| Common Name | Abbreviation | Chemical Name | Shorthand Notation |
|---|---|---|---|
| myristic | — | tetradecanoic | 14:0 |
| palmitic | PA | hexadecanoic | 16:0 |
| palmitoleic | — | 9-hexadecenoic | 16:1 |
| stearic | — | octadecanoic | 18:0 |
| oleic | — | cis-9-octadecenoic | 18:1 |
| linoleic | LA | cis-9,12-octadecadienoic | 18:2 ω-6 |
| gamma-linolenic | GLA | cis-6,9,12-octadecatrienoic | 18:3 ω-6 |
| eicosadienoic | EDA | cis-11,14-eicosadienoic | 20:2 ω-6 |
| dihomo-gamma-linolenic | DGLA | cis-8,11,14-eicosatrienoic | 20:3 ω-6 |
| sciadonic | SCI | cis-5,11,14-eicosatrienoic | 20:3b ω-6 |
| arachidonic | ARA | cis-5,8,11,14-eicosatetraenoic | 20:4 ω-6 |
| alpha-linolenic | ALA | cis-9,12,15-octadecatrienoic | 18:3 ω-3 |
| stearidonic | STA | cis-6,9,12,15-octadecatetraenoic | 18:4 ω-3 |
| eicosatrienoic | ETrA or ERA | cis-11,14,17-eicosatrienoic | 20:3 ω-3 |
| eicosa-tetraenoic | ETA | cis-8,11,14,17-eicosatetraenoic | 20:4 ω-3 |
| juniperonic | JUP | cis-5,11,14,17-eicosatetraenoic | 20:4b ω-3 |

TABLE 2-continued

Nomenclature of Polyunsaturated Fatty Acids and Precursors

| Common Name | Abbreviation | Chemical Name | Shorthand Notation |
|---|---|---|---|
| eicosa-pentaenoic | EPA | cis-5,8,11,14,17-eicosapentaenoic | 20:5 ω-3 |
| docosa-pentaenoic | DPA | cis-7,10,13,16,19-docosapentaenoic | 22:5 ω-3 |
| docosa-hexaenoic | DHA | cis-4,7,10,13,16,19-docosahexaenoic | 22:6 ω-3 |

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to LA, EDA, GLA, DGLA, ARA, ALA, STA, ETrA, ETA, EPA, DPA and DHA. This process is well described in the literature (e.g., see PCT Publication No. WO 2006/052870). Simplistically, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzyme" refers to any of the following enzymes (and genes which encode said enzymes) associated with the biosynthesis of a PUFA, including: a delta-4 desaturase, a delta-5 desaturase, a delta-6 desaturase, a delta-12 desaturase, a delta-15 desaturase, a delta-17 desaturase, a delta-9 desaturase, a delta-8 desaturase, a delta-9 elongase, a $C_{14/16}$ elongase, a $C_{16/18}$ elongase, a $C_{18/20}$ elongase and/or a $C_{20/22}$ elongase.

The term "omega-3/omega-6 fatty acid biosynthetic pathway" refers to a set of genes which, when expressed under the appropriate conditions encode enzymes that catalyze the production of either or both omega-3 and omega-6 fatty acids. Typically the genes involved in the omega-3/omega-6 fatty acid biosynthetic pathway encode PUFA biosynthetic pathway enzymes. A representative pathway is illustrated in FIG. 1, providing for the conversion of myristic acid through various intermediates to DHA, which demonstrates how both omega-3 and omega-6 fatty acids may be produced from a common source. The pathway is naturally divided into two portions where one portion will generate omega-3 fatty acids and the other portion, omega-6 fatty acids.

The term "functional" as used herein in context with the omega-3/omega-6 fatty acid biosynthetic pathway means that some (or all of) the genes in the pathway express active enzymes, resulting in in vivo catalysis or substrate conversion. It should be understood that "omega-3/omega-6 fatty acid biosynthetic pathway" or "functional omega-3/omega-6 fatty acid biosynthetic pathway" does not imply that all the PUFA biosynthetic pathway enzyme genes are required, as a number of fatty acid products will only require the expression of a subset of the genes of this pathway.

The term "delta-9 elongase/delta-8 desaturase pathway" refers to a biosynthetic pathway for production of long-chain PUFAs. This pathway, at a minimum, comprises a delta-9 elongase and a delta-8 desaturase, thereby enabling biosynthesis of DGLA and/or ETA from LA and ALA, respectively. With expression of other desaturases and elongases, ARA, EPA, DPA and DHA may also be synthesized. This pathway may be advantageous in some embodiments, as the biosynthesis of GLA and/or STA is excluded.

The term "intermediate fatty acid" refers to any fatty acid produced in a fatty acid metabolic pathway that can be further converted to an intended product fatty acid in this pathway by the action of other metabolic pathway enzymes. For instance, when EPA is produced using the delta-9 elongase/delta-8 desaturase pathway, EDA, ETrA, DGLA, ETA and ARA can be produced and are considered "intermediate fatty acids" since these fatty acids can be further converted to EPA via action of other metabolic pathway enzymes.

The term "by-product fatty acid" refers to any fatty acid produced in a fatty acid metabolic pathway that is not the intended fatty acid product of the pathway nor an "intermediate fatty acid" of the pathway. For instance, when EPA is produced using the delta-9 elongase/delta-8 desaturase pathway, sciadonic acid (SCI) and juniperonic acid (JUP) also can be produced by the action of a delta-5 desaturase on either EDA or ETrA, respectively. They are considered to be "by-product fatty acids" since neither can be further converted to EPA by the action of other metabolic pathway enzymes.

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long-chain PUFAs, as well as shorter saturated and unsaturated fatty acids and longer chain saturated fatty acids. Thus, "oil biosynthesis" generically refers to the synthesis of TAGs in the cell.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidyletanolamine (PE) fraction and triacylglycerol (TAG or oil) fraction. However, the terms "lipid" and "oil" will be used interchangeably throughout the specification.

The terms "conversion efficiency" and "percent substrate conversion" refer to the efficiency by which a particular enzyme (e.g., a desaturase) can convert substrate to product. The conversion efficiency is measured according to the following formula: ([product]/[substrate+product])*100, where 'product' includes the immediate product and all products in the pathway derived from it.

"Desaturase" is a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are delta-5 desaturases that will desaturate a fatty acid between the fifth and sixth carbon atom numbered from the carboxyl-terminal end of the molecule and that can, for example, catalyze the conversion of DGLA to ARA and/or ETA to EPA. Other useful fatty acid desaturases include, for example: (1) delta-8 desaturases that catalyze the conversion of EDA to DGLA and/or ERA to ETA; (2) delta-6 desaturases that catalyze the conversion of LA to GLA and/or ALA to STA; (3) delta-4 desaturases that catalyze the conversion of DPA to DHA; (4) delta-12 desaturases that catalyze the conversion of oleic acid to LA; (5) delta-15 desaturases that catalyze the conversion of LA to ALA and/or GLA to STA; (6) delta-17 desaturases that catalyze the conversion of ARA to EPA and/or DGLA to ETA; and (7) delta-9 desaturases that catalyze the conversion of palmitic acid to palmitoleic acid (16:1) and/or stearic acid to oleic acid (18:1). In the art, delta-15 and delta-17 desaturases are also occasionally referred to as "omega-3 desaturases", "w-3 desaturases", and/or "ω-3 desaturases", based on their ability to convert omega-6 fatty acids into their omega-3 counterparts (e.g., conversion of LA into ALA and ARA into EPA, respectively). In some embodiments, it is most desirable to empirically determine the specificity of a particular fatty acid desaturase by transforming a suitable host with the gene for the fatty acid desaturase and determining its effect on the fatty acid profile of the host.

The term "delta-5 desaturase" refers to an enzyme that desaturates a fatty acid between the fifth and sixth carbon atom numbered from the carboxyl-terminal end of the molecule. Preferably, a delta-5 desaturase converts dihomo-gamma-linolenic acid [20:3, DGLA] to arachidonic acid [20:4, ARA] or converts eicosatetraenoic acid [20:4, ETA] to eicosapentaenoic acid [20:5, EPA].

For the purposes herein, the terms "EaD5Des1" or "EaD5" refers to a delta-5 desaturase enzyme (SEQ ID NO:13) isolated from *Euglena anabaena*, encoded by SEQ ID NO:12 herein. Likewise, the term "EaD5S" (SEQ ID NO:45) refers to a delta-5 desaturase codon-optimized for expression in *Yarrowia lipolytica*.

For the purposes herein, the term "IgD9e" refers to a delta-9 elongase (SEQ ID NO:15) (NCBI Accession No. AAL37626 [GI 17226123], locus AAL37626, CDS AF390174; GenBank Accession No. AF390174) isolated from *Isochrysis galbana*. In contrast, the term "IgD9eS" refers to a synthetic (codon-optimized) delta-9 elongase derived from the DNA sequence of the *Isochrysis galbana* delta-9 elongase which can be used for expression in *Yarrowia lipolytica*.

Similarly for the purposes herein, the term "EgD9e" refers to a delta-9 elongase isolated from *Euglena gracilis*. EgD9e is described in U.S. application Ser. No. 11/601,563 (filed Nov. 16, 2006, which published May 24, 2007).

Similarly, the term "EgD8" refers to a delta-8 desaturase enzyme isolated from *Euglena gracilis*. EgD8 is 100% identical and functionally equivalent to "Eg5", as described in PCT Publication Nos. WO 2006/012325 and WO 2006/012326 (SEQ ID NO:2 of U.S. Publication No. 20050287652-A1).

The term "elongase system" refers to a suite of four enzymes that are responsible for elongation of a fatty acid carbon chain to produce a fatty acid that is two carbons longer than the fatty acid substrate that the elongase system acts upon. More specifically, the process of elongation occurs in association with fatty acid synthase, whereby CoA is the acyl carrier (Lassner et al., *Plant Cell* 8:281-292 (1996)). In the first step, which has been found to be both substrate-specific and also rate-limiting, malonyl-CoA is condensed with a long-chain acyl-CoA to yield carbon dioxide ($CO_2$) and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongase systems are the conversion of GLA to DGLA, STA to ETA, LA to EDA, ALA to ETrA and EPA to DPA.

For the purposes herein, an enzyme catalyzing the first condensation reaction (i.e., conversion of malonyl-CoA and long-chain acyl-CoA to β-ketoacyl-CoA) will be referred to generically as an "elongase". In general, the substrate selectivity of elongases is somewhat broad but segregated by both chain length and the degree of unsaturation. Accordingly, elongases can have different specificities. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase will utilize a $C_{18}$ substrate (e.g., GLA, STA) and a $C_{20/22}$ elongase will utilize a $C_{20}$ substrate (e.g., EPA). Similarly, a "delta-9 elongase" may be able to catalyze the conversion of LA to EDA and/or ALA to ETrA. It is important to note that some elongases have broad specificity and thus a single enzyme may be capable of catalyzing several elongase reactions. Thus, for example, a delta-9 elongase may also act as a $C_{16/18}$ elongase, $C_{18/20}$ elongase and/or $C_{20/22}$ elongase and may have alternate, but not preferred, specificities for delta-5 and delta-6 fatty acids such as EPA and/or GLA, respectively.

The term "conservative amino acid substitution" refers to a substitution of an amino acid residue in a given protein with another amino acid, without altering the chemical or functional nature of that protein. For example, it is well known in the art that alterations in a gene that result in the production of a chemically equivalent amino acid at a given site (but that do not affect the structural and functional properties of the encoded, folded protein) are common. For the purposes of the present invention, "conservative amino acid substitutions" are defined as exchanges within one of the following five groups:

1. small aliphatic, nonpolar or slightly polar residues: Ala [A], Ser [S], Thr [T] (Pro [P], Gly [G]);
2. polar, negatively charged residues and their amides: Asp [D], Asn [N], Glu [E], Gln [Q];
3. polar, positively charged residues: His [H], Arg [R], Lys [K];
4. large aliphatic, nonpolar residues: Met [M], Leu [L], Ile [I], Val [V] (Cys [C]); and,
5. large aromatic residues: Phe [F], Tyr [Y], Trp [W].

Conservative amino acid substitutions generally maintain: 1) the structure of the polypeptide backbone in the area of the substitution; 2) the charge or hydrophobicity of the molecule at the target site; or 3) the bulk of the side chain. Additionally, in many cases, alterations of the N-terminal and C-terminal portions of the protein molecule would also not be expected to alter the activity of the protein.

As used herein, "nucleic acid" means a polynucleotide and includes single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deosycytidylate, "G" for guanylate or deoxyguanylate, "U" for uridlate, "T" for deosythymidylate, "R" for purines (A or G), "Y" for pyrimidiens (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth et al., *Anal. Biochem.* 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, *CABIOS.* 5:151-153 (1989); Higgins, D. G. et al. (1992) *Comput. Appl. Biosci.* 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "genome" as it applies to a plant cells encompasses not only chromosomal DNA found within the nucleus, but organelle DNA found within subcellular components (e.g., mitochondrial, plastid) of the cell.

A "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same that plant is homozygous at that locus. If the alleles present at a given locus on a chromosome differ that plant is heterozygous at that locus.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B. *Biochemistry of Plants* 15:1-82 (1989).

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotechnol.* 3:225-236 (1995)).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. *Plant Cell* 1:671-680 (1989).

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989). Transformation methods are well known to those skilled in the art and are described infra.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

The term "recombinant" refers to an artificial combination of two otherwise separated segments of sequence, e.g., by chemical synthesis or by the manipulation of isolated segments of nucleic acids by genetic engineering techniques.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host (i.e., to a discrete nucleic acid fragment into which a nucleic acid sequence or fragment can be moved.)

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., a mRNA or a protein [either precursor or mature]).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

As used herein, "transgenic" refers to a plant or a cell which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of an expression construct. Transgenic is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the overexpressed sequence (Vaucheret et al., *Plant J.* 16:651-659 (1998); Gura, *Nature* 404:804-808 (2000)). The overall efficiency of this phenomenon is low, and the extent of the RNA reduction is widely variable. More recent work has described the use of "hairpin" structures that incorporate all, or part, of an mRNA encoding sequence in a complementary orientation that results in a potential "stem-loop" structure for the expressed RNA (PCT Publication No. WO 99/53050, published Oct. 21, 1999; PCT Publication No. WO 02/00904, published Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083, published Aug. 20, 1998). Both of these co-suppressing phenomena have not been elucidated mechanistically, although genetic evidence has begun to unravel this complex situation (Elmayan et al., *Plant Cell* 10:1747-1757 (1998)).

The term "oleaginous" refers to those organisms that tend to store their energy source in the form of lipid (Weete, In: Fungal Lipid Biochemistry, 2nd Ed., Plenum, 1980). A class of plants identified as oleaginous are commonly referred to as "oilseed" plants. Examples of oilseed plants include, but are not limited to: soybean (*Glycine* and *Soja* sp.), flax (*Linum* sp.), rapeseed (*Brassica* sp.), maize, cotton, safflower (*Carthamus* sp.) and sunflower (*Helianthus* sp.).

Within oleaginous microorganisms the cellular oil or TAG content generally follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)). The term "oleaginous yeast" refers to those microorganisms classified as yeasts that make oil. It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces.*

The term "Euglenophyceae" refers to a group of unicellular colorless or photosynthetic flagellates ("euglenoids") found living in freshwater, marine, soil, and parasitic environments. The class is characterized by solitary unicells, wherein most are free-swimming and have two flagella (one of which may be nonemergent) arising from an anterior invagination known as a reservoir. Photosynthetic euglenoids contain one to many grass-green chloroplasts, which vary from minute disks to expanded plates or ribbons. Colorless euglenoids depend on osmotrophy or phagotrophy for nutrient assimilation. About 1000 species have been described and classified into about 40 genera and 6 orders. Examples of Euglenophyceae include, but are no means limited to, the following genera: *Euglena, Eutreptiella* and *Tetruetreptia.*

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores.

"Progeny" comprises any subsequent generation of a plant.

An Overview: Microbial Biosynthesis of Fatty Acids and Triacylglycerols

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in PCT Publication No. WO 2004/101757. Palmitate is the precursor of longer-chain saturated and unsaturated fatty acid derivates, which are formed through the action of elongases and desaturases (FIG. 1).

TAGs (the primary storage unit for fatty acids) are formed by a series of reactions that involve: (1) the esterification of one molecule of acyl-CoA to glycerol-3-phosphate via an acyltransferase to produce lysophosphatidic acid; (2) the esterification of a second molecule of acyl-CoA via an acyltransferase to yield 1,2-diacylglycerol phosphate (commonly identified as phosphatidic acid); (3) removal of a phosphate by phosphatidic acid phosphatase to yield 1,2-diacylglycerol (DAG); and (4) the addition of a third fatty acid by the action of an acyltransferase to form TAG. A wide spectrum of fatty acids can be incorporated into TAGs, including saturated and unsaturated fatty acids and short-chain and long-chain fatty acids.

Biosynthesis of Omega Fatty Acids

The metabolic process wherein oleic acid is converted to long chain omega-3/omega-6 fatty acids involves elongation of the carbon chain through the addition of carbon atoms and desaturation of the molecule through the addition of double bonds. This requires a series of special desaturation and elongation enzymes present in the endoplasmic reticulim membrane. However, as seen in FIG. 1 and as described below, there are often multiple alternate pathways for production of a specific long chain omega-3/omega-6 fatty acid.

Specifically, all pathways require the initial conversion of oleic acid to LA, the first of the omega-6 fatty acids, by a delta-12 desaturase. Then, using the "delta-9 elongase/delta-8 desaturase pathway", long chain omega-6 fatty acids are formed as follows: (1) LA is converted to EDA by a delta-9 elongase; (2) EDA is converted to DGLA by a delta-8 desaturase; and (3) DGLA is converted to ARA by a delta-5 desaturase. Alternatively, the "delta-9 elongase/delta-8 desaturase pathway" can be utilized for formation of long chain omega-3 fatty acids as follows: (1) LA is converted to ALA, the first of the omega-3 fatty acids, by a delta-15 desaturase; (2) ALA is converted to ETrA by a delta-9 elongase; (3) ETrA is converted to ETA by a delta-8 desaturase; (4) ETA is converted to EPA by a delta-5 desaturase; (5) EPA is converted to DPA by a $C_{20/22}$ elongase; and (6) DPA is converted to DHA by a delta-4 desaturase. Optionally, omega-6 fatty acids may be converted to omega-3 fatty acids; for example, ETA and EPA are produced from DGLA and ARA, respectively, by delta-17 desaturase activity.

Alternate pathways for the biosynthesis of omega-3/omega-6 fatty acids utilize a delta-6 desaturase and $C_{18/20}$ elongase (also known as delta-6 elongase, the terms can be used interchangeably) (i.e., the "delta-6 desaturase/delta-6 elongase pathway"). More specifically, LA and ALA may be converted to GLA and STA, respectively, by a delta-6 desaturase; then, a $C_{18/20}$ elongase converts GLA to DGLA and/or STA to ETA.

It is contemplated that the particular functionalities required to be introduced into a specific host organism for production of omega-3/omega-6 fatty acids will depend on the host cell (and its native PUFA profile and/or desaturase/elongase profile), the availability of substrate, and the desired end product(s). For example, expression of the delta-9 elongase/delta-8 desaturase pathway may be preferred in some embodiments, as opposed to expression of the delta-6 desaturase/delta-6 elongase pathway, since PUFAs produced via the former pathway are devoid of GLA.

One skilled in the art will be able to identify various candidate genes encoding each of the enzymes desired for omega-3/omega-6 fatty acid biosynthesis. Useful desaturase and elongase sequences may be derived from any source, e.g., isolated from a natural source (from bacteria, algae, fungi, plants, animals, etc.), produced via a semi-synthetic route or synthesized de novo. Although the particular source of the desaturase and elongase genes introduced into the host is not critical, considerations for choosing a specific polypeptide having desaturase or elongase activity include: (1) the substrate specificity of the polypeptide; (2) whether the polypeptide or a component thereof is a rate-limiting enzyme; (3) whether the desaturase or elongase is essential for synthesis of a desired PUFA; and/or (4) co-factors required by the polypeptide. The expressed polypeptide preferably has parameters compatible with the biochemical environment of its location in the host cell (see PCT Publication No. WO 2004/101757 for additional details).

In additional embodiments, it will also be useful to consider the conversion efficiency of each particular desaturase and/or elongase. More specifically, since each enzyme rarely functions with 100% efficiency to convert substrate to product, the final lipid profile of unpurified oils produced in a host cell will typically be a mixture of various PUFAs consisting of the desired omega-3/omega-6 fatty acid, as well as various upstream intermediary PUFAs. Thus, consideration of each enzyme's conversion efficiency is also a variable when optimizing biosynthesis of a desired fatty acid that must be considered in light of the final desired lipid profile of the product.

With each of the considerations above in mind, candidate genes having the appropriate desaturase and elongase activities (e.g., delta-6 desaturases, $C_{18/20}$ elongases, delta-5 desaturases, delta-17 desaturases, delta-15 desaturases, delta-9 desaturases, delta-12 desaturases, $C_{14/16}$ elongases, $C_{16/18}$ elongases, delta-9 elongases, delta-8 desaturases, delta-4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

Sequence Identification of Novel Delta-5 Desaturases

In the present invention, nucleotide sequences encoding delta-5 desaturases have been isolated from *Euglena anabaena* (designated herein as "EaD5Des1").

Thus, the present invention concerns an isolated polynucleotide comprising:

(a) a nucleotide sequence encoding a polypeptide having delta-5 desaturase activity, wherein the polypeptide has at least 80% amino acid identity, based on the Clustal V method of alignment, when compared to an amino acid sequence as set forth in SEQ ID NO:13 [EaD5Des1];

(b) a nucleotide sequence encoding a polypeptide having delta-5 desaturase activity, wherein the nucleotide sequence has at least 80% sequence identity, based on the BLASTN method of alignment, when compared to a nucleotide sequence as set forth in SEQ ID NO:12 [EaD5Des1]; or, (c) a complement of the nucleotide sequence of (a) or (b), wherein the complement and the nucleotide sequence consist of the same number of nucleotides and are 100% complementary.

In still another aspect, this invention concerns an isolated polynucleotide comprising a nucleotide sequence encoding a polypeptide having delta-5 desaturase activity, wherein the nucleotide sequence has at least 90% sequence identity, based on the BLASTN method of alignment, when compared to a nucleotide sequence as set forth in SEQ ID NO:12.

The instant EaD5Des1 sequences can be codon-optimized for expression in a particular host organism (see SEQ ID NO:45). As is well known in the art, this can be a useful means to further optimize the expression of the enzyme in the alternate host, since use of host-preferred codons can substantially enhance the expression of the foreign gene encoding the polypeptide. In general, host-preferred codons can be determined within a particular host species of interest by examining codon usage in proteins (preferably those expressed in the largest amount) and determining which codons are used with highest frequency. Then, the coding sequence for a polypeptide of interest having e.g., desaturase activity can be synthesized in whole or in part using the codons preferred in the host species.

EaD5Des1 could be codon-optimized for expression in *Yarrowia lipolytica*, as taught in PCT Publication No. WO 04/101757 and U.S. Pat. No. 7,125,672. In one embodiment, it may be desirable to modify a portion of the codons encoding EaD5Des1 (as set forth in SEQ ID NO:12) to enhance expression of the gene in a host organism including, but not limited to, a plant or plant part.

One skilled in the art would be able to use the teachings herein to create various other codon-optimized delta-5 desaturase proteins suitable for optimal expression in alternate hosts, based on the wildtype EaD5Des1 sequence. Accordingly, the instant invention relates to any codon-optimized delta-5 desaturase protein that is derived from the wildtype EaD5Des1 (i.e., encoded by SEQ ID NO: 12).

Identification and Isolation of Homologs

Any of the instant desaturase sequences (i.e., EaD5Des1) or portions thereof may be used to search for delta-5 desaturase homologs in the same or other bacterial, algal, fungal, euglenoid or plant species using sequence analysis software. In general, such computer software matches similar sequences by assigning degrees of homology to various substitutions, deletions, and other modifications.

Alternatively, any of the instant desaturase sequences or portions thereof may also be employed as hybridization reagents for the identification of delta-5 desaturase homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the delta-5 desaturase nucleic acid fragments described herein (or any homologs identified thereof) may be used to isolate genes encoding homologous proteins from the same or other bacterial, algal, fungal, euglenoid or plant species. Isolation of homologous genes using sequence-dependent protocols is well known in the art. Examples of sequence-dependent protocols include, but are not limited to: (1) methods of nucleic acid hybridization; (2) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor et al., *Proc. Acad. Sci. USA* 82:1074 (1985); or strand displacement amplification (SDA), Walker et al., *Proc. Natl. Acad. Sci. U.S.A.,* 89:392 (1992)]; and (3) methods of library construction and screening by complementation.

For example, genes encoding similar proteins or polypeptides to the delta-5 desaturases described herein could be isolated directly by using all or a portion of the instant nucleic acid fragments as DNA hybridization probes to screen libraries from e.g., any desired yeast or fungus using methodology well known to those skilled in the art (wherein those organisms producing ARA and/or EPA would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *PNAS USA* 86:5673 (1989); Loh et al., *Science* 243:217 (1989)).

In other embodiments, any of the delta-5 desaturase nucleic acid fragments described herein (or any homologs identified thereof) may be used for creation of new and improved fatty acid desaturases. As is well known in the art, in vitro mutagenesis and selection, chemical mutagenesis, "gene shuffling" methods or other means can be employed to obtain mutations of naturally occurring desaturase genes. Alternatively, improved fatty acids may be synthesized by domain swapping, wherein a functional domain from any of the delta-5 desaturase nucleic acid fragments described herein are exchanged with a functional domain in an alternate desaturase gene to thereby result in a novel protein. As used herein, "domain" or "functional domain" refer to nucleic acid sequence(s) that are capable of eliciting a biological response in plants.

Methods for Production of Various Omega-3 and/or Omega-6 Fatty Acids

It is expected that introduction of chimeric genes encoding the delta-5 desaturases described herein (i.e., EaD5Des1 or other mutant enzymes, codon-optimized enzymes or homologs thereof), under the control of the appropriate promoters will result in increased production of ARA and/or EPA in the transformed host organism, respectively. As such, the present invention encompasses a method for the direct production of PUFAs comprising exposing a fatty acid substrate (i.e., DGLA and/or ETA) to the desaturase enzymes described herein (e.g., EaD5Des1), such that the substrate is converted to the desired fatty acid product (i.e., ARA and/or EPA).

More specifically, it is an object of the present invention to provide a method for the production of ARA in a plant host cell (e.g. soybean), wherein the plant host cell comprises:

(a) a recombinant construct encoding a delta-5 desaturase polypeptide selected from the group consisting of SEQ ID NO:13; and, (b) a source of DGLA;

wherein the host plant cell is grown under conditions such that the delta-5 desaturase is expressed and the DGLA is converted to ARA, and wherein the ARA is optionally recovered.

In alternate embodiments of the present invention, the delta-5 desaturase may be used for the use of the enzyme for the conversion of ETA to EPA. Accordingly the invention provides a method for the production of EPA, wherein the host cell comprises:

(a) a recombinant construct encoding a delta-5 desaturase polypeptide selected from the group consisting of SEQ ID NO:13; and, (b) a source of ETA;

wherein the host plant cell is grown under conditions such that the delta-5 desaturase is expressed and the ETA is converted to EPA, and wherein the EPA is optionally recovered.

Alternatively, each delta-5 desaturase gene and its corresponding enzyme product described herein can be used indirectly for the production of various omega-6 and omega-3 PUFAs, including e.g., DGLA, ETA, ARA, EPA, DPA and/or DHA (see FIG. 1; see also PCT Publication No. WO 2004/101757). Indirect production of omega-3/omega-6 PUFAs occurs wherein the fatty acid substrate is converted indirectly into the desired fatty acid product, via means of an intermediate step(s) or pathway intermediate(s). Thus, it is contemplated that the delta-5 desaturases described herein (i.e., EaD5Des1, or other mutant enzymes, codon-optimized enzymes or homologs thereof) may be expressed in conjunction with additional genes encoding enzymes of the PUFA biosynthetic pathway (e.g., delta-6 desaturases, $C_{18/20}$ elongases, delta-17 desaturases, delta-8 desaturases, delta-15 desaturases, delta-9 desaturases, delta-12 desaturases, $C_{14/16}$ elongases, $C_{16/18}$ elongases, delta-9 elongases, delta-5 desaturases, delta-4 desaturases, $C_{20/22}$ elongases) to result in higher levels of production of longer-chain omega-3/omega-6 fatty acids (e.g., ARA, EPA, DPA and DHA).

In preferred embodiments, the delta-5 desaturases of the present invention will minimally be expressed in conjunction with a delta-9 elongase and a delta-8 desaturases (e.g., a delta-8 desaturase or a codon-optimized delta-8 desaturase). The delta-5 desaturase could also be minimally expressed in conjunction with a delta-6 desaturase and $C_{18/20}$ elongases. However, the particular genes included within a particular expression cassette will depend on the host cell (and its PUFA profile and/or desaturase/elongase profile), the availability of substrate and the desired end product(s).

When the desired end product is SCI and/or JUP, then the delta-5 desaturase will be minimally expressed in conjunction with a delta-9 elongase in an organism which makes EDA and/or ERA, respectively.

The term "delta-6 desaturase/delta-6 elongase pathway" also refers to a biosynthetic pathway for production of long-chain PUFAs. This pathway, at a minimum, comprises a delta-6 desaturase and a delta-6 elongase, thereby enabling biosynthesis of DGLA and/or ETA from LA and ALA, respectively. With expression of other desaturases and elongases, ARA, EPA, DPA and DHA may also be synthesized. Occasionally, a delta-6 elongase may elongate fatty acids other than the intended fatty acid. For instance, delta-6 elongases generally convert GLA to DGLA but some delta-6 elongases may also convert unintended substrates such as LA or ALA to EDA or ETrA, respectively. In a delta-6 desaturase/delta-6 elongase pathway, EDA and ETrA would be considered "by-product fatty acids" as defined herein. Addition of a delta-8 desaturase to a delta-6 desaturase/delta-6 elongase pathway would provided a means to convert the "by-product fatty acids" EDA and ETrA back into the "intermediate fatty acids" (as defined previously) DGLA and ETA, respectively.

Plant Expression Systems, Cassettes and Vectors, and Transformation

In one embodiment, this invention concerns a recombinant construct comprising any one of the delta-5 desaturase polynucleotides of the invention operably linked to at least one regulatory sequence suitable for expression in a plant. A promoter is a DNA sequence that directs cellular machinery of a plant to produce RNA from the contiguous coding sequence downstream (3') of the promoter. The promoter region influences the rate, developmental stage, and cell type in which the RNA transcript of the gene is made. The RNA transcript is processed to produce mRNA which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cell to cause termination of the RNA transcript and the addition of polyadenylate nucleotides to the 3' end of the RNA.

The origin of the promoter chosen to drive expression of the delta-5 desaturase coding sequence is not important as long as it has sufficient transcriptional activity to accomplish the invention by expressing translatable mRNA for the desired nucleic acid fragments in the desired host tissue at the right time. Either heterologous or non-heterologous (i.e., endogenous) promoters can be used to practice the invention. For example, suitable promoters include, but are not limited to: the alpha prime subunit of beta conglycinin promoter, the Kunitz trypsin inhibitor 3 promoter, the annexin promoter, the glycinin Gy1 promoter, the beta subunit of beta conglycinin promoter, the P34/Gly Bd m 30K promoter, the albumin promoter, the Leg A1 promoter and the Leg A2 promoter.

The annexin, or P34, promoter is described in PCT Publication No. WO 2004/071178 (published Aug. 26, 2004). The level of activity of the annexin promoter is comparable to that of many known strong promoters, such as: (1) the CaMV 35S promoter (Atanassova et al., *Plant Mol. Biol.* 37:275-285 (1998); Battraw and Hall, *Plant Mol. Biol.* 15:527-538 (1990); Holtorf et al., *Plant Mol. Biol.* 29:637-646 (1995); Jefferson et al., *EMBO J.* 6:3901-3907 (1987); Wilmink et al., *Plant Mol. Biol.* 28:949-955 (1995)); (2) the *Arabidopsis* oleosin promoters (Plant et al., *Plant Mol. Biol.* 25:193-205 (1994); Li, Texas A&M University Ph.D. dissertation, pp. 107-128 (1997)); (3) the *Arabidopsis* ubiquitin extension protein promoters (Callis et al., *J. Biol. Chem.* 265(21):12486-93 (1990)); (4) a tomato ubiquitin gene promoter (Rollfinke et al., *Gene.* 211(2):267-76 (1998)); (5) a soybean heat shock protein promoter (Schoffl et al., *Mol Gen Genet.* 217(2-3):246-53 (1989)); and, (6) a maize H3 histone gene promoter (Atanassova et al., *Plant Mol. Biol.* 37(2):275-85 (1989)).

Another useful feature of the annexin promoter is its expression profile in developing seeds. The annexin promoter is most active in developing seeds at early stages (before 10 days after pollination) and is largely quiescent in later stages. The expression profile of the annexin promoter is different from that of many seed-specific promoters, e.g., seed storage protein promoters, which often provide highest activity in later stages of development (Chen et al., *Dev. Genet.* 10:112-122 (1989); Ellerstrom et al., *Plant Mol. Biol.* 32:1019-1027 (1996); Keddie et al., *Plant Mol. Biol.* 24:327-340 (1994); Plant et al., (supra); Li, (supra)). The annexin promoter has a more conventional expression profile but remains distinct from other known seed specific promoters. Thus, the annexin promoter will be a very attractive candidate when overexpression, or suppression, of a gene in embryos is desired at an early developing stage. For example, it may be desirable to overexpress a gene regulating early embryo development or a gene involved in the metabolism prior to seed maturation.

Following identification of an appropriate promoter suitable for expression of a specific delta-5 desaturase coding sequence, the promoter is then operably linked in a sense orientation using conventional means well known to those skilled in the art.

Standard recombinant DNA and molecular cloning techniques used herein are well known in the art and are described more fully in Sambrook, J. et al., In *Molecular Cloning: A Laboratory Manual;* 2nd ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In *Current Protocols in Molecular Biology*; John Wiley and Sons: New York, 1990 (hereinafter "Ausubel et al., 1990").

Once the recombinant construct has been made, it may then be introduced into a plant cell of choice by methods well known to those of ordinary skill in the art (e.g., transfection, transformation and electroporation). Oilseed plant cells are the preferred plant cells. The transformed plant cell is then cultured and regenerated under suitable conditions permitting expression of the long-chain PUFA which is then optionally recovered and purified.

The recombinant constructs of the invention may be introduced into one plant cell; or, alternatively, each construct may be introduced into separate plant cells.

Expression in a plant cell may be accomplished in a transient or stable fashion as is described above.

The desired long-chain PUFAs can be expressed in seed. Also within the scope of this invention are seeds or plant parts obtained from such transformed plants.

Plant parts include differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or a group of tissues that constitute a morphologically and functionally distinct part of a plant. The term "genome" refers to the following: (1) the entire complement of genetic material (genes and non-coding sequences) that is present in each cell of an organism, or virus or organelle; and/or (2) a complete set of chromosomes inherited as a (haploid) unit from one parent.

Thus, this invention also concerns a method for transforming a cell, comprising transforming a cell with the recombinant construct of the invention and selecting those cells transformed with the recombinant construct of the invention.

Also of interest is a method for producing a transformed plant comprising transforming a plant cell with the delta-5 desaturase polynucleotides of the instant invention and regenerating a plant from the transformed plant cell.

Methods for transforming dicots (primarily by use of *Agrobacterium tumefaciens*) and obtaining transgenic plants have been published, among others, for: cotton (U.S. Pat. No. 5,004,863; U.S. Pat. No. 5,159,135); soybean (U.S. Pat. No. 5,569,834; U.S. Pat. No. 5,416,011); *Brassica* (U.S. Pat. No. 5,463,174); peanut (Cheng et al. *Plant Cell Rep.* 15:653-657 (1996); McKently et al. *Plant Cell Rep.* 14:699-703 (1995)); papaya (Ling, K. et al. *Bio/technology* 9:752-758 (1991)); and pea (Grant et al. *Plant Cell Rep.* 15:254-258 (1995)). For a review of other commonly used methods of plant transformation see Newell, C. A. (*Mol. Biotechnol.* 16:53-65 (2000)). One of these methods of transformation uses *Agrobacterium rhizogenes* (Tepfler, M. and Casse-Delbart, F. *Microbiol. Sci.* 4:24-28 (1987)). Transformation of soybeans using direct delivery of DNA has been published using PEG fusion (PCT Publication No. WO 92/17598), electroporation (Chowrira, G. M. et al., *Mol. Biotechnol.* 3:17-23 (1995); Christou, P. et al., *Proc. Natl. Acad. Sci. U.S.A.* 84:3962-3966 (1987)), microinjection and particle bombardement (McCabe, D. E. et. al., *Bio/Technology* 6:923 (1988); Christou et al., *Plant Physiol.* 87:671-674 (1988)).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, In: Methods for Plant Molecular Biology, (Eds.), Academic: San Diego, Calif. (1988)). This regeneration and growth process typically includes the steps of selection of transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for: the construction, manipulation and isolation of macromolecules (e.g., DNA molecules, plasmids, etc.); the generation of recombinant DNA fragments and recombinant expression constructs; and, the screening and isolating of clones. See, for example: Sambrook et al., Molecular Cloning: A Laboratory Manual, Cold Spring Harbor: NY (1989); Maliga et al., Methods in Plant Molecular Biology, Cold Spring Harbor: NY (1995); Birren et al., Genome Analysis: Detecting Genes, Vol. 1, Cold Spring Harbor: NY (1998); Birren et al., Genome Analysis: Analyzing DNA, Vol. 2, Cold Spring Harbor: NY (1998); Plant Molecular Biology: A Laboratory Manual, eds. Clark, Springer: NY (1997).

Examples of oilseed plants include, but are not limited to: soybean, *Brassica* species, sunflower, maize, cotton, flax and safflower.

Examples of PUFAs having at least twenty carbon atoms and four or more carbon-carbon double bonds include, but are not limited to, omega-3 fatty acids such as EPA, DPA and DHA and the omega-6 fatty acid ARA. Seeds obtained from such plants are also within the scope of this invention as well as oil obtained from such seeds.

Thus, in one embodiment this invention concerns an oilseed plant comprising:

(a) a first recombinant DNA construct comprising an isolated polynucleotide encoding a delta-5 desaturase polypeptide, operably linked to at least one regulatory sequence; and, (b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-9 desaturase, a delta-9 elongase, a delta-12 desaturase, a delta-15 desaturase, a delta-17 desaturase, a $C_{14/16}$ elongase, a $C_{16/18}$ elongase, a $C_{18/20}$ elongase and a $C_{20/22}$ elongase.

Additional desaturases are discussed, for example, in U.S. Pat. Nos. 6,075,183, 5,968,809, 6,136,574, 5,972,664, 6,051,754, 6,410,288 and PCT Publication Nos. WO 98/46763, WO 98/46764, WO 00/12720 and WO 00/40705.

The choice of combination of cassettes used depends in part on the PUFA profile and/or desaturase/elongase profile of the oilseed plant cells to be transformed and the long-chain PUFA which is to be expressed.

In another aspect, this invention concerns a method for making long-chain PUFAs in a plant cell comprising:

(a) transforming a plant cell with the recombinant construct of the invention; and, (b) selecting those transformed plant cells that make long-chain PUFAs.

In still another aspect, this invention concerns a method for producing at least one PUFA in a soybean cell comprising:

(a) transforming a soybean cell with a first recombinant DNA construct comprising:
   (i) an isolated polynucleotide encoding a delta-5 desaturase polypeptide, operably linked to at least one regulatory sequence; and,
   (ii) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-9 desaturase, a delta-9 elongase, a delta-12 desaturase, a delta-15 desaturase, a delta-17 desaturase, a $C_{14/16}$ elongase, a $C_{16/18}$ elongase, a $C_{18/20}$ elongase and a $C_{20/22}$ elongase;

(b) regenerating a soybean plant from the transformed cell of step (a); and, (c) selecting those seeds obtained from the plants of step (b) having an altered level of PUFAs when compared to the level in seeds obtained from a nontransformed soybean plant.

In other preferred embodiments, the at least one additional recombinant DNA construct encodes a polypeptide having delta-9 elongase activity, e.g., the delta-9 elongase isolated or derived from *Isochrysis galbana* (GenBank Accession No. AF390174; IgD9e) or the delta-9 elongase isolated or derived from *Euglena gracilis.*

In other preferred embodiments, the at least one additional recombinant DNA construct encodes a polypeptide having delta-8 desaturase activity. For example, PCT Publication No. WO 2005/103253 (published Apr. 22, 2005) discloses amino acid and nucleic acid sequences for a delta-8 desaturase enzyme from *Pavlova salina* (see also U.S. Publication No. 2005/0273885). Sayanova et al. (*FEBS Lett.* 580:1946-1952 (2006)) describes the isolation and characterization of a cDNA from the free living soil amoeba *Acanthamoeba castellanii* that, when expressed in *Arabidopsis*, encodes a $C_{20}$ delta-8 desaturase. Also, Applicants' Assignee's co-pending application having U.S. patent application Ser. No. 11/737,772 (filed Apr. 20, 2007) discloses amino acid and nucleic acid sequences for a delta-8 desaturase enzyme from *Pavlova lutheri* (CCMP459). U.S. patent application Ser. No. 11/876,115 (filed Oct. 22, 2007) discloses amino acid and nucleic acid sequences for a delta-8 desaturase enzyme from *Tetru-*

*etreptia pomquetensis* CCMP1491, *Eutreptiella* sp. CCMP389 and *Eutreptiella* cf_*gymnastica* CCMP1594.

Microbial Expression Systems, Cassettes and Vectors, and Transformation

The delta-5 desaturase genes and gene products described herein (i.e., EaD5Des1, or other mutant enzymes, codon-optimized enzymes or homologs thereof) may also be produced in heterologous microbial host cells, particularly in the cells of oleaginous yeasts (e.g., *Yarrowia lipolytica*).

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high-level expression of the encoded enzymes.

Vectors or DNA cassettes useful for the transformation of suitable microbial host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed microbial host cell, although it is to be understood that such control regions need not be derived from the genes native to the specific species chosen as a production host.

Initiation control regions or promoters which are useful to drive expression of the instant delta-5 desaturase ORFs in the desired microbial host cell are numerous and familiar to those skilled in the art. Virtually any promoter capable of directing expression of these genes in the selected host cell is suitable for the present invention. Expression in a microbial host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species (e.g., see PCT Publication Nos. WO 2004/101757 and WO 2006/052870 for preferred transcriptional initiation regulatory regions for use in *Yarrowia lipolytica*). Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, when the microbial host is a yeast cell, the termination region is derived from a yeast gene (particularly *Saccharomyces, Schizosaccharomyces, Candida, Yarrowia* or *Kluyveromyces*). The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included. Although not intended to be limiting, termination regions useful in the disclosure herein include: ~100 bp of the 3' region of the *Yarrowia lipolytica* extracellular protease (XPR; GenBank Accession No. M17741); the acyl-coA oxidase (Aco3: GenBank Accession No. AJ001301 and No. CAA04661; Pox3: GenBank Accession No. XP_503244) terminators; the Pex20 (GenBank Accession No. AF054613) terminator; the Pex16 (GenBank Accession No. U75433) terminator; the Lip1 (GenBank Accession No. Z50020) terminator; the Lip2 (GenBank Accession No. AJ012632) terminator; and the 3-oxoacyl-coA thiolase (OCT; GenBank Accession No. X69988) terminator.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the microbial host cell. More specifically, some of the molecular features that have been manipulated to control gene expression include: (1) the nature of the relevant transcriptional promoter and terminator sequences; (2) the number of copies of the cloned gene and whether the gene is plasmid-borne or integrated into the genome of the host cell; (3) the final cellular location of the synthesized foreign protein; (4) the efficiency of translation and correct folding of the protein in the host organism; (5) the intrinsic stability of the mRNA and protein of the cloned gene within the host cell; and (6) the codon usage within the cloned gene, such that its frequency approaches the frequency of preferred codon usage of the host cell. Each of these types of modifications are encompassed in the present invention, as means to further optimize expression of the delta-5 desaturase described herein.

Once the DNA encoding a polypeptide suitable for expression in an appropriate microbial host cell (e.g., oleaginous yeast) has been obtained (e.g., a chimeric gene comprising a promoter, ORF and terminator), it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

The preferred method of expressing genes in *Yarrowia lipolytica* is by integration of linear DNA into the genome of the host; and, integration into multiple locations within the genome can be particularly useful when high level expression of genes are desired [e.g., in the Ura3 locus (GenBank Accession No. AJ306421), the Leu2 gene locus (GenBank Accession No. AF260230), the Lys5 gene (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the delta-12 desaturase gene locus (PCT Publication No. WO2004/104167), the Lip1 gene locus (GenBank Accession No. Z50020) and/or the Lip2 gene locus (GenBank Accession No. AJ012632)].

Advantageously, the Ura3 gene can be used repeatedly in combination with 5-fluoroorotic acid (5-fluorouracil-6-carboxylic acid monohydrate; "5-FOA") selection (infra), to readily permit genetic modifications to be integrated into the *Yarrowia* genome in a facile manner.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a microbial host cell by any standard technique. These techniques include transformation (e.g., lithium acetate transformation [*Methods in Enzymology,* 194:186-187 (1991)]), protoplast fusion, bolistic impact, electroporation, microinjection, or any other method that introduces the gene of interest into the host cell. More specific teachings applicable for oleaginous yeasts (i.e., *Yarrowia lipolytica*) include U.S. Pat. No. 4,880,741 and U.S. Pat. No. 5,071,764 and Chen, D. C. et al. (*Appl. Microbiol. Biotechnol.,* 48(2): 232-235 (1997)).

For convenience, a host cell that has been manipulated by any method to take up a DNA sequence (e.g., an expression cassette) will be referred to as "transformed" or "recombinant" herein. Thus, the term "transformed" and "recombinant" are used interchangeably herein. The transformed host will have at least one copy of the expression construct and may have two or more, depending upon whether the gene is integrated into the genome, amplified or is present on an extrachromosomal element having multiple copy numbers.

The transformed host cell can be identified by various selection techniques, as described in PCT Publication Nos. WO 2004/101757 and WO 2006/052870. Preferred selection methods for use herein are resistance to kanamycin, hygromycin and the amino glycoside G418, as well as ability to grow on media lacking uracil, leucine, lysine, tryptophan or histidine. In alternate embodiments, 5-FOA is used for selection of yeast Ura− mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of $Ura^-$ mutant yeast strains (Bartel, P. L. and Fields, S., Yeast 2-Hybrid System, Oxford University: New York, v. 7, pp 109-147, 1997). More specifically, one can first knockout the native Ura3 gene to produce a strain having a Ura− phenotype, wherein selection occurs based on 5-FOA resistance. Then, a cluster of multiple chimeric genes and a new Ura3 gene can be integrated into a different locus of the *Yarrowia* genome to thereby produce a new strain having a Ura+ phenotype. Subsequent integration produces a new Ura3− strain (again identified using 5-FOA selection), when the introduced Ura3 gene is knocked out. Thus, the Ura3 gene (in combination with 5-FOA selection) can be used as a selection marker in multiple rounds of transformation.

Following transformation, substrates suitable for the instant delta-5 desaturase (and, optionally other PUFA enzymes that are co-expressed within the host cell) may be produced by the host either naturally or transgenically, or they may be provided exogenously.

Microbial host cells for expression of the instant genes and nucleic acid fragments may include hosts that grow on a variety of feedstocks, including simple or complex carbohydrates, fatty acids, organic acids, oils and alcohols, and/or hydrocarbons over a wide range of temperature and pH values. Based on the needs of the Applicants' Assignee, the genes described in the instant invention will be expressed in an oleaginous yeast (and in particular *Yarrowia lipolytica*); however, it is contemplated that because transcription, translation and the protein biosynthetic apparatus is highly conserved, any bacteria, yeast, algae and/or fungus will be a suitable microbial host for expression of the present nucleic acid fragments.

Preferred microbial hosts, however, are oleaginous yeasts. These organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis*, and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.* 82(1):43-9 (2002)).

Historically, various strains of *Y. lipolytica* have been used for the manufacture and production of: isocitrate lyase; lipases; polyhydroxyalkanoates; citric acid; erythritol; 2-oxoglutaric acid; γ-decalactone; γ-dodecalatone; and pyruvic acid. Specific teachings applicable for engineering ARA, EPA and DHA production in *Y. lipolytica* are provided in U.S. patent application Ser. No. 11/264,784 (WO 2006/055322), U.S. patent application Ser. No. 11/265,761 (WO 2006/052870) and U.S. patent application Ser. No. 11/264,737 (WO 2006/052871), respectively.

Other preferred microbial hosts include oleaginous bacteria, algae and other fungi; and, within this broad group of microbial hosts, of particular interest are microorganisms that synthesize omega-3/omega-6 fatty acids (or those that can be genetically engineered for this purpose [e.g., other yeast such as *Saccharomyces cerevisiae*]). Thus, for example, transformation of *Mortierella alpina* (which is commercially used for production of ARA) with any of the present delta-5 desaturase genes under the control of inducible or regulated promoters could yield a transformant organism capable of synthesizing increased quantities of DGLA. The method of transformation of *M. alpina* is described by Mackenzie et al. (*Appl. Environ.*

*Microbiol.,* 66:4655 (2000)). Similarly, methods for transformation of Thraustochytriales microorganisms are disclosed in U.S. Pat. No. 7,001,772.

Metabolic Engineering of Omega-3 and/or Omega-6 Fatty Acid Biosynthesis in Microbes Methods for manipulating biochemical pathways are well known to those skilled in the art; and, it is expected that numerous manipulations will be possible to maximize omega-3 and/or omega-6 fatty acid biosynthesis in oleaginous yeasts, and particularly, in *Yarrowia lipolytica*. This manipulation may require metabolic engineering directly within the PUFA biosynthetic pathway or additional coordinated manipulation of various other metabolic pathways.

In the case of manipulations within the PUFA biosynthetic pathway, it may be desirable to increase the production of LA to enable increased production of omega-6 and/or omega-3 fatty acids. Introducing and/or amplifying genes encoding delta-9 and/or delta-12 desaturases may accomplish this. To maximize production of omega-6 unsaturated fatty acids, it is well known to one skilled in the art that production is favored in a host microorganism that is substantially free of ALA; thus, preferably, the host is selected or obtained by removing or inhibiting delta-15 or omega-3 type desaturase activity that permits conversion of LA to ALA. Alternatively, it may be desirable to maximize production of omega-3 fatty acids (and minimize synthesis of omega-6 fatty acids). In this example, one could utilize a host microorganism wherein the delta-12 desaturase activity that permits conversion of oleic acid to LA is removed or inhibited; subsequently, appropriate expression cassettes would be introduced into the host, along with appropriate substrates (e.g., ALA) for conversion to omega-3 fatty acid derivatives of ALA (e.g., STA, ETrA, ETA, EPA, DPA, DHA).

In alternate embodiments, biochemical pathways competing with the omega-3 and/or omega-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA).

Detailed discussion of manipulations within the PUFA biosynthetic pathway as a means to increase ARA, EPA or DHA (and associated techniques thereof) are presented in PCT Publication Nos. WO 2006/055322, WO 2006/052870 and WO 2006/052871, respectively, as are desirable manipulations in the TAG biosynthetic pathway and the TAG degradation pathway (and associated techniques thereof).

Within the context of the present invention, it may be useful to modulate the expression of the fatty acid biosynthetic pathway by any one of the strategies described above. For example, the present invention provides methods whereby genes encoding key enzymes in the delta-9 elongase/delta-8 desaturase biosynthetic pathway are introduced into plants for the production of omega-3 and/or omega-6 fatty acids. It will be particularly useful to express the present the delta-5 desaturase genes in plants that do not naturally possess omega-3 and/or omega-6 fatty acid biosynthetic pathways and coordinate the expression of these genes, to maximize production of preferred PUFA products using various means for metabolic engineering of the host organism.

Microbial Fermentation Processes for PUFA Production

The transformed host cell is grown under conditions that optimize expression of chimeric desaturase genes and produce the greatest and the most economical yield of desired PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. *Yarrowia lipolytica* are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media may contain a suitable carbon source. Suitable carbon sources are taught in PCT Publication No. WO 2004/101757. Although it is contemplated that the source of carbon utilized in may encompass a wide variety of carbon-containing sources, preferred carbon sources are sugars, glycerol, and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils, D. J. Kyle and R. Colin, eds. pp* 61-97 (1992)).

Preferred growth media are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast (e.g., *Yarrowia lipolytica*). This approach is described in PCT Publication No. WO 2004/101757, as are various suitable fermentation process designs (i.e., batch, fed-batch and continuous) and considerations during growth.

Purification and Processing of PUFA Oils

PUFAs may be found in the host microorganisms and plants as free fatty acids or in esterified forms such as acylglycerols, phospholipids, sulfolipids or glycolipids, and may be extracted from the host cells through a variety of means well-known in the art. One review of extraction techniques, quality analysis and acceptability standards for yeast lipids is that of Z. Jacobs (*Critical Reviews in Biotechnology,* 12(5/6): 463-491 (1992)). A brief review of downstream processing is also available by A. Singh and O. Ward (*Adv. Appl. Microbiol.,* 45:271-312 (1997)).

In general, means for the purification of PUFAs may include extraction with organic solvents, sonication, supercritical fluid extraction (e.g., using carbon dioxide), saponification and physical means such as presses, or combinations thereof. One is referred to the teachings of PCT Publication No. WO 2004/101757 for additional details. Methods of isolating seed oils are well known in the art: (Young et al., Processing of Fats and Oils, In *The Lipid Handbook*, Gunstone et al., eds., Chapter 5 pp 253-257; Chapman & Hall: London (1994)). For example, soybean oil is produced using a series of steps involving the extraction and purification of an edible oil product from the oil-bearing seed. Soybean oils and soybean byproducts are produced using the generalized steps shown in Table 3.

TABLE 3

Generalized Steps for Soybean Oil and Byproduct Production

| Process Step | Process | Impurities Removed and/or By-Products Obtained |
|---|---|---|
| # 1 | soybean seed | |
| # 2 | oil extraction | meal |
| # 3 | degumming | lecithin |
| # 4 | alkali or physical refining | gums, free fatty acids, pigments |
| # 5 | water washing | soap |
| # 6 | bleaching | color, soap, metal |
| # 7 | (hydrogenation) | |
| # 8 | (winterization) | stearine |
| # 9 | deodorization | free fatty acids, tocopherols, sterols, volatiles |
| # 10 | oil products | |

More specifically, soybean seeds are cleaned, tempered, dehulled and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., antisticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, Practical Handbook of Soybean Processing and Utilization, The American Oil Chemists' Society and United Soybean Board (1995). Soybean oil is liquid at room temperature because it is relatively low in saturated fatty acids when compared with oils such as coconut, palm, palm kernel and cocoa butter.

Plant and microbial oils containing PUFAs that have been refined and/or purified can be hydrogenated, to thereby result in fats with various melting properties and textures. Many processed fats (including spreads, confectionary fats, hard butters, margarines, baking shortenings, etc.) require varying degrees of solidity at room temperature and can only be produced through alteration of the source oil's physical properties. This is most commonly achieved through catalytic hydrogenation.

Hydrogenation is a chemical reaction in which hydrogen is added to the unsaturated fatty acid double bonds with the aid of a catalyst such as nickel. For example, high oleic soybean oil contains unsaturated oleic, LA and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction, which in turn alter the composition of the final product. Operating conditions including pressure, temperature, catalyst type and concentration, agitation and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings (used in the manufacture of baking products, solid fats and shortenings used for commercial frying and roasting operations) and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have become somewhat controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease.

PUFA-Containing Oils for Use in Foodstuffs

The market place currently supports a large variety of food and feed products, incorporating omega-3 and/or omega-6 fatty acids (particularly ARA, EPA and DHA). It is contemplated that the plant/seed oils, altered seeds and microbial oils of the invention comprising PUFAs will function in food and feed products to impart the health benefits of current formulations. Compared to other vegetable oils, the oils of the invention are believed to function similarly to other oils in food applications from a physical standpoint (for example, partially hydrogenated oils such as soybean oil are widely used as ingredients for soft spreads, margarine and shortenings for baking and frying).

Plant/seed oils, altered seeds and microbial oils containing omega-3 and/or omega-6 fatty acids as described herein will be suitable for use in a variety of food and feed products including, but not limited to: food analogs, meat products, cereal products, baked foods, snack foods and dairy products. Additionally, the present plant/seed oils, altered seeds and microbial oils may be used in formulations to impart health benefit in medical foods including medical nutritionals, dietary supplements, infant formula as well as pharmaceutical products. One of skill in the art of food processing and food formulation will understand how the amount and composition of the plant and microbial oils may be added to the food or feed product. Such an amount will be referred to herein as an "effective" amount and will depend on the food or feed product, the diet that the product is intended to supplement or the medical condition that the medical food or medical nutritional is intended to correct or treat.

Food analogs can be made using processes well known to those skilled in the art. There can be mentioned meat analogs, cheese analogs, milk analogs and the like. Meat analogs made from soybeans contain soy protein or tofu and other ingredients mixed together to simulate various kinds of meats. These meat alternatives are sold as frozen, canned or dried foods. Usually, they can be used the same way as the foods they replace. Meat alternatives made from soybeans are excellent sources of protein, iron and B vitamins. Examples of meat analogs include, but are not limited to: ham analogs, sausage analogs, bacon analogs, and the like.

Food analogs can be classified as imitation or substitutes depending on their functional and compositional characteristics. For example, an imitation cheese need only resemble the cheese it is designed to replace. However, a product can generally be called a substitute cheese only if it is nutritionally equivalent to the cheese it is replacing and meets the minimum compositional requirements for that cheese. Thus, substitute cheese will often have higher protein levels than imitation cheeses and be fortified with vitamins and minerals.

Milk analogs or nondairy food products include, but are not limited to, imitation milks and nondairy frozen desserts (e.g., those made from soybeans and/or soy protein products).

Meat products encompass a broad variety of products. In the United States "meat" includes "red meats" produced from cattle, hogs and sheep. In addition to the red meats there are poultry items which include chickens, turkeys, geese, guineas, ducks and the fish and shellfish. There is a wide assortment of seasoned and processed meat products: fresh, cured and fried, and cured and cooked. Sausages and hot dogs are examples of processed meat products. Thus, the term "meat products" as used herein includes, but is not limited to, processed meat products.

A cereal food product is a food product derived from the processing of a cereal grain. A cereal grain includes any plant from the grass family that yields an edible grain (seed). The most popular grains are barley, corn, millet, oats, quinoa, rice, rye, sorghum, triticale, wheat and wild rice. Examples of a cereal food product include, but are not limited to: whole grain, crushed grain, grits, flour, bran, germ, breakfast cereals, extruded foods, pastas, and the like.

A baked goods product comprises any of the cereal food products mentioned above and has been baked or processed in a manner comparable to baking (i.e., to dry or harden by subjecting to heat). Examples of a baked good product include, but are not limited to: bread, cakes, doughnuts, bars, pastas, bread crumbs, baked snacks, mini-biscuits, mini-crackers, mini-cookies, and mini-pretzels. As was mentioned above, oils of the invention can be used as an ingredient.

A snack food product comprises any of the above or below described food products.

A fried food product comprises any of the above or below described food products that has been fried.

A health food product is any food product that imparts a health benefit. Many oilseed-derived food products may be considered as health foods.

A beverage can be in a liquid or in a dry powdered form.

For example, there can be mentioned non-carbonated drinks such as fruit juices, fresh, frozen, canned or concentrate; flavored or plain milk drinks, etc. Adult and infant nutritional formulas are well known in the art and commercially available (e.g., Similac®, Ensure®, Jevity®, and Alimentum® from Ross Products Division, Abbott Laboratories).

Infant formulas are liquids or reconstituted powders fed to infants and young children. "Infant formula" is defined herein as an enteral nutritional product which can be substituted for human breast milk in feeding infants and typically is composed of a desired percentage of fat mixed with desired percentages of carbohydrates and proteins in an aqeuous solution (e.g., see U.S. Pat. No. 4,670,285). Based on the worldwide composition studies, as well as levels specified by expert groups, average human breast milk typically contains about 0.20% to 0.40% of total fatty acids (assuming about 50% of calories from fat); and, generally the ratio of DHA to ARA would range from about 1:1 to 1:2 (see, e.g., formulations of Enfamil LIPIL™ (Mead Johnson & Company) and Similac Advance™ (Ross Products Division, Abbott Laboratories)). Infant formulas have a special role to play in the diets of infants because they are often the only source of nutrients for infants; and, although breast-feeding is still the best nourishment for infants, infant formula is a close enough second that babies not only survive but thrive.

A dairy product is a product derived from milk. A milk analog or nondairy product is derived from a source other than milk, for example, soymilk as was discussed above. These products include, but are not limited to: whole milk, skim milk, fermented milk products such as yogurt or sour milk, cream, butter, condensed milk, dehydrated milk, coffee whitener, coffee creamer, ice cream, cheese, etc.

Additional food products into which the PUFA-containing oils of the invention could be included are, for example, chewing gums, confections and frostings, gelatins and puddings, hard and soft candies, jams and jellies, white granulated sugar, sugar substitutes, sweet sauces, toppings and syrups, and dry-blended powder mixes.

PUFA-Containing Oils for Use in Health Food Products and Pharmaceuticals

A health food product is any food product that imparts a health benefit and include functional foods, medical foods, medical nutritionals and dietary supplements. Additionally, the plant/seed oils, altered seeds and microbial oils of the invention may be used in standard pharmaceutical compositions (e.g., the long-chain PUFA containing oils could readily be incorporated into the any of the above mentioned food products, to thereby produce a functional or medical food). More concentrated formulations comprising PUFAs include capsules, powders, tablets, softgels, gelcaps, liquid concentrates and emulsions which can be used as a dietary supplement in humans or animals other than humans.

PUFA-Containing Oils for Use in Animal Feeds

Animal feeds are generically defined herein as products intended for use as feed or for mixing in feed for animals other than humans. The plant/seed oils, altered seeds and microbial oils of the invention can be used as an ingredient in various animal feeds.

More specifically, although not limited therein, it is expected that the oils of the invention can be used within pet food products, ruminant and poultry food products and aquacultural food products. Pet food products are those products intended to be fed to a pet (e.g., dog, cat, bird, reptile, rodent). These products can include the cereal and health food products above, as well as meat and meat byproducts, soy protein products, grass and hay products (e.g., alfalfa, timothy, oat or brome grass, vegetables). Ruminant and poultry food products are those wherein the product is intended to be fed to an animal (e.g., turkeys, chickens, cattle, swine). As with the pet foods above, these products can include cereal and health food products, soy protein products, meat and meat byproducts, and grass and hay products as listed above. Aquacultural food products (or "aquafeeds") are those products intended to be used in aquafarming, i.e., which concerns the propagation, cultivation or farming of aquatic organisms and/or animals in fresh or marine waters.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The meaning of abbreviations is as follows: "seq" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "pmole" mean micromole(s), "g" means gram(s), "μg" means microgram(s), "ng" means nanogram(s), "U" means unit(s), "bp" means base pair(s) and "kB" means kilobase(s).

General Methods:

Transformation and Cultivation of *Yarrowia lipolytica:*

*Yarrowia lipolytica* strains with ATCC Accession Nos. #20362, #76982 and #90812 were purchased from the American Type Culture Collection (Rockville, Md.). *Yarrowia lipolytica* strains were typically grown at 28° C. on YPD agar (1% yeast extract, 2% bactopeptone, 2% glucose, 2% agar).

Transformation of *Yarrowia lipolytica* was performed according to the method of Chen, D. C. et al. (*Appl. Microbiol. Biotechnol.* 48(2):232-235 (1997)), unless otherwise noted. Briefly, *Yarrowia* was streaked onto a YPD plate and grown at 30° C. for approximately 18 h. Several large loopfuls of cells were scraped from the plate and resuspended in 1 mL of transformation buffer, comprising: 2.25 mL of 50% PEG, average MW 3350; 0.125 mL of 2 M lithium acetate, pH 6.0; 0.125 mL of 2 M DTT; and 50 μg sheared salmon sperm DNA. Then, approximately 500 ng of linearized plasmid DNA was incubated in 100 μL of resuspended cells, and maintained at 39° C. for 1 h with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (Difco Laboratories, Detroit, Mich.) without ammonium sulfate or amino acids, 2% glucose, 0.1% proline, pH 6.1). Supplements of uracil were added as appropriate to a final concentration of 0.01% (thereby producing "MMU" selection media, prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (Difco Laboratories, Detroit, Mich.) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Fatty Acid Analysis of *Yarrowia lipolytica:*

For fatty acid analysis, cells were collected by centrifugation and lipids were extracted as described in Bligh, E. G. & Dyer, W. J. (*Can. J. Biochem. Physiol.* 37:911-917 (1959)). Fatty acid methyl esters were prepared by transesterification of the lipid extract with sodium methoxide (Roughan, G. and Nishida I., *Arch Biochem Biophys.* 276(1):38-46 (1990)) and subsequently analyzed with a Hewlett-Packard 6890 GC fitted with a 30 m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μL of 1%) was added to the sample, and then the sample was vortexed and rocked for 20 min. After adding 3 drops of 1 M NaCl and 400 μL hexane, the sample was vortexed and spun. The upper layer was removed and analyzed by GC as described above.

Example 1

Synthesis of a cDNA Library From *Euglena anabaena* UTEX 373

The present Example describes the synthesis of a cDNA library from *Euglena anabaena* UTEX 373. This work included the generation of RNA, synthesis of cDNA, and generation of a cDNA library.

Growth of *Euglena anabaena* UTEX 373 and Preparation of RNA

Figure 10:
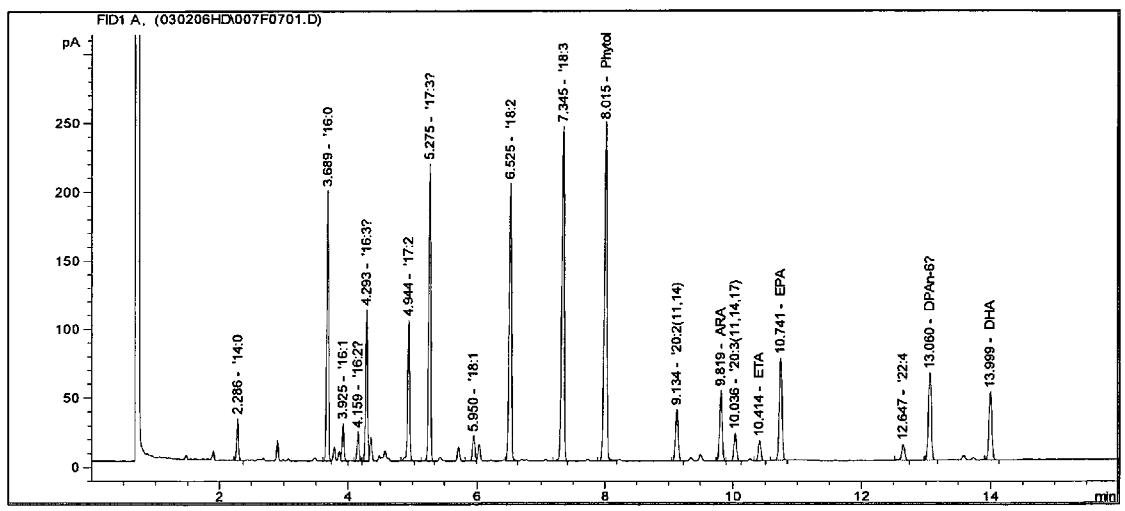
FIG. 10 shows a chromatogram of the lipid profile of an *Euglena anabaena* cell extract as described in the Examples.

*Euglena anabaena* UTEX 373 was obtained from Dr. Richard Triemer's lab at Michigan State University (East Lansing, Mich.). Approximately 2 mL of culture was removed for lipid analysis and centrifuged at 1,800×g for 5 min. The pellet was washed once with water and re-centrifuged. The resulting pellet was dried for 5 min under vacuum, resuspended in 100 μL of trimethylsulfonium hydroxide (TMSH) and incubated at room temperature for 15 min with shaking. After this step, 0.5 mL of hexane was added and the vials were incubated for 15 min at room temperature with shaking. Fatty acid methyl esters (5 μL injected from hexane layer) were separated and quantified using a Hewlett-Packard 6890 Gas Chromatograph fitted with an Omegawax 320 fused silica capillary column (Supelco Inc., Cat. No. 24152). The oven temperature was programmed to hold at 170° C. for 1.0 min, increase to 240° C. at 5° C./min and then hold for an additional 1.0 min. Carrier gas was supplied by a Whatman hydrogen generator. Retention times were compared to those for methyl esters of standards commercially available (Nu-Chek Prep, Inc. Cat. No. U-99-A) and the resulting chromatogram is shown in FIG. 10. The presence of EDA, ERA, EPA and DHA in the fatty acid profile, with the absence of GLA and STA, suggested that *Euglena anabaena* uses the delta-9 elongase/delta-8 desaturase pathway for LC-PUFA biosynthesis and would be a good source for LC-PUFA biosynthetic genes such as, but not limited to, delta-5 desaturases.

The remaining 5 mL of an actively growing culture was transferred into 25 mL of AF-6 Medium (Watanabe & Hiroki, NIES-Collection List of Strains, $5^{th}$ ed., National Institute for Environmental Studies, Tsukuba, 127 pp (2004)) in a 125 mL glass flask. *Euglena anabaena* cultures were grown at 22° C. with a 16 h light, 8 h dark cycle for 2 weeks with very gentle agitation.

After 2 weeks, the culture (25 mL) was transferred to 100 mL of AF-6 medium in a 500 mL glass bottle and the culture was grown for 1 month as described above. After this time, two 50 mL aliquots were transferred into two separate 500 mL glass bottles containing 250 mL of AF-6 medium and the cultures were grown for two months as described above (giving a total of ~600 mL of culture). Next, the cultures were pelleted by centrifugation at 1,800×g for 10 min, washed once with water and re-centrifuged. Total RNA was extracted from one of the resulting pellets using the RNA STAT-60™ reagent (TEL-TEST, Inc., Friendswood, Tex.) and following the manufacturer's protocol provided (use 5 mL of reagent, dissolved RNA in 0.5 mL of water). In this way, 340 μg of total RNA (680 μg/mL) was obtained from the pellet. The remaining pellet was frozen in liquid nitrogen and stored at −80° C. The mRNA was isolated from all 340 μg of total RNA using the mRNA Purification Kit (Amersham Biosciences, Piscataway, N.J.) following the manufacturer's protocol provided. In this way, 9.0 μg of mRNA was obtained.

Preparation of *Euglena anabaena* cDNA and Generation of cDNA Library eug1c

A cDNA library was generated using the Cloneminer™ cDNA Library Construction Kit (Cat. No. 18249-029, Invitrogen Corporation, Carlsbad, Calif.) and following the manufacturer's protocol provided (Version B, 25-0608). Using the non-radiolabeling method, cDNA was synthesized from 5.12 μg of mRNA (described above) using the Biotin-attB2-Oligo (dT) primer. After synthesis of the first and second strand, the attB1 adapter was added, ligated and the cDNA was size fractionated using column chromatography. DNA from fractions were concentrated, recombined into pDONR™222 and transformed into *E. coli* ElectroMAX™ DH10B™ T1 Phage-Resistant cells (Invitrogen Corporation). The *Euglena anabaena* library was named eug1c.

The cDNA library eug1c was plated onto LBKan plates (approx. 100,000 colonies), the colonies were scraped off and DNA was isolated using the QIAprep® Spin Miniprep Kit (Qiagen Inc., Valencia, Calif.) following the manufacturer's protocol. In this way, a plasmid DNA sub-library from eug1c was obtained.

Example 2

Isolation of the Full-Length Delta-5 Desaturases from *Euglena anabaena* UTEX 373

The present Example describes the identification of a cDNA (SEQ ID NO:1) encoding delta-5 desaturase from *Euglena anabaena* UTEX 373. This work included the generation of a probe derived from the *Euglena gracilis* delta-5 desaturase (EgD5; SEQ ID NO:2; which is described in U.S. Provisional Application No. 60/801,172 (filed May 17, 2006) and the hybridization of the probe to the cDNA library eug1c in order to identify delta-5 desaturase homologs from *Euglena anabaena* UTEX 373.

Figure 2:
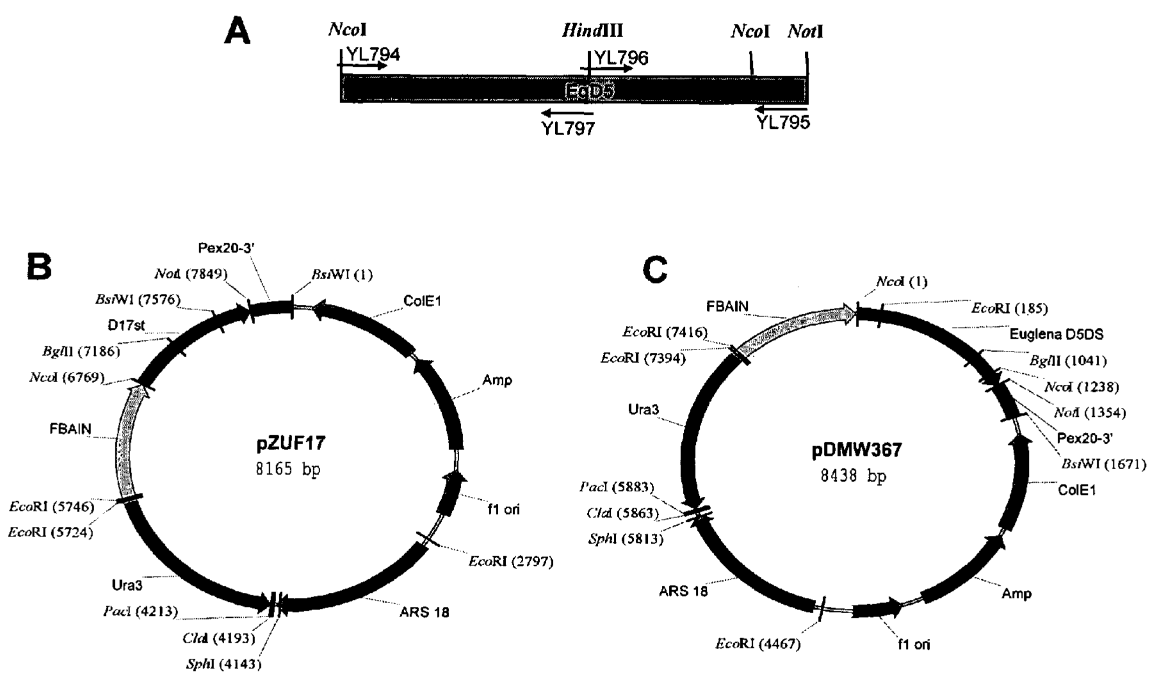
FIG. 2A is a schematic of EgD5.
FIG. 2B is a map of plasmid pZUF17 (SEQ ID NO:7).
FIG. 2C is a map of plasmid pDMW267 (SEQ ID NO:8).

Generation of Construct pDMW367, Comprising EgD5:

Based on the cDNA sequence of the *Euglena gracilis* delta-5 desaturase (EgD5; SEQ ID NO:2) oligonucleotides YL794 and YL797 (SEQ ID NOs:3 and 4, respectively) were used as primers to amplify the first portion of EgD5 (FIG. 2A). Primer YL794 contained a NcoI site and primer YL797 contained a HindIII site. Then, primers YL796 and YL795 (SEQ ID NOs:5 and 6, respectively) were used as primers to amplify the second portion of EgD5. Primer YL796 contained a HindIII site, while primer YL797 contained a NotI site. The PCR reactions, using primer pairs YL794/YL797 or YL796/YL795, with *Euglena gracilis* cDNA (the generation of which is described in U.S. Provisional Application No. 60/801,172 (filed May 17, 2006)) as template, were individually carried out in a 50 μL total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 μg/mL BSA (final concentration), 200 μM each deoxyribonucleotide triphosphate, 10 pmole of each primer and 1 μl of Pfu DNA polymerase (Stratagene, San Diego, Calif.). The thermocycler conditions were set for 35 cycles at 95° C. for 1 min, 56° C. for 30 sec and 72° C. for 1 min, followed by a final extension at 7° C. for 10 min. The individual PCR products were purified using a Qiagen PCR purification kit. The PCR product from the reaction amplified with primers YL794/797 was digested with NcoI and HindIII, while the PCR product from the reaction amplified with primers YL796/YL795 was digested with HindIII and NotI. The NcoI/HindIII and the HindIII/NotI digested DNA fragments were purified following gel electrophoresis in 1% (w/v) agarose, and then directionally ligated with NcoI/NotI digested pZUF17 (FIG. 2B; SEQ ID NO:7; comprising a synthetic delta-17 desaturase gene ["D17st"] derived from *S. diclina* (U.S. Publication No. 2003/0196217 A1), codon-optimized for *Yarrowia lipolytica* (PCT Publication No. WO 2004/101757)). The product of this ligation was pDMW367 (FIG. 2C; SEQ ID NO:8), which thereby contained the following components:

TABLE 4

Components of Plasmid pDMW367 (SEQ ID NO: 8)

| RE Sites and Nucleotides Within SEQ ID NO: 8 | Description Of Fragment And Chimeric Gene Components |
|---|---|
| EcoR I/BsiW I (7416-1617) | FBAIN::EgD5::Pex20, comprising: FBAIN: *Yarrowia lipolytica* FBAIN promoter (WO 2005/049805) EgD5: *Euglena gracilis* delta-5 desaturase (SEQ ID NO: 2 described herein) Pex20: Pex20 terminator sequence of *Yarrowia* Pex20 gene (GenBank Accession No. AF054613) |
| 2707-1827 | ColE1 plasmid origin of replication |
| 3637-2777 | ampicillin-resistance gene ($Amp^R$) for selection in *E. coli* |
| 4536-5840 | *Yarrowia* autonomous replication sequence (ARS18; GenBank Accession No. A17608) |
| 7373-5886 | *Yarrowia* Ura 3 gene (GenBank Accession No. AJ306421) |

The term "FBAIN promoter" or "FBAIN promoter region" refers to the 5' upstream untranslated region in front of the 'ATG' translation initiation codon of the *Yarrowia lipolytica* fructose-bisphosphate aldolase enzyme (E.C. 4.1.2.13) encoded by the fba1 gene and that is necessary for expression, plus a portion of 5' coding region that has an intron of the fba1 gene.

Colony Lifts:

Approximately 17,000 clones of cDNA library eug1c were plated onto three large square (24 cm×24 cm) petri plates (Corning, Corning, N.Y.) each containing LB+50 μg/mL kanamycin agar media. Cells were grown overnight at 37° C. and plates were then cooled to room temperature.

Biodyne B 0.45 μm membrane (Cat. No. 60207, Pall Corporation, Pensacola, Fla.) was trimmed to approximately 22 cm×22 cm and the membrane was carefully layed on top of the agar to avoid air bubbles. After incubation for 2 min at room temperature, the membrane was marked for orientation, lifted off with tweezers and placed colony-side up on filter paper soaked with 0.5 M sodium hydroxide and 1.5 M sodium chloride. After denaturation for 4 min, the sodium hydroxide was neutralized by placing the membrane on filter paper soaked with 0.5 M Tris-HCL (pH 7.5) and 1.5 M sodium chloride for 4 min. This step was repeated and the membrane was rinsed briefly in 2×SSC buffer (20×SSC is 3M sodium chloride, 0.3 M sodium citrate; pH 7.0) and air dried on filter paper.

Hybridization:

Membranes were pre-hybridized at 65° C. in 200 mL hybridization solution for 2 h. Hybridization solution contained 6×SSPE (20×SSPE is 3 M sodium chloride, 0.2 M sodium phosphate, 20 mM EDTA; pH 7.4), 5×Denhardt's reagent (100×Denhardt's reagent is 2% (w/v) Ficoll, 2% (w/v) polyvinylpyrrolidone, 2% (w/v) acetylated bovine serum albumin), 0.5% sodium dodecyl sulfate (SDS), 100 μg/mL sheared salmon sperm DNA and 5% dextran sulfate.

A DNA probe was made using an agarose gel purified NcoI/NotI DNA fragment, containing the *Euglena gracilis* delta-5 desaturase gene, from pDMW367 (SEQ ID NO:8) labeled with $P^{32}$ dCTP using the RadPrime DNA Labeling System (Cat. No. 18428-011, Invitrogen, Carlsbad, Calif.) following the manufacture's instructions. Unincorporated $P^{32}$ dCTP was separated using a NICK column (Cat. No. 17-0855-02, Amersham Biosciences, Piscataway, N.J.) following the manufacturer's instructions. The probe was denatured for 5 min at 100° C., placed on ice for 3 min and half was added to the hybridization solution.

The membrane was hybridized with the probe overnight at 65° C. with gentle shaking and then washed the following day twice with 2×SSC containing 0.5% SDS (5 min each) and twice with 0.2×SSC containing 0.1% SDS (15 min each). After washing, hyperfilm (Cat. No. RPN30K, Amersham Biosciences, Piscataway, N.J.) was exposed to the membrane overnight at −80° C.

Based on alignment of plates with the exposed hyperfilm, positive colonies were picked using the blunt end of a Pasteur pipette into 1 mL of water and vortexed. Several dilutions were made and plated onto small round Petri dishes (82 mm) containing LB media plus 50 μg/mL kanamycin to obtain around 100 well isolated colonies on a single plate. Lifts were done as described above except NytranN membrane circles (Cat, No. 10416116, Schleicher & Schuell, Keene, N.H.) were used and hybridization was carried out in 100 mL using the remaining radiolabeled probe. In this way, positive clones were confirmed.

Individual positive clones were grown at 37° C. in LB+50 μg/mL kanamycin liquid media and plasmid was purified using the QIAprep® Spin Miniprep Kit (Qiagen Inc.) following the manufacturer's protocol.

DNA inserts were end-sequenced in 384-well plates, using vector-primed M13F universal primer (SEQ ID NO:9), M13rev-28 primer (SEQ ID NO:10) and the poly(A) tail-primed WobbleT oligonucleotides, with the ABI BigDye version 3 Prism sequencing kit. For the sequencing reaction, 100-200 ng of template and 6.4 pmol of primer were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3700 automated sequencers. The WobbleT primer is an equimolar mix of 21 mer poly(T)A, poly(T)C, and poly(T)G, used to sequence the 3' end of cDNA clones.

Sequences were aligned and compared using Sequencher™ (Version 4.2, Gene Codes Corporation, Ann Arbor, Mich.) and in this way, it was determined that all all of the CDS in each cDNA were identical. A representative clone containing a cDNA (pLF119) is shown in SEQ ID NO:11 and the gene contained within the cDNA was called EaD5Des1. The coding sequence for EaD5Des1 is shown in SEQ ID NO:12. The corresponding amino acid sequence for EaD5Des1 is shown in SEQ ID NO:13.

Example 3

Primary Sequence Analysis of the Delta-5 Desaturase Sequence of *Euglena anabaena* UTEX 373 (EaD5Des1) and Comparison to the Delta-5 Desaturase Sequence of *Euglena gracilis* (EgD5)

The amino acid sequence for EaD5Des1 (SEQ ID NO:13) was evaluated by BLASTP (Basic Local Alignment Search Tool; Altschul et al., *J. Mol. Biol.* 215:403-410 (1993)) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL and DDBJ databases) using default parameters with the filter turned off. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

BLASTP analysis with EaD5Des1 yielded a pLog value of 76.52 (P value of 3e-77) versus the *Thalassiosira pseudonana* delta-8 fatty acid desaturase (TpsD8; SEQ ID NO:14) (NCBI Accession No. AAX14502(GI 60172920), locus AAX14502, CDS AY817152; Tonon et al., *FEBS J.* 272:3401-3412 (2005)) when compared to the "nr" database. Although identified as a delta-8 fatty acid desaturase in the NCBI database, AY817152 was identified as a delta-5 desaturase in Tonon et al. and the NCBI designation as a delta-8 fatty acid desaturase is likely an error. BLASTP analysis with EaD5Des1 also yielded a pLog value of 75.70 (P value of 2e-76) versus the *Phaeodactylum tricornutum* delta-5 fatty acid desaturase (SEQ ID NO:15) (NCBI Accession No. AAL92562(GI 19879687), locus AAL92562, CDS AY082392; Domergue et al., *Eur. J. Biochem.* 269:4105-4113 (2002)) when compared to the "nr" database.

The amino acid sequence for EaD5Des1 (SEQ ID NO:13) was compared to the *Thalassiosira pseudonana* delta-8 fatty acid desaturase (SEQ ID NO:14) and the *Euglena gracilis* delta-5 desaturase amino acid sequence (EgD5; SEQ ID NO:16; which is described in U.S. Provisional Application No. 60/801,172 (filed May 17, 2006)) using BlastP, Clustal V and the Jotun Hein methods of sequence comparison. The % identity against the TpsD8 and EgD5 using each method is shown in Table 5 and Table 6, respectively.

Sequence percent identity calculations performed by the BlastP method are as described above. Sequence percent identity calculations were performed by the Clustal V method (Higgins, D. G. and Sharp, P. M., *Comput. Appl. Biosci.* 5:151-153 (1989); Higgins et al., *Comput. Appl. Biosci.* 8:189-191 (1992)) using the MegAlign™ v6.1 program of the LASERGENE bioinformatics computing suite (DNASTAR Inc., Madison, Wis.) with the default parameters for pairwise alignment (KTUPLE=1, GAP PENALTY=3, WINDOW=5 and DIAGONALS SAVED=5 and GAP LENGTH PENALTY=10).

Sequence percent identity calculations performed by the Jotun Hein method (Hein, J. J., *Meth. Enz.* 183:626-645 (1990)) were done using the MegAlign™ v6.1 program of the LASERGENE bioinformatics computing suite (DNASTAR Inc., Madison, Wis.) with the default parameters for pairwise alignment (KTUPLE=2).

TABLE 5

Sequence Comparison of EaD5Des1 (SEQ ID NO: 13) to TpsD8 (SEQ ID NO: 14)

| Desaturase | % Identity to TpsD8 by BLASTP | % Identity to TpsD8 by the Jotun Hein Method | % Identity to TpsD8 by the Clustal V Method |
|---|---|---|---|
| EaD5Des1 (SEQ ID NO: 13) | 37% | 40.8% | 30.8% |

TABLE 6

Sequence Comparison of EaD5Des1 (SEQ ID NO: 13) to EgD5 (SEQ ID NO: 16)

| Desaturase | % Identity to EgD5 by BLASTP | % Identity to EgD5 by the Jotun Hein Method | % Identity to EgD5 by the Clustal V Method |
|---|---|---|---|
| EaD5Des1 (SEQ ID NO: 13) | 73% | 72.4% | 77.1% |

Example 4

Functional Analysis of the *Euglena gracilis* UTEX 373 Delta-5 Desaturase (EaD5Des1) in *Yarrowia lipolytica*

The present Example describes functional analysis of EaD5Des1 (SEQ ID NO:13) in *Yarrowia lipolytica*. This work included the following steps: (1) Construction of Gateway®-compatible *Yarrowia* expression vector pY159; (2) transfer of EaD5Des1 (SEQ ID NO:12) into pY159 to produce pY169; and, (3) comparison of lipid profiles within transformant organisms comprising pY169.

Construction of Gateway®-Compatible *Yarrowia* Expression Vector pY159

Plasmid pY5-30 (which was previously described in PCT Publication No. WO 2005/003310 (the contents of which are hereby incorporated by reference)), is a shuttle plasmid that can replicate both in *E. coli* and *Yarrowia lipolytica*. Plasmid pY5-30 contains the following: a *Yarrowia* autonomous replication sequence (ARS18); a ColE1 plasmid origin of replication; an ampicillin-resistance gene ($Amp^R$), for selection in *E. coli*; a *Yarrowia* LEU2 gene, for selection in *Yarrowia*; and a chimeric TEF::GUS::XPR gene. Plasmid pDMW263 (SEQ ID NO:17) was created from pY5-30, by replacing the TEF promoter with the *Yarrowia lipolytica* FBAINm promoter (PCT Publication No. WO 2005/049805) using techniques well known to one skilled in the art. Briefly, this promoter refers to a modified promoter which is located in the 5' upstream untranslated region in front of the 'ATG' translation initiation codon of the fructose-bisphosphate aldolase enzyme (E.C. 4.1.2.13) encoded by the fba1 gene and that is necessary for expression, plus a portion of 5' coding region that has an intron, wherein FBAINm has a 52 bp deletion between the ATG translation initiation codon and the intron of the FBAIN promoter (thereby including only 22 amino acids of the N-terminus) and a new translation consensus motif after the intron. Table 7 summarizes the components of pDMW263 (SEQ ID NO:17).

TABLE 7

Components of Plasmid pDMW263 (SEQ ID NO: 17)

| RE Sites and Nucleotides Within SEQ ID NO: 17 | Description of Fragment and Chimeric Gene Components |
|---|---|
| 4992-4296 | ARS18 sequence (GenBank Accession No. A17608) |
| SalI/SacII (8505-2014) | FBAINm::GUS::XPR, comprising:<br>FBAINm: FBAINm promoter (WO2005/049805)<br>GUS: *E. coli* gene encoding β-glucuronidase (Jefferson, R. A. Nature. 14: 342: 837-838 (1989)<br>XPR: ~100 bp of the 3' region of the *Yarrowia* Xpr gene (GenBank Accession No. M17741) |
| 6303-8505 | *Yarrowia* Leu2 gene (GenBank Accession No. AF260230) |

Figure 3:
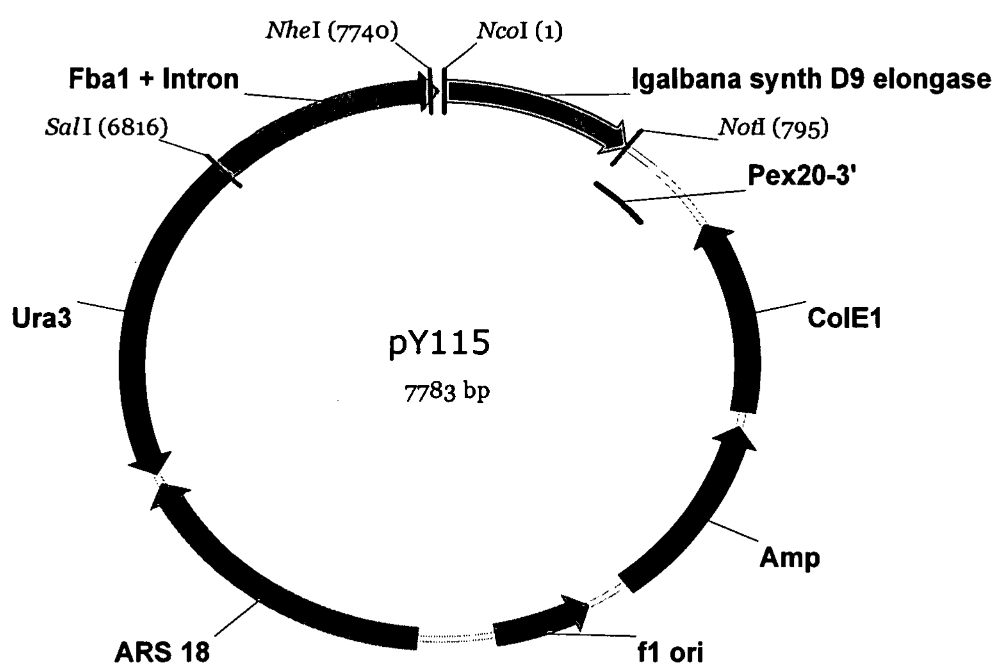
FIG. 3 is a map of plasmid pY115 (SEQ ID NO:19).

The NcoI/SalI DNA fragment from pDMW263 (SEQ ID NO:17), containing the *Yarrowia lipolytica* FBAINm promoter, was cloned into the NcoI/SalI DNA fragment of pDMW237 (SEQ ID NO:18), previously described in PCT Publication No. WO 2006/012325 (the contents of which are hereby incorporated by reference), containing a synthetic delta-9 elongase gene derived from *Isochrysis galbana* and codon-optimized for expression in *Yarrowia lipolytica* (IgD9eS), to produce pY115 (SEQ ID NO:19; FIG. 3). In FIG. 3, the modified FBAINm promoter is called FBA1+Intron. It is also FBA1+Intron in other figures, as well as YAR FBA1 PRO+Intron and these terms are used interchangeably with FBAINm.

The FBAINm promoter was amplified from plasmid pY115 (SEQ ID NO:19), using PCR with oligonucleotide primers oYFBA1 (SEQ ID NO:20) and oYFBA1-6 (SEQ ID NO:21). Primer oYFBA1 (SEQ ID NO:20) was designed to introduce an BglII site at the 5' end of the promoter and primer oYFBA1-6 (SEQ ID NO:21) was designed to introduce a NotI site at the 3' end of the promoter while removing the NcoI site and thus, the ATG start codon. The resulting PCR fragment was digested with BglII and NotI and cloned into the BglII/NotI fragment of pY115, containing the vector backbone, to form pY158 (SEQ ID NO:22).

Figure 4:
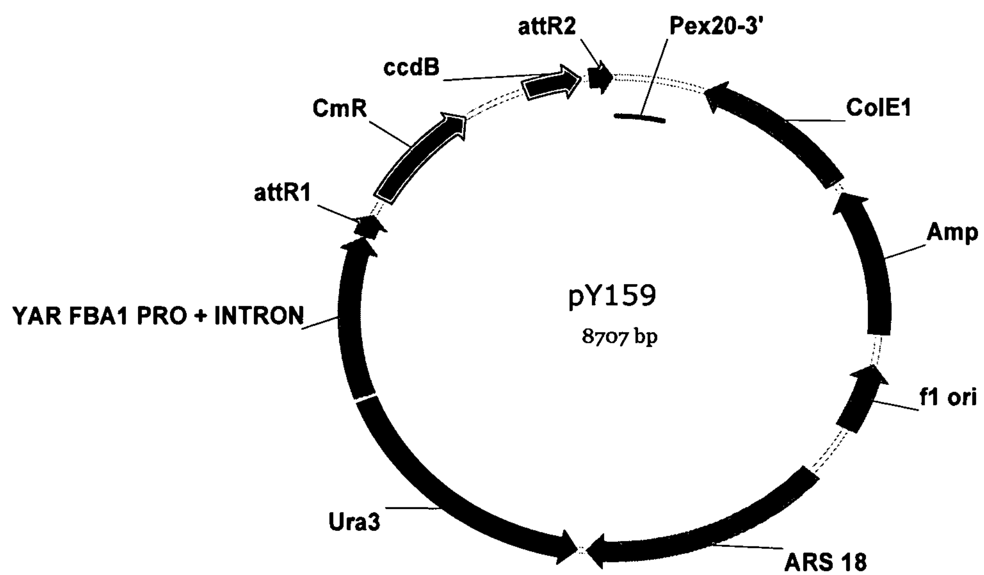
FIG. 4 is a map of plasmid pY159 (SEQ ID NO:23).

Plasmid pY158 (SEQ ID NO:22) was digested with NotI and the resulting DNA ends were filled. After filling to form blunt ends, the DNA fragments were treated with calf intestinal alkaline phosphatase and separated using agarose gel electrophoresis. The 6992 bp fragment containing the *Yarrowia lipolytica* FBAINm promoter was excised from the agarose gel and purified using the QIAquick® Gel Extraction Kit (Qiagen Inc., Valencia, Calif.) following the manufacturer's protocol. The purified 6992 bp fragment was ligated with cassette rfA using the Gateway Vector Conversion System (Cat. No. 11823-029, Invitrogen Corporation) following the manufacturer's protocol to form *Yarrowia lipolytica* Gateway® destination vector pY159 (SEQ ID NO:23; FIG. 4).

Construction of *Yarrowia* Expression Vectors pY169

Figure 5:
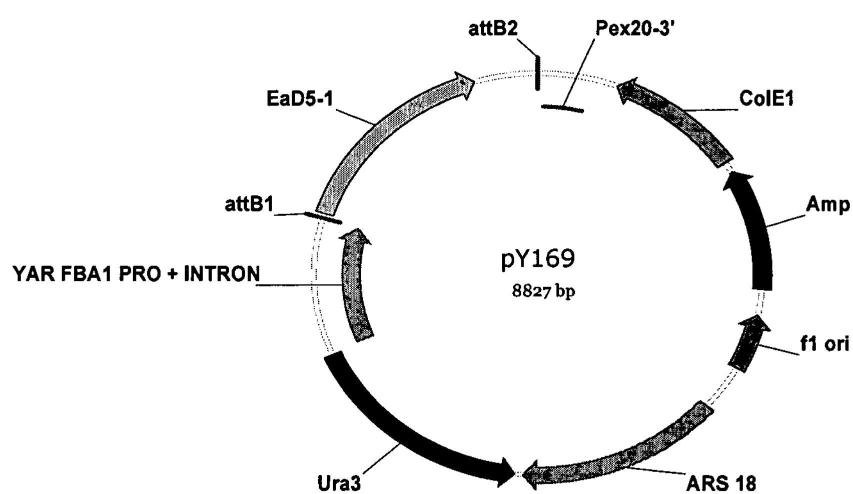
FIG. 5 is a map of plasmid pY169 (SEQ ID NO:24).

Using the Gateway® LR Clonase™ II enzyme mix (Cat. No. 11791-020, Invitrogen Corporation) and following the manufacturer's protocol, the cDNA insert from pLF119 (SEQ ID NO:11) was transferred to pY159 (SEQ ID NO:23) to form pY169 (SEQ ID NO:24, FIG. 5). In FIG. 5, EaD5Des1 is identified as EaD5-1 but they are identical.

Functional analysis of EaD5Des1 in *Yarrowia lipolytica*

Strain Y2224 was isolated in the following manner: *Yarrowia lipolytica* ATCC #20362 cells from a YPD agar plate (1% yeast extract, 2% bactopeptone, 2% glucose, 2% agar) were streaked onto a MM plate (75 mg/L each of uracil and uridine, 6.7 g/L YNB with ammonia sulfate, without amino acid, and 20 g/L glucose) containing 250 mg/L 5-FOA (Zymo Research). Plates were incubated at 28° C. and four of the resulting colonies were patched separately onto MM plates containing 200 mg/mL 5-FOA and MM plates lacking uracil and uridine to confirm uracil Ura3 auxotrophy.

Strain Y2224 was transformed with pY169 (SEQ ID NO:24, FIG. 5) as described in the General Methods.

Single colonies of transformant *Yarrowia lipolytica* containing pY169 were grown in 3 mL minimal media lacking uracil supplemented with 0.2% tergitol at 30° C. for 1 day. After this, 0.1 mL was transferred to 3 mL of the same medium supplemented with either ALA, EDA, ERA, DGLA, ETA, EPA, DPA or no fatty acid. These were incubated for 16 h at 30° C., 250 rpm and then pellets were obtained by centrifugation. Cells were washed once with water, pelleted by centrifugation and air dried. Pellets were transesterified (Roughan, G. and Nishida, I., *Arch. Biochem. Biophys.* 276 (1):38-46 (1990)) with 500 μL of 1% sodium methoxide for 30 min. at 50° C. after which 500 μL of 1 M sodium chloride and 100 μL of heptane were added. After thorough mixing and centrifugation, fatty acid methyl esters (FAMEs) were analyzed by GC. FAMEs (5 μL injected from hexane layer) were separated and quantified using a Hewlett-Packard 6890 Gas Chromatograph fitted with an Omegawax 320 fused silica capillary column (Cat. No. 24152, Supelco Inc.). The oven temperature was programmed to hold at 220° C. for 2.6 min, increase to 240° C. at 20° C./min and then hold for an additional 2.4 min. Carrier gas was supplied by a Whatman hydrogen generator. In the case of DPA feeding, GC analysis was carried out in a similar way except that the oven temperature was programmed to hold at 170° C. for 1.0 min, increase to 240° C. at 5° C./min and then hold for an additional 1.0 min. Retention times were compared to those for methyl esters of standards commercially available (Nu-Chek Prep, Inc.).

The fatty acid profiles for *Yarrowia lipolytica* expressing pY169 and fed various substrates are shown in FIG. 6. Substrates (either LA—when no fatty acid fed, ALA, EDA, ERA, DGLA, ETA or DPA) were fed to assess delta-4 (DPA to DHA), delta-5 (DGLA to ARA, DTA to EPA, EDA to SCI, ERA to JUP), delta-6 (LA to GLA, ALA to STA), delta-8 (EDA to DGLA, ERA to ETA) or omega-3 (LA to ALA, EDA to ERA, DGLA to ETA) desaturase activities. Percent desaturation (% desat) was calculated by dividing the wt. % for substrate (either LA—when no fatty acid fed, ALA, EDA, ERA, DGLA, ETA or DPA) by the sum of the wt. % for the substrate (either LA—when no fatty acid fed, ALA, EDA, ERA, DGLA, ETA or DPA) and product (either GLA, STA, DGLA, ETA, ARA, EPA or DHA, respectively) and multiplying by 100 to express as a %, depending on which substrate was fed. In FIG. 6. shading indicates the substrates fed and products produced. Averages are indicated by Ave. followed by appropriate header. From the results in FIG. 6, it is clear that EaD5Des1 functions as a delta-5 desaturase with preference for DGLA and ETA over EDA and ERA. The ratio of desaturation of omega-6 substrate to omega-3 substrate (Ratio n-6/n-3) is calculated by dividing the Ave. % desat for either DGLA by ETA or EDA by ERA. In both cases, EaD5Des1 prefers n-6 substrates over n-3 substrates. The ratio of desaturation of the preferred substrate to that of the non-preferred substrate (Ratio Prod/By-Prod) is calculated by dividing the Ave. % desat for either DGLA by EDA or ETA by ERA. In both cases, EaD5Des1 has an approximately 3.5-fold preference for DGLA or ETA over EDA or ERA, respectively.

Example 5

Construction of Soybean Expression Vector pKR1153 for Co-Expression of the *Euglena anabaena* UTEX 373 Delta-5 Desaturase (EaD5Des1) with a Delta-9 Elongase Derived from *Euglena gracilis* (EgD9e) and a Delta-8 Desaturase Derived from *Euglena gracilis* (EgD8)

The present Example describes construction of a soybean vector for co-expression of EaD5Des1 with EgD9e (SEQ ID NO:25; which is described in U.S. application Ser. No. 11/601,563 (filed Nov. 16, 2006, which published May 24, 2007) and EgD8 (SEQ ID NO:26; described as Eg5 in PCT Publication No. WO 2006/012325)

*Euglena gracilis* Delta-9 Elongase (EgD9e):

A clone from the *Euglena* cDNA library (eeg1c), called eeg1c.pk001.n5f, containing the *Euglena gracilis* delta-9 elongase (EgD9e; SEQ ID NO:25; which is described in U.S. application Ser. No. 11/601,563 (filed Nov. 16, 2006, which published May 24, 2007) the contents of which are hereby incorporated by reference) was used as template to amplify EgD9e with oligonucleotide primers oEugEL1-1 (SEQ ID NO:27) and oEugEL1-2 (SEQ ID NO:28) using the VentR® DNA Polymerase (Cat. No. M0254S, New England Biolabs Inc., Beverly, Mass.) following the manufacturer's protocol. The resulting DNA fragment was cloned into the pCR-Blunt® cloning vector using the Zero Blunt® PCR Cloning Kit (Invitrogen Corporation), following the manufacturer's protocol, to produce pKR906 (SEQ ID NO:29).

A starting plasmid pKR72 (ATCC Accession No. PTA-6019; SEQ ID NO:30, 7085 bp sequence), a derivative of pKS123 which was previously described in PCT Publication No. WO 02/008269 (the contents of which are hereby incorporated by reference), contains the hygromycin B phosphotransferase gene (HPT) (Gritz, L. and Davies, J., *Gene* 25:179-188 (1983)), flanked by the T7 promoter and transcription terminator (T7prom/HPT/T7term cassette), and a bacterial origin of replication (ori) for selection and replication in bacteria (e.g., *E. coli*). In addition, pKR72 also contains HPT, flanked by the 35S promoter (Odell et al., *Nature* 313:810-812 (1985)) and NOS 3' transcription terminator (Depicker et al., *J. Mol. Appl. Genet.* 1:561-570 (1982)) (35S/HPT/NOS3' cassette) for selection in plants such as soybean. pKR72 also contains a NotI restriction site, flanked by the promoter for the α' subunit of β-conglycinin (Beachy et al., *EMBO J.* 4:3047-3053 (1985)) and the 3' transcription termination region of the phaseolin gene (Doyle et al., *J. Biol. Chem.* 261:9228-9238 (1986)), thus allowing for strong tissue-specific expression in the seeds of soybean of genes cloned into the NotI site.

The AscI fragment from plasmid pKS102 (SEQ ID NO:31), previously described in PCT Publication No. WO 02/00905 (the contents of which are hereby incorporated by reference), containing the T7prom/hpt/T7term cassette and bacterial ori, was combined with the AscI fragment of plasmid pKR72 (SEQ ID NO:30), containing the βcon/NotI/Phas cassette to produce pKR197 (SEQ ID NO:32), previously described in PCT Publication No. WO 04/071467 (the contents of which are hereby incorporated by reference).

The gene for the *Euglena gracilis* delta-9 elongase was released from pKR906 (SEQ ID NO:29) by digestion with NotI and cloned into the NotI site of pKR197 to produce intermediate cloning vector pKR911 (SEQ ID NO:33).

*Euglena gracilis* Delta-8 Desaturase (EgD8):

Plasmid pKR680 (SEQ ID NO:34), which was previously described in PCT Publication No. WO 2006/012325 (the contents of which are hereby incorporated by reference), contains the *Euglena gracilis* delta-8 desaturase (EgD8; SEQ ID NO:26; described as Eg5 in WO 2006/012325) flanked by the Kunitz soybean Trypsin Inhibitor (KTi) promoter (Jofuku et al., *Plant Cell* 1:1079-1093 (1989)) and the KTi 3' termination region, the isolation of which is described in U.S. Pat. No. 6,372,965, followed by the soy albumin transcription terminator, which was previously described in PCT Publication No. WO 2004/071467 (Kti/NotI/Kti3'Salb3' cassette).

Plasmid pKR680 (SEQ ID NO:34) was digested with BsiWI and the fragment containing EgD8 was cloned into the BsiWI site of pKR911 (SEQ ID NO:33) to produce pKR913 (SEQ ID NO:35).

*Euglena anabaena* UTEX 373 Delta-5 Desaturase (EaD5Des1):

In order to introduce NotI sites at the 5' and 3' ends of the coding sequence, EaD5Des1 was PCR amplified from pLF119 (SEQ ID NO:11) with oligonucleotide primers oEAd5-1-1 (SEQ ID NO:36) and oEAd5-1-2 (SEQ ID NO:37) using the Phusion™ High-Fidelity DNA Polymerase (Cat. No. F553S, Finnzymes Oy, Finland) following the manufacturer's protocol. The resulting DNA fragment was cloned into the pCR-Blunt® cloning vector using the Zero Blunt® PCR Cloning Kit (Invitrogen Corporation), following the manufacturer's protocol, to produce pKR1136 (SEQ ID NO:38).

Plasmid pKR767 (SEQ ID NO:39), which was previously described in PCT Publication No. WO 2006/012325 (the contents of which are hereby incorporated by reference), contains the *Mortierella alpina* delta-5 desaturase (MaD5; SEQ ID NO:40, which is described in U.S. Pat. No. 6,075,183 and PCT Publication Nos. WO 2004/071467 and WO 2005/047479) flanked by the promoter for the soybean glycinin Gy1 gene and the pea leguminA2 3' transcription termination region (Gy1/MaD5/legA2 cassette; the construction of which is described in WO 2006/012325). Plasmid pKR974 (SEQ ID NO:41) is identical to pKR767 (SEQ ID NO:40) except the NotI fragment containing MaD5 has been replaced with a NotI fragment containing the *Saprolegnia diclina* delta-5 desaturase (SaD5; SEQ ID NO:42, which is described in PCT Publication No. WO 2004/071467. In addition, an MfeI site in the legA2 terminator of pKR974 (SEQ ID NO:41) was removed by digestion with MfeI, filling the MfeI site and religating (i.e., CAATTG converted to CAATTAATTG) and therefore, the legA2 terminator of pKR974 (SEQ ID NO:41) is 770 bp versus 766 bp for pKR767 (SEQ ID NO:40).

The gene for the *Euglena anabaena* delta-5 desaturase was released from pKR1136 (SEQ ID NO:38) by digestion with NotI and cloned into the NotI site of pKR974 (SEQ ID NO:41) to produce pKR1139 (SEQ ID NO:43).

Figure 7:
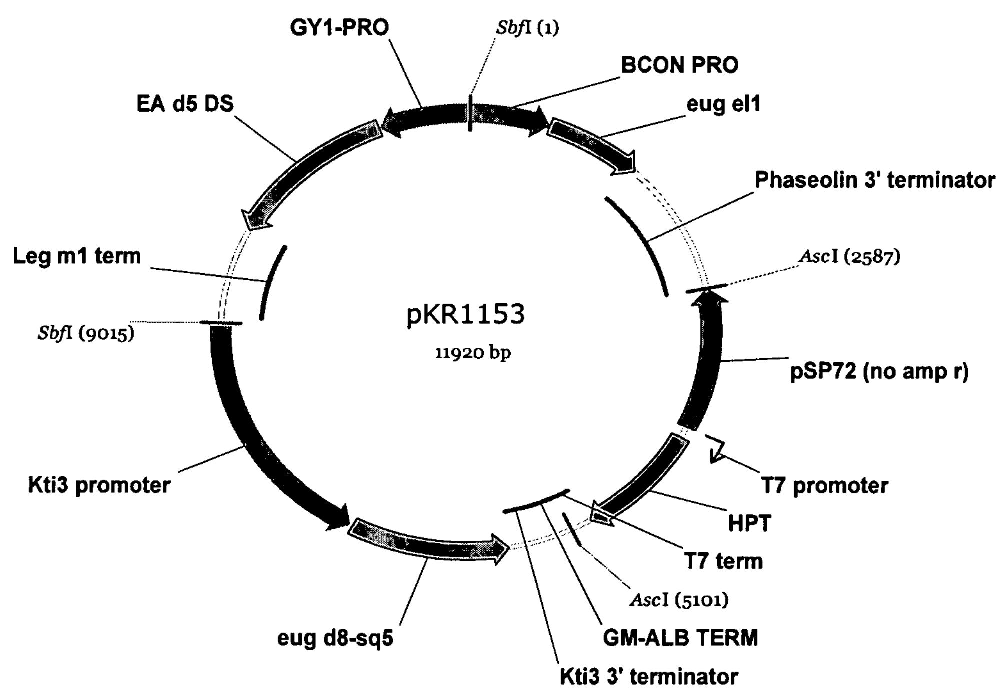
FIG. 7 is a map of pKR1153 (SEQ ID NO:44).

Plasmid pKR1139 (SEQ ID NO:43) was digested with SbfI and the fragment containing the *Euglena anabaena* delta-5 desaturase was cloned into the SbfI site of pKR913 (SEQ ID NO:35) to produce pKR1153 (SEQ ID NO:44, FIG. 7). In this way, the *Euglena anabaena* delta-5 desaturase (EaD5Des1) could be co-expressed with the *Euglena gracilis* delta-8 desaturase (EgD8) and the *Euglena gracilis* delta-9 elongase (EgD9e) behind strong, seed-specific promoters. In FIG. 7, EaD5Des1, EgD8 and EgD9e are referred to as EA d5 DS, eug d8-sq5 and eug el1, respectively.

Example 6

Production and Model System Transformation of Somatic Soybean Embryo Cultures with Soybean Expression Vectors and Plant Regeneration Culture Conditions Soybean embryogenic suspension cultures (cv. Jack) are maintained in 35 mL liquid medium SB196 (infra) on a rotary shaker, 150 rpm, 26° C. with cool white fluorescent lights on 16:8 hr day/night photoperiod at light intensity of 60-85 μE/m2/s. Cultures are subcultured every 7 days to two weeks by inoculating approximately 35 mg of tissue into 35 mL of fresh liquid SB196 (the preferred subculture interval is every 7 days).

Soybean embryogenic suspension cultures are transformed with the soybean expression plasmids by the method of particle gun bombardment (Klein et al., *Nature* 327:70 (1987)) using a DuPont Biolistic PDS1000/HE instrument (helium retrofit) for all transformations.

Soybean Embryogenic Suspension Culture Initiation:

Soybean cultures are initiated twice each month with 5-7 days between each initiation. Pods with immature seeds from available soybean plants are picked 45-55 days after planting. Seeds are removed from the pods and placed into a sterilized magenta box. The soybean seeds are sterilized by shaking them for 15 min in a 5% Clorox solution with 1 drop of Ivory soap (i.e., 95 mL of autoclaved distilled water plus 5 mL Clorox and 1 drop of soap, mixed well). Seeds are rinsed using 2 1-liter bottles of sterile distilled water and those less than 4 mm are placed on individual microscope slides. The small end of the seed is cut and the cotyledons pressed out of the seed coat. When cultures are being prepared for production transformation, cotyledons are transferred to plates containing SB1 medium (25-30 cotyledons per plate). Plates are wrapped with fiber tape and are maintained at 26° C. with cool white fluorescent lights on 16:8 h day/night photoperiod at light intensity of 60-80 μE/m2/s for eight weeks, with a media change after 4 weeks. When cultures are being prepared for model system experiments, cotyledons are transferred to plates containing SB199 medium (25-30 cotyledons per plate) for 2 weeks, and then transferred to SB1 for 2-4 weeks. Light and temperature conditions are the same as described above. After incubation on SB1 medium, secondary embryos are cut and placed into SB196 liquid media for 7 days.

Preparation of DNA for Bombardment:

Either an intact plasmid or a DNA plasmid fragment containing the genes of interest and the selectable marker gene are used for bombardment. Fragments from soybean expression plasmids are obtained by gel isolation of digested plasmids. In each case, 100 μg of plasmid DNA is used in 0.5 mL of the specific enzyme mix described below. Plasmids are digested with AscI (100 units) in NEBuffer 4 (20 mM Tris-acetate, 10 mM magnesium acetate, 50 mM potassium acetate, 1 mM dithiothreitol, pH 7.9), 100 μg/mL BSA, and 5 mM beta-mercaptoethanol at 37° C. for 1.5 hr. The resulting DNA fragments are separated by gel electrophoresis on 1% SeaPlaque GTG agarose (BioWhitaker Molecular Applications) and the DNA fragments containing gene cassettes are cut from the agarose gel. DNA is purified from the agarose using the GELase digesting enzyme following the manufacturer's protocol.

A 50 μL aliquot of sterile distilled water containing 3 mg of gold particles (3 mg gold) is added to 30 μL of a 10 ng/μL DNA solution (either intact plasmid or DNA fragment prepared as described herein), 25 μL 5M $CaCl_2$ and 20 μL of 0.1

M spermidine. The mixture is shaken 3 min on level 3 of a vortex shaker and spun for 10 sec in a bench microfuge. The supernatant is removed, followed by a wash with 400 μL 100% ethanol and another brief centrifugation. The 400 μl ethanol is removed and the pellet is resuspended in 40 μL of 100% ethanol. Five μL of DNA suspension is dispensed to each flying disk of the Biolistic PDS1000/HE instrument disk. Each 5 μL aliquot contains approximately 0.375 mg gold per bombardment (e.g., per disk).

For model system transformations, the protocol is identical except for a few minor changes (ie, 1 mg of gold particles is added to 5 μL of a 1 μg/μL DNA solution, 50 μL of a 2.5M $CaCl_2$ is used and the pellet is ultimately resuspended in 85 μL of 100% ethanol thus providing 0.058 mg of gold particles per bombardment).

Tissue Preparation and Bombardment with DNA:

Approximately 150-200 mg of seven day old embryogenic suspension cultures is placed in an empty, sterile 60×15 mm petri dish and the dish is covered with plastic mesh. The chamber is evacuated to a vacuum of 27-28 inches of mercury, and tissue is bombarded one or two shots per plate with membrane rupture pressure set at 1100 PSI. Tissue is placed approximately 3.5 inches from the retaining/stopping screen. Model system transformation conditions are identical except 100-150 mg of embryogenic tissue is used, rupture pressure is set at 650 PSI and tissue is place approximately 2.5 inches from the retaining screen.

Selection of Transformed Embryos:

Transformed embryos are selected either using hygromycin (when the hygromycin B phosphotransferase (HPT) gene is used as the selectable marker) or chlorsulfuron (when the acetolactate synthase (ALS) gene is used as the selectable marker).

Following bombardment, the tissue is placed into fresh SB196 media and cultured as described above. Six to eight days post-bombardment, the SB196 is exchanged with fresh SB196 containing either 30 mg/L hygromycin or 100 ng/mL chlorsulfuron, depending on the selectable marker used. The selection media is refreshed weekly. Four to six weeks post-selection, green, transformed tissue is observed growing from untransformed, necrotic embryogenic clusters.

Embryo Maturation:

For production transformations, isolated, green tissue is removed and inoculated into multiwell plates to generate new, clonally propagated, transformed embryogenic suspension cultures. Transformed embryogenic clusters are cultured for four-six weeks in multiwell plates at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 $\mu E/m^2s$. After this time embryo clusters are removed to a solid agar media, SB166, for one-two weeks and then subcultured to SB103 medium for 3-4 weeks to mature embryos. After maturation on plates in SB103, individual embryos are removed from the clusters, dried and screened for alterations in their fatty acid compositions as described in Example 7.

For model system transformations, embryos are matured in soybean histodifferentiation and maturation liquid medium (SHaM liquid media; Schmidt et al., *Cell Biology and Morphogenesis* 24:393 (2005)) using a modified procedure. Briefly, after 4 weeks of selection in SB196 as described above, embryo clusters are removed to 35 mL of SB228 (SHaM liquid media) in a 250 mL Erlenmeyer flask. Tissue is maintained in SHaM liquid media on a rotary shaker at 130 rpm and 26° C. with cool white fluorescent lights on a 16:8 hr day/night photoperiod at a light intensity of 60-85 μE/m2/s for 2 weeks as embryos mature. Embryos grown for 2 weeks in SHaM liquid media are equivalent in size and fatty acid content to embryos cultured on SB166/SB103 for 5-8 weeks.

After maturation in SHaM liquid media, individual embryos are removed from the clusters, dried and screened for alterations in their fatty acid compositions as described in Example 7.

Media Recipes:

| SB 196 - FN Lite Liquid Proliferation Medium (per liter) | |
|---|---|
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| asparagine | 1.0 gm |
| sucrose (1%) | 10 gm |
| pH 5.8 | |

FN Lite Stock Solutions

| Stock Number | | 1000 mL | 500 mL |
|---|---|---|---|
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| *Add first, dissolve in dark bottle while stirring | | | |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

SB1 Solid Medium (per liter)

1 package MS salts (Gibco/BRL - Cat. No. 11117-066)
1 mL B5 vitamins 1000X stock
31.5 g glucose
2 mL 2,4-D (20 mg/L final concentration)
pH 5.7
8 g TC agar SB199 Solid Medium (per liter)

1 package MS salts (Gibco/BRL - Cat. No. 11117-066)
1 mL B5 vitamins 1000X stock
30 g Sucrose
4 ml 2,4-D (40 mg/L final concentration)
pH 7.0
2 gm Gelrite SB 166 Solid Medium (per liter)

1 package MS salts (Gibco/BRL - Cat. No. 11117-066)
1 mL B5 vitamins 1000X stock
60 g maltose
750 mg $MgCl_2$ hexahydrate
5 g activated charcoal
pH 5.7
2 g gelrite SB 103 Solid Medium (per liter)

1 package MS salts (Gibco/BRL - Cat. No. 11117-066)
1 mL B5 vitamins 1000X stock
60 g maltose
750 mg MgCl2 hexahydrate
pH 5.7
2 g gelrite -continued

| SB 71-4 Solid Medium (per liter) |
|---|
| 1 bottle Gamborg's B5 salts w/ sucrose (Gibco/BRL - Cat. No. 21153-036) |
| pH 5.7 |
| 5 g TC agar |
| 2,4-D Stock |

| |
|---|
| Obtain premade from Phytotech Cat. No. D 295 - concentration 1 mg/mL |
| B5 Vitamins Stock (per 100 mL) |

| |
|---|
| Store aliquots at −20° C. |
| 10 g myo-inositol |
| 100 mg nicotinic acid |
| 100 mg pyridoxine HCl |
| 1 g thiamine |

If the solution does not dissolve quickly enough, apply a low level of heat via the hot stir plate.

| SB 228 - Soybean Histodifferentiation & Maturation (SHaM) (per liter) | |
|---|---|
| DDI $H_2O$ | 600 mL |
| FN-Lite Macro Salts for SHaM 10X | 100 mL |
| MS Micro Salts 1000x | 1 mL |
| MS FeEDTA 100x | 10 mL |
| CaCl 100x | 6.82 mL |
| B5 Vitamins 1000x | 1 mL |
| L-Methionine | 0.149 g |
| Sucrose | 30 g |
| Sorbitol | 30 g |
| Adjust volume to 900 mL | |
| pH 5.8 | |
| Autoclave | |
| Add to cooled media (≤30° C.): | |
| *Glutamine (final concentration 30 mM) 4% | 110 mL |

*Note:
Final volume will be 1010 mL after glutamine addition.
Since glutamine degrades relatively rapidly, it may be preferable to add immediately prior to using media. Expiration 2 weeks after glutamine is added; base media can be kept longer w/o glutamine.

| FN-lite Macro for SHAM 10X - Stock #1 (per liter) | |
|---|---|
| $(NH_4)2SO_4$ (ammonium sulfate) | 4.63 g |
| $KNO_3$ (potassium nitrate) | 28.3 g |
| $MgSO_4$*$7H_20$ (magnesium sulfate heptahydrate) | 3.7 g |
| $KH_2PO_4$ (potassium phosphate, monobasic) | 1.85 g |
| Bring to volume | |
| Autoclave | |

| MS Micro 1000X - Stock #2 (per 1 liter) | |
|---|---|
| $H_3BO_3$ (boric acid) | 6.2 g |
| $MnSO_4$*$H_2O$ (manganese sulfate monohydrate) | 16.9 g |
| $ZnSO_4$*7H20 (zinc sulfate heptahydrate) | 8.6 g |
| $Na_2MoO_4$*2H20 (sodium molybdate dihydrate) | 0.25 g |
| $CuSO_4$*$5H_20$ (copper sulfate pentahydrate) | 0.025 g |
| $CoCl_2$*$6H_20$ (cobalt chloride hexahydrate) | 0.025 g |
| KI (potassium iodide) | 0.8300 g |
| Bring to volume | |
| Autoclave | |

| FeEDTA 100X - Stock #3 (per liter) | |
|---|---|
| $Na_2EDTA$* (sodium EDTA) | 3.73 g |
| $FeSO_4$*$7H_20$ (iron sulfate heptahydrate) | 2.78 g |
| *EDTA must be completely dissolved before adding iron. | |
| Bring to Volume | |
| Solution is photosensitive. Bottle(s) should be wrapped in foil to omit light. | |
| Autoclave | |

| Ca 100X - Stock #4 (per liter) | |
|---|---|
| $CaCl_2$*$2H_20$ (calcium chloride dihydrate) | 44 g |
| Bring to Volume | |
| Autoclave | |

| B5 Vitamin 1000X - Stock #5 (per liter) | |
|---|---|
| Thiamine*HCl | 10 g |
| Nicotinic Acid | 1 g |
| Pyridoxine*HCl | 1 g |

-continued

| | |
|---|---|
| Myo-Inositol | 100 g |
| Bring to Volume | |
| Store frozen | |

| 4% Glutamine - Stock #6 (per liter) | |
|---|---|
| DDI water heated to 30° C. | 900 mL |
| L-Glutamine | 40 g |

Gradually add while stirring and applying low heat.
Do not exceed 35° C.
Bring to Volume
Filter Sterilize
Store frozen*
*Note: Warm thawed stock in 31° C. bath to fully dissolve crystals.

Regeneration of Soybean Somatic Embryos into Plants:

In order to obtain whole plants from embryogenic suspension cultures, the tissue must be regenerated. Embyros are matured as described in above. After subculturing on medium SB103 for 3 weeks, individual embryos can be removed from the clusters and screened for alterations in their fatty acid compositions as described in Example 7. It should be noted that any detectable phenotype, resulting from the expression of the genes of interest, could be screened at this stage. This would include, but not be limited to, alterations in fatty acid profile, protein profile and content, carbohydrate content, growth rate, viability, or the ability to develop normally into a soybean plant.

Matured individual embryos are desiccated by placing them into an empty, small petri dish (35×10 mm) for approximately 4 to 7 days. The plates are sealed with fiber tape (creating a small humidity chamber). Desiccated embryos are planted into SB71-4 medium where they are left to germinate under the same culture conditions described above. Germinated plantlets are removed from germination medium and rinsed thoroughly with water and then are planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot. After 10 to 16 weeks, mature seeds are harvested, chipped and analyzed for fatty acids.

Example 7

Fatty Acid Analysis of Transgenic Somatic Soybean Embryos

Mature somatic soybean embryos are a good model for zygotic embryos. While in the globular embryo state in liquid culture, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α'-subunit of β-conglycinin, kunitz trypsin inhibitor 3, and seed lectin are essentially absent. Upon transfer to hormone-free media to allow differentiation to the maturing somatic embryo state, triacylglycerol becomes the most abundant lipid class. As well, mRNAs for α'-subunit of β-conglycinin, kunitz trypsin inhibitor 3 and seed lectin become very abundant messages in the total mRNA population. On this basis, the somatic soybean embryo system behaves very similarly to maturing zygotic soybean embryos in vivo, and is thus a good and rapid model system for analyzing the phenotypic effects of modifying the expression of genes in the fatty acid biosynthesis pathway (see PCT Publication No. WO 2002/00904, Example 3). Most importantly, the model system is also predictive of the fatty acid composition of seeds from plants derived from transgenic embryos.

A subset of soybean embryos for each event generated from either production transformation or model system transformation (as described in Example 6) are harvested in the following way. Embryos (5-10 embryos) from each event are picked into glass GC vials and fatty acid methyl esters are prepared by transesterification. For transesterification, 50 μL of trimethylsulfonium hydroxide (TMSH) and 0.5 mL of hexane is added to the embryos in glass vials and incubated for 30 min at room temperature while shaking. Fatty acid methyl esters (5 μL injected from hexane layer) are separated and quantified using a Hewlett-Packard 6890 Gas Chromatograph fitted with an Omegawax 320 fused silica capillary column (Cat. No. 24152, Supelco Inc.). The oven temperature is programmed to hold at 220° C. for 2.6 min, increase to 240° C. at 20° C./min and then hold for an additional 2.4 min. Carrier gas is supplied by a Whatman hydrogen generator. Retention times are compared to those for methyl esters of standards commercially available (Nu-Chek Prep, Inc.). Events having good phenotype can be re-analyzed by GC using identical conditions except the oven temperature is held at 150° C. for 1 min and then increased to 240° C. at 5° C./min.

Example 8

Construction of Alternate Soybean Expression Vectors for Expression of *Euglena anabaena* UTEX 373 Delta-5 Desaturase (EaD5Des1)

In addition to the genes, promoters, terminators and gene cassettes described herein, one skilled in the art can appreciate that other promoter/gene/terminator cassette combinations can be synthesized in a way similar to, but not limited to, that described herein for expression of EaD5Des1. Similarly, it may be desirable to express other PUFA genes (such as those described below in Table 10), for co-expression with the delta-5 desaturase of the present invention.

For instance, PCT Publication Nos. WO 2004/071467 and WO 2004/071178 describe the isolation of a number of promoter and transcription terminator sequences for use in embryo-specific expression in soybean. Furthermore, PCT Publication Nos. WO 2004/071467, WO 2005/047479 and WO 2006/012325 describe the synthesis of multiple promoter/gene/terminator cassette combinations by ligating individual promoters, genes and transcription terminators together in unique combinations. Generally, a NotI site flanked by the suitable promoter (such as those listed in, but not limited to, Table 8) and a transcription terminator (such as those listed in, but not limited to, Table 9) is used to clone the desired gene. NotI sites can be added to a gene of interest such as those listed in, but not limited to, Table 7 using PCR amplification with oligonucleotides designed to introduce NotI sites at the 5' and 3' ends of the gene. The resulting PCR product is then digested with NotI and cloned into a suitable promoter/NotI/terminator cassette.

In addition, PCT Publication Nos. WO 2004/071467, WO 2005/047479 and WO 2006/012325 describe the further linking together of individual gene cassettes in unique combinations, along with suitable selectable marker cassettes, in order to obtain the desired phenotypic expression. Although this is done mainly using different restriction enzymes sites, one skilled in the art can appreciate that a number of techniques can be utilized to achieve the desired promoter/gene/transcription terminator combination. In so doing, any combination of embryo-specific promoter/gene/transcription terminator cassettes can be achieved. One skilled in the art can also appreciate that these cassettes can be located on individual DNA fragments or on multiple fragments where co-expression of genes is the outcome of co-transformation of multiple DNA fragments.

TABLE 8

| Seed-specific Promoters | | |
|---|---|---|
| Promoter | Organism | Promoter Reference |
| β-conglycinin α'-subunit | soybean | Beachy et al., EMBO J. 4: 3047-3053 (1985) |
| kunitz trypsin inhibitor | soybean | Jofuku et al., Plant Cell 1: 1079-1093 (1989) |
| Annexin | soybean | WO 2004/071467 |
| glycinin Gy1 | soybean | WO 2004/071467 |
| albumin 2S | soybean | U.S. Pat. No. 6,177,613 |
| legumin A1 | pea | Rerie et al., Mol. Gen. Genet. 225: 148-157 (1991) |
| β-conglycinin β-subunit | soybean | WO 2004/071467 |
| BD30 (also called P34) | soybean | WO 2004/071467 |
| legumin A2 | pea | Rerie et al., Mol. Gen. Genet. 225: 148-157 (1991) |

TABLE 9

| Transcription Terminators | | |
|---|---|---|
| Transcription Terminator | Organism | Reference |
| phaseolin 3' | bean | WO 2004/071467 |
| kunitz trypsin inhibitor 3' | soybean | WO 2004/071467 |
| BD30 (also called P34) 3' | soybean | WO 2004/071467 |
| legumin A2 3' | pea | WO 2004/071467 |
| albumin 2S 3' | soybean | WO 2004/071467 |

TABLE 10

| PUFA Biosynthetic Pathway Genes | | |
|---|---|---|
| Gene | Organism | Reference |
| delta-6 desaturase | *Saprolegnia diclina* | WO 2002/081668 |
| delta-6 desaturase | *Mortierella alpina* | U.S. Pat. No. 5,968,809 |
| elongase | *Mortierella alpina* | WO 2000/12720 U.S. Pat. No. 6,403,349 |
| delta-5 desaturase | *Mortierella alpina* | U.S. Pat. No. 6,075,183 |
| delta-5 desaturase | *Saprolegnia diclina* | WO 2002/081668 |
| delta-5 desaturase | *Peridinium* sp. | U.S. Provisional Application No. 60/801,119 |
| delta-5 desaturase | *Euglena gracilis* | U.S. Provisional Application No. 60/801,172 |
| delta-15 desaturase | *Fusarium moniliforme* | WO 2005/047479 |
| delta-17 desaturase | *Saprolegnia diclina* | WO 2002/081668 |
| elongase | *Thraustochytrium aureum* | WO 2002/08401 U.S. Pat. No. 6,677,145 |
| elongase | *Pavlova* sp. | Pereira et al., Biochem. J. 384: 357-366 (2004) |
| delta-4 desaturase | *Schizochytrium aggregatum* | WO 2002/090493 U.S. Pat. No. 7,045,683 |
| delta-4 desaturase | *Isochrysis galbana* | WO 2002/090493 U.S. Pat. No. 7,045,683 |
| delta-4 desaturase | *Thraustochytrium aureum* | WO 2002/090493 U.S. Pat. No. 7,045,683 |
| delta-4 desaturase | *Euglena gracilis* | U.S. Patent Application No. 10/552,127 |
| delta-9 elongase | *Isochrysis galbana* | WO 2002/077213 |
| delta-9 elongase | *Euglena gracilis* | U.S. Patent Application No. 11/601,563 |

TABLE 10-continued

PUFA Biosynthetic Pathway Genes

| Gene | Organism | Reference |
| --- | --- | --- |
| delta-9 elongase | *Eutreptiella* sp. CCMP389 | U.S. Patent Application No. 11/601,564 |
| delta-8 desaturase | *Euglena gracilis* | WO 2000/34439<br>U.S. Pat. No. 6,825,017<br>WO 2004/057001<br>WO 2006/012325 |
| delta-8 desaturase | *Acanthamoeba castellanii* | Sayanova et al., FEBS Lett. 580: 1946-1952 (2006) |
| delta-8 desaturase | *Pavlova salina* | WO 2005/103253 |
| delta-8 desaturase | *Pavlova lutheri* | U.S. Provisional Application No. 60/795,810 |
| delta-8 desaturase | *Tetruetreptia pomquetensis* CCMP1491 | U.S. Provisional Application No. 60/853,563 |
| delta-8 desaturase | *Eutreptiella* sp. CCMP389 | U.S. Provisional Application No. 60/853,563 |
| delta-8 desaturase | *Eutreptiella* cf_gymnastica CCMP1594 | U.S. Provisional Application No. 60/853,563 |

Example 9

Synthesis of a Codon-Optimized Delta-5 Desaturase Gene for *Yarrowia lipolytica* (EaD5S)

Figure 8B:
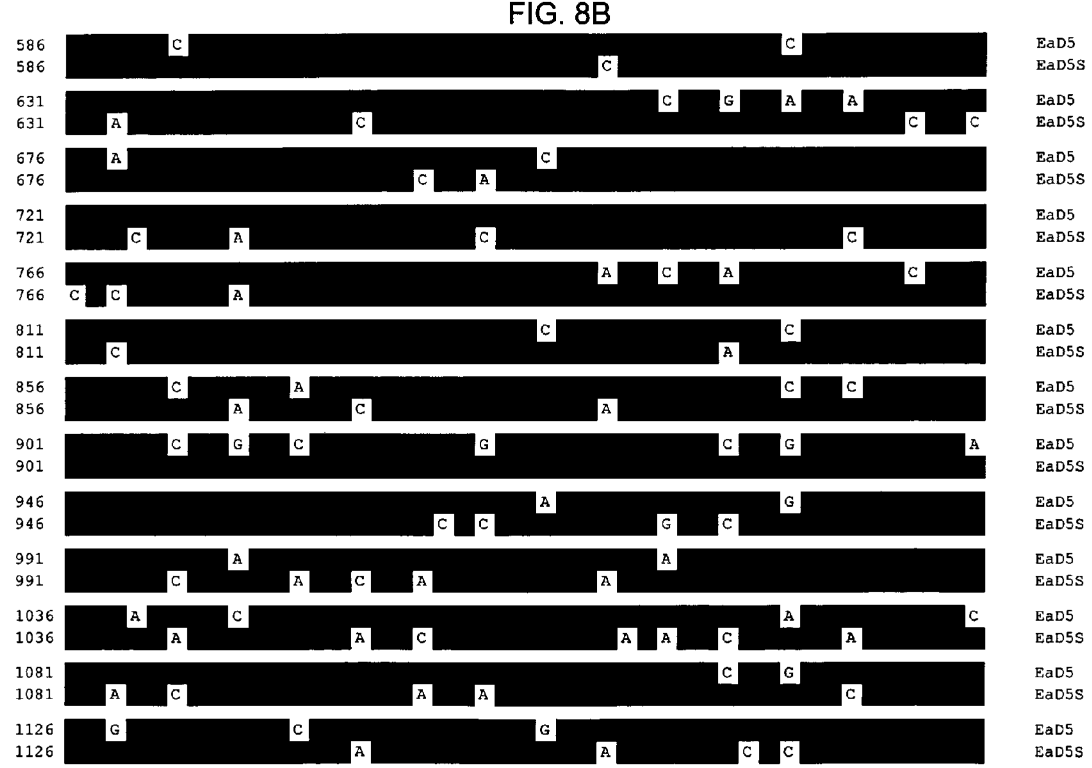
Figure 8C:
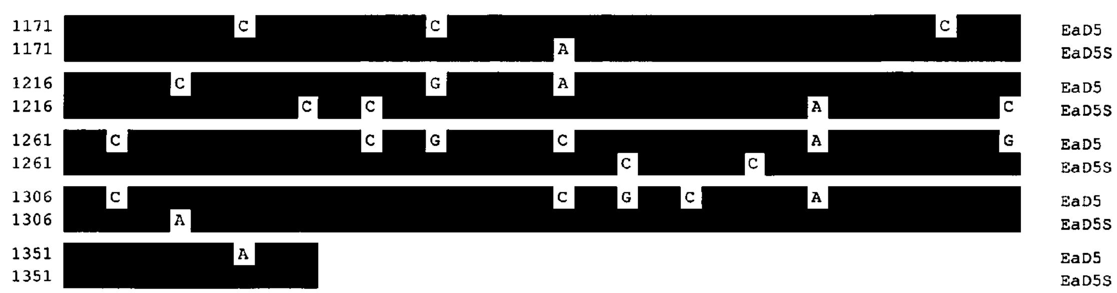
Figure 9:
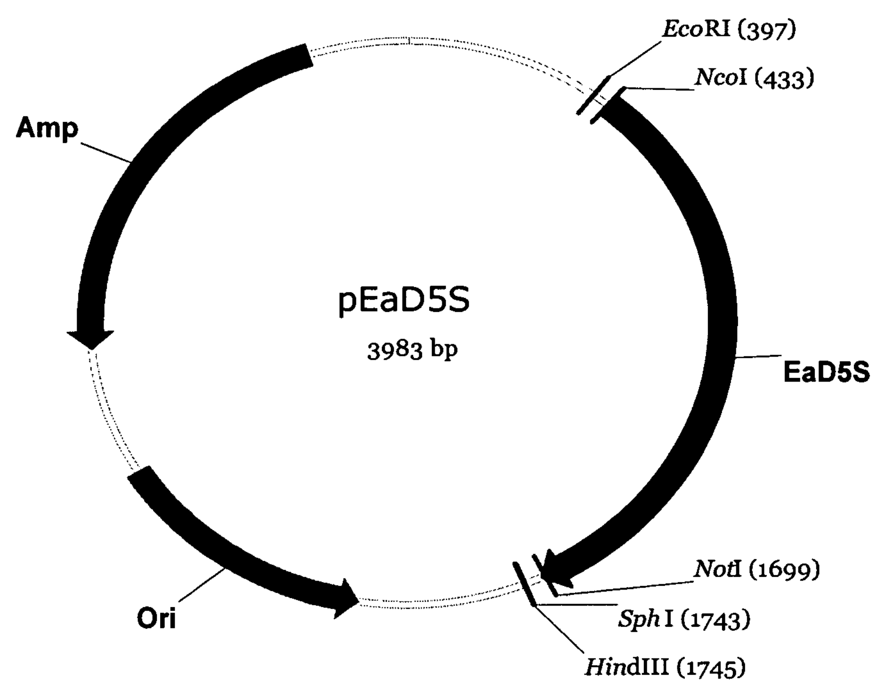
FIG. 9 is a map of plasmid pEaD5S (SEQ ID NO:46).

The codon usage of the delta-5 desaturase gene (EaD5) of *Euglena anabaena* was optimized for expression in *Yarrowia lipolytica*, in a manner similar to that described in PCT Publication No. WO 2004/101753. Specifically, a codon-optimized delta-5 desaturase gene (designated "EaD5S", SEQ ID NO:45) was designed based on the coding sequence of EaD5Des1 (SEQ ID NOs:12 and 13), according to the *Yarrowia* codon usage pattern (PCT Publication No. WO 2004/101753), the consensus sequence around the 'ATG' translation initiation codon, and the general rules of RNA stability (Guhaniyogi, G. and J. Brewer, *Gene* 265(1-2):11-23 (2001)). In addition to modification of the translation initiation site, 183 bp of the 1362 bp coding region were modified (13.4%) and 174 codons were optimized (38.3%). The GC content was reduced from 57.6% within the wild type gene (i.e., EaD5Des1) to 54.6% within the synthetic gene (i.e., EaD5S). A NcoI site and NotI sites were incorporated around the translation initiation codon and after the stop codon of EaD5S (SEQ ID NO:45), respectively. FIGS. 8A, 8B and 8C show a comparison of the nucleotide sequences of EaD5Des1 (SEQ ID NO:12) and EaD5S (SEQ ID NO:45). The codon optimized EaD5S gene did not change any amino acid sequence of EaD5Des1 (SEQ ID NO:13). The designed EaD5S gene was synthesized by GenScript Corporation (Piscataway, N.J.) and cloned into pUC57 (GenBank Accession No. Y14837) to generate pEaD5S (SEQ ID NO:46; FIG. 9).

Based on the teachings herein concerning vector construction and suitable promoter and terminators for use in *Yarrowia lipolytica*, one of skill in the art will be able to construct additional plasmids suitable for expression of EaD5S (SEQ ID NO:45).

Example 10

Functional Analysis of the *Euglena anabaena* UTEX 373 Delta-5 Desaturase (EaD5Des1) Co-Expressed with a Delta-9 Elongase Derived from *Euglena gracilis* (EgD9e) a Delta-8 Desaturase Derived from *Euglena gracilis* (EgD8) and a Delta-17 Desaturase from *Saprolegnia diclina* in Soy Somatic Embryos The present example describes the transformation and expression in soybean somatic embryos of pKR1153 (SEQ ID NO:44; Example 5) comprising EaD5Des1, EgD9e and EgD8 along with pKR328 (described in PCT Publication No. WO 04/071467) comprising the *Saprolegnia diclina* delta-17 desaturase SdD17 under control of the annexin promoter and having a hygromycin resistance gene for selection in plants.

Soybean embryogenic suspension culture (cv. Jack) was transformed with pKR1153 (SEQ ID NO:44) and pKR328, and embryos were matured in soybean histodifferentiation and maturation liquid medium (SHaM liquid media; Schmidt et al., *Cell Biology and Morphogenesis,* 24:393 (2005)) as described in Example 6 and previously described in PCT Publication No. WO 2007/136877 (the contents of which are hereby incorporated by reference).

After maturation in SHaM liquid media, a subset of transformed soybean embryos (i.e., 5 embryos per event) were harvested and analyzed for fatty acid profiles by GC as described in Example 7 and herein.

In this way, approximately 30 events transformed with pKR1153 and pKR328 (Experiment MSE2140) were analyzed, and the ten events having the highest average correct delta-5 desaturase activities (average of the 5 embryos analyzed) are shown in FIG. 11.

In FIG. 11, fatty acids are identified as 16:0 (palmitate), 18:0 (stearic acid), 18:1 (oleic acid), LA, ALA, EDA, SCI, DGLA, ARA, ERA, JUP, ETA and EPA. Fatty acid compositions for an individual embryo were expressed as the weight percent (wt. %) of total fatty acids and the average fatty acid composition is an average of six individual embryos for each event.

The activity of the delta-5 desaturase is expressed as percent delta-5 desaturation ("% delta-5 desat"), calculated according to the following formula: ([product]/[substrate+product])*100. More specifically, the percent delta-5 desaturation was determined as: ([ARA+EPA]/[DGLA+ETA+ARA+EPA])*100.

What is claimed is:

1. A recombinant DNA construct comprising:

(a) a nucleotide sequence encoding a polypeptide having delta-5 desaturase activity, wherein the polypeptide has at least 95% amino acid identity, based on the Clustal V method of alignment, when compared to an amino acid sequence as set forth in SEQ ID NO:13;

(b) a nucleotide sequence encoding a polypeptide having delta-5 desaturase activity, wherein the nucleotide sequence has at least 95% sequence identity, based on the BLASTN method of alignment, when compared to a nucleotide sequence as set forth in SEQ ID NO:12; or (c) a nucleotide sequence comprising the complement of the nucleotide sequence of (a) or (b), wherein the complement and the nucleotide sequence of (a) or (b) consist of the same number of nucleotides and are 100% complementary;

wherein said recombinant DNA construct is operably linked to at least one regulatory sequence.

2. The recombinant DNA construct of claim 1 wherein the nucleotide sequence comprises SEQ ID NO:12.

3. The recombinant DNA construct of claim 1, wherein the amino acid sequence of the polypeptide comprises SEQ ID NO:13.

4. A plant cell comprising in its genome the recombinant DNA construct of claim 1, 2, or 3.

5. A method for transforming a plant cell, comprising transforming a plant cell with the recombinant DNA construct of claim 1, 2, or 3 and selecting those plant cells transformed with the recombinant DNA construct.

6. A method for producing a transformed plant comprising regenerating a plant from the transformed plant cell of claim 5.

7. The method of claim 6 wherein the plant is a soybean plant.

8. A transgenic seed comprising in its genome the recombinant DNA construct of claim 1, 2, or 3.

9. A transgenic seed obtained from the plant made by the method of claim 7.

10. A method for making long-chain polyunsaturated fatty acids in a plant cell comprising:

(a) transforming a plant cell with the recombinant DNA construct of claim 1, 2, or 3; and (b) selecting those transformed plant cells that make long-chain polyunsaturated fatty acids.

11. A method for producing at least one polyunsaturated fatty acid in an oilseed plant cell comprising:

(a) transforming an oilseed plant cell with a first recombinant DNA construct comprising an isolated polynucleotide encoding at least one delta-5 desaturase polypeptide, operably linked to at least one regulatory sequence and at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase, wherein the isolated polynucleotide encoding at least one delta-5 desaturase polypeptide comprises a nucleotide sequence selected from the group consisting of, (i) a nucleotide sequence comprising the sequence set forth in SEQ ID NO:12, (ii) a nucleotide sequence encoding the amino acid sequence set forth in SEQ ID NO:13, (iii) a nucleotide sequence encoding a polypeptide having delta-5 desaturase activity, wherein the polypeptide has at least 95% amino acid identity, based on the Clustal V method of alignment, when compared to an amino acid sequence as set forth in SEQ ID NO:13;

(iv) a nucleotide sequence encoding a polypeptide having delta-5 desaturase activity, wherein the nucleotide sequence has at least 95% sequence identity, based on the BLASTN method of alignment, when compared to a nucleotide sequence as set forth in SEQ ID NO:12; and (v) a nucleotide sequence comprising the complement of the nucleotide sequence of (i), (ii), (iii), or (iv), wherein the complement and the nucleotide sequence of (i), (ii), (iii), or (iv) consist of the same number of nucleotides and are 100% complementary;

(b) regenerating an oilseed plant from the transformed cell of step (a); and (c) selecting those seeds obtained from the plants of step (b) having an altered level of at least one polyunsaturated fatty acids when compared to the level in a seed obtained from a nontransformed oilseed plant.

12. The method of claim 11 wherein the oilseed plant is selected from the group consisting of soybean, *Brassica* species, sunflower, maize, cotton, flax, and safflower.

13. An oilseed plant comprising in its genome the recombinant DNA construct of claim 1.

14. An oilseed plant comprising:

(a) a first recombinant DNA construct comprising an isolated polynucleotide encoding at least one delta-5 desaturase polypeptide, operably linked to at least one regulatory sequence, wherein the isolated polynucleotide encoding at least one delta-5 desaturase polypeptide comprises a nucleotide sequence selected from the group consisting of, (i) a nucleotide sequence comprising the sequence set forth in SEQ ID NO:12, (ii) a nucleotide sequence encoding the amino acid sequence set forth in SEQ ID NO:13, (iii) a nucleotide sequence encoding a polypeptide having delta-5 desaturase activity, wherein the polypeptide has at least 95% amino acid identity, based on the Clustal V method of alignment, when compared to an amino acid sequence as set forth in SEQ ID NO:13;

(iv) a nucleotide sequence encoding a polypeptide having delta-5 desaturase activity, wherein the nucleotide sequence has at least 95% sequence identity, based on the BLASTN method of alignment, when compared to a nucleotide sequence as set forth in SEQ ID NO:12; and (v) a nucleotide sequence comprising the complement of the nucleotide sequence of (i), (ii), (iii), or (iv), wherein the complement and the nucleotide sequence of (i), (ii), (iii), or (iv) consist of the same number of nucleotides and are 100% complementary; and (b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase.

15. The oilseed plant of claim 13 or 14, wherein the oilseed plant is selected from the group consisting of soybean, *Brassica* species, sunflower, maize, cotton, flax and safflower.

16. A transgenic seed obtained from the oilseed plant of claim 13, wherein the transgenic seed comprises the recombinant DNA construct.

17. A transgenic seed obtained from the oilseed plant of claim 14, wherein the transgenic seed comprises the first recombinant DNA construct.

18. Food or feed comprising the seed of claim 16.

19. Food or feed comprising the seed of claim 17.

20. Progeny plants obtained from the plant made by the method of claim 7, wherein said progeny plants comprise said recombinant DNA construct.

21. Progeny plants obtained from the oilseed plant of claim 13 or 14, wherein said progeny plants comprise said recombinant DNA construct.

* * * * *

SEQUENCE LISTING

```
<160> NUMBER OF SEQ ID NOS: 46

<210> SEQ ID NO 1
<211> LENGTH: 1524
<212> TYPE: DNA
<213> ORGANISM: Euglena anabaena

<400> SEQUENCE: 1

acccagtgta cacctttgac agtcccttcg cccaggatgt caagcagagc gttcgggagg     60
```

```
tcatgaaggg gcgcaactgg tacgccacgc ccggcttttg gctgcggacc gcgctgatca    120

tcgcgtgcac tgccataggc gaatggtatt ggatcactac cggggcagtg atgtggggca    180

tcttcaccgg gtacttccac agccagattg ggttggcgat tcaacacgat gcctctcacg    240

gagccatcag caaaaagccc tgggtgaacg cctttttcgc ctacggcatc gacgccattg    300

gatcctcccg ctggatctgg ctgcagtccc acattatgcg ccaccacacc tacaccaacc    360

agcatggcct ggacctggac gctgcctcgg cggagccgtt cattttgttc cactcctacc    420

cggcaacaaa tgcgtcacga aagtggtacc atcggttcca ggcgtggtac atgtacatcg    480

ttttggggat gtatggtgtg tcgatggtgt acaatccgat gtacttgttc acgatgcagc    540

acaacgacac aatcccagag gccacctctc ttagaccagg cagctttttc aaccggcagc    600

gcgccttcgc cgtttccctc cgcctactgt tcatcttccg caacgccttc ctcccctggt    660

acatcgcggg cgcctctccg ctgctcacca tcctgctggt gccaacggtc acaggcatct    720

tcttgacatt tgtttttgtg ctgtcccata actttgaagg cgctgagcgg acccccgaaa    780

agaactgcaa ggccaaaagg gccaaggagg ggaaggaggt ccgcgatgta gaggaggacc    840

gggtggactg gtaccgggcg caggccgaga ccgcggcgac ctacgggggc agcgtcggga    900

tgatgctgac cggcggtttg aacctgcaga tcgagcacca cttgttcccc cgcatgtcct    960

cttggcacta ccccttcatc caagatacgg tgcgggaatg ttgcaagcgc catggcgtgc   1020

gctacacata ctacccgacc atcctggaga atataatgtc cacgctccgc tacatgcaga   1080

aggtgggcgt ggcccacaca attcaggatg cccaggaatt ctgagtgagt tcgatccgca   1140

tcgacgtcta ccatttttga tgctgtctat tcctgttttc agtcacctcc agcattctca   1200

tggctggtga ccactgcccc tctaacccat tgtgacacac cgccaaagac tttgcctctt   1260

ttttttccct ttcttttgtc ctcggggtgc tttggccggt gtttactcgc cttgcagtcc   1320

ccgcaaacga ccgacgttta agctccgttg ttgactgggc cgctcgtaaa cccatctgca   1380

ggttgaggct cccatggaga attgtgatgg ctgattagga ggtggcgggg catacatgcc   1440

tcgacactca aagccgggcg gcttctggat tcgaaaacgc aaatgggcgc tttggaaaaa   1500

aaaaaaaaaa aaaaaaaaaa aaaa                                          1524
```

<210> SEQ ID NO 2
<211> LENGTH: 1347
<212> TYPE: DNA
<213> ORGANISM: Euglena gracilis

<400> SEQUENCE: 2

```
atggctctca gtcttaccac agaacagctg ttagaacgcc ctgatttggt tgcgattgat     60

ggcatcctct acgaccttga agggcttgcc aaagttcatc caggaggaga tttgattctc    120

gcttctggtg cctctgatgc ctcccctctc ttttattcaa tgcatccata cgtcaaaccg    180

gagaattcca aattgcttca acagttcgtc cgagggaagc atgaccgcac ctcgaaggac    240

attgtctaca cgtatgattc tcccttcgca caagacgtta agcggacaat gcgcgaggtg    300

atgaaaggga ggaactggta cgcaacccct ggcttctggc tgcgcaccgt tgggatcatc    360

gccgtgacgg cctttttgcga gtggcactgg gctaccacgg ggatggtgct gtggggcctg    420

ttgactggat tcatgcacat gcagatcggc ttatccatcc agcatgatgc gtcccacggg    480

gccatcagca agaagccttg ggtcaacgcc ctcttcgcct acggcattga cgtcatcgga    540

tcgtcccggt ggatttggct gcagtcgcac atcatgcggc accacaccta caccaaccag    600
```

```
cacggcctcg acctggatgc ggagtcggca gagccgttcc tggtgttcca caactacccc    660

gccgcaaaca ccgcccgaaa gtggttccac cgcttccaag cttggtacat gtaccttgtg    720

ctgggggcat acggggtatc gctggtgtac aacccgctct acattttccg gatgcagcac    780

aatgacacca tcccagagtc tgtcacggcc atgcgggaaa atggctttct gcggcgctac    840

cgcacacttg cattcgtgat gcgagctttc ttcatcttcc ggaccgcatt cttgccctgg    900

tacctcactg ggacctcatt gctgatcacc attcctctgg tgcccaccgc aactggtgcc    960

ttcttgacgt tcttcttcat tttgtcccac aattttgatg gctccgaacg gatccccgac   1020

aagaactgca aggttaagag atctgagaag gacgttgagg ctgaccaaat tgactggtat   1080

cgggcgcagg tggagacgtc ctccacatac ggtggcccca tcgccatgtt cttcactggc   1140

ggtctcaatt tccagatcga gcaccacctc tttccccgga tgtcgtcttg gcactacccc   1200

ttcgtccagc aggcggtccg ggagtgttgc gaacgccatg gagtgcgata tgttttctac   1260

cctaccatcg tcggcaacat catctccacc ctgaagtaca tgcataaggt gggtgtcgtc   1320

cactgcgtga aggacgcaca ggattcc                                        1347


<210> SEQ ID NO 3
<211> LENGTH: 32
<212> TYPE: DNA
<213> ORGANISM: Artificial Sequence
<220> FEATURE:
<223> OTHER INFORMATION: Euglena gracilis delta-5 desaturase
      oligonucleotide YL794

<400> SEQUENCE: 3

tttccatggc tctcagtctt accacagaac ag                                    32


<210> SEQ ID NO 4
<211> LENGTH: 27
<212> TYPE: DNA
<213> ORGANISM: Artificial Sequence
<220> FEATURE:
<223> OTHER INFORMATION: Euglena gracilis delta-5 desaturase
      oligonucleotide YL797

<400> SEQUENCE: 4

gtacatgtac caagcttgga agcggtg                                          27


<210> SEQ ID NO 5
<211> LENGTH: 27
<212> TYPE: DNA
<213> ORGANISM: Artificial Sequence
<220> FEATURE:
<223> OTHER INFORMATION: Euglena gracilis delta-5 desaturase
      oligonucleotide YL796

<400> SEQUENCE: 5

caccgcttcc aagcttggta catgtac                                          27


<210> SEQ ID NO 6
<211> LENGTH: 39
<212> TYPE: DNA
<213> ORGANISM: Artificial Sequence
<220> FEATURE:
<223> OTHER INFORMATION: Euglena gracilis delta-5 desaturase
      oligonucleotide YL795

<400> SEQUENCE: 6

tttgcggccg cttaggaatc ctgtgcgtcc ttcacgcag                             39
```

<210> SEQ ID NO 7
<211> LENGTH: 8165
<212> TYPE: DNA
<213> ORGANISM: Artificial Sequence
<220> FEATURE:
<223> OTHER INFORMATION: plasmid pZUF17

<400> SEQUENCE: 7

```
gtacgagccg gaagcataaa gtgtaaagcc tggggtgcct aatgagtgag ctaactcaca     60

ttaattgcgt tgcgctcact gcccgctttc cagtcgggaa acctgtcgtg ccagctgcat    120

taatgaatcg gccaacgcgc ggggagaggc ggtttgcgta ttgggcgctc ttccgcttcc    180

tcgctcactg actcgctgcg ctcggtcgtt cggctgcggc gagcggtatc agctcactca    240

aaggcggtaa tacggttatc cacagaatca ggggataacg caggaaagaa catgtgagca    300

aaaggccagc aaaaggccag gaaccgtaaa aaggccgcgt tgctggcgtt tttccatagg    360

ctccgccccc ctgacgagca tcacaaaaat cgacgctcaa gtcagaggtg gcgaaacccg    420

acaggactat aaagatacca ggcgtttccc cctggaagct ccctcgtgcg ctctcctgtt    480

ccgaccctgc cgcttaccgg atacctgtcc gcctttctcc cttcgggaag cgtggcgctt    540

tctcatagct cacgctgtag gtatctcagt tcggtgtagg tcgttcgctc caagctgggc    600

tgtgtgcacg aaccccccgt tcagcccgac cgctgcgcct tatccggtaa ctatcgtctt    660

gagtccaacc cggtaagaca cgacttatcg ccactggcag cagccactgg taacaggatt    720

agcagagcga ggtatgtagg cggtgctaca gagttcttga agtggtggcc taactacggc    780

tacactagaa ggacagtatt tggtatctgc gctctgctga agccagttac cttcggaaaa    840

agagttggta gctcttgatc cggcaaacaa accaccgctg gtagcggtgg tttttttgtt    900

tgcaagcagc agattacgcg cagaaaaaaa ggatctcaag aagatccttt gatcttttct    960

acggggtctg acgctcagtg gaacgaaaac tcacgttaag ggattttggt catgagatta   1020

tcaaaaagga tcttcaccta gatcctttta aattaaaaat gaagttttaa atcaatctaa   1080

agtatatatg agtaaacttg gtctgacagt taccaatgct taatcagtga ggcacctatc   1140

tcagcgatct gtctatttcg ttcatccata gttgcctgac tccccgtcgt gtagataact   1200

acgatacggg agggcttacc atctggcccc agtgctgcaa tgataccgcg agacccacgc   1260

tcaccggctc cagatttatc agcaataaac cagccagccg gaagggccga gcgcagaagt   1320

ggtcctgcaa ctttatccgc ctccatccag tctattaatt gttgccggga agctagagta   1380

agtagttcgc cagttaatag tttgcgcaac gttgttgcca ttgctacagg catcgtggtg   1440

tcacgctcgt cgtttggtat ggcttcattc agctccggtt cccaacgatc aaggcgagtt   1500

acatgatccc ccatgttgtg caaaaaagcg gttagctcct tcggtcctcc gatcgttgtc   1560

agaagtaagt tggccgcagt gttatcactc atggttatgg cagcactgca taattctctt   1620

actgtcatgc catccgtaag atgcttttct gtgactggtg agtactcaac caagtcattc   1680

tgagaatagt gtatgcggcg accgagttgc tcttgcccgg cgtcaatacg ggataatacc   1740

gcgccacata gcagaacttt aaaagtgctc atcattggaa aacgttcttc ggggcgaaaa   1800

ctctcaagga tcttaccgct gttgagatcc agttcgatgt aacccactcg tgcacccaac   1860

tgatcttcag catcttttac tttcaccagc gtttctgggt gagcaaaaac aggaaggcaa   1920

aatgccgcaa aaaagggaat aagggcgaca cggaaatgtt gaatactcat actcttcctt   1980

tttcaatatt attgaagcat ttatcagggt tattgtctca tgagcggata catatttgaa   2040

tgtatttaga aaaataaaca aataggggtt ccgcgcacat ttccccgaaa agtgccacct   2100
```

```
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tatttttatt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aatttttttgc ttaaattcaa tccccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca atcgatttcg   4200
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
cagttaaatt acatatccat agtctaacct ctaacagtta atcttctggt aagcctccca   4500
```

```
gccagccttc tggtatcgct tggcctcctc aataggatct cggttctggc cgtacagacc   4560
tcggccgaca attatgatat ccgttccggt agacatgaca tcctcaacag ttcggtactg   4620
ctgtccgaga gcgtctccct tgtcgtcaag acccaccccg ggggtcagaa taagccagtc   4680
ctcagagtcg cccttaggtc ggttctgggc aatgaagcca accacaaact cggggtcgga   4740
tcgggcaagc tcaatggtct gcttggagta ctcgccagtg gccagagagc ccttgcaaga   4800
cagctcggcc agcatgagca gacctctggc cagcttctcg ttgggagagg ggactaggaa   4860
ctccttgtac tgggagttct cgtagtcaga gacgtcctcc ttcttctgtt cagagacagt   4920
ttcctcggca ccagctcgca ggccagcaat gattccggtt ccgggtacac cgtgggcgtt   4980
ggtgatatcg gaccactcgg cgattcggtg acaccggtac tggtgcttga cagtgttgcc   5040
aatatctgcg aactttctgt cctcgaacag gaagaaaccg tgcttaagag caagttcctt   5100
gagggggagc acagtgccgg cgtaggtgaa gtcgtcaatg atgtcgatat gggttttgat   5160
catgcacaca taaggtccga ccttatcggc aagctcaatg agctccttgg tggtggtaac   5220
atccagagaa gcacacaggt tggttttctt ggctgccacg agcttgagca ctcgagcggc   5280
aaaggcggac ttgtggacgt tagctcgagc ttcgtaggag ggcattttgg tggtgaagag   5340
gagactgaaa taaatttagt ctgcagaact ttttatcgga accttatctg gggcagtgaa   5400
gtatatgtta tggtaatagt tacgagttag ttgaacttat agatagactg gactatacgg   5460
ctatcggtcc aaattagaaa gaacgtcaat ggctctctgg gcgtcgcctt tgccgacaaa   5520
aatgtgatca tgatgaaagc cagcaatgac gttgcagctg atattgttgt cggccaaccg   5580
cgccgaaaac gcagctgtca gacccacagc ctccaacgaa gaatgtatcg tcaaagtgat   5640
ccaagcacac tcatagttgg agtcgtactc caaaggcggc aatgacgagt cagacagata   5700
ctcgtcgact caggcgacga cggaattcct gcagcccatc tgcagaattc aggagagacc   5760
gggttggcgg cgtatttgtg tcccaaaaaa cagccccaat tgccccggag aagacggcca   5820
ggccgcctag atgacaaatt caacaactca cagctgactt tctgccattg ccactagggg   5880
ggggcctttt tatatggcca agccaagctc tccacgtcgg ttgggctgca cccaacaata   5940
aatgggtagg gttgcaccaa caaagggatg ggatgggggg tagaagatac gaggataacg   6000
gggctcaatg gcacaaataa gaacgaatac tgccattaag actcgtgatc cagcgactga   6060
caccattgca tcatctaagg gcctcaaaac tacctcggaa ctgctgcgct gatctggaca   6120
ccacagaggt tccgagcact ttaggttgca ccaaatgtcc caccaggtgc aggcagaaaa   6180
cgctggaaca gcgtgtacag tttgtcttaa caaaaagtga gggcgctgag gtcgagcagg   6240
gtggtgtgac ttgttatagc ctttagagct gcgaaagcgc gtatggattt ggctcatcag   6300
gccagattga gggtctgtgg acacatgtca tgttagtgta cttcaatcgc cccctggata   6360
tagccccgac aataggccgt ggcctcattt ttttgccttc cgcacatttc cattgctcgg   6420
tacccacacc ttgcttctcc tgcacttgcc aaccttaata ctggtttaca ttgaccaaca   6480
tcttacaagc ggggggcttg tctagggtat atataaacag tggctctccc aatcggttgc   6540
cagtctcttt tttcctttct ttccccacag attcgaaatc taaactacac atcacacaat   6600
gcctgttact gacgtcctta agcgaaagtc cggtgtcatc gtcggcgacg atgtccgagc   6660
cgtgagtatc cacgacaaga tcagtgtcga gacgacgcgt tttgtgtaat gacacaatcc   6720
gaaagtcgct agcaacacac actctctaca caaactaacc cagctctcca tggctgagga   6780
taagaccaag gtcgagttcc ctaccctgac tgagctgaag cactctatcc ctaacgcttg   6840
```

```
ctttgagtcc aacctcggac tctcgctcta ctacactgcc cgagcgatct tcaacgcatc   6900

tgcctctgct gctctgctct acgctgcccg atctactccc ttcattgccg ataacgttct   6960

gctccacgct ctggtttgcg ccacctacat ctacgtgcag ggtgtcatct tctggggttt   7020

ctttaccgtc ggtcacgact gtggtcactc tgccttctcc cgataccact ccgtcaactt   7080

catcattggc tgcatcatgc actctgccat tctgactccc ttcgagtcct ggcgagtgac   7140

ccaccgacac catcacaaga acactggcaa cattgataag gacgagatct tctaccctca   7200

tcggtccgtc aaggacctcc aggacgtgcg acaatgggtc tacaccctcg gaggtgcttg   7260

gtttgtctac ctgaaggtcg gatatgctcc tcgaaccatg tcccactttg acccctggga   7320

ccctctcctg cttcgacgag cctccgctgt catcgtgtcc ctcggagtct gggctgcctt   7380

cttcgctgcc tacgcctacc tcacatactc gctcggcttt gccgtcatgg gcctctacta   7440

ctatgctcct ctctttgtct ttgcttcgtt cctcgtcatt actaccttct tgcatcacaa   7500

cgacgaagct actccctggt acggtgactc ggagtggacc tacgtcaagg gcaacctgag   7560

ctccgtcgac cgatcgtacg gagctttcgt ggacaacctg tctcaccaca ttggcaccca   7620

ccaggtccat cacttgttcc ctatcattcc ccactacaag ctcaacgaag ccaccaagca   7680

ctttgctgcc gcttaccctc acctcgtgag acgtaacgac gagcccatca ttactgcctt   7740

cttcaagacc gctcacctct ttgtcaacta cggagctgtg cccgagactg ctcagatttt   7800

caccctcaaa gagtctgccg ctgcagccaa ggccaagagc gactaagcgg ccgcaagtgt   7860

ggatggggaa gtgagtgccc ggttctgtgt gcacaattgg caatccaaga tggatggatt   7920

caacacaggg atatagcgag ctacgtggtg gtgcgaggat atagcaacgg atatttatgt   7980

ttgacacttg agaatgtacg atacaagcac tgtccaagta caatactaaa catactgtac   8040

atactcatac tcgtacccgg gcaacggttt cacttgagtg cagtggctag tgctcttact   8100

cgtacagtgt gcaatactgc gtatcatagt ctttgatgta tatcgtattc attcatgtta   8160

gttgc                                                               8165
```

<210> SEQ ID NO 8
<211> LENGTH: 8438
<212> TYPE: DNA
<213> ORGANISM: Artificial Sequence
<220> FEATURE:
<223> OTHER INFORMATION: plasmid pDMW367

<400> SEQUENCE: 8

```
catggctctc agtcttacca cagaacagct gttagaacgc cctgatttgg ttgcgattga     60

tggcatcctc tacgaccttg aagggcttgc caaagttcat ccaggaggag atttgattct    120

cgcttctggt gcctctgatg cctcccctct cttttattca atgcatccat acgtcaaacc    180

ggagaattcc aaattgcttc aacagttcgt ccgagggaag catgaccgca cctcgaagga    240

cattgtctac acgtatgatt ctcccttcgc acaagacgtt aagcggacaa tgcgcgaggt    300

gatgaaaggg aggaactggt acgcaacccc tggcttctgg ctgcgcaccg ttgggatcat    360

cgccgtgacg gccttttgcg agtggcactg ggctaccacg gggatggtgc tgtggggcct    420

gttgactgga ttcatgcaca tgcagatcgg cttatccatc cagcatgatg cgtcccacgg    480

ggccatcagc aagaagcctt gggtcaacgc cctcttcgcc tacggcattg acgtcatcgg    540

atcgtcccgg tggatttggc tgcagtcgca catcatgcgg caccacacct acaccaacca    600

gcacggcctc gacctggatg cggagtcggc agagccgttc ctggtgttcc acaactaccc    660

cgccgcaaac accgcccgaa agtggttcca ccgcttccaa gcttggtaca tgtaccttgt    720
```

```
gctgggggca tacggggtat cgctggtgta caacccgctc tacattttcc ggatgcagca    780

caatgacacc atcccagagt ctgtcacggc catgcgggaa aatggctttc tgcggcgcta    840

ccgcacactt gcattcgtga tgcgagcttt cttcatcttc cggaccgcat tcttgccctg    900

gtacctcact gggacctcat tgctgatcac cattcctctg gtgcccaccg caactggtgc    960

cttcttgacg ttcttcttca ttttgtccca caattttgat ggctccgaac ggatccccga   1020

caagaactgc aaggttaaga gatctgagaa ggacgttgag gctgaccaaa ttgactggta   1080

tcgggcgcag gtggagacgt cctccacata cggtggcccc atcgccatgt tcttcactgg   1140

cggtctcaat ttccagatcg agcaccacct ctttccccgg atgtcgtctt ggcactaccc   1200

cttcgtccag caggcggtcc gggagtgttg cgaacgccat ggagtgcgat atgttttcta   1260

ccctaccatc gtcggcaaca tcatctccac cctgaagtac atgcataagg tgggtgtcgt   1320

ccactgcgtg aaggacgcac aggattccta agcggccgca agtgtggatg gggaagtgag   1380

tgcccggttc tgtgtgcaca attggcaatc caagatggat ggattcaaca cagggatata   1440

gcgagctacg tggtggtgcg aggatatagc aacggatatt tatgtttgac acttgagaat   1500

gtacgataca agcactgtcc aagtacaata ctaaacatac tgtacatact catactcgta   1560

cccgggcaac ggtttcactt gagtgcagtg gctagtgctc ttactcgtac agtgtgcaat   1620

actgcgtatc atagtctttg atgtatatcg tattcattca tgttagttgc gtacgagccg   1680

gaagcataaa gtgtaaagcc tggggtgcct aatgagtgag ctaactcaca ttaattgcgt   1740

tgcgctcact gcccgctttc cagtcgggaa acctgtcgtg ccagctgcat taatgaatcg   1800

gccaacgcgc ggggagaggc ggtttgcgta ttgggcgctc ttccgcttcc tcgctcactg   1860

actcgctgcg ctcggtcgtt cggctgcggc gagcggtatc agctcactca aaggcggtaa   1920

tacggttatc cacagaatca ggggataacg caggaaagaa catgtgagca aaaggccagc   1980

aaaaggccag gaaccgtaaa aaggccgcgt tgctggcgtt tttccatagg ctccgccccc   2040

ctgacgagca tcacaaaaat cgacgctcaa gtcagaggtg gcgaaacccg acaggactat   2100

aaagatacca ggcgtttccc cctggaagct ccctcgtgcg ctctcctgtt ccgaccctgc   2160

cgcttaccgg atacctgtcc gcctttctcc cttcgggaag cgtggcgctt tctcatagct   2220

cacgctgtag gtatctcagt tcggtgtagg tcgttcgctc caagctgggc tgtgtgcacg   2280

aaccccccgt tcagcccgac cgctgcgcct tatccggtaa ctatcgtctt gagtccaacc   2340

cggtaagaca cgacttatcg ccactggcag cagccactgg taacaggatt agcagagcga   2400

ggtatgtagg cggtgctaca gagttcttga agtggtggcc taactacggc tacactagaa   2460

ggacagtatt tggtatctgc gctctgctga agccagttac cttcggaaaa agagttggta   2520

gctcttgatc cggcaaacaa accaccgctg gtagcggtgg tttttttgtt tgcaagcagc   2580

agattacgcg cagaaaaaaa ggatctcaag aagatccttt gatcttttct acggggtctg   2640

acgctcagtg gaacgaaaac tcacgttaag ggattttggt catgagatta tcaaaaagga   2700

tcttcaccta gatcctttta aattaaaaat gaagttttaa atcaatctaa agtatatatg   2760

agtaaacttg gtctgacagt taccaatgct taatcagtga ggcacctatc tcagcgatct   2820

gtctatttcg ttcatccata gttgcctgac tccccgtcgt gtagataact acgatacggg   2880

agggcttacc atctggcccc agtgctgcaa tgataccgcg agacccacgc tcaccggctc   2940

cagatttatc agcaataaac cagccagccg gaagggccga gcgcagaagt ggtcctgcaa   3000

ctttatccgc ctccatccag tctattaatt gttgccggga agctagagta agtagttcgc   3060
```

```
cagttaatag tttgcgcaac gttgttgcca ttgctacagg catcgtggtg tcacgctcgt   3120
cgtttggtat ggcttcattc agctccggtt cccaacgatc aaggcgagtt acatgatccc   3180
ccatgttgtg caaaaaagcg gttagctcct tcggtcctcc gatcgttgtc agaagtaagt   3240
tggccgcagt gttatcactc atggttatgg cagcactgca taattctctt actgtcatgc   3300
catccgtaag atgcttttct gtgactggtg agtactcaac caagtcattc tgagaatagt   3360
gtatgcggcg accgagttgc tcttgcccgg cgtcaatacg ggataatacc gcgccacata   3420
gcagaacttt aaaagtgctc atcattggaa aacgttcttc ggggcgaaaa ctctcaagga   3480
tcttaccgct gttgagatcc agttcgatgt aacccactcg tgcacccaac tgatcttcag   3540
catcttttac tttcaccagc gtttctgggt gagcaaaaac aggaaggcaa aatgccgcaa   3600
aaaagggaat aagggcgaca cggaaatgtt gaatactcat actcttcctt tttcaatatt   3660
attgaagcat ttatcagggt tattgtctca tgagcggata catatttgaa tgtatttaga   3720
aaaataaaca aataggggtt ccgcgcacat ttccccgaaa agtgccacct gacgcgccct   3780
gtagcggcgc attaagcgcg gcgggtgtgg tggttacgcg cagcgtgacc gctacacttg   3840
ccagcgccct agcgcccgct cctttcgctt tcttcccttc ctttctcgcc acgttcgccg   3900
gctttccccg tcaagctcta aatcgggggc tccctttagg gttccgattt agtgctttac   3960
ggcacctcga ccccaaaaaa cttgattagg gtgatggttc acgtagtggg ccatcgccct   4020
gatagacggt ttttcgccct ttgacgttgg agtccacgtt ctttaatagt ggactcttgt   4080
tccaaactgg aacaacactc aaccctatct cggtctattc ttttgattta taagggattt   4140
tgccgatttc ggcctattgg ttaaaaaatg agctgattta acaaaaattt aacgcgaatt   4200
ttaacaaaat attaacgctt acaatttcca ttcgccattc aggctgcgca actgttggga   4260
agggcgatcg gtgcgggcct cttcgctatt acgccagctg gcgaaagggg gatgtgctgc   4320
aaggcgatta agttgggtaa cgccagggtt ttcccagtca cgacgttgta aaacgacggc   4380
cagtgaattg taatacgact cactataggg cgaattgggt accgggcccc ccctcgaggt   4440
cgatggtgtc gataagcttg atatcgaatt catgtcacac aaaccgatct tcgcctcaag   4500
gaaacctaat tctacatccg agagactgcc gagatccagt ctacactgat taattttcgg   4560
gccaataatt taaaaaaatc gtgttatata atattatatg tattatatat atacatcatg   4620
atgatactga cagtcatgtc ccattgctaa atagacagac tccatctgcc gcctccaact   4680
gatgttctca atatttaagg ggtcatctcg cattgtttaa taataaacag actccatcta   4740
ccgcctccaa atgatgttct caaaatatat tgtatgaact tatttttatt acttagtatt   4800
attagacaac ttacttgctt tatgaaaaac acttcctatt taggaaacaa tttataatgg   4860
cagttcgttc atttaacaat ttatgtagaa taaatgttat aaatgcgtat gggaaatctt   4920
aaatatggat agcataaatg atatctgcat tgcctaattc gaaatcaaca gcaacgaaaa   4980
aaatcccttg tacaacataa atagtcatcg agaaatatca actatcaaag aacagctatt   5040
cacacgttac tattgagatt attattggac gagaatcaca cactcaactg tctttctctc   5100
ttctagaaat acaggtacaa gtatgtacta ttctcattgt tcatacttct agtcatttca   5160
tcccacatat tccttggatt tctctccaat gaatgacatt ctatcttgca aattcaacaa   5220
ttataataag atataccaaa gtagcggtat agtggcaatc aaaaagcttc tctggtgtgc   5280
ttctcgtatt tatttttatt ctaatgatcc attaaaggta tatatttatt tcttgttata   5340
taatcctttt gtttattaca tgggctggat acataaaggt attttgattt aattttttgc   5400
ttaaattcaa tccccccctcg ttcagtgtca actgtaatgg taggaaatta ccatactttt   5460
```

```
gaagaagcaa aaaaaatgaa agaaaaaaaa aatcgtattt ccaggttaga cgttccgcag   5520

aatctagaat gcggtatgcg gtacattgtt cttcgaacgt aaaagttgcg ctccctgaga   5580

tattgtacat ttttgctttt acaagtacaa gtacatcgta caactatgta ctactgttga   5640

tgcatccaca acagtttgtt ttgttttttt ttgttttttt tttttctaat gattcattac   5700

cgctatgtat acctacttgt acttgtagta agccgggtta ttggcgttca attaatcata   5760

gacttatgaa tctgcacggt gtgcgctgcg agttactttt agcttatgca tgctacttgg   5820

gtgtaatatt gggatctgtt cggaaatcaa cggatgctca atcgatttcg acagtaatta   5880

attaagtcat acacaagtca gctttcttcg agcctcatat aagtataagt agttcaacgt   5940

attagcactg tacccagcat ctccgtatcg agaaacacaa caacatgccc cattggacag   6000

atcatgcgga tacacaggtt gtgcagtatc atacatactc gatcagacag gtcgtctgac   6060

catcatacaa gctgaacaag cgctccatac ttgcacgctc tctatataca cagttaaatt   6120

acatatccat agtctaacct ctaacagtta atcttctggt aagcctccca gccagccttc   6180

tggtatcgct tggcctcctc aataggatct cggttctggc cgtacagacc tcggccgaca   6240

attatgatat ccgttccggt agacatgaca tcctcaacag ttcggtactg ctgtccgaga   6300

gcgtctccct tgtcgtcaag acccaccccg gggtcagaa taagccagtc ctcagagtcg   6360

cccttaggtc ggttctgggc aatgaagcca accacaaact cggggtcgga tcgggcaagc   6420

tcaatggtct gcttggagta ctcgccagtg gccagagagc ccttgcaaga cagctcggcc   6480

agcatgagca gacctctggc cagcttctcg ttgggagagg ggactaggaa ctccttgtac   6540

tgggagttct cgtagtcaga gacgtcctcc ttcttctgtt cagagacagt ttcctcggca   6600

ccagctcgca ggccagcaat gattccggtt ccgggtacac cgtgggcgtt ggtgatatcg   6660

gaccactcgg cgattcggtg acaccggtac tggtgcttga cagtgttgcc aatatctgcg   6720

aactttctgt cctcgaacag gaagaaaccg tgcttaagag caagttcctt gagggggagc   6780

acagtgccgg cgtaggtgaa gtcgtcaatg atgtcgatat gggttttgat catgcacaca   6840

taaggtccga ccttatcggc aagctcaatg agctccttgg tggtggtaac atccagagaa   6900

gcacacaggt tggttttctt ggctgccacg agcttgagca ctcgagcggc aaaggcggac   6960

ttgtggacgt tagctcgagc ttcgtaggag ggcattttgg tggtgaagag gagactgaaa   7020

taaatttagt ctgcagaact ttttatcgga accttatctg gggcagtgaa gtatatgtta   7080

tggtaatagt tacgagttag ttgaacttat agatagactg gactatacgg ctatcggtcc   7140

aaattagaaa gaacgtcaat ggctctctgg gcgtcgcctt tgccgacaaa aatgtgatca   7200

tgatgaaagc cagcaatgac gttgcagctg atattgttgt cggccaaccg cgccgaaaac   7260

gcagctgtca gacccacagc ctccaacgaa gaatgtatcg tcaaagtgat ccaagcacac   7320

tcatagttgg agtcgtactc caaaggcggc aatgacgagt cagacagata ctcgtcgact   7380

caggcgacga cggaattcct gcagcccatc tgcagaattc aggagagacc gggttggcgg   7440

cgtatttgtg tcccaaaaaa cagccccaat tgccccggag aagacggcca ggccgcctag   7500

atgacaaatt caacaactca cagctgactt tctgccattg ccactagggg ggggcctttt   7560

tatatggcca agccaagctc tccacgtcgg ttgggctgca cccaacaata aatgggtagg   7620

gttgcaccaa caaagggatg ggatgggggg tagaagatac gaggataacg gggctcaatg   7680

gcacaaataa gaacgaatac tgccattaag actcgtgatc cagcgactga caccattgca   7740

tcatctaagg gcctcaaaac tacctcggaa ctgctgcgct gatctggaca ccacagaggt   7800
```

```
tccgagcact ttaggttgca ccaaatgtcc caccaggtgc aggcagaaaa cgctggaaca   7860

gcgtgtacag tttgtcttaa caaaaagtga gggcgctgag gtcgagcagg gtggtgtgac   7920

ttgttatagc ctttagagct gcgaaagcgc gtatggattt ggctcatcag gccagattga   7980

gggtctgtgg acacatgtca tgttagtgta cttcaatcgc cccctggata tagccccgac   8040

aataggccgt ggcctcattt ttttgccttc cgcacatttc cattgctcgg tacccacacc   8100

ttgcttctcc tgcacttgcc aaccttaata ctggtttaca ttgaccaaca tcttacaagc   8160

ggggggcttg tctagggtat atataaacag tggctctccc aatcggttgc cagtctcttt   8220

tttcctttct ttccccacag attcgaaatc taaactacac atcacacaat gcctgttact   8280

gacgtcctta agcgaaagtc cggtgtcatc gtcggcgacg atgtccgagc cgtgagtatc   8340

cacgacaaga tcagtgtcga gacgacgcgt tttgtgtaat gacacaatcc gaaagtcgct   8400

agcaacacac actctctaca caaactaacc cagctctc                           8438
```

```
<210> SEQ ID NO 9
<211> LENGTH: 18
<212> TYPE: DNA
<213> ORGANISM: Artificial Sequence
<220> FEATURE:
<223> OTHER INFORMATION: M13F universal primer

<400> SEQUENCE: 9

tgtaaaacga cggccagt                                                  18
```

```
<210> SEQ ID NO 10
<211> LENGTH: 22
<212> TYPE: DNA
<213> ORGANISM: Artificial Sequence
<220> FEATURE:
<223> OTHER INFORMATION: primer M13-28Rev

<400> SEQUENCE: 10

gtaatacgac tcactatagg gc                                             22
```

```
<210> SEQ ID NO 11
<211> LENGTH: 4276
<212> TYPE: DNA
<213> ORGANISM: Artificial Sequence
<220> FEATURE:
<223> OTHER INFORMATION: plasmid pLF119

<400> SEQUENCE: 11

gtacaaagtt ggcattataa gaaagcattg cttatcaatt tgttgcaacg aacaggtcac     60

tatcagtcaa aataaaatca ttatttgcca tccagctgat atcccctata gtgagtcgta    120

ttacatggtc atagctgttt cctggcagct ctggcccgtg tctcaaaatc tctgatgtta    180

cattgcacaa gataaaaata tatcatcatg ttagaaaaac tcatcgagca tcaaatgaaa    240

ctgcaattta ttcatatcag gattatcaat accatatttt tgaaaaagcc gtttctgtaa    300

tgaaggagaa aactcaccga ggcagttcca taggatggca agatcctggt atcggtctgc    360

gattccgact cgtccaacat caatacaacc tattaatttc ccctcgtcaa aaataaggtt    420

atcaagtgag aaatcaccat gagtgacgac tgaatccggt gagaatggca aaagcttatg    480

catttctttc cagacttgtt caacaggcca gccattacgc tcgtcatcaa aatcactcgc    540

atcaaccaaa ccgttattca ttcgtgattg cgcctgagcg agacgaaata cgcgatcgct    600

gttaaaagga caattacaaa caggaatcga atgcaaccgg cgcaggaaca ctgccagcgc    660

atcaacaata ttttcacctg aatcaggata ttcttctaat acctggaatg ctgttttccc    720
```

```
ggggatcgca gtggtgagta accatgcatc atcaggagta cggataaaat gcttgatggt    780
cggaagaggc ataaattccg tcagccagtt tagtctgacc atctcatctg taacatcatt    840
ggcaacgcta cctttgccat gtttcagaaa caactctggc gcatcgggct tcccatacaa    900
tcgatagatt gtcgcacctg attgcccgac attatcgcga gcccatttat acccatataa    960
atcagcatcc atgttggaat ttaatcgcgg cctcgagcaa gacgtttccc gttgaatatg   1020
gctcatagat cttttctcca tcactgatag ggagtggtaa aataactcca tcaatgatag   1080
agtgtcaaca acatgaccaa aatcccttaa cgtgagttac gcgtattaat tgcgttgcgc   1140
tcactgcccg ctttccagtc gggaaacctg tcgtgccagc tgcattaatg aatcggccaa   1200
cgcgcgggga gaggcggttt gcgtattggg cgctcttccg cttcctcgct cactgactcg   1260
ctgcgctcgg tcgttcggct gcggcgagcg gtatcagctc actcaaaggc ggtaatacgg   1320
ttatccacag aatcagggga taacgcagga aagaacatgt gagcaaaagg ccagcaaaag   1380
gccaggaacc gtaaaaaggc cgcgttgctg gcgtttttcc ataggctccg cccccctgac   1440
gagcatcaca aaaatcgacg ctcaagtcag aggtggcgaa acccgacagg actataaaga   1500
taccaggcgt ttccccctgg aagctccctc gtgcgctctc ctgttccgac cctgccgctt   1560
accggatacc tgtccgcctt tctcccttcg ggaagcgtgg cgctttctca atgctcacgc   1620
tgtaggtatc tcagttcggt gtaggtcgtt cgctccaagc tgggctgtgt gcacgaaccc   1680
cccgttcagc ccgaccgctg cgccttatcc ggtaactatc gtcttgagtc caacccggta   1740
agacacgact tatcgccact ggcagcagcc actggtaaca ggattagcag agcgaggtat   1800
gtaggcggtg ctacagagtt cttgaagtgg tggcctaact acggttacac tagaagaaca   1860
gtatttggta tctgcgctct gctgaagcca gttaccttcg gaaaaagagt tggtagctct   1920
tgatccggca aacaaaccac cgctggtagc ggtggttttt ttgtttgcaa gcagcagatt   1980
acgcgcagaa aaaaaggatc tcaagaagat cctttgatct tttctacggg gtctgacgct   2040
cagggaacga cgcgtaccgc tagccaggaa gagtttgtag aaacgcaaaa aggccatccg   2100
tcaggatggc cttctgctta gtttgatgcc tggcagttta tggcgggcgt cctgcccgcc   2160
accctccggg ccgttgcttc acaacgttca aatccgctcc cggcggattt gtcctactca   2220
ggagagcgtt caccgacaaa caacagataa aacgaaaggc ccagtcttcc gactgagcct   2280
ttcgttttat ttgatgcctg gcagttccct actctcgcgt taacgctagc atggatgttt   2340
tcccagtcac gacgttgtaa aacgacggcc agtcttaagc tcgggcccca aataatgatt   2400
ttattttgac tgatagtgac ctgttcgttg caacaaattg atgagcaatg cttttttata   2460
atgccaactt tgtacaaaaa agttggattt tttttcggga tggccaccat ctctttgact   2520
actgagcaac ttttagaaca cccagaactg gttgcaattg atggggtgtt gtacgatctc   2580
ttcggactgg cgaaagtgca tccaggtggc aacctcattg aagccgccgg tgcctccgac   2640
ggaaccgccc tgttctactc catgcaccct ggagtgaagc cagagaattc gaagctgctg   2700
cagcaatttg cccgaggcaa acacgaacga agctcgaagg acccagtgta cacctttgac   2760
agtcccttcg cccaggatgt caagcagagc gttcgggagg tcatgaaggg gcgcaactgg   2820
tacgccacgc ccggcttttg gctgcggacc gcgctgatca tcgcgtgcac tgccataggc   2880
gaatggtatt ggatcactac cggggcagtg atgtggggca tcttcaccgg gtacttccac   2940
agccagattg ggttggcgat tcaacacgat gcctctcacg gagccatcag caaaaagccc   3000
tgggtgaacg cctttttcgc ctacggcatc gacgccattg gatcctcccg ctggatctgg   3060
```

```
ctgcagtccc acattatgcg ccaccacacc tacaccaacc agcatggcct ggacctggac   3120
gctgcctcgg cggagccgtt cattttgttc cactcctacc cggcaacaaa tgcgtcacga   3180
aagtggtacc atcggttcca ggcgtggtac atgtacatcg ttttggggat gtatggtgtg   3240
tcgatggtgt acaatccgat gtacttgttc acgatgcagc acaacgacac aatcccagag   3300
gccacctctc ttagaccagg cagctttttc aaccggcagc gcgccttcgc cgtttccctc   3360
cgcctactgt tcatcttccg caacgccttc ctcccctggt acatcgcggg cgcctctccg   3420
ctgctcacca tcctgctggt gccaacggtc acaggcatct tcttgacatt tgtttttgtg   3480
ctgtcccata actttgaagg cgctgagcgg accccccgaaa agaactgcaa ggccaaaagg   3540
gccaaggagg ggaaggaggt ccgcgatgta gaggaggacc gggtggactg gtaccgggcg   3600
caggccgaga ccgcggcgac ctacgggggc agcgtcggga tgatgctgac cggcggtttg   3660
aacctgcaga tcgagcacca cttgttcccc cgcatgtcct cttggcacta ccccttcatc   3720
caagatacgg tgcgggaatg ttgcaagcgc catggcgtgc gctacacata ctacccgacc   3780
atcctggaga atataatgtc cacgctccgc tacatgcaga aggtgggcgt ggcccacaca   3840
attcaggatg cccaggaatt ctgagtgagt tcgatccgca tcgacgtcta ccatttttga   3900
tgctgtctat tcctgttttc agtcacctcc agcattctca tggctggtga ccactgcccc   3960
tctaacccat tgtgacacac cgccaaagac tttgcctctt ttttttccct ttcttttgtc   4020
ctcggggtgc tttggccggt gtttactcgc cttgcagtcc ccgcaaacga ccgacgttta   4080
agctccgttg ttgactgggc cgctcgtaaa cccatctgca ggttgaggct cccatggaga   4140
attgtgatgg ctgattagga ggtggcgggg catacatgcc tcgacactca aagccgggcg   4200
gcttctggat tcgaaaacgc aaatgggcgc tttggaaaaa aaaaaaaaaa aaaaaaaaaa   4260
aaaacccaac tttctt                                                   4276
```

<210> SEQ ID NO 12
<211> LENGTH: 1362
<212> TYPE: DNA
<213> ORGANISM: Euglena anabaena

<400> SEQUENCE: 12

```
atggccacca tctctttgac tactgagcaa cttttagaac acccagaact ggttgcaatt     60
gatggggtgt tgtacgatct cttcggactg gcgaaagtgc atccaggtgg caacctcatt    120
gaagccgccg gtgcctccga cggaaccgcc ctgttctact ccatgcaccc tggagtgaag    180
ccagagaatt cgaagctgct gcagcaattt gcccgaggca aacacgaacg aagctcgaag    240
gacccagtgt acacctttga cagtcccttc gcccaggatg tcaagcagag cgttcgggag    300
gtcatgaagg ggcgcaactg gtacgccacg cccggctttt ggctgcggac cgcgctgatc    360
atcgcgtgca ctgccatagg cgaatggtat tggatcacta ccggggcagt gatgtggggc    420
atcttcaccg ggtacttcca cagccagatt gggttggcga ttcaacacga tgcctctcac    480
ggagccatca gcaaaaagcc ctgggtgaac gcctttttcg cctacggcat cgacgccatt    540
ggatcctccc gctggatctg gctgcagtcc cacattatgc gccaccacac ctacaccaac    600
cagcatggcc tggacctgga cgctgcctcg gcggagccgt tcattttgtt ccactcctac    660
ccggcaacaa atgcgtcacg aaagtggtac catcggttcc aggcgtggta catgtacatc    720
gttttgggga tgtatggtgt gtcgatggtg tacaatccga tgtacttgtt cacgatgcag    780
cacaacgaca caatcccaga ggccacctct cttagaccag gcagcttttt caaccggcag    840
cgcgccttcg ccgtttccct ccgcctactg ttcatcttcc gcaacgcctt cctcccctgg    900
```

```
tacatcgcgg gcgcctctcc gctgctcacc atcctgctgg tgccaacggt cacaggcatc    960

ttcttgacat ttgtttttgt gctgtcccat aactttgaag gcgctgagcg gacccccgaa   1020

aagaactgca aggccaaaag ggccaaggag gggaaggagg tccgcgatgt agaggaggac   1080

cgggtggact ggtaccgggc gcaggccgag accgcggcga cctacggggg cagcgtcggg   1140

atgatgctga ccggcggttt gaacctgcag atcgagcacc acttgttccc ccgcatgtcc   1200

tcttggcact accccttcat ccaagatacg gtgcgggaat gttgcaagcg ccatggcgtg   1260

cgctacacat actacccgac catcctggag aatataatgt ccacgctccg ctacatgcag   1320

aaggtgggcg tggcccacac aattcaggat gcccaggaat tc                      1362
```

```
<210> SEQ ID NO 13
<211> LENGTH: 454
<212> TYPE: PRT
<213> ORGANISM: Euglena anabaena

<400> SEQUENCE: 13

Met Ala Thr Ile Ser Leu Thr Thr Glu Gln Leu Leu Glu His Pro Glu
1               5                   10                  15

Leu Val Ala Ile Asp Gly Val Leu Tyr Asp Leu Phe Gly Leu Ala Lys
            20                  25                  30

Val His Pro Gly Gly Asn Leu Ile Glu Ala Ala Gly Ala Ser Asp Gly
        35                  40                  45

Thr Ala Leu Phe Tyr Ser Met His Pro Gly Val Lys Pro Glu Asn Ser
    50                  55                  60

Lys Leu Leu Gln Gln Phe Ala Arg Gly Lys His Glu Arg Ser Ser Lys
65                  70                  75                  80

Asp Pro Val Tyr Thr Phe Asp Ser Pro Phe Ala Gln Asp Val Lys Gln
                85                  90                  95

Ser Val Arg Glu Val Met Lys Gly Arg Asn Trp Tyr Ala Thr Pro Gly
            100                 105                 110

Phe Trp Leu Arg Thr Ala Leu Ile Ile Ala Cys Thr Ala Ile Gly Glu
        115                 120                 125

Trp Tyr Trp Ile Thr Thr Gly Ala Val Met Trp Gly Ile Phe Thr Gly
    130                 135                 140

Tyr Phe His Ser Gln Ile Gly Leu Ala Ile Gln His Asp Ala Ser His
145                 150                 155                 160

Gly Ala Ile Ser Lys Lys Pro Trp Val Asn Ala Phe Phe Ala Tyr Gly
                165                 170                 175

Ile Asp Ala Ile Gly Ser Ser Arg Trp Ile Trp Leu Gln Ser His Ile
            180                 185                 190

Met Arg His His Thr Tyr Thr Asn Gln His Gly Leu Asp Leu Asp Ala
        195                 200                 205

Ala Ser Ala Glu Pro Phe Ile Leu Phe His Ser Tyr Pro Ala Thr Asn
    210                 215                 220

Ala Ser Arg Lys Trp Tyr His Arg Phe Gln Ala Trp Tyr Met Tyr Ile
225                 230                 235                 240

Val Leu Gly Met Tyr Gly Val Ser Met Val Tyr Asn Pro Met Tyr Leu
                245                 250                 255

Phe Thr Met Gln His Asn Asp Thr Ile Pro Glu Ala Thr Ser Leu Arg
            260                 265                 270

Pro Gly Ser Phe Phe Asn Arg Gln Arg Ala Phe Ala Val Ser Leu Arg
        275                 280                 285
```

-continued

```
Leu Leu Phe Ile Phe Arg Asn Ala Phe Leu Pro Trp Tyr Ile Ala Gly
    290                 295                 300

Ala Ser Pro Leu Leu Thr Ile Leu Leu Val Pro Thr Val Thr Gly Ile
305                 310                 315                 320

Phe Leu Thr Phe Val Phe Val Leu Ser His Asn Phe Glu Gly Ala Glu
                325                 330                 335

Arg Thr Pro Glu Lys Asn Cys Lys Ala Lys Arg Ala Lys Glu Gly Lys
            340                 345                 350

Glu Val Arg Asp Val Glu Glu Asp Arg Val Asp Trp Tyr Arg Ala Gln
        355                 360                 365

Ala Glu Thr Ala Ala Thr Tyr Gly Gly Ser Val Gly Met Met Leu Thr
    370                 375                 380

Gly Gly Leu Asn Leu Gln Ile Glu His His Leu Phe Pro Arg Met Ser
385                 390                 395                 400

Ser Trp His Tyr Pro Phe Ile Gln Asp Thr Val Arg Glu Cys Cys Lys
                405                 410                 415

Arg His Gly Val Arg Tyr Thr Tyr Tyr Pro Thr Ile Leu Glu Asn Ile
            420                 425                 430

Met Ser Thr Leu Arg Tyr Met Gln Lys Val Gly Val Ala His Thr Ile
        435                 440                 445

Gln Asp Ala Gln Glu Phe
    450


<210> SEQ ID NO 14
<211> LENGTH: 476
<212> TYPE: PRT
<213> ORGANISM: Thalassiosira pseudonana

<400> SEQUENCE: 14

Met Pro Pro Asn Ala Asp Ile Ser Arg Ile Arg Asn Arg Ile Pro Thr
1               5                   10                  15

Lys Thr Gly Thr Val Ala Ser Ala Asp Asn Asn Asp Pro Ala Thr Gln
            20                  25                  30

Ser Val Arg Thr Leu Lys Ser Leu Lys Gly Asn Glu Val Val Ile Asn
        35                  40                  45

Gly Thr Ile Tyr Asp Ile Ala Asp Phe Val His Pro Gly Gly Glu Val
    50                  55                  60

Val Lys Phe Phe Gly Gly Asn Asp Val Thr Ile Gln Tyr Asn Met Ile
65                  70                  75                  80

His Pro Tyr His Thr Gly Lys His Leu Glu Lys Met Lys Ala Val Gly
                85                  90                  95

Lys Val Val Asp Trp Gln Ser Asp Tyr Lys Phe Asp Thr Pro Phe Glu
            100                 105                 110

Arg Glu Ile Lys Ser Glu Val Phe Lys Ile Val Arg Arg Gly Arg Glu
        115                 120                 125

Phe Gly Thr Thr Gly Tyr Phe Leu Arg Ala Phe Phe Tyr Ile Ala Leu
    130                 135                 140

Phe Phe Thr Met Gln Tyr Thr Phe Ala Thr Cys Thr Thr Phe Thr Thr
145                 150                 155                 160

Tyr Asp His Trp Tyr Gln Ser Gly Val Phe Ile Ala Ile Val Phe Gly
                165                 170                 175

Ile Ser Gln Ala Phe Ile Gly Leu Asn Val Gln His Asp Ala Asn His
            180                 185                 190

Gly Ala Ala Ser Lys Arg Pro Trp Val Asn Asp Leu Leu Gly Phe Gly
        195                 200                 205
```

Thr Asp Leu Ile Gly Ser Asn Lys Trp Asn Trp Met Ala Gln His Trp
210 215 220

Thr His His Ala Tyr Thr Asn His Ser Glu Lys Asp Pro Asp Ser Phe
225 230 235 240

Ser Ser Glu Pro Met Phe Ala Phe Asn Asp Tyr Pro Ile Gly His Pro
245 250 255

Lys Arg Lys Trp Trp His Arg Phe Gln Gly Gly Tyr Phe Leu Phe Met
260 265 270

Leu Gly Leu Tyr Trp Leu Pro Thr Val Phe Asn Pro Gln Phe Ile Asp
275 280 285

Leu Arg Gln Arg Gly Ala Gln Tyr Val Gly Ile Gln Met Glu Asn Asp
290 295 300

Phe Ile Val Lys Arg Arg Lys Tyr Ala Val Ala Leu Arg Met Met Tyr
305 310 315 320

Ile Tyr Leu Asn Ile Val Ser Pro Phe Met Asn Asn Gly Leu Ser Trp
325 330 335

Ser Thr Phe Gly Ile Ile Met Leu Met Gly Ile Ser Glu Ser Leu Thr
340 345 350

Leu Ser Val Leu Phe Ser Leu Ser His Asn Phe Ile Asn Ser Asp Arg
355 360 365

Asp Pro Thr Ala Asp Phe Lys Lys Thr Gly Glu Gln Val Cys Trp Phe
370 375 380

Lys Ser Gln Val Glu Thr Ser Ser Thr Tyr Gly Gly Phe Ile Ser Gly
385 390 395 400

Cys Leu Thr Gly Gly Leu Asn Phe Gln Val Glu His His Leu Phe Pro
405 410 415

Arg Met Ser Ser Ala Trp Tyr Pro Tyr Ile Ala Pro Thr Val Arg Glu
420 425 430

Val Cys Lys Lys His Gly Met Ser Tyr Ala Tyr Tyr Pro Trp Ile Gly
435 440 445

Gln Asn Leu Val Ser Thr Phe Lys Tyr Met His Arg Ala Gly Ser Gly
450 455 460

Ala Asn Trp Glu Leu Lys Pro Leu Ser Gly Ser Ala
465 470 475

<210> SEQ ID NO 15
<211> LENGTH: 469
<212> TYPE: PRT
<213> ORGANISM: Phaeodactylum tricornutum

<400> SEQUENCE: 15

Met Ala Pro Asp Ala Asp Lys Leu Arg Gln Arg Gln Thr Thr Ala Val
1 5 10 15

Ala Lys His Asn Ala Ala Thr Ile Ser Thr Gln Glu Arg Leu Cys Ser
20 25 30

Leu Ser Ser Leu Lys Gly Glu Glu Val Cys Ile Asp Gly Ile Ile Tyr
35 40 45

Asp Leu Gln Ser Phe Asp His Pro Gly Gly Glu Thr Ile Lys Met Phe
50 55 60

Gly Gly Asn Asp Val Thr Val Gln Tyr Lys Met Ile His Pro Tyr His
65 70 75 80

Thr Glu Lys His Leu Glu Lys Met Lys Arg Val Gly Lys Val Thr Asp
85 90 95

Phe Val Cys Glu Tyr Lys Phe Asp Thr Glu Phe Glu Arg Glu Ile Lys

```
            100                 105                 110

Arg Glu Val Phe Lys Ile Val Arg Arg Gly Lys Asp Phe Gly Thr Leu
        115                 120                 125

Gly Trp Phe Phe Arg Ala Phe Cys Tyr Ile Ala Ile Phe Phe Tyr Leu
    130                 135                 140

Gln Tyr His Trp Val Thr Thr Gly Thr Ser Trp Leu Leu Ala Val Ala
145                 150                 155                 160

Tyr Gly Ile Ser Gln Ala Met Ile Gly Met Asn Val Gln His Asp Ala
                165                 170                 175

Asn His Gly Ala Thr Ser Lys Arg Pro Trp Val Asn Asp Met Leu Gly
            180                 185                 190

Leu Gly Ala Asp Phe Ile Gly Gly Ser Lys Trp Leu Trp Gln Glu Gln
        195                 200                 205

His Trp Thr His His Ala Tyr Thr Asn His Ala Glu Met Asp Pro Asp
    210                 215                 220

Ser Phe Gly Ala Glu Pro Met Leu Leu Phe Asn Asp Tyr Pro Leu Asp
225                 230                 235                 240

His Pro Ala Arg Thr Trp Leu His Arg Phe Gln Ala Phe Phe Tyr Met
                245                 250                 255

Pro Val Leu Ala Gly Tyr Trp Leu Ser Ala Val Phe Asn Pro Gln Ile
            260                 265                 270

Leu Asp Leu Gln Gln Arg Gly Ala Leu Ser Val Gly Ile Arg Leu Asp
        275                 280                 285

Asn Ala Phe Ile His Ser Arg Arg Lys Tyr Ala Val Phe Trp Arg Ala
    290                 295                 300

Val Tyr Ile Ala Val Asn Val Ile Ala Pro Phe Tyr Thr Asn Ser Gly
305                 310                 315                 320

Leu Glu Trp Ser Trp Arg Val Phe Gly Asn Ile Met Leu Met Gly Val
                325                 330                 335

Ala Glu Ser Leu Ala Leu Ala Val Leu Phe Ser Leu Ser His Asn Phe
            340                 345                 350

Glu Ser Ala Asp Arg Asp Pro Thr Ala Pro Leu Lys Lys Thr Gly Glu
        355                 360                 365

Pro Val Asp Trp Phe Lys Thr Gln Val Glu Thr Ser Cys Thr Tyr Gly
    370                 375                 380

Gly Phe Leu Ser Gly Cys Phe Thr Gly Gly Leu Asn Phe Gln Val Glu
385                 390                 395                 400

His His Leu Phe Pro Arg Met Ser Ser Ala Trp Tyr Pro Tyr Ile Ala
                405                 410                 415

Pro Lys Val Arg Glu Ile Cys Ala Lys His Gly Val His Tyr Ala Tyr
            420                 425                 430

Tyr Pro Trp Ile His Gln Asn Phe Leu Ser Thr Val Arg Tyr Met His
        435                 440                 445

Ala Ala Gly Thr Gly Ala Asn Trp Arg Gln Met Ala Arg Glu Asn Pro
    450                 455                 460

Leu Thr Gly Arg Ala
465


<210> SEQ ID NO 16
<211> LENGTH: 449
<212> TYPE: PRT
<213> ORGANISM: Euglena gracilis

<400> SEQUENCE: 16
```

```
Met Ala Leu Ser Leu Thr Thr Glu Gln Leu Leu Glu Arg Pro Asp Leu
1               5                   10                  15

Val Ala Ile Asp Gly Ile Leu Tyr Asp Leu Glu Gly Leu Ala Lys Val
            20                  25                  30

His Pro Gly Gly Asp Leu Ile Leu Ala Ser Gly Ala Ser Asp Ala Ser
        35                  40                  45

Pro Leu Phe Tyr Ser Met His Pro Tyr Val Lys Pro Glu Asn Ser Lys
    50                  55                  60

Leu Leu Gln Gln Phe Val Arg Gly Lys His Asp Arg Thr Ser Lys Asp
65                  70                  75                  80

Ile Val Tyr Thr Tyr Asp Ser Pro Phe Ala Gln Asp Val Lys Arg Thr
                85                  90                  95

Met Arg Glu Val Met Lys Gly Arg Asn Trp Tyr Ala Thr Pro Gly Phe
            100                 105                 110

Trp Leu Arg Thr Val Gly Ile Ile Ala Val Thr Ala Phe Cys Glu Trp
        115                 120                 125

His Trp Ala Thr Thr Gly Met Val Leu Trp Gly Leu Leu Thr Gly Phe
    130                 135                 140

Met His Met Gln Ile Gly Leu Ser Ile Gln His Asp Ala Ser His Gly
145                 150                 155                 160

Ala Ile Ser Lys Lys Pro Trp Val Asn Ala Leu Phe Ala Tyr Gly Ile
                165                 170                 175

Asp Val Ile Gly Ser Ser Arg Trp Ile Trp Leu Gln Ser His Ile Met
            180                 185                 190

Arg His His Thr Tyr Thr Asn Gln His Gly Leu Asp Leu Asp Ala Glu
        195                 200                 205

Ser Ala Glu Pro Phe Leu Val Phe His Asn Tyr Pro Ala Ala Asn Thr
    210                 215                 220

Ala Arg Lys Trp Phe His Arg Phe Gln Ala Trp Tyr Met Tyr Leu Val
225                 230                 235                 240

Leu Gly Ala Tyr Gly Val Ser Leu Val Tyr Asn Pro Leu Tyr Ile Phe
                245                 250                 255

Arg Met Gln His Asn Asp Thr Ile Pro Glu Ser Val Thr Ala Met Arg
            260                 265                 270

Glu Asn Gly Phe Leu Arg Arg Tyr Arg Thr Leu Ala Phe Val Met Arg
        275                 280                 285

Ala Phe Phe Ile Phe Arg Thr Ala Phe Leu Pro Trp Tyr Leu Thr Gly
    290                 295                 300

Thr Ser Leu Leu Ile Thr Ile Pro Leu Val Pro Thr Ala Thr Gly Ala
305                 310                 315                 320

Phe Leu Thr Phe Phe Phe Ile Leu Ser His Asn Phe Asp Gly Ser Glu
                325                 330                 335

Arg Ile Pro Asp Lys Asn Cys Lys Val Lys Arg Ser Glu Lys Asp Val
            340                 345                 350

Glu Ala Asp Gln Ile Asp Trp Tyr Arg Ala Gln Val Glu Thr Ser Ser
        355                 360                 365

Thr Tyr Gly Gly Pro Ile Ala Met Phe Phe Thr Gly Gly Leu Asn Phe
    370                 375                 380

Gln Ile Glu His His Leu Phe Pro Arg Met Ser Ser Trp His Tyr Pro
385                 390                 395                 400

Phe Val Gln Gln Ala Val Arg Glu Cys Cys Glu Arg His Gly Val Arg
                405                 410                 415

Tyr Val Phe Tyr Pro Thr Ile Val Gly Asn Ile Ile Ser Thr Leu Lys
```

```
            420                 425                 430

Tyr Met His Lys Val Gly Val Val His Cys Val Lys Asp Ala Gln Asp
        435                 440                 445

Ser


<210> SEQ ID NO 17
<211> LENGTH: 9472
<212> TYPE: DNA
<213> ORGANISM: Artificial Sequence
<220> FEATURE:
<223> OTHER INFORMATION: plasmid pDMW263

<400> SEQUENCE: 17

catggcatgg atggtacgtc ctgtagaaac cccaacccgt gaaatcaaaa aactcgacgg      60

cctgtgggca ttcagtctgg atcgcgaaaa ctgtggaatt gatcagcgtt ggtgggaaag     120

cgcgttacaa gaaagccggg caattgctgt gccaggcagt tttaacgatc agttcgccga     180

tgcagatatt cgtaattatg cgggcaacgt ctggtatcag cgcgaagtct ttataccgaa     240

aggttgggca ggccagcgta tcgtgctgcg tttcgatgcg gtcactcatt acggcaaagt     300

gtgggtcaat aatcaggaag tgatggagca tcagggcggc tatacgccat ttgaagccga     360

tgtcacgccg tatgttattg ccgggaaaag tgtacgtatc accgtttgtg tgaacaacga     420

actgaactgg cagactatcc cgccgggaat ggtgattacc gacgaaaacg gcaagaaaaa     480

gcagtcttac ttccatgatt tctttaacta tgccgggatc catcgcagcg taatgctcta     540

caccacgccg aacacctggg tggacgatat caccgtggtg acgcatgtcg cgcaagactg     600

taaccacgcg tctgttgact ggcaggtggt ggccaatggt gatgtcagcg ttgaactgcg     660

tgatgcggat caacaggtgg ttgcaactgg acaaggcact agcgggactt tgcaagtggt     720

gaatccgcac ctctggcaac cgggtgaagg ttatctctat gaactgtgcg tcacagccaa     780

aagccagaca gagtgtgata tctacccgct tcgcgtcggc atccggtcag tggcagtgaa     840

gggcgaacag ttcctgatta accacaaacc gttctacttt actggctttg gtcgtcatga     900

agatgcggac ttacgtggca aaggattcga taacgtgctg atggtgcacg accacgcatt     960

aatggactgg attggggcca actcctaccg tacctcgcat tacccttacg ctgaagagat    1020

gctcgactgg gcagatgaac atggcatcgt ggtgattgat gaaactgctg ctgtcggctt    1080

taacctctct ttaggcattg gtttcgaagc gggcaacaag ccgaaagaac tgtacagcga    1140

agaggcagtc aacggggaaa ctcagcaagc gcacttacag gcgattaaag agctgatagc    1200

gcgtgacaaa aaccacccaa gcgtggtgat gtggagtatt gccaacgaac cggatacccg    1260

tccgcaagtg cacgggaata tttcgccact ggcggaagca acgcgtaaac tcgacccgac    1320

gcgtccgatc acctgcgtca atgtaatgtt ctgcgacgct cacaccgata ccatcagcga    1380

tctctttgat gtgctgtgcc tgaaccgtta ttacggatgg tatgtccaaa gcggcgattt    1440

ggaaacggca gagaaggtac tggaaaaaga acttctggcc tggcaggaga aactgcatca    1500

gccgattatc atcaccgaat acggcgtgga tacgttagcc gggctgcact caatgtacac    1560

cgacatgtgg agtgaagagt atcagtgtgc atggctggat atgtatcacc gcgtctttga    1620

tcgcgtcagc gccgtcgtcg gtgaacaggt atggaatttc gccgattttg cgacctcgca    1680

aggcatattg cgcgttggcg gtaacaagaa agggatcttc actcgcgacc gcaaaccgaa    1740

gtcggcggct tttctgctgc aaaaacgctg gactggcatg aacttcggtg aaaaaccgca    1800

gcagggaggc aaacaatgat taattaacta gagcggccgc caccgcggcc cgagattccg    1860
```

-continued

```
gcctcttcgg ccgccaagcg acccgggtgg acgtctagag gtacctagca attaacagat   1920
agtttgccgg tgataattct cttaacctcc cacactcctt tgacataacg atttatgtaa   1980
cgaaactgaa atttgaccag atattgtgtc cgcggtggag ctccagcttt tgttcccttt   2040
agtgagggtt aatttcgagc ttggcgtaat catggtcata gctgtttcct gtgtgaaatt   2100
gttatccgct cacaattcca cacaacatac gagccggaag cataaagtgt aaagcctggg   2160
gtgcctaatg agtgagctaa ctcacattaa ttgcgttgcg ctcactgccc gctttccagt   2220
cgggaaacct gtcgtgccag ctgcattaat gaatcggcca acgcgcgggg agaggcggtt   2280
tgcgtattgg gcgctcttcc gcttcctcgc tcactgactc gctgcgctcg gtcgttcggc   2340
tgcggcgagc ggtatcagct cactcaaagg cggtaatacg gttatccaca gaatcagggg   2400
ataacgcagg aaagaacatg tgagcaaaag gccagcaaaa ggccaggaac cgtaaaaagg   2460
ccgcgttgct ggcgtttttc cataggctcc gcccccctga cgagcatcac aaaaatcgac   2520
gctcaagtca gaggtggcga aacccgacag gactataaag ataccaggcg tttccccctg   2580
gaagctccct cgtgcgctct cctgttccga ccctgccgct taccggatac ctgtccgcct   2640
ttctcccttc gggaagcgtg gcgctttctc atagctcacg ctgtaggtat ctcagttcgg   2700
tgtaggtcgt tcgctccaag ctgggctgtg tgcacgaacc ccccgttcag cccgaccgct   2760
gcgccttatc cggtaactat cgtcttgagt ccaacccggt aagacacgac ttatcgccac   2820
tggcagcagc cactggtaac aggattagca gagcgaggta tgtaggcggt gctacagagt   2880
tcttgaagtg gtggcctaac tacggctaca ctagaaggac agtatttggt atctgcgctc   2940
tgctgaagcc agttaccttc ggaaaaagag ttggtagctc ttgatccggc aaacaaacca   3000
ccgctggtag cggtggtttt tttgtttgca agcagcagat tacgcgcaga aaaaaaggat   3060
ctcaagaaga tcctttgatc ttttctacgg ggtctgacgc tcagtggaac gaaaactcac   3120
gttaagggat tttggtcatg agattatcaa aaaggatctt cacctagatc cttttaaatt   3180
aaaaatgaag ttttaaatca atctaaagta tatatgagta aacttggtct gacagttacc   3240
aatgcttaat cagtgaggca cctatctcag cgatctgtct atttcgttca tccatagttg   3300
cctgactccc cgtcgtgtag ataactacga tacgggaggg cttaccatct ggccccagtg   3360
ctgcaatgat accgcgagac ccacgctcac cggctccaga tttatcagca ataaaccagc   3420
cagccggaag ggccgagcgc agaagtggtc ctgcaacttt atccgcctcc atccagtcta   3480
ttaattgttg ccgggaagct agagtaagta gttcgccagt taatagtttg cgcaacgttg   3540
ttgccattgc tacaggcatc gtggtgtcac gctcgtcgtt tggtatggct tcattcagct   3600
ccggttccca acgatcaagg cgagttacat gatcccccat gttgtgcaaa aaagcggtta   3660
gctccttcgg tcctccgatc gttgtcagaa gtaagttggc cgcagtgtta tcactcatgg   3720
ttatggcagc actgcataat tctcttactg tcatgccatc cgtaagatgc ttttctgtga   3780
ctggtgagta ctcaaccaag tcattctgag aatagtgtat gcggcgaccg agttgctctt   3840
gcccggcgtc aatacgggat aataccgcgc cacatagcag aactttaaaa gtgctcatca   3900
ttggaaaacg ttcttcgggg cgaaaactct caaggatctt accgctgttg agatccagtt   3960
cgatgtaacc cactcgtgca cccaactgat cttcagcatc ttttactttc accagcgttt   4020
ctgggtgagc aaaaacagga aggcaaaatg ccgcaaaaaa gggaataagg gcgacacgga   4080
aatgttgaat actcatactc ttcctttttc aatattattg aagcatttat cagggttatt   4140
gtctcatgag cggatacata tttgaatgta tttagaaaaa taaacaaata ggggttccgc   4200
gcacatttcc ccgaaaagtg ccacctgacg cgccctgtag cggcgcatta agcgcggcgg   4260
```

```
gtgtggtggt tacgcgcagc gtgaccgcta cacttgccag cgccctagcg cccgctcctt   4320
tcgctttctt cccttccttt ctcgccacgt tcgccggctt tccccgtcaa gctctaaatc   4380
gggggctccc tttagggttc cgatttagtg ctttacggca cctcgacccc aaaaaacttg   4440
attagggtga tggttcacgt agtgggccat cgccctgata gacggttttt cgccctttga   4500
cgttggagtc cacgttcttt aatagtggac tcttgttcca aactggaaca acactcaacc   4560
ctatctcggt ctattctttt gatttataag ggattttgcc gatttcggcc tattggttaa   4620
aaaatgagct gatttaacaa aaatttaacg cgaattttaa caaaatatta acgcttacaa   4680
tttccattcg ccattcaggc tgcgcaactg ttgggaaggg cgatcggtgc gggcctcttc   4740
gctattacgc cagctggcga aagggggatg tgctgcaagg cgattaagtt gggtaacgcc   4800
agggttttcc cagtcacgac gttgtaaaac gacggccagt gaattgtaat acgactcact   4860
atagggcgaa ttgggtaccg ggccccccct cgaggtcgat ggtgtcgata agcttgatat   4920
cgaattcatg tcacacaaac cgatcttcgc ctcaaggaaa cctaattcta catccgagag   4980
actgccgaga tccagtctac actgattaat ttcgggcca ataatttaaa aaaatcgtgt   5040
tatataatat tatatgtatt atatatatac atcatgatga tactgacagt catgtcccat   5100
tgctaaatag acagactcca tctgccgcct ccaactgatg ttctcaatat ttaaggggtc   5160
atctcgcatt gtttaataat aaacagactc catctaccgc ctccaaatga tgttctcaaa   5220
atatattgta tgaacttatt tttattactt agtattatta gacaacttac ttgctttatg   5280
aaaaacactt cctatttagg aaacaattta taatggcagt tcgttcattt aacaatttat   5340
gtagaataaa tgttataaat gcgtatggga aatcttaaat atggatagca taaatgatat   5400
ctgcattgcc taattcgaaa tcaacagcaa cgaaaaaaat cccttgtaca acataaatag   5460
tcatcgagaa atatcaacta tcaaagaaca gctattcaca cgttactatt gagattatta   5520
ttggacgaga atcacacact caactgtctt tctctcttct agaaatacag gtacaagtat   5580
gtactattct cattgttcat acttctagtc atttcatccc acatattcct tggatttctc   5640
tccaatgaat gacattctat cttgcaaatt caacaattat aataagatat accaaagtag   5700
cggtatagtg gcaatcaaaa agcttctctg gtgtgcttct cgtatttatt tttattctaa   5760
tgatccatta aaggtatata tttatttctt gttatataat ccttttgttt attacatggg   5820
ctggatacat aaaggtattt tgatttaatt ttttgcttaa attcaatccc ccctcgttca   5880
gtgtcaactg taatggtagg aaattaccat acttttgaag aagcaaaaaa aatgaaagaa   5940
aaaaaaaatc gtatttccag gttagacgtt ccgcagaatc tagaatgcgg tatgcggtac   6000
attgttcttc gaacgtaaaa gttgcgctcc ctgagatatt gtacattttt gcttttacaa   6060
gtacaagtac atcgtacaac tatgtactac tgttgatgca tccacaacag tttgttttgt   6120
tttttttgt ttttttttt tctaatgatt cattaccgct atgtatacct acttgtactt   6180
gtagtaagcc gggttattgg cgttcaatta atcatagact tatgaatctg cacggtgtgc   6240
gctgcgagtt acttttagct tatgcatgct acttgggtgt aatattggga tctgttcgga   6300
aatcaacgga tgctcaaccg atttcgacag taataatttg aatcgaatcg gagcctaaaa   6360
tgaacccgag tatatctcat aaaattctcg gtgagaggtc tgtgactgtc agtacaaggt   6420
gccttcatta tgccctcaac cttaccatac ctcactgaat gtagtgtacc tctaaaaatg   6480
aaatacagtg ccaaaagcca aggcactgag ctcgtctaac ggacttgata tacaaccaat   6540
taaaacaaat gaaaagaaat acagttcttt gtatcatttg taacaattac cctgtacaaa   6600
```

```
ctaaggtatt gaaatcccac aatattccca aagtccaccc ctttccaaat tgtcatgcct   6660
acaactcata taccaagcac taacctacca aacaccacta aaaccccaca aaatatatct   6720
taccgaatat acagtaacaa gctaccacca cactcgttgg gtgcagtcgc cagcttaaag   6780
atatctatcc acatcagcca caactccctt cctttaataa accgactaca cccttggcta   6840
ttgaggttat gagtgaatat actgtagaca agacactttc aagaagactg tttccaaaac   6900
gtaccactgt cctccactac aaacacaccc aatctgcttc ttctagtcaa ggttgctaca   6960
ccggtaaatt ataaatcatc atttcattag cagggcaggg cccttttat agagtcttat   7020
acactagcgg accctgccgg tagaccaacc cgcaggcgcg tcagtttgct ccttccatca   7080
atgcgtcgta gaaacgactt actccttctt gagcagctcc ttgaccttgt tggcaacaag   7140
tctccgacct cggaggtgga ggaagagcct ccgatatcgg cggtagtgat accagcctcg   7200
acggactcct tgacggcagc ctcaacagcg tcaccggcgg gcttcatgtt aagagagaac   7260
ttgagcatca tggcggcaga cagaatggtg gcaatggggt tgaccttctg cttgccgaga   7320
tcgggggcag atccgtgaca gggctcgtac agaccgaacg cctcgttggt gtcgggcaga   7380
gaagccagag aggcggaggg cagcagaccc agagaaccgg ggatgacgga ggcctcgtcg   7440
gagatgatat cgccaaacat gttggtggtg atgatgatac cattcatctt ggagggctgc   7500
ttgatgagga tcatggcggc cgagtcgatc agctggtggt tgagctcgag ctgggggaat   7560
tcgtccttga ggactcgagt gacagtcttt cgccaaagtc gagaggaggc cagcacgttg   7620
gccttgtcaa gagaccacac gggaagaggg gggttgtgct gaagggccag gaaggcggcc   7680
attcgggcaa ttcgctcaac ctcaggaacg gagtaggtct cggtgtcgga agcgacgcca   7740
gatccgtcat cctcctttcg ctctccaaag tagatacctc cgacgagctc tcggacaatg   7800
atgaagtcgg tgccctcaac gtttcggatg ggggagagat cggcgagctt gggcgacagc   7860
agctggcagg gtcgcaggtt ggcgtacagg ttcaggtcct ttcgcagctt gaggagaccc   7920
tgctcgggtc gcacgtcggt tcgtccgtcg ggagtggtcc atacggtgtt ggcagcgcct   7980
ccgacagcac cgagcataat agagtcagcc tttcggcaga tgtcgagagt agcgtcggtg   8040
atgggctcgc cctccttctc aatggcagct cctccaatga gtcggtcctc aaacacaaac   8100
tcggtgccgg aggcctcagc aacagacttg agcaccttga cggcctcggc aatcacctcg   8160
gggccacaga agtcgccgcc gagaagaaca atcttcttgg agtcagtctt ggtcttctta   8220
gtttcgggtt ccattgtgga tgtgtgtggt tgtatgtgtg atgtggtgtg tggagtgaaa   8280
atctgtggct ggcaaacgct cttgtatata tacgcacttt tgcccgtgct atgtggaaga   8340
ctaaacctcc gaagattgtg actcaggtag tgcggtatcg gctagggacc caaaccttgt   8400
cgatgccgat agcgctatcg aacgtacccc agccggccgg gagtatgtcg gaggggacat   8460
acgagatcgt caagggtttg tggccaactg gtaaataaat gatgtcgacg tttaaacagt   8520
gtacgcagat ctactataga ggaacattta aattgccccg gagaagacgg ccaggccgcc   8580
tagatgacaa attcaacaac tcacagctga ctttctgcca ttgccactag gggggggcct   8640
ttttatatgg ccaagccaag ctctccacgt cggttgggct gcacccaaca ataaatgggt   8700
agggttgcac caacaaaggg atgggatggg gggtagaaga tacgaggata acggggctca   8760
atggcacaaa taagaacgaa tactgccatt aagactcgtg atccagcgac tgacaccatt   8820
gcatcatcta agggcctcaa aactacctcg gaactgctgc gctgatctgg acaccacaga   8880
ggttccgagc actttaggtt gcaccaaatg tcccaccagg tgcaggcaga aaacgctgga   8940
acagcgtgta cagtttgtct taacaaaaag tgagggcgct gaggtcgagc agggtggtgt   9000
```

gacttgttat agcctttaga gctgcgaaag cgcgtatgga tttggctcat caggccagat 9060
tgagggtctg tggacacatg tcatgttagt gtacttcaat cgccccctgg atatagcccc 9120
gacaataggc cgtggcctca tttttttgcc ttccgcacat ttccattgct cgatacccac 9180
accttgcttc tcctgcactt gccaacctta atactggttt acattgacca acatcttaca 9240 agcgggggc ttgtctaggg tatatataaa cagtggctct cccaatcggt tgccagtctc 9300
ttttttcctt tctttcccca cagattcgaa atctaaacta cacatcacag aattccgagc 9360
cgtgagtatc cacgacaaga tcagtgtcga gacgacgcgt tttgtgtaat gacacaatcc 9420
gaaagtcgct agcaacacac actctctaca caaactaacc cagctctggt ac 9472

<210> SEQ ID NO 18
<211> LENGTH: 7879
<212> TYPE: DNA
<213> ORGANISM: Artificial Sequence
<220> FEATURE:
<223> OTHER INFORMATION: plasmid pDMW237

<400> SEQUENCE: 18
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120
ggatatttat gtttgacact tgagaatgta cgatacaagc actgtccaag tacaatacta 180
aacatactgt acatactcat actcgtaccc gggcaacggt ttcacttgag tgcagtggct 240
agtgctctta ctcgtacagt gtgcaatact gcgtatcata gtctttgatg tatatcgtat 300
tcattcatgt tagttgcgta cgagccggaa gcataaagtg taaagcctgg ggtgcctaat 360
gagtgagcta actcacatta attgcgttgc gctcactgcc cgctttccag tcgggaaacc 420
tgtcgtgcca gctgcattaa tgaatcggcc aacgcgcggg gagaggcggt ttgcgtattg 480
ggcgctcttc cgcttcctcg ctcactgact cgctgcgctc ggtcgttcgg ctgcggcgag 540
cggtatcagc tcactcaaag gcggtaatac ggttatccac agaatcaggg gataacgcag 600
gaaagaacat gtgagcaaaa ggccagcaaa aggccaggaa ccgtaaaaag gccgcgttgc 660
tggcgttttt ccataggctc cgcccccctg acgagcatca caaaaatcga cgctcaagtc 720
agaggtggcg aaacccgaca ggactataaa gataccaggc gtttccccct ggaagctccc 780
tcgtgcgctc tcctgttccg accctgccgc ttaccggata cctgtccgcc tttctccctt 840
cgggaagcgt ggcgctttct catagctcac gctgtaggta tctcagttcg gtgtaggtcg 900
ttcgctccaa gctgggctgt gtgcacgaac cccccgttca gcccgaccgc tgcgccttat 960
ccggtaacta tcgtcttgag tccaacccgg taagacacga cttatcgcca ctggcagcag 1020
ccactggtaa caggattagc agagcgaggt atgtaggcgg tgctacagag ttcttgaagt 1080
ggtggcctaa ctacggctac actagaagga cagtatttgg tatctgcgct ctgctgaagc 1140
cagttacctt cggaaaaaga gttggtagct cttgatccgg caaacaaacc accgctggta 1200
gcggtggttt ttttgtttgc aagcagcaga ttacgcgcag aaaaaaagga tctcaagaag 1260
atcctttgat cttttctacg gggtctgacg ctcagtggaa cgaaaactca cgttaaggga 1320
ttttggtcat gagattatca aaaaggatct tcacctagat ccttttaaat taaaaatgaa 1380
gttttaaatc aatctaaagt atatatgagt aaacttggtc tgacagttac caatgcttaa 1440
tcagtgaggc acctatctca gcgatctgtc tatttcgttc atccatagtt gcctgactcc 1500
ccgtcgtgta gataactacg atacgggagg gcttaccatc tggccccagt gctgcaatga 1560

```
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cgggggctcc   2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
```

```
aaaggtatat atttatttct tgttatataa tccttttgtt tattacatgg gctggataca   4020
taaaggtatt ttgatttaat tttttgctta aattcaatcc cccctcgttc agtgtcaact   4080
gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg tttttttttg   4320
tttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag gggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgactcag gcgacgacgg aattcctgca gcccatctgc   6060
agaattcagg agagaccggg ttggcggcgt atttgtgtcc caaaaaacag ccccaattgc   6120
cccggagaag acggccaggc cgcctagatg acaaattcaa caactcacag ctgactttct   6180
gccattgcca ctaggggggg gcctttttat atggccaagc caagctctcc acgtcggttg   6240
ggctgcaccc aacaataaat gggtagggtt gcaccaacaa agggatggga tgggggtag    6300
```

aagatacgag gataacgggg ctcaatggca caaataagaa cgaatactgc cattaagact 6360
cgtgatccag cgactgacac cattgcatca tctaagggcc tcaaaactac ctcggaactg 6420
ctgcgctgat ctggacacca cagaggttcc gagcacttta ggttgcacca aatgtcccac 6480
caggtgcagg cagaaaacgc tggaacagcg tgtacagttt gtcttaacaa aaagtgaggg 6540
cgctgaggtc gagcagggtg gtgtgacttg ttatagcctt tagagctgcg aaagcgcgta 6600
tggatttggc tcatcaggcc agattgaggg tctgtggaca catgtcatgt tagtgtactt 6660
caatcgcccc ctggatatag ccccgacaat aggccgtggc ctcatttttt tgccttccgc 6720
acatttccat tgctcggtac ccacaccttg cttctcctgc acttgccaac cttaatactg 6780
gtttacattg accaacatct tacaagcggg gggcttgtct agggtatata taaacagtgg 6840
ctctcccaat cggttgccag tctctttttt cctttctttc cccacagatt cgaaatctaa 6900
actacacatc acacaatgcc tgttactgac gtccttaagc gaaagtccgg tgtcatcgtc 6960
ggcgacgatg tccgagccgt gagtatccac gacaagatca gtgtcgagac gacgcgtttt 7020
gtgtaatgac acaatccgaa agtcgctagc aacacacact ctctacacaa actaacccag 7080
ctctccatgg ctctggccaa cgacgctggc gagcgaatct gggctgccgt caccgatccc 7140
gaaatcctca ttggcacctt ctcctacctg ctcctgaagc ctctcctgcg aaactctggt 7200
ctcgtggacg agaagaaagg agcctaccga acctccatga tctggtacaa cgtcctcctg 7260
gctctcttct ctgccctgtc cttctacgtg actgccaccg ctctcggctg ggactacggt 7320
actggagcct ggctgcgaag acagaccggt gatactcccc agcctctctt tcagtgtccc 7380
tctcctgtct gggactccaa gctgttcacc tggactgcca aggccttcta ctattctaag 7440
tacgtggagt acctcgacac cgcttggctg gtcctcaagg gcaagcgagt gtcctttctg 7500
caggccttcc atcactttgg agctccctgg gacgtctacc tcggcattcg actgcacaac 7560
gagggtgtgt ggatcttcat gttctttaac tcgttcattc acaccatcat gtacacctac 7620
tatggactga ctgccgctgg ctacaagttc aaggccaagc ctctgatcac tgccatgcag 7680
atttgccagt tcgtcggtgg ctttctcctg gtctgggact acatcaacgt tccctgcttc 7740
aactctgaca agggcaagct gttctcctgg gctttcaact acgcctacgt cggatctgtc 7800
tttctcctgt tctgtcactt cttttaccag gacaacctgg ccaccaagaa atccgctaag 7860
gctggtaagc agctttagc 7879

<210> SEQ ID NO 19
<211> LENGTH: 7783
<212> TYPE: DNA
<213> ORGANISM: Artificial Sequence
<220> FEATURE:
<223> OTHER INFORMATION: plasmid pY115

<400> SEQUENCE: 19
catggctctg gccaacgacg ctggcgagcg aatctgggct gccgtcaccg atcccgaaat 60
cctcattggc accttctcct acctgctcct gaagcctctc ctgcgaaact ctggtctcgt 120
ggacgagaag aaaggagcct accgaacctc catgatctgg tacaacgtcc tcctggctct 180
cttctctgcc ctgtccttct acgtgactgc caccgctctc ggctgggact acggtactgg 240
agcctggctg cgaagacaga ccggtgatac tccccagcct ctctttcagt gtccctctcc 300
tgtctgggac tccaagctgt tcacctggac tgccaaggcc ttctactatt ctaagtacgt 360
ggagtacctc gacaccgctt ggctggtcct caagggcaag cgagtgtcct ttctgcaggc 420
cttccatcac tttggagctc cctgggacgt ctacctcggc attcgactgc acaacgaggg 480

```
tgtgtggatc ttcatgttct ttaactcgtt cattcacacc atcatgtaca cctactatgg    540
actgactgcc gctggctaca agttcaaggc caagcctctg atcactgcca tgcagatttg    600
ccagttcgtc ggtggctttc tcctggtctg ggactacatc aacgttccct gcttcaactc    660
tgacaagggc aagctgttct cctgggcttt caactacgcc tacgtcggat ctgtctttct    720
cctgttctgt cacttctttt accaggacaa cctggccacc aagaaatccg ctaaggctgg    780
taagcagctt tagcggccgc aagtgtggat ggggaagtga gtgcccggtt ctgtgtgcac    840
aattggcaat ccaagatgga tggattcaac acagggatat agcgagctac gtggtggtgc    900
gaggatatag caacggatat ttatgtttga cacttgagaa tgtacgatac aagcactgtc    960
caagtacaat actaaacata ctgtacatac tcatactcgt acccgggcaa cggtttcact   1020
tgagtgcagt ggctagtgct cttactcgta cagtgtgcaa tactgcgtat catagtcttt   1080
gatgtatatc gtattcattc atgttagttg cgtacgagcc ggaagcataa agtgtaaagc   1140
ctggggtgcc taatgagtga gctaactcac attaattgcg ttgcgctcac tgcccgcttt   1200
ccagtcggga aacctgtcgt gccagctgca ttaatgaatc ggccaacgcg cggggagagg   1260
cggtttgcgt attgggcgct cttccgcttc ctcgctcact gactcgctgc gctcggtcgt   1320
tcggctgcgg cgagcggtat cagctcactc aaaggcggta atacggttat ccacagaatc   1380
aggggataac gcaggaaaga acatgtgagc aaaaggccag caaaaggcca ggaaccgtaa   1440
aaaggccgcg ttgctggcgt ttttccatag gctccgcccc cctgacgagc atcacaaaaa   1500
tcgacgctca agtcagaggt ggcgaaaccc gacaggacta taaagatacc aggcgtttcc   1560
ccctggaagc tccctcgtgc gctctcctgt tccgaccctg ccgcttaccg gatacctgtc   1620
cgcctttctc ccttcgggaa gcgtggcgct ttctcatagc tcacgctgta ggtatctcag   1680
ttcggtgtag gtcgttcgct ccaagctggg ctgtgtgcac gaaccccccg ttcagcccga   1740
ccgctgcgcc ttatccggta actatcgtct tgagtccaac ccggtaagac acgacttatc   1800
gccactggca gcagccactg gtaacaggat tagcagagcg aggtatgtag gcggtgctac   1860
agagttcttg aagtggtggc ctaactacgg ctacactaga aggacagtat ttggtatctg   1920
cgctctgctg aagccagtta ccttcggaaa aagagttggt agctcttgat ccggcaaaca   1980
aaccaccgct ggtagcggtg gtttttttgt ttgcaagcag cagattacgc gcagaaaaaa   2040
aggatctcaa gaagatcctt tgatcttttc tacggggtct gacgctcagt ggaacgaaaa   2100
ctcacgttaa gggattttgg tcatgagatt atcaaaaagg atcttcacct agatcctttt   2160
aaattaaaaa tgaagtttta aatcaatcta aagtatatat gagtaaactt ggtctgacag   2220
ttaccaatgc ttaatcagtg aggcacctat ctcagcgatc tgtctatttc gttcatccat   2280
agttgcctga ctccccgtcg tgtagataac tacgatacgg gagggcttac catctggccc   2340
cagtgctgca atgataccgc gagacccacg ctcaccggct ccagatttat cagcaataaa   2400
ccagccagcc ggaagggccg agcgcagaag tggtcctgca actttatccg cctccatcca   2460
gtctattaat tgttgccggg aagctagagt aagtagttcg ccagttaata gtttgcgcaa   2520
cgttgttgcc attgctacag gcatcgtggt gtcacgctcg tcgtttggta tggcttcatt   2580
cagctccggt tcccaacgat caaggcgagt tacatgatcc cccatgttgt gcaaaaaagc   2640
ggttagctcc ttcggtcctc cgatcgttgt cagaagtaag ttggccgcag tgttatcact   2700
catggttatg gcagcactgc ataattctct tactgtcatg ccatccgtaa gatgcttttc   2760
tgtgactggt gagtactcaa ccaagtcatt ctgagaatag tgtatgcggc gaccgagttg   2820
```

-continued

```
ctcttgcccg gcgtcaatac gggataatac cgcgccacat agcagaactt taaaagtgct   2880
catcattgga aaacgttctt cggggcgaaa actctcaagg atcttaccgc tgttgagatc   2940
cagttcgatg taacccactc gtgcacccaa ctgatcttca gcatctttta ctttcaccag   3000
cgtttctggg tgagcaaaaa caggaaggca aaatgccgca aaaaagggaa taagggcgac   3060
acggaaatgt tgaatactca tactcttcct ttttcaatat tattgaagca tttatcaggg   3120
ttattgtctc atgagcggat acatatttga atgtatttag aaaaataaac aaataggggt   3180
tccgcgcaca tttccccgaa aagtgccacc tgacgcgccc tgtagcggcg cattaagcgc   3240
ggcgggtgtg gtggttacgc gcagcgtgac cgctacactt gccagcgccc tagcgcccgc   3300
tcctttcgct ttcttccctt cctttctcgc cacgttcgcc ggctttcccc gtcaagctct   3360
aaatcggggg ctccctttag ggttccgatt tagtgcttta cggcacctcg accccaaaaa   3420
acttgattag ggtgatggtt cacgtagtgg gccatcgccc tgatagacgg tttttcgccc   3480
tttgacgttg gagtccacgt tctttaatag tggactcttg ttccaaactg gaacaacact   3540
caaccctatc tcggtctatt cttttgattt ataagggatt ttgccgattt cggcctattg   3600
gttaaaaaat gagctgattt aacaaaaatt taacgcgaat tttaacaaaa tattaacgct   3660
tacaatttcc attcgccatt caggctgcgc aactgttggg aagggcgatc ggtgcgggcc   3720
tcttcgctat tacgccagct ggcgaaaggg ggatgtgctg caaggcgatt aagttgggta   3780
acgccagggt tttcccagtc acgacgttgt aaaacgacgg ccagtgaatt gtaatacgac   3840
tcactatagg gcgaattggg taccgggccc cccctcgagg tcgatggtgt cgataagctt   3900
gatatcgaat tcatgtcaca caaaccgatc ttcgcctcaa ggaaacctaa ttctacatcc   3960
gagagactgc cgagatccag tctacactga ttaattttcg ggccaataat ttaaaaaaat   4020
cgtgttatat aatattatat gtattatata tatacatcat gatgatactg acagtcatgt   4080
cccattgcta aatagacaga ctccatctgc cgcctccaac tgatgttctc aatatttaag   4140
gggtcatctc gcattgttta ataataaaca gactccatct accgcctcca aatgatgttc   4200
tcaaaatata ttgtatgaac ttatttttat tacttagtat tattagacaa cttacttgct   4260
ttatgaaaaa cacttcctat ttaggaaaca atttataatg gcagttcgtt catttaacaa   4320
tttatgtaga ataaatgtta taaatgcgta tgggaaatct taaatatgga tagcataaat   4380
gatatctgca ttgcctaatt cgaaatcaac agcaacgaaa aaaatccctt gtacaacata   4440
aatagtcatc gagaaatatc aactatcaaa gaacagctat tcacacgtta ctattgagat   4500
tattattgga cgagaatcac acactcaact gtctttctct cttctagaaa tacaggtaca   4560
agtatgtact attctcattg ttcatacttc tagtcatttc atcccacata ttccttggat   4620
ttctctccaa tgaatgacat tctatcttgc aaattcaaca attataataa gatataccaa   4680
agtagcggta tagtggcaat caaaaagctt ctctggtgtg cttctcgtat ttattttat   4740
tctaatgatc cattaaaggt atatatttat ttcttgttat ataatccttt tgtttattac   4800
atgggctgga tacataaagg tattttgatt taatttttg cttaaattca atccccctc    4860
gttcagtgtc aactgtaatg gtaggaaatt accatacttt tgaagaagca aaaaaaatga   4920
aagaaaaaaa aaatcgtatt tccaggttag acgttccgca gaatctagaa tgcggtatgc   4980
ggtacattgt tcttcgaacg taaaagttgc gctccctgag atattgtaca tttttgcttt   5040
tacaagtaca agtacatcgt acaactatgt actactgttg atgcatccac aacagtttgt   5100
tttgtttttt tttgtttttt tttttctaa tgattcatta ccgctatgta tacctacttg    5160
tacttgtagt aagccgggtt attggcgttc aattaatcat agacttatga atctgcacgg   5220
```

```
tgtgcgctgc gagttacttt tagcttatgc atgctacttg ggtgtaatat tgggatctgt   5280
tcggaaatca acggatgctc aatcgatttc gacagtaatt aattaagtca tacacaagtc   5340
agctttcttc gagcctcata taagtataag tagttcaacg tattagcact gtacccagca   5400
tctccgtatc gagaaacaca acaacatgcc ccattggaca gatcatgcgg atacacaggt   5460
tgtgcagtat catacatact cgatcagaca ggtcgtctga ccatcataca agctgaacaa   5520
gcgctccata cttgcacgct ctctatatac acagttaaat tacatatcca tagtctaacc   5580
tctaacagtt aatcttctgg taagcctccc agccagcctt ctggtatcgc ttggcctcct   5640
caataggatc tcggttctgg ccgtacagac ctcggccgac aattatgata tccgttccgg   5700
tagacatgac atcctcaaca gttcggtact gctgtccgag agcgtctccc ttgtcgtcaa   5760
gacccacccc gggggtcaga ataagccagt cctcagagtc gcccttaggt cggttctggg   5820
caatgaagcc aaccacaaac tcggggtcgg atcgggcaag ctcaatggtc tgcttggagt   5880
actcgccagt ggccagagag cccttgcaag acagctcggc cagcatgagc agacctctgg   5940
ccagcttctc gttgggagag gggactagga actccttgta ctgggagttc tcgtagtcag   6000
agacgtcctc cttcttctgt tcagagacag tttcctcggc accagctcgc aggccagcaa   6060
tgattccggt tccgggtaca ccgtgggcgt tggtgatatc ggaccactcg gcgattcggt   6120
gacaccggta ctggtgcttg acagtgttgc caatatctgc gaactttctg tcctcgaaca   6180
ggaagaaacc gtgcttaaga gcaagttcct tgagggggag cacagtgccg gcgtaggtga   6240
agtcgtcaat gatgtcgata tgggttttga tcatgcacac ataaggtccg accttatcgg   6300
caagctcaat gagctccttg gtggtggtaa catccagaga agcacacagg ttggttttct   6360
tggctgccac gagcttgagc actcgagcgg caaaggcgga cttgtggacg ttagctcgag   6420
cttcgtagga gggcattttg gtggtgaaga ggagactgaa ataaatttag tctgcagaac   6480
tttttatcgg aaccttatct ggggcagtga agtatatgtt atggtaatag ttacgagtta   6540
gttgaactta tagatagact ggactatacg gctatcggtc caaattagaa agaacgtcaa   6600
tggctctctg ggcgtcgcct ttgccgacaa aaatgtgatc atgatgaaag ccagcaatga   6660
cgttgcagct gatattgttg tcggccaacc gcgccgaaaa cgcagctgtc agacccacag   6720
cctccaacga agaatgtatc gtcaaagtga tccaagcaca ctcatagttg gagtcgtact   6780
ccaaaggcgg caatgacgag tcagacagat actcgtcgac gtttaaacag tgtacgcaga   6840
tctactatag aggaacattt aaattgcccc ggagaagacg gccaggccgc ctagatgaca   6900
aattcaacaa ctcacagctg actttctgcc attgccacta ggggggggcc tttttatatg   6960
gccaagccaa gctctccacg tcggttgggc tgcacccaac aataaatggg tagggttgca   7020
ccaacaaagg gatgggatgg ggggtagaag atacgaggat aacggggctc aatggcacaa   7080
ataagaacga atactgccat taagactcgt gatccagcga ctgacaccat tgcatcatct   7140
aagggcctca aaactacctc ggaactgctg cgctgatctg gacaccacag aggttccgag   7200
cactttaggt tgcaccaaat gtcccaccag gtgcaggcag aaaacgctgg aacagcgtgt   7260
acagtttgtc ttaacaaaaa gtgagggcgc tgaggtcgag cagggtggtg tgacttgtta   7320
tagcctttag agctgcgaaa gcgcgtatgg atttggctca tcaggccaga ttgagggtct   7380
gtggacacat gtcatgttag tgtacttcaa tcgccccctg gatatagccc cgacaatagg   7440
ccgtggcctc attttttgc cttccgcaca tttccattgc tcgataccca caccttgctt   7500
ctcctgcact tgccaacctt aatactggtt tacattgacc aacatcttac aagcgggggg   7560
```

```
cttgtctagg gtatatataa acagtggctc tcccaatcgg ttgccagtct ctttttttcct   7620

ttctttcccc acagattcga aatctaaact acacatcaca gaattccgag ccgtgagtat   7680

ccacgacaag atcagtgtcg agacgacgcg ttttgtgtaa tgacacaatc cgaaagtcgc   7740

tagcaacaca cactctctac acaaactaac ccagctctgg tac                     7783
```

<210> SEQ ID NO 20
<211> LENGTH: 19
<212> TYPE: DNA
<213> ORGANISM: Artificial Sequence
<220> FEATURE:
<223> OTHER INFORMATION: oligonucleotide oYFBA1

<400> SEQUENCE: 20

```
acgcagatct actatagag                                                  19
```

<210> SEQ ID NO 21
<211> LENGTH: 27
<212> TYPE: DNA
<213> ORGANISM: Artificial Sequence
<220> FEATURE:
<223> OTHER INFORMATION: oligonucleotide oYFBA1-6

<400> SEQUENCE: 21

```
agcggccgct ggtaccagag ctgggtt                                         27
```

<210> SEQ ID NO 22
<211> LENGTH: 6992
<212> TYPE: DNA
<213> ORGANISM: Artificial Sequence
<220> FEATURE:
<223> OTHER INFORMATION: plasmid pY158

<400> SEQUENCE: 22

```
ggccgcaagt gtggatgggg aagtgagtgc ccggttctgt gtgcacaatt ggcaatccaa     60

gatggatgga ttcaacacag ggatatagcg agctacgtgg tggtgcgagg atatagcaac    120

ggatatttat gtttgacact tgagaatgta cgatacaagc actgtccaag tacaatacta    180

aacatactgt acatactcat actcgtaccc ggcaacggtt tcacttgagt gcagtggcta    240

gtgctcttac tcgtacagtg tgcaatactg cgtatcatag tctttgatgt atatcgtatt    300

cattcatgtt agttgcgtac gagccggaag cataaagtgt aaagcctggg gtgcctaatg    360

agtgagctaa ctcacattaa ttgcgttgcg ctcactgccc gctttccagt cgggaaacct    420

gtcgtgccag ctgcattaat gaatcggcca acgcgcgggg agaggcggtt tgcgtattgg    480

gcgctcttcc gcttcctcgc tcactgactc gctgcgctcg gtcgttcggc tgcggcgagc    540

ggtatcagct cactcaaagg cggtaatacg gttatccaca gaatcagggg ataacgcagg    600

aaagaacatg tgagcaaaag gccagcaaaa ggccaggaac cgtaaaaagg ccgcgttgct    660

ggcgtttttc cataggctcc gcccccctga cgagcatcac aaaaatcgac gctcaagtca    720

gaggtggcga aacccgacag gactataaag ataccaggcg tttccccctg gaagctccct    780

cgtgcgctct cctgttccga ccctgccgct taccggatac ctgtccgcct ttctcccttc    840

gggaagcgtg gcgctttctc atagctcacg ctgtaggtat ctcagttcgg tgtaggtcgt    900

tcgctccaag ctgggctgtg tgcacgaacc ccccgttcag cccgaccgct gcgccttatc    960

cggtaactat cgtcttgagt ccaacccggt aagacacgac ttatcgccac tggcagcagc   1020

cactggtaac aggattagca gagcgaggta tgtaggcggt gctacagagt tcttgaagtg   1080

gtggcctaac tacggctaca ctagaaggac agtatttggt atctgcgctc tgctgaagcc   1140
```

```
agttaccttc ggaaaaagag ttggtagctc ttgatccggc aaacaaacca ccgctggtag   1200
cggtggtttt tttgtttgca agcagcagat tacgcgcaga aaaaaaggat ctcaagaaga   1260
tcctttgatc ttttctacgg ggtctgacgc tcagtggaac gaaaactcac gttaagggat   1320
tttggtcatg agattatcaa aaaggatctt cacctagatc cttttaaatt aaaaatgaag   1380
ttttaaatca atctaaagta tatatgagta aacttggtct gacagttacc aatgcttaat   1440
cagtgaggca cctatctcag cgatctgtct atttcgttca tccatagttg cctgactccc   1500
cgtcgtgtag ataactacga tacgggaggg cttaccatct ggccccagtg ctgcaatgat   1560
accgcgagac ccacgctcac cggctccaga tttatcagca ataaaccagc cagccggaag   1620
ggccgagcgc agaagtggtc ctgcaacttt atccgcctcc atccagtcta ttaattgttg   1680
ccgggaagct agagtaagta gttcgccagt taatagtttg cgcaacgttg ttgccattgc   1740
tacaggcatc gtggtgtcac gctcgtcgtt tggtatggct tcattcagct ccggttccca   1800
acgatcaagg cgagttacat gatcccccat gttgtgcaaa aaagcggtta gctccttcgg   1860
tcctccgatc gttgtcagaa gtaagttggc cgcagtgtta tcactcatgg ttatggcagc   1920
actgcataat tctcttactg tcatgccatc cgtaagatgc ttttctgtga ctggtgagta   1980
ctcaaccaag tcattctgag aatagtgtat gcggcgaccg agttgctctt gcccggcgtc   2040
aatacgggat aataccgcgc cacatagcag aactttaaaa gtgctcatca ttggaaaacg   2100
ttcttcgggg cgaaaactct caaggatctt accgctgttg agatccagtt cgatgtaacc   2160
cactcgtgca cccaactgat cttcagcatc ttttactttc accagcgttt ctgggtgagc   2220
aaaaacagga aggcaaaatg ccgcaaaaaa gggaataagg gcgacacgga aatgttgaat   2280
actcatactc ttcctttttc aatattattg aagcatttat cagggttatt gtctcatgag   2340
cggatacata tttgaatgta tttagaaaaa taaacaaata ggggttccgc gcacatttcc   2400
ccgaaaagtg ccacctgacg cgccctgtag cggcgcatta agcgcggcgg gtgtggtggt   2460
tacgcgcagc gtgaccgcta cacttgccag cgccctagcg cccgctcctt tcgctttctt   2520
cccttccttt ctcgccacgt tcgccggctt tccccgtcaa gctctaaatc gggggctccc   2580
tttagggttc cgatttagtg ctttacggca cctcgacccc aaaaaacttg attagggtga   2640
tggttcacgt agtgggccat cgccctgata gacggttttt cgccctttga cgttggagtc   2700
cacgttcttt aatagtggac tcttgttcca aactggaaca acactcaacc ctatctcggt   2760
ctattctttt gatttataag ggattttgcc gatttcggcc tattggttaa aaaatgagct   2820
gatttaacaa aaatttaacg cgaattttaa caaaatatta acgcttacaa tttccattcg   2880
ccattcaggc tgcgcaactg ttgggaaggg cgatcggtgc gggcctcttc gctattacgc   2940
cagctggcga aagggggatg tgctgcaagg cgattaagtt gggtaacgcc agggttttcc   3000
cagtcacgac gttgtaaaac gacggccagt gaattgtaat acgactcact atagggcgaa   3060
ttgggtaccg ggccccccct cgaggtcgat ggtgtcgata agcttgatat cgaattcatg   3120
tcacacaaac cgatcttcgc ctcaaggaaa cctaattcta catccgagag actgccgaga   3180
tccagtctac actgattaat tttcgggcca ataatttaaa aaaatcgtgt tatataatat   3240
tatatgtatt atatatatac atcatgatga tactgacagt catgtcccat tgctaaatag   3300
acagactcca tctgccgcct ccaactgatg ttctcaatat ttaaggggtc atctcgcatt   3360
gtttaataat aaacagactc catctaccgc ctccaaatga tgttctcaaa atatattgta   3420
tgaacttatt tttattactt agtattatta gacaacttac ttgctttatg aaaaacactt   3480
```

```
cctatttagg aaacaattta taatggcagt tcgttcattt aacaatttat gtagaataaa   3540
tgttataaat gcgtatggga aatcttaaat atggatagca taaatgatat ctgcattgcc   3600
taattcgaaa tcaacagcaa cgaaaaaaat cccttgtaca acataaatag tcatcgagaa   3660
atatcaacta tcaaagaaca gctattcaca cgttactatt gagattatta ttggacgaga   3720
atcacacact caactgtctt tctctcttct agaaatacag gtacaagtat gtactattct   3780
cattgttcat acttctagtc atttcatccc acatattcct tggatttctc tccaatgaat   3840
gacattctat cttgcaaatt caacaattat aataagatat accaaagtag cggtatagtg   3900
gcaatcaaaa agcttctctg gtgtgcttct cgtatttatt tttattctaa tgatccatta   3960
aaggtatata tttatttctt gttatataat ccttttgttt attacatggg ctggatacat   4020
aaaggtattt tgatttaatt ttttgcttaa attcaatccc ccctcgttca gtgtcaactg   4080
taatggtagg aaattaccat acttttgaag aagcaaaaaa aatgaaagaa aaaaaaaatc   4140
gtatttccag gttagacgtt ccgcagaatc tagaatgcgg tatgcggtac attgttcttc   4200
gaacgtaaaa gttgcgctcc ctgagatatt gtacattttt gcttttacaa gtacaagtac   4260
atcgtacaac tatgtactac tgttgatgca tccacaacag tttgttttgt tttttttttgt   4320
ttttttttt tctaatgatt cattaccgct atgtatacct acttgtactt gtagtaagcc   4380
gggttattgg cgttcaatta atcatagact tatgaatctg cacggtgtgc gctgcgagtt   4440
acttttagct tatgcatgct acttgggtgt aatattggga tctgttcgga aatcaacgga   4500
tgctcaatcg atttcgacag taattaatta agtcatacac aagtcagctt tcttcgagcc   4560
tcatataagt ataagtagtt caacgtatta gcactgtacc cagcatctcc gtatcgagaa   4620
acacaacaac atgccccatt ggacagatca tgcggataca caggttgtgc agtatcatac   4680
atactcgatc agacaggtcg tctgaccatc atacaagctg aacaagcgct ccatacttgc   4740
acgctctcta tatacacagt taaattacat atccatagtc taacctctaa cagttaatct   4800
tctggtaagc ctcccagcca gccttctggt atcgcttggc ctcctcaata ggatctcggt   4860
tctggccgta cagacctcgg ccgacaatta tgatatccgt tccggtagac atgacatcct   4920
caacagttcg gtactgctgt ccgagagcgt ctcccttgtc gtcaagaccc accccggggg   4980
tcagaataag ccagtcctca gagtcgccct taggtcggtt ctgggcaatg aagccaacca   5040
caaactcggg gtcggatcgg gcaagctcaa tggtctgctt ggagtactcg ccagtggcca   5100
gagagccctt gcaagacagc tcggccagca tgagcagacc tctggccagc ttctcgttgg   5160
gagaggggac taggaactcc ttgtactggg agttctcgta gtcagagacg tcctccttct   5220
tctgttcaga gacagtttcc tcggcaccag ctcgcaggcc agcaatgatt ccggttccgg   5280
gtacaccgtg ggcgttggtg atatcggacc actcggcgat tcggtgacac cggtactggt   5340
gcttgacagt gttgccaata tctgcgaact ttctgtcctc gaacaggaag aaaccgtgct   5400
taagagcaag ttccttgagg gggagcacag tgccggcgta ggtgaagtcg tcaatgatgt   5460
cgatatgggt tttgatcatg cacacataag gtccgacctt atcggcaagc tcaatgagct   5520
ccttggtggt ggtaacatcc agagaagcac acaggttggt tttcttggct gccacgagct   5580
tgagcactcg agcggcaaag gcggacttgt ggacgttagc tcgagcttcg taggagggca   5640
ttttggtggt gaagaggaga ctgaaataaa tttagtctgc agaacttttt atcggaacct   5700
tatctggggc agtgaagtat atgttatggt aatagttacg agttagttga acttatagat   5760
agactggact atacggctat cggtccaaat tagaaagaac gtcaatggct ctctgggcgt   5820
cgcctttgcc gacaaaaatg tgatcatgat gaaagccagc aatgacgttg cagctgatat   5880
```

```
tgttgtcggc caaccgcgcc gaaaacgcag ctgtcagacc cacagcctcc aacgaagaat   5940

gtatcgtcaa agtgatccaa gcacactcat agttggagtc gtactccaaa ggcggcaatg   6000

acgagtcaga cagatactcg tcgacgttta aacagtgtac gcagatctac tatagaggaa   6060

catttaaatt gccccggaga agacggccag gccgcctaga tgacaaattc aacaactcac   6120

agctgacttt ctgccattgc cactaggggg gggccttttt atatggccaa gccaagctct   6180

ccacgtcggt tgggctgcac ccaacaataa atgggtaggg ttgcaccaac aaagggatgg   6240

gatggggggt agaagatacg aggataacgg ggctcaatgg cacaaataag aacgaatact   6300

gccattaaga ctcgtgatcc agcgactgac accattgcat catctaaggg cctcaaaact   6360

acctcggaac tgctgcgctg atctggacac cacagaggtt ccgagcactt taggttgcac   6420

caaatgtccc accaggtgca ggcagaaaac gctggaacag cgtgtacagt ttgtcttagc   6480

aaaaagtgaa ggcgctgagg tcgagcaggg tggtgtgact tgttatagcc tttagagctg   6540

cgaaagcgcg tatggatttg gctcatcagg ccagattgag ggtctgtgga cacatgtcat   6600

gttagtgtac ttcaatcgcc ccctggatat agccccgaca ataggccgtg gcctcatttt   6660

tttgccttcc gcacatttcc attgctcgat acccacacct tgcttctcct gcacttgcca   6720

accttaatac tggtttacat tgaccaacat cttacaagcg gggggcttgt ctagggtata   6780

tataaacagt ggctctccca atcggttgcc agtctctttt ttcctttctt tccccacaga   6840

ttcgaaatct aaactacaca tcacagaatt ccgagccgtg agtatccacg acaagatcag   6900

tgtcgagacg acgcgttttg tgtaatgaca caatccgaaa gtcgctagca acacacactc   6960

tctacacaaa ctaacccagc tctggtacca gc                                  6992
```

<210> SEQ ID NO 23
<211> LENGTH: 8707
<212> TYPE: DNA
<213> ORGANISM: Artificial Sequence
<220> FEATURE:
<223> OTHER INFORMATION: plasmid pY159

<400> SEQUENCE: 23

```
ggccgcaagt gtggatgggg aagtgagtgc ccggttctgt gtgcacaatt ggcaatccaa     60

gatggatgga ttcaacacag ggatatagcg agctacgtgg tggtgcgagg atatagcaac    120

ggatatttat gtttgacact tgagaatgta cgatacaagc actgtccaag tacaatacta    180

aacatactgt acatactcat actcgtaccc ggcaacggtt tcacttgagt gcagtggcta    240

gtgctcttac tcgtacagtg tgcaatactg cgtatcatag tctttgatgt atatcgtatt    300

cattcatgtt agttgcgtac gagccggaag cataaagtgt aaagcctggg gtgcctaatg    360

agtgagctaa ctcacattaa ttgcgttgcg ctcactgccc gctttccagt cgggaaacct    420

gtcgtgccag ctgcattaat gaatcggcca acgcgcgggg agaggcggtt tgcgtattgg    480

gcgctcttcc gcttcctcgc tcactgactc gctgcgctcg gtcgttcggc tgcggcgagc    540

ggtatcagct cactcaaagg cggtaatacg gttatccaca gaatcagggg ataacgcagg    600

aaagaacatg tgagcaaaag gccagcaaaa ggccaggaac cgtaaaaagg ccgcgttgct    660

ggcgtttttc cataggctcc gcccccctga cgagcatcac aaaaatcgac gctcaagtca    720

gaggtggcga aacccgacag gactataaag ataccaggcg tttccccctg gaagctccct    780

cgtgcgctct cctgttccga ccctgccgct taccggatac ctgtccgcct ttctcccttc    840

gggaagcgtg gcgctttctc atagctcacg ctgtaggtat ctcagttcgg tgtaggtcgt    900
```

-continued

```
tcgctccaag ctgggctgtg tgcacgaacc ccccgttcag cccgaccgct gcgccttatc    960

cggtaactat cgtcttgagt ccaacccggt aagacacgac ttatcgccac tggcagcagc   1020

cactggtaac aggattagca gagcgaggta tgtaggcggt gctacagagt tcttgaagtg   1080

gtggcctaac tacggctaca ctagaaggac agtatttggt atctgcgctc tgctgaagcc   1140

agttaccttc ggaaaaagag ttggtagctc ttgatccggc aaacaaacca ccgctggtag   1200

cggtggtttt tttgtttgca agcagcagat tacgcgcaga aaaaaaggat ctcaagaaga   1260

tcctttgatc ttttctacgg ggtctgacgc tcagtggaac gaaaactcac gttaagggat   1320

tttggtcatg agattatcaa aaaggatctt cacctagatc cttttaaatt aaaaatgaag   1380

ttttaaatca atctaaagta tatatgagta aacttggtct gacagttacc aatgcttaat   1440

cagtgaggca cctatctcag cgatctgtct atttcgttca tccatagttg cctgactccc   1500

cgtcgtgtag ataactacga tacgggaggg cttaccatct ggccccagtg ctgcaatgat   1560

accgcgagac ccacgctcac cggctccaga tttatcagca ataaaccagc cagccggaag   1620

ggccgagcgc agaagtggtc ctgcaacttt atccgcctcc atccagtcta ttaattgttg   1680

ccgggaagct agagtaagta gttcgccagt taatagtttg cgcaacgttg ttgccattgc   1740

tacaggcatc gtggtgtcac gctcgtcgtt tggtatggct tcattcagct ccggttccca   1800

acgatcaagg cgagttacat gatcccccat gttgtgcaaa aaagcggtta gctccttcgg   1860

tcctccgatc gttgtcagaa gtaagttggc cgcagtgtta tcactcatgg ttatggcagc   1920

actgcataat tctcttactg tcatgccatc cgtaagatgc ttttctgtga ctggtgagta   1980

ctcaaccaag tcattctgag aatagtgtat gcggcgaccg agttgctctt gcccggcgtc   2040

aatacgggat aataccgcgc cacatagcag aactttaaaa gtgctcatca ttggaaaacg   2100

ttcttcgggg cgaaaactct caaggatctt accgctgttg agatccagtt cgatgtaacc   2160

cactcgtgca cccaactgat cttcagcatc ttttactttc accagcgttt ctgggtgagc   2220

aaaaacagga aggcaaaatg ccgcaaaaaa gggaataagg gcgacacgga aatgttgaat   2280

actcatactc ttcctttttc aatattattg aagcatttat cagggttatt gtctcatgag   2340

cggatacata tttgaatgta tttagaaaaa taaacaaata ggggttccgc gcacatttcc   2400

ccgaaaagtg ccacctgacg cgccctgtag cggcgcatta agcgcggcgg gtgtggtggt   2460

tacgcgcagc gtgaccgcta cacttgccag cgccctagcg cccgctcctt tcgctttctt   2520

cccttccttt ctcgccacgt tcgccggctt tccccgtcaa gctctaaatc gggggctccc   2580

tttagggttc cgatttagtg ctttacggca cctcgacccc aaaaaacttg attagggtga   2640

tggttcacgt agtgggccat cgccctgata gacggttttt cgccctttga cgttggagtc   2700

cacgttcttt aatagtggac tcttgttcca aactggaaca acactcaacc ctatctcggt   2760

ctattctttt gatttataag ggattttgcc gatttcggcc tattggttaa aaaatgagct   2820

gatttaacaa aaatttaacg cgaattttaa caaaatatta acgcttacaa tttccattcg   2880

ccattcaggc tgcgcaactg ttgggaaggg cgatcggtgc gggcctcttc gctattacgc   2940

cagctggcga aagggggatg tgctgcaagg cgattaagtt gggtaacgcc agggttttcc   3000

cagtcacgac gttgtaaaac gacggccagt gaattgtaat acgactcact atagggcgaa   3060

ttgggtaccg ggccccccct cgaggtcgat ggtgtcgata agcttgatat cgaattcatg   3120

tcacacaaac cgatcttcgc ctcaaggaaa cctaattcta catccgagag actgccgaga   3180

tccagtctac actgattaat tttcgggcca ataatttaaa aaaatcgtgt tatataatat   3240

tatatgtatt atatatatac atcatgatga tactgacagt catgtcccat tgctaaatag   3300
```

acagactcca tctgccgcct ccaactgatg ttctcaatat ttaaggggtc atctcgcatt 3360
gtttaataat aaacagactc catctaccgc ctccaaatga tgttctcaaa atatattgta 3420
tgaacttatt tttattactt agtattatta gacaacttac ttgctttatg aaaaacactt 3480
cctatttagg aaacaattta taatggcagt tcgttcattt aacaatttat gtagaataaa 3540
tgttataaat gcgtatggga aatcttaaat atggatagca taaatgatat ctgcattgcc 3600
taattcgaaa tcaacagcaa cgaaaaaaat cccttgtaca acataaatag tcatcgagaa 3660
atatcaacta tcaaagaaca gctattcaca cgttactatt gagattatta ttggacgaga 3720
atcacacact caactgtctt tctctcttct agaaatacag gtacaagtat gtactattct 3780
cattgttcat acttctagtc atttcatccc acatattcct tggatttctc tccaatgaat 3840
gacattctat cttgcaaatt caacaattat aataagatat accaaagtag cggtatagtg 3900
gcaatcaaaa agcttctctg gtgtgcttct cgtatttatt tttattctaa tgatccatta 3960
aaggtatata tttatttctt gttatataat ccttttgttt attacatggg ctggatacat 4020
aaaggtattt tgatttaatt ttttgcttaa attcaatccc ccctcgttca gtgtcaactg 4080
taatggtagg aaattaccat acttttgaag aagcaaaaaa aatgaaagaa aaaaaaaatc 4140
gtatttccag gttagacgtt ccgcagaatc tagaatgcgg tatgcggtac attgttcttc 4200
gaacgtaaaa gttgcgctcc ctgagatatt gtacattttt gcttttacaa gtacaagtac 4260
atcgtacaac tatgtactac tgttgatgca tccacaacag tttgttttgt tttttttttgt 4320 ttttttttt tctaatgatt cattaccgct atgtatacct acttgtactt gtagtaagcc 4380
gggttattgg cgttcaatta atcatagact tatgaatctg cacggtgtgc gctgcgagtt 4440
acttttagct tatgcatgct acttgggtgt aatattggga tctgttcgga aatcaacgga 4500
tgctcaatcg atttcgacag taattaatta agtcatacac aagtcagctt tcttcgagcc 4560
tcatataagt ataagtagtt caacgtatta gcactgtacc cagcatctcc gtatcgagaa 4620
acacaacaac atgccccatt ggacagatca tgcggataca caggttgtgc agtatcatac 4680
atactcgatc agacaggtcg tctgaccatc atacaagctg aacaagcgct ccatacttgc 4740
acgctctcta tatacacagt taaattacat atccatagtc taacctctaa cagttaatct 4800
tctggtaagc ctcccagcca gccttctggt atcgcttggc ctcctcaata ggatctcggt 4860
tctggccgta cagacctcgg ccgacaatta tgatatccgt tccggtagac atgacatcct 4920
caacagttcg gtactgctgt ccgagagcgt ctcccttgtc gtcaagaccc accccggggg 4980
tcagaataag ccagtcctca gagtcgccct taggtcggtt ctgggcaatg aagccaacca 5040
caaactcggg gtcggatcgg gcaagctcaa tggtctgctt ggagtactcg ccagtggcca 5100
gagagccctt gcaagacagc tcggccagca tgagcagacc tctggccagc ttctcgttgg 5160
gagaggggac taggaactcc ttgtactggg agttctcgta gtcagagacg tcctccttct 5220
tctgttcaga gacagtttcc tcggcaccag ctcgcaggcc agcaatgatt ccggttccgg 5280
gtacaccgtg ggcgttggtg atatcggacc actcggcgat tcggtgacac cggtactggt 5340
gcttgacagt gttgccaata tctgcgaact ttctgtcctc gaacaggaag aaaccgtgct 5400
taagagcaag ttccttgagg gggagcacag tgccggcgta ggtgaagtcg tcaatgatgt 5460
cgatatgggt tttgatcatg cacacataag gtccgacctt atcggcaagc tcaatgagct 5520
ccttggtggt ggtaacatcc agagaagcac acaggttggt tttcttggct gccacgagct 5580
tgagcactcg agcggcaaag gcggacttgt ggacgttagc tcgagcttcg taggagggca 5640

```
ttttggtggt gaagaggaga ctgaaataaa tttagtctgc agaacttttt atcggaacct   5700
tatctggggc agtgaagtat atgttatggt aatagttacg agttagttga acttatagat   5760
agactggact atacggctat cggtccaaat tagaaagaac gtcaatggct ctctgggcgt   5820
cgcctttgcc gacaaaaatg tgatcatgat gaaagccagc aatgacgttg cagctgatat   5880
tgttgtcggc caaccgcgcc gaaaacgcag ctgtcagacc cacagcctcc aacgaagaat   5940
gtatcgtcaa agtgatccaa gcacactcat agttggagtc gtactccaaa ggcggcaatg   6000
acgagtcaga cagatactcg tcgacgttta aacagtgtac gcagatctac tatagaggaa   6060
catttaaatt gccccggaga agacggccag gccgcctaga tgacaaattc aacaactcac   6120
agctgacttt ctgccattgc cactaggggg gggccttttt atatggccaa gccaagctct   6180
ccacgtcggt tgggctgcac ccaacaataa atgggtaggg ttgcaccaac aaagggatgg   6240
gatgggggt agaagatacg aggataacgg ggctcaatgg cacaaataag aacgaatact   6300
gccattaaga ctcgtgatcc agcgactgac accattgcat catctaaggg cctcaaaact   6360
acctcggaac tgctgcgctg atctggacac cacagaggtt ccgagcactt taggttgcac   6420
caaatgtccc accaggtgca ggcagaaaac gctggaacag cgtgtacagt ttgtcttagc   6480
aaaaagtgaa ggcgctgagg tcgagcaggg tggtgtgact tgttatagcc tttagagctg   6540
cgaaagcgcg tatggatttg gctcatcagg ccagattgag ggtctgtgga cacatgtcat   6600
gttagtgtac ttcaatcgcc ccctggatat agccccgaca ataggccgtg gcctcatttt   6660
tttgccttcc gcacatttcc attgctcgat acccacacct tgcttctcct gcacttgcca   6720
accttaatac tggtttacat tgaccaacat cttacaagcg gggggcttgt ctagggtata   6780
tataaacagt ggctctccca atcggttgcc agtctctttt ttcctttctt tccccacaga   6840
ttcgaaatct aaactacaca tcacagaatt ccgagccgtg agtatccacg acaagatcag   6900
tgtcgagacg acgcgttttg tgtaatgaca caatccgaaa gtcgctagca acacacactc   6960
tctacacaaa ctaacccagc tctggtacca gcggccatca caagtttgta caaaaaagct   7020
gaacgagaaa cgtaaaatga tataaatatc aatatattaa attagatttt gcataaaaaa   7080
cagactacat aatactgtaa aacacaacat atccagtcat attggcggcc gcattaggca   7140
ccccaggctt tacactttat gcttccggct cgtataatgt gtggattttg agttaggatc   7200
cgtcgagatt ttcaggagct aaggaagcta aaatggagaa aaaaatcact ggatatacca   7260
ccgttgatat atcccaatgg catcgtaaag aacattttga ggcatttcag tcagttgctc   7320
aatgtaccta taaccagacc gttcagctgg atattacggc ctttttaaag accgtaaaga   7380
aaaataagca caagttttat ccggccttta ttcacattct tgcccgcctg atgaatgctc   7440
atccggaatt ccgtatggca atgaaagacg gtgagctggt gatatgggat agtgttcacc   7500
cttgttacac cgttttccat gagcaaactg aaacgttttc atcgctctgg agtgaatacc   7560
acgacgattt ccggcagttt ctacacatat attcgcaaga tgtggcgtgt tacggtgaaa   7620
acctggccta tttccctaaa gggtttattg agaatatgtt tttcgtctca gccaatccct   7680
gggtgagttt caccagtttt gatttaaacg tggccaatat ggacaacttc ttcgcccccg   7740
ttttcaccat gggcaaatat tatacgcaag gcgacaaggt gctgatgccg ctggcgattc   7800
aggttcatca tgccgtttgt gatggcttcc atgtcggcag aatgcttaat gaattacaac   7860
agtactgcga tgagtggcag ggcggggcgt aaacgcgtgg atccggctta ctaaaagcca   7920
gataacagta tgcgtatttg cgcgctgatt tttgcggtat aagaatatat actgatatgt   7980
atacccgaag tatgtcaaaa agaggtatgc tatgaagcag cgtattacag tgacagttga   8040
```

```
cagcgacagc tatcagttgc tcaaggcata tatgatgtca atatctccgg tctggtaagc   8100
acaaccatgc agaatgaagc ccgtcgtctg cgtgccgaac gctggaaagc ggaaaatcag   8160
gaagggatgg ctgaggtcgc ccggtttatt gaaatgaacg gctcttttgc tgacgagaac   8220
aggggctggt gaaatgcagt ttaaggttta cacctataaa agagagagcc gttatcgtct   8280
gtttgtggat gtacagagtg atattattga cacgcccggg cgacggatgg tgatccccct   8340
ggccagtgca cgtctgctgt cagataaagt ctcccgtgaa ctttacccgg tggtgcatat   8400
cggggatgaa agctggcgca tgatgaccac cgatatggcc agtgtgccgg tctccgttat   8460
cggggaagaa gtggctgatc tcagccaccg cgaaaatgac atcaaaaacg ccattaacct   8520
gatgttctgg ggaatataaa tgtcaggctc ccttatacac agccagtctg caggtcgacc   8580
atagtgactg gatatgttgt gttttacagc attatgtagt ctgtttttta tgcaaaatct   8640
aatttaatat attgatattt atatcatttt acgtttctcg ttcagctttc ttgtacaaag   8700
tggtgat                                                             8707
```

```
<210> SEQ ID NO 24
<211> LENGTH: 8827
<212> TYPE: DNA
<213> ORGANISM: Artificial Sequence
<220> FEATURE:
<223> OTHER INFORMATION: plasmid pY169

<400> SEQUENCE: 24

cttgtacaaa gtggtgatgg ccgcaagtgt ggatggggaa gtgagtgccc ggttctgtgt     60
gcacaattgg caatccaaga tggatggatt caacacaggg atatagcgag ctacgtggtg    120
gtgcgaggat atagcaacgg atatttatgt ttgacacttg agaatgtacg atacaagcac    180
tgtccaagta caatactaaa catactgtac atactcatac tcgtacccgg caacggtttc    240
acttgagtgc agtggctagt gctcttactc gtacagtgtg caatactgcg tatcatagtc    300
tttgatgtat atcgtattca ttcatgttag ttgcgtacga gccggaagca taaagtgtaa    360
agcctggggt gcctaatgag tgagctaact cacattaatt gcgttgcgct cactgcccgc    420
tttccagtcg ggaaacctgt cgtgccagct gcattaatga atcggccaac gcgcggggag    480
aggcggtttg cgtattgggc gctcttccgc ttcctcgctc actgactcgc tgcgctcggt    540
cgttcggctg cggcgagcgg tatcagctca ctcaaaggcg gtaatacggt tatccacaga    600
atcaggggat aacgcaggaa agaacatgtg agcaaaaggc cagcaaaagg ccaggaaccg    660
taaaaaggcc gcgttgctgg cgtttttcca taggctccgc ccccctgacg agcatcacaa    720
aaatcgacgc tcaagtcaga ggtggcgaaa cccgacagga ctataaagat accaggcgtt    780
tccccctgga agctccctcg tgcgctctcc tgttccgacc ctgccgctta ccggatacct    840
gtccgccttt ctcccttcgg gaagcgtggc gctttctcat agctcacgct gtaggtatct    900
cagttcggtg taggtcgttc gctccaagct gggctgtgtg cacgaacccc ccgttcagcc    960
cgaccgctgc gccttatccg gtaactatcg tcttgagtcc aacccggtaa gacacgactt   1020
atcgccactg gcagcagcca ctggtaacag gattagcaga gcgaggtatg taggcggtgc   1080
tacagagttc ttgaagtggt ggcctaacta cggctacact agaaggacag tatttggtat   1140
ctgcgctctg ctgaagccag ttaccttcgg aaaaagagtt ggtagctctt gatccggcaa   1200
acaaaccacc gctggtagcg gtggtttttt tgtttgcaag cagcagatta cgcgcagaaa   1260
aaaaggatct caagaagatc tttgatcttt tctacggggt ctgacgctc agtggaacga    1320
```

```
aaactcacgt taagggattt tggtcatgag attatcaaaa aggatcttca cctagatcct   1380
tttaaattaa aaatgaagtt ttaaatcaat ctaaagtata tatgagtaaa cttggtctga   1440
cagttaccaa tgcttaatca gtgaggcacc tatctcagcg atctgtctat ttcgttcatc   1500
catagttgcc tgactccccg tcgtgtagat aactacgata cgggagggct taccatctgg   1560
ccccagtgct gcaatgatac cgcgagaccc acgctcaccg gctccagatt tatcagcaat   1620
aaaccagcca gccggaaggg ccgagcgcag aagtggtcct gcaactttat ccgcctccat   1680
ccagtctatt aattgttgcc gggaagctag agtaagtagt tcgccagtta atagtttgcg   1740
caacgttgtt gccattgcta caggcatcgt ggtgtcacgc tcgtcgtttg gtatggcttc   1800
attcagctcc ggttcccaac gatcaaggcg agttacatga tcccccatgt tgtgcaaaaa   1860
agcggttagc tccttcggtc ctccgatcgt tgtcagaagt aagttggccg cagtgttatc   1920
actcatggtt atggcagcac tgcataattc tcttactgtc atgccatccg taagatgctt   1980
ttctgtgact ggtgagtact caaccaagtc attctgagaa tagtgtatgc ggcgaccgag   2040
ttgctcttgc ccggcgtcaa tacgggataa taccgcgcca catagcagaa ctttaaaagt   2100
gctcatcatt ggaaaacgtt cttcggggcg aaaactctca aggatcttac cgctgttgag   2160
atccagttcg atgtaaccca ctcgtgcacc caactgatct tcagcatctt ttactttcac   2220
cagcgtttct gggtgagcaa aaacaggaag gcaaaatgcc gcaaaaaagg gaataagggc   2280
gacacggaaa tgttgaatac tcatactctt cctttttcaa tattattgaa gcatttatca   2340
gggttattgt ctcatgagcg gatacatatt tgaatgtatt tagaaaaata aacaaatagg   2400
ggttccgcgc acatttcccc gaaaagtgcc acctgacgcg ccctgtagcg gcgcattaag   2460
cgcggcgggt gtggtggtta cgcgcagcgt gaccgctaca cttgccagcg ccctagcgcc   2520
cgctcctttc gctttcttcc cttcctttct cgccacgttc gccggctttc cccgtcaagc   2580
tctaaatcgg gggctccctt tagggttccg atttagtgct ttacggcacc tcgaccccaa   2640
aaaacttgat tagggtgatg gttcacgtag tgggccatcg ccctgataga cggtttttcg   2700
ccctttgacg ttggagtcca cgttctttaa tagtggactc ttgttccaaa ctggaacaac   2760
actcaaccct atctcggtct attcttttga tttataaggg attttgccga tttcggccta   2820
ttggttaaaa aatgagctga tttaacaaaa atttaacgcg aattttaaca aaatattaac   2880
gcttacaatt tccattcgcc attcaggctg cgcaactgtt gggaagggcg atcggtgcgg   2940
gcctcttcgc tattacgcca gctggcgaaa gggggatgtg ctgcaaggcg attaagttgg   3000
gtaacgccag ggttttccca gtcacgacgt tgtaaaacga cggccagtga attgtaatac   3060
gactcactat agggcgaatt gggtaccggg ccccccctcg aggtcgatgg tgtcgataag   3120
cttgatatcg aattcatgtc acacaaaccg atcttcgcct caaggaaacc taattctaca   3180
tccgagagac tgccgagatc cagtctacac tgattaattt tcgggccaat aatttaaaaa   3240
aatcgtgtta tataatatta tatgtattat atatatacat catgatgata ctgacagtca   3300
tgtcccattg ctaaatagac agactccatc tgccgcctcc aactgatgtt ctcaatattt   3360
aaggggtcat ctcgcattgt ttaataataa acagactcca tctaccgcct ccaaatgatg   3420
ttctcaaaat atattgtatg aacttatttt tattacttag tattattaga caacttactt   3480
gctttatgaa aaacacttcc tatttaggaa acaatttata atggcagttc gttcatttaa   3540
caatttatgt agaataaatg ttataaatgc gtatgggaaa tcttaaatat ggatagcata   3600
aatgatatct gcattgccta attcgaaatc aacagcaacg aaaaaaatcc cttgtacaac   3660
ataaatagtc atcgagaaat atcaactatc aaagaacagc tattcacacg ttactattga   3720
```

```
gattattatt ggacgagaat cacacactca actgtctttc tctcttctag aaatacaggt   3780
acaagtatgt actattctca ttgttcatac ttctagtcat ttcatcccac atattccttg   3840
gatttctctc caatgaatga cattctatct tgcaaattca acaattataa taagatatac   3900
caaagtagcg gtatagtggc aatcaaaaag cttctctggt gtgcttctcg tatttatttt   3960
tattctaatg atccattaaa ggtatatatt tatttcttgt tatataatcc ttttgtttat   4020
tacatgggct ggatacataa aggtattttg atttaatttt ttgcttaaat tcaatccccc   4080
ctcgttcagt gtcaactgta atggtaggaa attaccatac ttttgaagaa gcaaaaaaaa   4140
tgaaagaaaa aaaaaatcgt atttccaggt tagacgttcc gcagaatcta gaatgcggta   4200
tgcggtacat tgttcttcga acgtaaaagt tgcgctccct gagatattgt acatttttgc   4260
ttttacaagt acaagtacat cgtacaacta tgtactactg ttgatgcatc cacaacagtt   4320
tgttttgttt tttttgttt ttttttttc taatgattca ttaccgctat gtatacctac    4380
ttgtacttgt agtaagccgg gttattggcg ttcaattaat catagactta tgaatctgca   4440
cggtgtgcgc tgcgagttac ttttagctta tgcatgctac ttgggtgtaa tattgggatc   4500
tgttcggaaa tcaacggatg ctcaatcgat ttcgacagta attaattaag tcatacacaa   4560
gtcagctttc ttcgagcctc atataagtat aagtagttca acgtattagc actgtaccca   4620
gcatctccgt atcgagaaac acaacaacat gccccattgg acagatcatg cggatacaca   4680
ggttgtgcag tatcatacat actcgatcag acaggtcgtc tgaccatcat acaagctgaa   4740
caagcgctcc atacttgcac gctctctata tacacagtta aattacatat ccatagtcta   4800
acctctaaca gttaatcttc tggtaagcct cccagccagc cttctggtat cgcttggcct   4860
cctcaatagg atctcggttc tggccgtaca gacctcggcc gacaattatg atatccgttc   4920
cggtagacat gacatcctca acagttcggt actgctgtcc gagagcgtct cccttgtcgt   4980
caagacccac cccgggggtc agaataagcc agtcctcaga gtcgccctta ggtcggttct   5040
gggcaatgaa gccaaccaca aactcggggt cggatcgggc aagctcaatg gtctgcttgg   5100
agtactcgcc agtggccaga gagcccttgc aagacagctc ggccagcatg agcagacctc   5160
tggccagctt ctcgttggga gaggggacta ggaactcctt gtactgggag ttctcgtagt   5220
cagagacgtc ctccttcttc tgttcagaga cagtttcctc ggcaccagct cgcaggccag   5280
caatgattcc ggttccgggt acaccgtggg cgttggtgat atcggaccac tcggcgattc   5340
ggtgacaccg gtactggtgc ttgacagtgt tgccaatatc tgcgaacttt ctgtcctcga   5400
acaggaagaa accgtgctta agagcaagtt ccttgagggg gagcacagtg ccggcgtagg   5460
tgaagtcgtc aatgatgtcg atatgggttt tgatcatgca cacataaggt ccgaccttat   5520
cggcaagctc aatgagctcc ttggtggtgg taacatccag agaagcacac aggttggttt   5580
tcttggctgc cacgagcttg agcactcgag cggcaaaggc ggacttgtgg acgttagctc   5640
gagcttcgta ggagggcatt ttggtggtga agaggagact gaaataaatt tagtctgcag   5700
aactttttat cggaacctta tctggggcag tgaagtatat gttatggtaa tagttacgag   5760
ttagttgaac ttatagatag actggactat acggctatcg gtccaaatta gaaagaacgt   5820
caatggctct ctgggcgtcg cctttgccga caaaaatgtg atcatgatga aagccagcaa   5880
tgacgttgca gctgatattg ttgtcggcca accgcgccga aaacgcagct gtcagaccca   5940
cagcctccaa cgaagaatgt atcgtcaaag tgatccaagc acactcatag ttggagtcgt   6000
actccaaagg cggcaatgac gagtcagaca gatactcgtc gacgtttaaa cagtgtacgc   6060
```

```
agatctacta tagaggaaca tttaaattgc cccggagaag acggccaggc cgcctagatg   6120
acaaattcaa caactcacag ctgactttct gccattgcca ctaggggggg gcctttttat   6180
atggccaagc caagctctcc acgtcggttg ggctgcaccc aacaataaat gggtagggtt   6240
gcaccaacaa agggatggga tggggggtag aagatacgag gataacgggg ctcaatggca   6300
caaataagaa cgaatactgc cattaagact cgtgatccag cgactgacac cattgcatca   6360
tctaagggcc tcaaaactac ctcggaactg ctgcgctgat ctggacacca cagaggttcc   6420
gagcacttta ggttgcacca aatgtcccac caggtgcagg cagaaaacgc tggaacagcg   6480
tgtacagttt gtcttagcaa aaagtgaagg cgctgaggtc gagcagggtg gtgtgacttg   6540
ttatagcctt tagagctgcg aaagcgcgta tggatttggc tcatcaggcc agattgaggg   6600
tctgtggaca catgtcatgt tagtgtactt caatcgcccc ctggatatag ccccgacaat   6660
aggccgtggc ctcatttttt tgccttccgc acatttccat tgctcgatac ccacaccttg   6720
cttctcctgc acttgccaac cttaatactg gtttacattg accaacatct tacaagcggg   6780
gggcttgtct agggtatata taaacagtgg ctctcccaat cggttgccag tctctttttt   6840
cctttctttc cccacagatt cgaaatctaa actacacatc acagaattcc gagccgtgag   6900
tatccacgac aagatcagtg tcgagacgac gcgttttgtg taatgacaca atccgaaagt   6960
cgctagcaac acacactctc tacacaaact aacccagctc tggtaccagc ggccatcaca   7020
agtttgtaca aaaaagttgg atttttttc gggatggcca ccatctcttt gactactgag   7080
caacttttag aacacccaga actggttgca attgatgggg tgttgtacga tctcttcgga   7140
ctggcgaaag tgcatccagg tggcaacctc attgaagccg ccggtgcctc cgacggaacc   7200
gccctgttct actccatgca ccctggagtg aagccagaga attcgaagct gctgcagcaa   7260
tttgcccgag gcaaacacga acgaagctcg aaggacccag tgtacacctt tgacagtccc   7320
ttcgcccagg atgtcaagca gagcgttcgg gaggtcatga aggggcgcaa ctggtacgcc   7380
acgcccggct tttggctgcg gaccgcgctg atcatcgcgt gcactgccat aggcgaatgg   7440
tattggatca ctaccggggc agtgatgtgg ggcatcttca ccgggtactt ccacagccag   7500
attgggttgg cgattcaaca cgatgcctct cacggagcca tcagcaaaaa gccctgggtg   7560
aacgcctttt tcgcctacgg catcgacgcc attggatcct cccgctggat ctggctgcag   7620
tcccacatta tgcgccacca cacctacacc aaccagcatg gcctggacct ggacgctgcc   7680
tcggcggagc cgttcatttt gttccactcc tacccggcaa caaatgcgtc acgaaagtgg   7740
taccatcggt tccaggcgtg gtacatgtac atcgttttgg ggatgtatgg tgtgtcgatg   7800
gtgtacaatc cgatgtactt gttcacgatg cagcacaacg acacaatccc agaggccacc   7860
tctcttagac caggcagctt tttcaaccgg cagcgcgcct tcgccgtttc cctccgccta   7920
ctgttcatct tccgcaacgc cttcctcccc tggtacatcg cgggcgcctc tccgctgctc   7980
accatcctgc tggtgccaac ggtcacaggc atcttcttga catttgtttt tgtgctgtcc   8040
cataactttg aaggcgctga gcggaccccc gaaaagaact gcaaggccaa aagggccaag   8100
gaggggaagg aggtccgcga tgtagaggag gaccgggtgg actggtaccg ggcgcaggcc   8160
gagaccgcgg cgacctacgg gggcagcgtc gggatgatgc tgaccggcgg tttgaacctg   8220
cagatcgagc accacttgtt cccccgcatg tcctcttggc actacccctt catccaagat   8280
acggtgcggg aatgttgcaa gcgccatggc gtgcgctaca catactaccc gaccatcctg   8340
gagaatataa tgtccacgct ccgctacatg cagaaggtgg gcgtggccca cacaattcag   8400
gatgcccagg aattctgagt gagttcgatc cgcatcgacg tctaccattt ttgatgctgt   8460
```

```
ctattcctgt tttcagtcac ctccagcatt ctcatggctg gtgaccactg cccctctaac   8520

ccattgtgac acaccgccaa agactttgcc tctttttttt ccctttcttt tgtcctcggg   8580

gtgctttggc cggtgtttac tcgccttgca gtccccgcaa acgaccgacg tttaagctcc   8640

gttgttgact gggccgctcg taaacccatc tgcaggttga ggctcccatg gagaattgtg   8700

atggctgatt aggaggtggc ggggcataca tgcctcgaca ctcaaagccg ggcggcttct   8760

ggattcgaaa acgcaaatgg gcgctttgga aaaaaaaaaa aaaaaaaaaa aaaaaaaacc   8820

caacttt                                                             8827
```

<210> SEQ ID NO 25
<211> LENGTH: 774
<212> TYPE: DNA
<213> ORGANISM: Euglena gracilis

<400> SEQUENCE: 25

```
atggaggtgg tgaatgaaat agtctcaatt gggcaggaag ttttacccaa agttgattat     60

gcccaactct ggagtgatgc cagtcactgt gaggtgcttt acttgtccat cgcatttgtc    120

atcttgaagt tcactcttgg ccccccttggt ccaaaaggtc agtctcgtat gaagtttgtt   180

ttcaccaatt acaaccttct catgtccatt tattcgttgg gatcattcct ctcaatggca    240

tatgccatgt acaccatcgg tgttatgtct gacaactgcg agaaggcttt tgacaacaac    300

gtcttcagga tcaccacgca gttgttctat ttgagcaagt tcctggagta tattgactcc    360

ttctatttgc cactgatggg caagcctctg acctggttgc aattcttcca tcatttgggg    420

gcaccgatgg atatgtggct gttctataat taccgaaatg aagctgtttg gatttttgtg    480

ctgttgaatg gtttcatcca ctggatcatg tacggttatt attggaccag attgatcaag    540

ctgaagttcc ccatgccaaa atccctgatt acatcaatgc agatcattca attcaatgtt    600

ggtttctaca ttgtctggaa gtacaggaac attccctgtt atcgccaaga tgggatgagg    660

atgtttggct ggttcttcaa ttacttttat gttggcacag tcttgtgttt gttcttgaat    720

ttctatgtgc aaacgtatat cgtcaggaag cacaagggag ccaaaaagat tcag          774
```

<210> SEQ ID NO 26
<211> LENGTH: 1263
<212> TYPE: DNA
<213> ORGANISM: Euglena gracilis

<400> SEQUENCE: 26

```
atgaagtcaa agcgccaagc gcttcccctt acaattgatg gaacaacata tgatgtgtct     60

gcctgggtca atttccaccc tggtggtgcg gaaattatag agaattacca aggaagggat    120

gccactgatg ccttcatggt tatgcactct caagaagcct tcgacaagct caagcgcatg    180

cccaaaatca atcccagttc tgagttgcca ccccaggctg cagtgaatga agctcaagag    240

gatttccgga agctccgaga agagttgatc gcaactggca tgtttgatgc ctcccccctc    300

tggtactcat acaaaatcag caccacactg ggccttggag tgctgggtta tttcctgatg    360

gttcagtatc agatgtattt cattggggca gtgttgcttg ggatgcacta tcaacagatg    420

ggctggcttt ctcatgacat ttgccaccac cagactttca agaaccggaa ctggaacaac    480

ctcgtgggac tggtatttgg caatggtctg caaggttttt ccgtgacatg gtggaaggac    540

agacacaatg cacatcattc ggcaaccaat gttcaagggc acgaccctga tattgacaac    600

ctcccccctct tagcctggtc tgaggatgac gtcacacggg cgtcaccgat ttcccgcaag   660
```

```
ctcattcagt tccagcagta ctatttcttg gtcatctgta tcttgttgcg gttcatttgg    720

tgtttccaga gcgtgttgac cgtgcgcagt ttgaaggaca gagataacca attctatcgc    780

tctcagtata agaaggaggc cattggcctc gccctgcact ggaccttgaa gaccctgttc    840

cacttattct ttatgcccag catcctcaca tcgctgttgg tgtttttcgt ttcggagctg    900

gttggcggct tcggcattgc gatcgtggtg ttcatgaacc actacccact ggagaagatc    960

ggggactcag tctgggatgg ccatggattc tcggttggcc agatccatga gaccatgaac   1020

attcggcgag ggattatcac agattggttt ttcggaggct tgaattacca gattgagcac   1080

catttgtggc cgaccctccc tcgccacaac ctgacagcgg ttagctacca ggtggaacag   1140

ctgtgccaga agcacaacct gccgtatcgg aacccgctgc cccatgaagg gttggtcatc   1200

ctgctgcgct atctggcggt gttcgcccgg atggcggaga agcaacccgc ggggaaggct   1260

cta                                                                 1263
```

<210> SEQ ID NO 27
<211> LENGTH: 30
<212> TYPE: DNA
<213> ORGANISM: Artificial Sequence
<220> FEATURE:
<223> OTHER INFORMATION: Euglena gracilis elongase sense oligonucleotide oEugEL1-1

<400> SEQUENCE: 27

```
agcggccgca ccatggaggt ggtgaatgaa                                      30
```

<210> SEQ ID NO 28
<211> LENGTH: 30
<212> TYPE: DNA
<213> ORGANISM: Artificial Sequence
<220> FEATURE:
<223> OTHER INFORMATION: Euglena gracilis elongase anti-sense oligonucleotide oEugEL1-2

<400> SEQUENCE: 28

```
tgcggccgct cactgaatct tttggctcc                                       30
```

<210> SEQ ID NO 29
<211> LENGTH: 4311
<212> TYPE: DNA
<213> ORGANISM: Artificial Sequence
<220> FEATURE:
<223> OTHER INFORMATION: plasmid pKR906

<400> SEQUENCE: 29

```
agcggccgca ccatggaggt ggtgaatgaa atagtctcaa ttgggcagga agttttaccc     60

aaagttgatt atgcccaact ctggagtgat gccagtcact gtgaggtgct ttacttgtcc    120

atcgcatttg tcatcttgaa gttcactctt ggcccccttg gtccaaaagg tcagtctcgt    180

atgaagtttg ttttcaccaa ttacaacctt ctcatgtcca tttattcgtt gggatcattc    240

ctctcaatgg catatgccat gtacaccatc ggtgttatgt ctgacaactg cgagaaggct    300

tttgacaaca acgtcttcag gatcaccacg cagttgttct atttgagcaa gttcctggag    360

tatattgact ccttctattt gccactgatg ggcaagcctc tgacctggtt gcaattcttc    420

catcatttgg gggcaccgat ggatatgtgg ctgttctata attaccgaaa tgaagctgtt    480

tggatttttg tgctgttgaa tggtttcatc cactggatca tgtacggtta ttattggacc    540

agattgatca agctgaagtt ccccatgcca aaatccctga ttacatcaat gcagatcatt    600

caattcaatg ttggtttcta cattgtctgg aagtacagga acattccctg ttatcgccaa    660
```

```
gatgggatga ggatgtttgg ctggttcttc aattactttt atgttggcac agtcttgtgt    720
ttgttcttga atttctatgt gcaaacgtat atcgtcagga agcacaaggg agccaaaaag    780
attcagtgag cggccgcacc tgaattccag cacactggcg gccgttacta gtggatccga    840
gctcggtacc aagcttgatg catagcttga gtattctaac gcgtcaccta aatagcttgg    900
cgtaatcatg gtcatagctg tttcctgtgt gaaattgtta tccgctcaca attccacaca    960
acatacgagc cggaagcata aagtgtaaag cctggggtgc ctaatgagtg agctaactca   1020
cattaattgc gttgcgctca ctgcccgctt tccagtcggg aaacctgtcg tgccagctgc   1080
attaatgaat cggccaacgc gcggggagag gcggtttgcg tattgggcgc tcttccgctt   1140
cctcgctcac tgactcgctg cgctcggtcg ttcggctgcg gcgagcggta tcagctcact   1200
caaaggcggt aatacggtta tccacagaat caggggataa cgcaggaaag aacatgtgag   1260
caaaaggcca gcaaaagccc aggaaccgta aaaaggccgc gttgctggcg tttttccata   1320
ggctccgccc ccctgacgag catcacaaaa atcgacgctc aagtcagagg tggcgaaacc   1380
cgacaggact ataaagatac caggcgtttc cccctggaag ctccctcgtg cgctctcctg   1440
ttccgaccct gccgcttacc ggatacctgt ccgcctttct cccttcggga agcgtggcgc   1500
tttctcatag ctcacgctgt aggtatctca gttcggtgta ggtcgttcgc tccaagctgg   1560
gctgtgtgca cgaacccccc gttcagcccg accgctgcgc cttatccggt aactatcgtc   1620
ttgagtccaa cccggtaaga cacgacttat cgccactggc agcagccact ggtaacagga   1680
ttagcagagc gaggtatgta ggcggtgcta cagagttctt gaagtggtgg cctaactacg   1740
gctacactag aaggacagta tttggtatct gcgctctgct gaagccagtt accttcggaa   1800
aaagagttgg tagctcttga tccggcaaac aaaccaccgc tggtagcggt ggtttttttg   1860
tttgcaagca gcagattacg cgcagaaaaa aaggatctca agaagatcct ttgatctttt   1920
ctacggggtc tgacgctcag tggaacgaaa actcacgtta agggattttg gtcatgagat   1980
tatcaaaaag gatcttcacc tagatccttt taaattaaaa atgaagtttt agcacgtgtc   2040
agtcctgctc ctcggccacg aagtgcacgc agttgccggc cgggtcgcgc agggcgaact   2100
cccgccccca cggctgctcg ccgatctcgg tcatggccgg cccggaggcg tcccggaagt   2160
tcgtggacac gacctccgac cactcggcgt acagctcgtc caggccgcgc acccacaccc   2220
aggccagggt gttgtccggc accacctggt cctggaccgc gctgatgaac agggtcacgt   2280
cgtcccggac cacaccggcg aagtcgtcct ccacgaagtc ccgggagaac ccgagccggt   2340
cggtccagaa ctcgaccgct ccggcgacgt cgcgcgcggt gagcaccgga acggcactgg   2400
tcaacttggc catggtggcc ctcctcacgt gctattattg aagcatttat cagggttatt   2460
gtctcatgag cggatacata tttgaatgta tttagaaaaa taaacaaata ggggttccgc   2520
gcacatttcc ccgaaaagtg ccacctgtat gcggtgtgaa ataccgcaca gatgcgtaag   2580
gagaaaatac cgcatcagga aattgtaagc gttaataatt cagaagaact cgtcaagaag   2640
gcgatagaag gcgatgcgct gcgaatcggg agcggcgata ccgtaaagca cgaggaagcg   2700
gtcagcccat tcgccgccaa gctcttcagc aatatcacgg gtagccaacg ctatgtcctg   2760
atagcggtcc gccacaccca gccggccaca gtcgatgaat ccagaaaagc ggccattttc   2820
caccatgata ttcggcaagc aggcatcgcc atgggtcacg acgagatcct cgccgtcggg   2880
catgctcgcc ttgagcctgg cgaacagttc ggctggcgcg agcccctgat gctcttcgtc   2940
cagatcatcc tgatcgacaa gaccggcttc catccgagta cgtgctcgct cgatgcgatg   3000
```

```
tttcgcttgg tggtcgaatg ggcaggtagc cggatcaagc gtatgcagcc gccgcattgc   3060

atcagccatg atggatactt tctcggcagg agcaaggtga gatgacagga gatcctgccc   3120

cggcacttcg cccaatagca gccagtccct tcccgcttca gtgacaacgt cgagcacagc   3180

tgcgcaagga acgcccgtcg tggccagcca cgatagccgc gctgcctcgt cttgcagttc   3240

attcagggca ccggacaggt cggtcttgac aaaaagaacc gggcgcccct gcgctgacag   3300

ccggaacacg gcggcatcag agcagccgat tgtctgttgt gcccagtcat agccgaatag   3360

cctctccacc caagcggccg gagaacctgc gtgcaatcca tcttgttcaa tcatgcgaaa   3420

cgatcctcat cctgtctctt gatcagagct tgatcccctg cgccatcaga tccttggcgg   3480

cgagaaagcc atccagttta ctttgcaggg cttcccaacc ttaccagagg gcgccccagc   3540

tggcaattcc ggttcgcttg ctgtccataa aaccgcccag tctagctatc gccatgtaag   3600

cccactgcaa gctacctgct ttctctttgc gcttgcgttt tcccttgtcc agatagccca   3660

gtagctgaca ttcatccggg gtcagcaccg tttctgcgga ctggctttct acgtgaaaag   3720

gatctaggtg aagatccttt ttgataatct catgcctgac atttatattc cccagaacat   3780

caggttaatg gcgtttttga tgtcattttc gcggtggctg agatcagcca cttcttcccc   3840

gataacggag accggcacac tggccatatc ggtggtcatc atgcgccagc tttcatcccc   3900

gatatgcacc accgggtaaa gttcacggga gactttatct gacagcagac gtgcactggc   3960

caggggatc accatccgtc gccccggcgt gtcaataata tcactctgta catccacaaa   4020

cagacgataa cggctctctc ttttataggt gtaaacctta aactgccgta cgtataggct   4080

gcgcaactgt tgggaagggc gatcggtgcg ggcctcttcg ctattacgcc agctggcgaa   4140

aggggatgt gctgcaaggc gattaagttg ggtaacgcca gggttttccc agtcacgacg   4200

ttgtaaaacg acggccagtg aattgtaata cgactcacta tagggcgaat tgggccctct   4260

agatgcatgc tcgagcggcc gccagtgtga tggatatctg cagaattcag g            4311
```

```
<210> SEQ ID NO 30
<211> LENGTH: 7085
<212> TYPE: DNA
<213> ORGANISM: Artificial Sequence
<220> FEATURE:
<223> OTHER INFORMATION: plasmid pKR72

<400> SEQUENCE: 30
```

```
gtacggatcc gtcgacggcg cgcccgatca tccggatata gttcctcctt tcagcaaaaa     60

acccctcaag acccgtttag aggccccaag gggttatgct agttattgct cagcggtggc    120

agcagccaac tcagcttcct ttcgggcttt gttagcagcc ggatcgatcc aagctgtacc    180

tcactattcc tttgccctcg gacgagtgct ggggcgtcgg tttccactat cggcgagtac    240

ttctacacag ccatcggtcc agacggccgc gcttctgcgg gcgatttgtg tacgcccgac    300

agtcccggct ccggatcgga cgattgcgtc gcatcgaccc tgcgcccaag ctgcatcatc    360

gaaattgccg tcaaccaagc tctgatagag ttggtcaaga ccaatgcgga gcatatacgc    420

ccggagccgc ggcgatcctg caagctccgg atgcctccgc tcgaagtagc gcgtctgctg    480

ctccatacaa gccaaccacg gcctccagaa gaagatgttg gcgacctcgt attgggaatc    540

cccgaacatc gcctcgctcc agtcaatgac cgctgttatg cggccattgt ccgtcaggac    600

attgttggag ccgaaatccg cgtgcacgag gtgccggact tcggggcagt cctcggccca    660

aagcatcagc tcatcgagag cctgcgcgac ggacgcactg acggtgtcgt ccatcacagt    720

ttgccagtga tacacatggg gatcagcaat cgcgcatatg aaatcacgcc atgtagtgta    780
```

```
ttgaccgatt ccttgcggtc cgaatgggcc gaacccgctc gtctggctaa gatcggccgc    840
agcgatcgca tccatagcct ccgcgaccgg ctgcagaaca gcgggcagtt cggtttcagg    900
caggtcttgc aacgtgacac cctgtgcacg gcgggagatg caataggtca ggctctcgct    960
gaattcccca atgtcaagca cttccggaat cgggagcgcg gccgatgcaa agtgccgata   1020
aacataacga tctttgtaga aaccatcggc gcagctattt acccgcagga catatccacg   1080
ccctcctaca tcgaagctga aagcacgaga ttcttcgccc tccgagagct gcatcaggtc   1140
ggagacgctg tcgaactttt cgatcagaaa cttctcgaca gacgtcgcgg tgagttcagg   1200
cttttccatg ggtatatctc cttcttaaag ttaaacaaaa ttatttctag agggaaaccg   1260
ttgtggtctc cctatagtga gtcgtattaa tttcgcggga tcgagatcga tccaattcca   1320
atcccacaaa aatctgagct taacagcaca gttgctcctc tcagagcaga atcgggtatt   1380
caacaccctc atatcaacta ctacgttgtg tataacggtc cacatgccgg tatatacgat   1440
gactggggtt gtacaaaggc ggcaacaaac ggcgttcccg gagttgcaca caagaaattt   1500
gccactatta cagaggcaag agcagcagct gacgcgtaca caacaagtca gcaaacagac   1560
aggttgaact tcatccccaa aggagaagct caactcaagc ccaagagctt tgctaaggcc   1620
ctaacaagcc caccaaagca aaaagcccac tggctcacgc taggaaccaa aaggcccagc   1680
agtgatccag ccccaaaaga gatctccttt gccccggaga ttacaatgga cgatttcctc   1740
tatctttacg atctaggaag gaagttcgaa ggtgaaggtg acgacactat gttcaccact   1800
gataatgaga aggttagcct cttcaatttc agaaagaatg ctgacccaca gatggttaga   1860
gaggcctacg cagcaggtct catcaagacg atctacccga gtaacaatct ccaggagatc   1920
aaataccttc ccaagaaggt taaagatgca gtcaaaagat tcaggactaa ttgcatcaag   1980
aacacagaga aagacatatt tctcaagatc agaagtacta ttccagtatg gacgattcaa   2040
ggcttgcttc ataaaccaag gcaagtaata gagattggag tctctaaaaa ggtagttcct   2100
actgaatcta aggccatgca tggagtctaa gattcaaatc gaggatctaa cagaactcgc   2160
cgtgaagact ggcgaacagt tcatacagag tcttttacga ctcaatgaca agaagaaaat   2220
cttcgtcaac atggtggagc acgacactct ggtctactcc aaaaatgtca aagatacagt   2280
ctcagaagac caaagggcta ttgagacttt tcaacaaagg ataatttcgg gaaacctcct   2340
cggattccat tgcccagcta tctgtcactt catcgaaagg acagtagaaa aggaaggtgg   2400
ctcctacaaa tgccatcatt gcgataaagg aaaggctatc attcaagatg cctctgccga   2460
cagtggtccc aaagatggac ccccacccac gaggagcatc gtggaaaaag aagacgttcc   2520
aaccacgtct tcaaagcaag tggattgatg tgacatctcc actgacgtaa gggatgacgc   2580
acaatcccac tatccttcgc aagacccttc ctctatataa ggaagttcat ttcatttgga   2640
gaggacacgc tcgagctcat ttctctatta cttcagccat aacaaaagaa ctcttttctc   2700
ttcttattaa accatgaaaa agcctgaact caccgcgacg tctgtcgaga agtttctgat   2760
cgaaaagttc gacagcgtct ccgacctgat gcagctctcg gagggcgaag aatctcgtgc   2820
tttcagcttc gatgtaggag ggcgtggata tgtcctgcgg gtaaatagct gcgccgatgg   2880
tttctacaaa gatcgttatg tttatcggca ctttgcatcg gccgcgctcc cgattccgga   2940
agtgcttgac attggggaat tcagcgagag cctgacctat tgcatctccc gccgtgcaca   3000
gggtgtcacg ttgcaagacc tgcctgaaac cgaactgccc gctgttctgc agccggtcgc   3060
ggaggccatg gatgcgatcg ctgcggccga tcttagccag acgagcgggt tcggcccatt   3120
```

```
cggaccgcaa ggaatcggtc aatacactac atggcgtgat ttcatatgcg cgattgctga   3180
tccccatgtg tatcactggc aaactgtgat ggacgacacc gtcagtgcgt ccgtcgcgca   3240
ggctctcgat gagctgatgc tttgggccga ggactgcccc gaagtccggc acctcgtgca   3300
cgcggatttc ggctccaaca atgtcctgac ggacaatggc cgcataacag cggtcattga   3360
ctggagcgag gcgatgttcg gggattccca atacgaggtc gccaacatct tcttctggag   3420
gccgtggttg gcttgtatgg agcagcagac gcgctacttc gagcggaggc atccggagct   3480
tgcaggatcg ccgcggctcc gggcgtatat gctccgcatt ggtcttgacc aactctatca   3540
gagcttggtt gacggcaatt tcgatgatgc agcttgggcg cagggtcgat gcgacgcaat   3600
cgtccgatcc ggagccggga ctgtcgggcg tacacaaatc gcccgcagaa gcgcggccgt   3660
ctggaccgat ggctgtgtag aagtactcgc cgatagtgga aaccgacgcc ccagcactcg   3720
tccgagggca aaggaatagt gaggtaccta aagaaggagt gcgtcgaagc agatcgttca   3780
aacatttggc aataaagttt cttaagattg aatcctgttg ccggtcttgc gatgattatc   3840
atataatttc tgttgaatta cgttaagcat gtaataatta acatgtaatg catgacgtta   3900
tttatgagat gggtttttat gattagagtc ccgcaattat acatttaata cgcgatagaa   3960
aacaaaatat agcgcgcaaa ctaggataaa ttatcgcgcg cggtgtcatc tatgttacta   4020
gatcgatgtc gaatcgatca acctgcatta atgaatcggc caacgcgcgg ggagaggcgg   4080
tttgcgtatt gggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
acgctcaagt cagaggtggc gaaacccgac aggactataa agataccagg cgtttccccc   4380
tggaagctcc ctcgtgcgct ctcctgttcc gaccctgccg cttaccggat acctgtccgc   4440
ctttctccct tcgggaagcg tggcgctttc tcaatgctca cgctgtaggt atctcagttc   4500
ggtgtaggtc gttcgctcca agctgggctg tgtgcacgaa ccccccgttc agcccgaccg   4560
ctgcgcctta tccggtaact atcgtcttga gtccaacccg gtaagacacg acttatcgcc   4620
actggcagca gccactggta acaggattag cagagcgagg tatgtaggcg gtgctacaga   4680
gttcttgaag tggtggccta actacggcta cactagaagg acagtatttg gtatctgcgc   4740
tctgctgaag ccagttacct tcggaaaaag agttggtagc tcttgatccg gcaaacaaac   4800
caccgctggt agcggtggtt tttttgtttg caagcagcag attacgcgca gaaaaaaagg   4860
atctcaagaa gatcctttga tcttttctac ggggtctgac gctcagtgga acgaaaactc   4920
acgttaaggg attttggtca tgacattaac ctataaaaat aggcgtatca cgaggccctt   4980
tcgtctcgcg cgtttcggtg atgacggtga aaacctctga cacatgcagc tcccggagac   5040
ggtcacagct tgtctgtaag cggatgccgg gagcagacaa gcccgtcagg gcgcgtcagc   5100
gggtgttggc gggtgtcggg gctggcttaa ctatgcggca tcagagcaga ttgtactgag   5160
agtgcaccat atggacatat tgtcgttaga acgcggctac aattaataca taaccttatg   5220
tatcatacac atacgattta ggtgacacta tagaacggcg cgccaagctt gttgaaacat   5280
ccctgaagtg tctcatttta ttttatttat tctttgctga taaaaaaata aaataaaaga   5340
agctaagcac acggtcaacc attgctctac tgctaaaagg gttatgtgta gtgttttact   5400
gcataaatta tgcagcaaac aagacaactc aaattaaaaa atttcctttg cttgtttttt   5460
tgttgtctct gacttgactt tcttgtggaa gttggttgta taaggattgg gacaccattg   5520
```

```
tccttcttaa tttaatttta ttctttgctg ataaaaaaaa aaatttcata tagtgttaaa   5580
taataatttg ttaaataacc aaaaagtcaa atatgtttac tctcgtttaa ataattgaga   5640
ttcgtccagc aaggctaaac gattgtatag atttatgaca atatttactt ttttatagat   5700
aaatgttata ttataataaa tttatataca tatattatat gttatttatt attattttaa   5760
atccttcaat attttatcaa accaactcat aatttttttt ttatctgtaa gaagcaataa   5820
aattaaatag acccacttta aggatgatcc aacctttata cagagtaaga gagttcaaat   5880
agtacccttt catatacata tcaactaaaa tattagaaat atcatggatc aaaccttata   5940
aagacattaa ataagtggat aagtataata tataaatggg tagtatataa tatataaatg   6000
gatacaaact tctctcttta taattgttat gtctccttaa catcctaata taatacataa   6060
gtgggtaata tataatatat aaatggagac aaacttcttc cattataatt gttatgtctt   6120
cttaacactt atgtctcgtt cacaatgcta aggttagaat tgtttagaaa gtcttatagt   6180
acacatttgt ttttgtacta tttgaagcat tccataagcc gtcacgattc agatgattta   6240
taataataag aggaaattta tcatagaaca ataaggtgca tagatagagt gttaatatat   6300
cataacatcc tttgtttatt catagaagaa gtgagatgga gctcagttat tatactgtta   6360
catggtcgga tacaatattc catgctctcc atgagctctt acacctacat gcattttagt   6420
tcatacttgc ggccgcagta tatcttaaat tctttaatac ggtgtactag gatattgaac   6480
tggttcttga tgatgaaaac ctgggccgag attgcagcta tttatagtca taggtcttgt   6540
taacatgcat ggacatttgg ccacggggtg gcatgcagtt tgacgggtgt tgaaataaac   6600
aaaaatgagg tggcggaaga gaatacgagt ttgaggttgg gttagaaaca acaaatgtga   6660
gggctcatga tgggttgagt tggtgaatgt tttgggctgc tcgattgaca cctttgtgag   6720
tacgtgttgt tgtgcatggc ttttggggtc cagttttttt ttcttgacgc ggcgatcctg   6780
atcagctagt ggataagtga tgtccactgt gtgtgattgc gtttttgttt gaattttatg   6840
aacttagaca ttgctatgca aaggatactc tcattgtgtt ttgtcttctt ttgttccttg   6900
gctttttctt atgatccaag agactagtca gtgttgtggc attcgagact accaagatta   6960
attatgatgg gggaaggata agtaactgat tagtacggac tgttaccaaa ttaattaata   7020
agcggcaaat gaagggcatg gatcaaaagc ttggatctcc tgcaggatct ggccggccgg   7080
atctc                                                               7085
```

<210> SEQ ID NO 31
<211> LENGTH: 2540
<212> TYPE: DNA
<213> ORGANISM: Artificial Sequence
<220> FEATURE:
<223> OTHER INFORMATION: plasmid KS102

<400> SEQUENCE: 31

```
cgatcatccg gatatagttc ctcctttcag caaaaaaccc ctcaagaccc gtttagaggc     60
cccaaggggt tatgctagtt attgctcagc ggtggcagca gccaactcag cttcctttcg    120
ggctttgtta gcagccggat cgatccaagc tgtacctcac tattcctttg ccctcggacg    180
agtgctgggg cgtcggtttc cactatcggc gagtacttct acacagccat cggtccagac    240
ggccgcgctt ctgcgggcga tttgtgtacg cccgacagtc ccggctccgg atcggacgat    300
tgcgtcgcat cgaccctgcg cccaagctgc atcatcgaaa ttgccgtcaa ccaagctctg    360
atagagttgg tcaagaccaa tgcggagcat atacgcccgg agccgcggcg atcctgcaag    420
```

```
ctccggatgc ctccgctcga agtagcgcgt ctgctgctcc atacaagcca accacggcct    480
ccagaagaag atgttggcga cctcgtattg ggaatccccg aacatcgcct cgctccagtc    540
aatgaccgct gttatgcggc cattgtccgt caggacattg ttggagccga aatccgcgtg    600
cacgaggtgc cggacttcgg ggcagtcctc ggcccaaagc atcagctcat cgagagcctg    660
cgcgacggac gcactgacgg tgtcgtccat cacagtttgc cagtgataca catggggatc    720
agcaatcgcg catatgaaat cacgccatgt agtgtattga ccgattcctt gcggtccgaa    780
tgggccgaac ccgctcgtct ggctaagatc ggccgcagcg atcgcatcca tagcctccgc    840
gaccggctgc agaacagcgg gcagttcggt ttcaggcagg tcttgcaacg tgacaccctg    900
tgcacggcgg gagatgcaat aggtcaggct ctcgctgaat tccccaatgt caagcacttc    960
cggaatcggg agcgcggccg atgcaaagtg ccgataaaca taacgatctt tgtagaaacc   1020
atcggcgcag ctatttaccc gcaggacata tccacgccct cctacatcga agctgaaagc   1080
acgagattct tcgccctccg agagctgcat caggtcggag acgctgtcga acttttcgat   1140
cagaaacttc tcgacagacg tcgcggtgag ttcaggcttt tccatgggta tatctccttc   1200
ttaaagttaa acaaaattat ttctagaggg aaaccgttgt ggtctcccta tagtgagtcg   1260
tattaatttc gcgggatcga gatctgatca acctgcatta atgaatcggc caacgcgcgg   1320
ggagaggcgg tttgcgtatt gggcgctctt ccgcttcctc gctcactgac tcgctgcgct   1380
cggtcgttcg gctgcggcga gcggtatcag ctcactcaaa ggcggtaata cggttatcca   1440
cagaatcagg ggataacgca ggaaagaaca tgtgagcaaa aggccagcaa aaggccagga   1500
accgtaaaaa ggccgcgttg ctggcgtttt tccataggct ccgcccccct gacgagcatc   1560
acaaaaatcg acgctcaagt cagaggtggc gaaacccgac aggactataa agataccagg   1620
cgtttccccc tggaagctcc ctcgtgcgct ctcctgttcc gaccctgccg cttaccggat   1680
acctgtccgc ctttctccct tcgggaagcg tggcgctttc tcaatgctca cgctgtaggt   1740
atctcagttc ggtgtaggtc gttcgctcca agctgggctg tgtgcacgaa ccccccgttc   1800
agcccgaccg ctgcgcctta tccggtaact atcgtcttga gtccaacccg gtaagacacg   1860
acttatcgcc actggcagca gccactggta acaggattag cagagcgagg tatgtaggcg   1920
gtgctacaga gttcttgaag tggtggccta actacggcta cactagaagg acagtatttg   1980
gtatctgcgc tctgctgaag ccagttacct tcggaaaaag agttggtagc tcttgatccg   2040
gcaaacaaac caccgctggt agcggtggtt tttttgtttg caagcagcag attacgcgca   2100
gaaaaaaagg atctcaagaa gatcctttga tcttttctac ggggtctgac gctcagtgga   2160
acgaaaactc acgttaaggg attttggtca tgacattaac ctataaaaat aggcgtatca   2220
cgaggccctt tcgtctcgcg cgtttcggtg atgacggtga aaacctctga cacatgcagc   2280
tcccggagac ggtcacagct tgtctgtaag cggatgccgg gagcagacaa gcccgtcagg   2340
gcgcgtcagc gggtgttggc gggtgtcggg gctggcttaa ctatgcggca tcagagcaga   2400
ttgtactgag agtgcaccat atggacatat tgtcgttaga acgcggctac aattaataca   2460
taaccttatg tatcatacac atacgattta ggtgacacta tagaacggcg cgccaagctt   2520
ggatccgtcg acggcgcgcc                                                2540
```

<210> SEQ ID NO 32
<211> LENGTH: 4359
<212> TYPE: DNA
<213> ORGANISM: Artificial Sequence
<220> FEATURE:
<223> OTHER INFORMATION: plasmid pKR197

<400> SEQUENCE: 32

```
cgcgcccgat catccggata tagttcctcc tttcagcaaa aaacccctca agacccgttt     60
agaggcccca aggggttatg ctagttattg ctcagcggtg gcagcagcca actcagcttc    120
ctttcgggct ttgttagcag ccggatcgat ccaagctgta cctcactatt cctttgccct    180
cggacgagtg ctggggcgtc ggtttccact atcggcgagt acttctacac agccatcggt    240
ccagacggcc gcgcttctgc gggcgatttg tgtacgcccg acagtcccgg ctccggatcg    300
gacgattgcg tcgcatcgac cctgcgccca agctgcatca tcgaaattgc cgtcaaccaa    360
gctctgatag agttggtcaa gaccaatgcg gagcatatac gcccggagcc gcggcgatcc    420
tgcaagctcc ggatgcctcc gctcgaagta gcgcgtctgc tgctccatac aagccaacca    480
cggcctccag aagaagatgt tggcgacctc gtattgggaa tccccgaaca tcgcctcgct    540
ccagtcaatg accgctgtta tgcggccatt gtccgtcagg acattgttgg agccgaaatc    600
cgcgtgcacg aggtgccgga cttcggggca gtcctcggcc caaagcatca gctcatcgag    660
agcctgcgcg acggacgcac tgacggtgtc gtccatcaca gtttgccagt gatacacatg    720
gggatcagca atcgcgcata tgaaatcacg ccatgtagtg tattgaccga ttccttgcgg    780
tccgaatggg ccgaacccgc tcgtctggct aagatcggcc gcagcgatcg catccatagc    840
ctccgcgacc ggctgcagaa cagcgggcag ttcggtttca ggcaggtctt gcaacgtgac    900
accctgtgca cggcgggaga tgcaataggt caggctctcg ctgaattccc caatgtcaag    960
cacttccgga atcgggagcg cggccgatgc aaagtgccga taaacataac gatctttgta   1020
gaaaccatcg gcgcagctat ttacccgcag gacatatcca cgccctccta catcgaagct   1080
gaaagcacga gattcttcgc cctccgagag ctgcatcagg tcggagacgc tgtcgaactt   1140
ttcgatcaga aacttctcga cagacgtcgc ggtgagttca ggcttttcca tgggtatatc   1200
tccttcttaa agttaaacaa aattatttct agagggaaac cgttgtggtc tccctatagt   1260
gagtcgtatt aatttcgcgg gatcgagatc tgatcaacct gcattaatga atcggccaac   1320
gcgcggggag aggcggtttg cgtattgggc gctcttccgc ttcctcgctc actgactcgc   1380
tgcgctcggt cgttcggctg cggcgagcgg tatcagctca ctcaaaggcg gtaatacggt   1440
tatccacaga atcaggggat aacgcaggaa agaacatgtg agcaaaaggc cagcaaaagg   1500
ccaggaaccg taaaaaggcc gcgttgctgg cgtttttcca taggctccgc ccccctgacg   1560
agcatcacaa aaatcgacgc tcaagtcaga ggtggcgaaa cccgacagga ctataaagat   1620
accaggcgtt tccccctgga agctccctcg tgcgctctcc tgttccgacc ctgccgctta   1680
ccggatacct gtccgccttt ctcccttcgg gaagcgtggc gctttctcaa tgctcacgct   1740
gtaggtatct cagttcggtg taggtcgttc gctccaagct gggctgtgtg cacgaacccc   1800
ccgttcagcc cgaccgctgc gccttatccg gtaactatcg tcttgagtcc aacccggtaa   1860
gacacgactt atcgccactg gcagcagcca ctggtaacag gattagcaga gcgaggtatg   1920
taggcggtgc tacagagttc ttgaagtggt ggcctaacta cggctacact agaaggacag   1980
tatttggtat ctgcgctctg ctgaagccag ttaccttcgg aaaaagagtt ggtagctctt   2040
gatccggcaa acaaaccacc gctggtagcg gtggtttttt tgtttgcaag cagcagatta   2100
cgcgcagaaa aaaaggatct caagaagatc ctttgatctt ttctacgggg tctgacgctc   2160
agtggaacga aaactcacgt taagggattt tggtcatgac attaacctat aaaaataggc   2220
gtatcacgag gccctttcgt ctcgcgcgtt tcggtgatga cggtgaaaac ctctgacaca   2280
```

```
tgcagctccc ggagacggtc acagcttgtc tgtaagcgga tgccgggagc agacaagccc   2340
gtcagggcgc gtcagcgggt gttggcgggt gtcggggctg gcttaactat gcggcatcag   2400
agcagattgt actgagagtg caccatatgg acatattgtc gttagaacgc ggctacaatt   2460
aatacataac cttatgtatc atacacatac gatttaggtg acactataga acggcgcgcc   2520
aagcttgttg aaacatccct gaagtgtctc attttatttt atttattctt tgctgataaa   2580
aaaataaaat aaaagaagct aagcacacgg tcaaccattg ctctactgct aaaagggtta   2640
tgtgtagtgt tttactgcat aaattatgca gcaaacaaga caactcaaat taaaaaattt   2700
cctttgcttg tttttttgtt gtctctgact tgactttctt gtggaagttg gttgtataag   2760
gattgggaca ccattgtcct tcttaattta attttattct ttgctgataa aaaaaaaaat   2820
ttcatatagt gttaaataat aatttgttaa ataaccaaaa agtcaaatat gtttactctc   2880
gtttaaataa ttgagattcg tccagcaagg ctaaacgatt gtatagattt atgacaatat   2940
ttactttttt atagataaat gttatattat aataaattta tatacatata ttatatgtta   3000
tttattatta ttttaaatcc ttcaatattt tatcaaacca actcataatt ttttttttat   3060
ctgtaagaag caataaaatt aaatagaccc actttaagga tgatccaacc tttatacaga   3120
gtaagagagt tcaaatagta ccctttcata tacatatcaa ctaaaatatt agaaatatca   3180
tggatcaaac cttataaaga cattaaataa gtggataagt ataatatata aatgggtagt   3240
atataatata taaatggata caaacttctc tctttataat tgttatgtct ccttaacatc   3300
ctaatataat acataagtgg gtaatatata atatataaat ggagacaaac ttcttccatt   3360
ataattgtta tgtcttctta acacttatgt ctcgttcaca atgctaaggt tagaattgtt   3420
tagaaagtct tatagtacac atttgttttt gtactatttg aagcattcca taagccgtca   3480
cgattcagat gatttataat aataagagga aatttatcat agaacaataa ggtgcataga   3540
tagagtgtta atatatcata acatcctttg tttattcata gaagaagtga gatggagctc   3600
agttattata ctgttacatg gtcggataca atattccatg ctctccatga gctcttacac   3660
ctacatgcat tttagttcat acttgcggcc gcagtatatc ttaaattctt taatacggtg   3720
tactaggata ttgaactggt tcttgatgat gaaaacctgg gccgagattg cagctattta   3780
tagtcatagg tcttgttaac atgcatggac atttggccac ggggtggcat gcagtttgac   3840
gggtgttgaa ataaacaaaa atgaggtggc ggaagagaat acgagtttga ggttgggtta   3900
gaaacaacaa atgtgagggc tcatgatggg ttgagttggt gaatgttttg ggctgctcga   3960
ttgacacctt tgtgagtacg tgttgttgtg catggctttt ggggtccagt ttttttttct   4020
tgacgcggcg atcctgatca gctagtggat aagtgatgtc cactgtgtgt gattgcgttt   4080
ttgtttgaat tttatgaact tagacattgc tatgcaaagg atactctcat tgtgttttgt   4140
cttcttttgt tccttggctt tttcttatga tccaagagac tagtcagtgt tgtggcattc   4200
gagactacca agattaatta tgatgggga aggataagta actgattagt acggactgtt   4260
accaaattaa ttaataagcg gcaaatgaag ggcatggatc aaaagcttgg atctcctgca   4320
ggatctggcc ggccggatct cgtacggatc cgtcgacgg                          4359
```

<210> SEQ ID NO 33
<211> LENGTH: 5147
<212> TYPE: DNA
<213> ORGANISM: Artificial Sequence
<220> FEATURE:
<223> OTHER INFORMATION: plasmid pKR911

<400> SEQUENCE: 33

```
ggccgcaagt atgaactaaa atgcatgtag gtgtaagagc tcatggagag catggaatat     60
tgtatccgac catgtaacag tataataact gagctccatc tcacttcttc tatgaataaa    120
caaaggatgt tatgatatat taacactcta tctatgcacc ttattgttct atgataaatt    180
tcctcttatt attataaatc atctgaatcg tgacggctta tggaatgctt caaatagtac    240
aaaaacaaat gtgtactata agactttcta aacaattcta accttagcat tgtgaacgag    300
acataagtgt taagaagaca taacaattat aatggaagaa gtttgtctcc atttatatat    360
tatatattac ccacttatgt attatattag gatgttaagg agacataaca attataaaga    420
gagaagtttg tatccattta tatattatat actacccatt tatatattat acttatccac    480
ttatttaatg tctttataag gtttgatcca tgatatttct aatattttag ttgatatgta    540
tatgaaaggg tactatttga actctcttac tctgtataaa ggttggatca tccttaaagt    600
gggtctattt aattttattg cttcttacag ataaaaaaaa aattatgagt tggtttgata    660
aaatattgaa ggatttaaaa taataataaa taacatataa tatatgtata taaatttatt    720
ataatataac atttatctat aaaaaagtaa atattgtcat aaatctatac aatcgtttag    780
ccttgctgga cgaatctcaa ttatttaaac gagagtaaac atatttgact ttttggttat    840
ttaacaaatt attatttaac actatatgaa attttttttt ttatcagcaa agaataaaat    900
taaattaaga aggacaatgg tgtcccaatc cttatacaac caacttccac aagaaagtca    960
agtcagagac aacaaaaaaa caagcaaagg aaattttta atttgagttg tcttgtttgc    1020
tgcataattt atgcagtaaa acactacaca taaccctttt agcagtagag caatggttga   1080
ccgtgtgctt agcttctttt attttatttt tttatcagca aagaataaat aaaataaaat   1140
gagacacttc agggatgttt caacaagctt ggcgcgccgt tctatagtgt cacctaaatc   1200
gtatgtgtat gatacataag gttatgtatt aattgtagcc gcgttctaac gacaatatgt   1260
ccatatggtg cactctcagt acaatctgct ctgatgccgc atagttaagc cagccccgac   1320
acccgccaac acccgctgac gcgccctgac gggcttgtct gctcccggca tccgcttaca   1380
gacaagctgt gaccgtctcc gggagctgca tgtgtcagag gttttcaccg tcatcaccga   1440
aacgcgcgag acgaaagggc ctcgtgatac gcctattttt ataggttaat gtcatgacca   1500
aaatccctta acgtgagttt tcgttccact gagcgtcaga ccccgtagaa aagatcaaag   1560
gatcttcttg agatcctttt tttctgcgcg taatctgctg cttgcaaaca aaaaaaccac   1620
cgctaccagc ggtggtttgt ttgccggatc aagagctacc aactcttttt ccgaaggtaa   1680
ctggcttcag cagagcgcag ataccaaata ctgtccttct agtgtagccg tagttaggcc   1740
accacttcaa gaactctgta gcaccgccta catacctcgc tctgctaatc ctgttaccag   1800
tggctgctgc cagtggcgat aagtcgtgtc ttaccgggtt ggactcaaga cgatagttac   1860
cggataaggc gcagcggtcg ggctgaacgg ggggttcgtg cacacagccc agcttggagc   1920
gaacgaccta caccgaactg agatacctac agcgtgagca ttgagaaagc gccacgcttc   1980
ccgaagggag aaaggcggac aggtatccgg taagcggcag ggtcggaaca ggagagcgca   2040
cgagggagct tccaggggga aacgcctggt atctttatag tcctgtcggg tttcgccacc   2100
tctgacttga gcgtcgattt ttgtgatgct cgtcaggggg gcggagccta tggaaaaacg   2160
ccagcaacgc ggccttttta cggttcctgg ccttttgctg gccttttgct cacatgttct   2220
ttcctgcgtt atcccctgat tctgtggata accgtattac cgcctttgag tgagctgata   2280
ccgctcgccg cagccgaacg accgagcgca gcgagtcagt gagcgaggaa gcggaagagc   2340
```

```
gcccaatacg caaaccgcct ctccccgcgc gttggccgat tcattaatgc aggttgatca   2400
gatctcgatc ccgcgaaatt aatacgactc actataggga gaccacaacg gtttccctct   2460
agaaataatt ttgtttaact ttaagaagga gatataccca tggaaaagcc tgaactcacc   2520
gcgacgtctg tcgagaagtt tctgatcgaa aagttcgaca gcgtctccga cctgatgcag   2580
ctctcggagg gcgaagaatc tcgtgctttc agcttcgatg taggagggcg tggatatgtc   2640
ctgcgggtaa atagctgcgc cgatggtttc tacaaagatc gttatgttta tcggcacttt   2700
gcatcggccg cgctcccgat tccggaagtg cttgacattg gggaattcag cgagagcctg   2760
acctattgca tctcccgccg tgcacagggt gtcacgttgc aagacctgcc tgaaaccgaa   2820
ctgcccgctg ttctgcagcc ggtcgcggag gctatggatg cgatcgctgc ggccgatctt   2880
agccagacga gcgggttcgg cccattcgga ccgcaaggaa tcggtcaata cactacatgg   2940
cgtgatttca tatgcgcgat tgctgatccc catgtgtatc actggcaaac tgtgatggac   3000
gacaccgtca gtgcgtccgt cgcgcaggct ctcgatgagc tgatgctttg ggccgaggac   3060
tgccccgaag tccggcacct cgtgcacgcg gatttcggct ccaacaatgt cctgacggac   3120
aatggccgca taacagcggt cattgactgg agcgaggcga tgttcgggga ttcccaatac   3180
gaggtcgcca acatcttctt ctggaggccg tggttggctt gtatggagca gcagacgcgc   3240
tacttcgagc ggaggcatcc ggagcttgca ggatcgccgc ggctccgggc gtatatgctc   3300
cgcattggtc ttgaccaact ctatcagagc ttggttgacg gcaatttcga tgatgcagct   3360
tgggcgcagg gtcgatgcga cgcaatcgtc cgatccggag ccgggactgt cgggcgtaca   3420
caaatcgccc gcagaagcgc ggccgtctgg accgatggct gtgtagaagt actcgccgat   3480
agtggaaacc gacgccccag cactcgtccg agggcaaagg aatagtgagg tacagcttgg   3540
atcgatccgg ctgctaacaa agcccgaaag gaagctgagt tggctgctgc caccgctgag   3600
caataactag cataacccct tggggcctct aaacgggtct tgaggggttt tttgctgaaa   3660
ggaggaacta tatccggatg atcgggcgcg ccgtcgacgg atccgtacga gatccggccg   3720
gccagatcct gcaggagatc caagcttttg atccatgccc ttcatttgcc gcttattaat   3780
taatttggta acagtccgta ctaatcagtt acttatcctt cccccatcat aattaatctt   3840
ggtagtctcg aatgccacaa cactgactag tctcttggat cataagaaaa agccaaggaa   3900
caaaagaaga caaaacacaa tgagagtatc ctttgcatag caatgtctaa gttcataaaa   3960
ttcaaacaaa aacgcaatca cacacagtgg acatcactta tccactagct gatcaggatc   4020
gccgcgtcaa gaaaaaaaaa ctggacccca aaagccatgc acaacaacac gtactcacaa   4080
aggtgtcaat cgagcagccc aaaacattca ccaactcaac ccatcatgag ccctcacatt   4140
tgttgtttct aacccaacct caaactcgta ttctcttccg ccacctcatt tttgtttatt   4200
tcaacacccg tcaaactgca tgccaccccg tggccaaatg tccatgcatg ttaacaagac   4260
ctatgactat aaatagctgc aatctcggcc caggttttca tcatcaagaa ccagttcaat   4320
atcctagtac accgtattaa agaatttaag atatactgcg gccgcaccat ggaggtggtg   4380
aatgaaatag tctcaattgg gcaggaagtt ttacccaaag ttgattatgc ccaactctgg   4440
agtgatgcca gtcactgtga ggtgctttac ttgtccatcg catttgtcat cttgaagttc   4500
actcttggcc cccttggtcc aaaaggtcag tctcgtatga agtttgtttt caccaattac   4560
aaccttctca tgtccattta ttcgttggga tcattcctct caatggcata tgccatgtac   4620
accatcggtg ttatgtctga caactgcgag aaggcttttg acaacaacgt cttcaggatc   4680
accacgcagt tgttctattt gagcaagttc ctggagtata ttgactcctt ctatttgcca   4740
```

```
ctgatgggca agcctctgac ctggttgcaa ttcttccatc atttgggggc accgatggat   4800

atgtggctgt tctataatta ccgaaatgaa gctgtttgga tttttgtgct gttgaatggt   4860

ttcatccact ggatcatgta cggttattat tggaccagat tgatcaagct gaagttcccc   4920

atgccaaaat ccctgattac atcaatgcag atcattcaat tcaatgttgg tttctacatt   4980

gtctggaagt acaggaacat tccctgttat cgccaagatg ggatgaggat gtttggctgg   5040

ttcttcaatt acttttatgt tggcacagtc ttgtgtttgt tcttgaattt ctatgtgcaa   5100

acgtatatcg tcaggaagca caagggagcc aaaaagattc agtgagc                 5147
```

```
<210> SEQ ID NO 34
<211> LENGTH: 6559
<212> TYPE: DNA
<213> ORGANISM: Artificial Sequence
<220> FEATURE:
<223> OTHER INFORMATION: plasmid pKR680
<220> FEATURE:
<221> NAME/KEY: misc_feature
<222> LOCATION: (4340)..(4340)
<223> OTHER INFORMATION: n is a, c, g, or t

<400> SEQUENCE: 34
```

```
ggccgcgaca caagtgtgag agtactaaat aaatgctttg gttgtacgaa atcattacac     60

taaataaaat aatcaaagct tatatatgcc ttccgctaag gccgaatgca aagaaattgg    120

ttctttctcg ttatcttttg ccacttttac tagtacgtat taattactac ttaatcatct    180

ttgtttacgg ctcattatat ccggtctaga ggatccaagg ccgcgaagtt aaaagcaatg    240

ttgtcacttg tcgtactaac acatgatgtg atagtttatg ctagctagct ataacataag    300

ctgtctctga gtgtgttgta tattaataaa gatcatcact ggtgaatggt gatcgtgtac    360

gtaccctact tagtaggcaa tggaagcact tagagtgtgc tttgtgcatg gccttgcctc    420

tgttttgaga cttttgtaat gttttcgagt ttaaatcttt gcctttgcgt acgtgggcgg    480

atcccccggg ctgcaggaat tcactggccg tcgttttaca acgtcgtgac tgggaaaacc    540

ctggcgttac ccaacttaat cgccttgcag cacatccccc tttcgccagc tggcgtaata    600

gcgaagaggc ccgcaccgat cgcccttccc aacagttgcg cagcctgaat ggcgaatggc    660

gcctgatgcg gtattttctc cttacgcatc tgtgcggtat ttcacaccgc atatggtgca    720

ctctcagtac aatctgctct gatgccgcat agttaagcca gccccgacac ccgccaacac    780

ccgctgacgc gccctgacgg gcttgtctgc tcccggcatc cgcttacaga caagctgtga    840

ccgtctccgg gagctgcatg tgtcagaggt tttcaccgtc atcaccgaaa cgcgcgagac    900

gaaagggcct cgtgatacgc ctatttttat aggttaatgt catgataata atggtttctt    960

agacgtcagg tggcactttt cggggaaatg tgcgcggaac ccctatttgt ttatttttct   1020

aaatacattc aaatatgtat ccgctcatga gacaataacc ctgataaatg cttcaataat   1080

attgaaaaag gaagagtatg agtattcaac atttccgtgt cgcccttatt cccttttttg   1140

cggcattttg ccttcctgtt tttgctcacc cagaaacgct ggtgaaagta aaagatgctg   1200

aagatcagtt gggtgcacga gtgggttaca tcgaactgga tctcaacagc ggtaagatcc   1260

ttgagagttt tcgccccgaa gaacgttttc caatgatgag cacttttaaa gttctgctat   1320

gtggcgcggt attatcccgt attgacgccg ggcaagagca actcggtcgc cgcatacact   1380

attctcagaa tgacttggtt gagtactcac cagtcacaga aaagcatctt acggatggca   1440

tgacagtaag agaattatgc agtgctgcca taaccatgag tgataacact gcggccaact   1500
```

```
tacttctgac aacgatcgga ggaccgaagg agctaaccgc ttttttgcac aacatggggg   1560
atcatgtaac tcgccttgat cgttgggaac cggagctgaa tgaagccata ccaaacgacg   1620
agcgtgacac cacgatgcct gtagcaatgg caacaacgtt gcgcaaacta ttaactggcg   1680
aactacttac tctagcttcc cggcaacaat taatagactg gatggaggcg gataaagttg   1740
caggaccact tctgcgctcg gcccttccgg ctggctggtt tattgctgat aaatctggag   1800
ccggtgagcg tgggtctcgc ggtatcattg cagcactggg gccagatggt aagccctccc   1860
gtatcgtagt tatctacacg acggggagtc aggcaactat ggatgaacga aatagacaga   1920
tcgctgagat aggtgcctca ctgattaagc attggtaact gtcagaccaa gtttactcat   1980
atatacttta gattgattta aaacttcatt tttaatttaa aaggatctag gtgaagatcc   2040
tttttgataa tctcatgacc aaaatccctt aacgtgagtt ttcgttccac tgagcgtcag   2100
accccgtaga aaagatcaaa ggatcttctt gagatccttt ttttctgcgc gtaatctgct   2160
gcttgcaaac aaaaaaacca ccgctaccag cggtggtttg tttgccggat caagagctac   2220
caactctttt tccgaaggta actggcttca gcagagcgca gataccaaat actgtccttc   2280
tagtgtagcc gtagttaggc caccacttca agaactctgt agcaccgcct acatacctcg   2340
ctctgctaat cctgttacca gtggctgctg ccagtggcga taagtcgtgt cttaccgggt   2400
tggactcaag acgatagtta ccggataagg cgcagcggtc gggctgaacg gggggttcgt   2460
gcacacagcc cagcttggag cgaacgacct acaccgaact gagataccta cagcgtgagc   2520
tatgagaaag cgccacgctt cccgaaggga gaaaggcgga caggtatccg gtaagcggca   2580
gggtcggaac aggagagcgc acgagggagc ttccaggggg aaacgcctgg tatctttata   2640
gtcctgtcgg gtttcgccac ctctgacttg agcgtcgatt tttgtgatgc tcgtcagggg   2700
ggcggagcct atggaaaaac gccagcaacg cggccttttt acggttcctg gccttttgct   2760
ggccttttgc tcacatgttc tttcctgcgt tatcccctga ttctgtggat aaccgtatta   2820
ccgcctttga gtgagctgat accgctcgcc gcagccgaac gaccgagcgc agcgagtcag   2880
tgagcgagga agcggaagag cgcccaatac gcaaaccgcc tctccccgcg cgttggccga   2940
ttcattaatg cagctggcac gacaggtttc ccgactggaa agcgggcagt gagcgcaacg   3000
caattaatgt gagttagctc actcattagg caccccaggc tttacacttt atgcttccgg   3060
ctcgtatgtt gtgtggaatt gtgagcggat aacaatttca cacaggaaac agctatgacc   3120
atgattacgc caagcttgca tgcctgcagg tcgactcgac gtacgtcctc gaagagaagg   3180
gttaataaca catttttaa catttttaac acaaatttta gttatttaaa aatttattaa   3240
aaaatttaaa ataagaagag gaactcttta aataaatcta acttacaaaa tttatgattt   3300
ttaataagtt ttcaccaata aaaaatgtca taaaaatatg ttaaaaagta tattatcaat   3360
attctcttta tgataaataa aaagaaaaaa aaaataaaag ttaagtgaaa atgagattga   3420
agtgacttta ggtgtgtata aatatatcaa ccccgccaac aatttattta atccaaatat   3480
attgaagtat attattccat agcctttatt tatttatata tttattatat aaaagcttta   3540
tttgttctag gttgttcatg aaatattttt ttggttttat ctccgttgta agaaaatcat   3600
gtgctttgtg tcgccactca ctattgcagc tttttcatgc attggtcaga ttgacggttg   3660
attgtatttt tgttttttat ggttttgtgt tatgacttaa gtcttcatct ctttatctct   3720
tcatcaggtt tgatggttac ctaatatggt ccatgggtac atgcatggtt aaattaggtg   3780
gccaactttg ttgtgaacga tagaattttt tttatattaa gtaaactatt tttatattat   3840
gaaataataa taaaaaaaat attttatcat tattaacaaa atcatattag ttaatttgtt   3900
```

```
aactctataa taaaagaaat actgtaacat tcacattaca tggtaacatc tttccaccct   3960
ttcatttgtt ttttgtttga tgactttttt tcttgtttaa atttatttcc cttcttttaa   4020
atttggaata cattatcatc atatataaac taaaatacta aaaacaggat tacacaaatg   4080
ataaataata acacaaatat ttataaatct agctgcaata tatttaaact agctatatcg   4140
atattgtaaa ataaaactag ctgcattgat actgataaaa aaatatcatg tgctttctgg   4200
actgatgatg cagtatactt ttgacattgc ctttatttta tttttcagaa aagctttctt   4260
agttctgggt tcttcattat ttgtttccca tctccattgt gaattgaatc atttgcttcg   4320
tgtcacaaat acaatttagn taggtacatg cattggtcag attcacggtt tattatgtca   4380
tgacttaagt tcatggtagt acattacctg ccacgcatgc attatattgg ttagatttga   4440
taggcaaatt tggttgtcaa caatataaat ataaataatg tttttatatt acgaaataac   4500
agtgatcaaa acaaacagtt ttatctttat taacaagatt ttgtttttgt ttgatgacgt   4560
tttttaatgt ttacgctttc cccttcttt tgaatttaga acactttatc atcataaaat   4620
caaatactaa aaaaattaca tatttcataa ataataacac aaatattttt aaaaaatctg   4680
aaataataat gaacaatatt acatattatc acgaaaattc attaataaaa atattatata   4740
aataaaatgt aatagtagtt atatgtagga aaaaagtact gcacgcataa tatatacaaa   4800
aagattaaaa tgaactatta taaataataa cactaaatta atggtgaatc atatcaaaat   4860
aatgaaaaag taaataaaat ttgtaattaa cttctatatg tattacacac acaaataata   4920
aataatagta aaaaaaatta tgataaatat ttaccatctc ataagatatt taaaataatg   4980
ataaaaatat agattatttt ttatgcaact agctagccaa aaagagaaca cgggtatata   5040
taaaaagagt acctttaaat tctactgtac ttcctttatt cctgacgttt ttatatcaag   5100
tggacatacg tgaagatttt aattatcagt ctaaatattt cattagcact taatactttt   5160
ctgttttatt cctatcctat aagtagtccc gattctccca acattgctta ttcacacaac   5220
taactaagaa agtcttccat agccccccaa gcggccgcgg gaattcgatt gaaatgaagt   5280
caaagcgcca agcgcttccc cttacaattg atggaacaac atatgatgtg tctgcctggg   5340
tcaatttcca ccctggtggt gcggaaatta tagagaatta ccaaggaagg gatgccactg   5400
atgccttcat ggttatgcac tctcaagaag ccttcgacaa gctcaagcgc atgcccaaaa   5460
tcaatcccag ttctgagttg ccaccccagg ctgcagtgaa tgaagctcaa gaggatttcc   5520
ggaagctccg agaagagttg atcgcaactg gcatgtttga tgcctccccc ctctggtact   5580
catacaaaat cagcaccaca ctgggccttg gagtgctggg ttatttcctg atggttcagt   5640
atcagatgta tttcattggg gcagtgttgc ttgggatgca ctatcaacag atgggctggc   5700
tttctcatga catttgccac caccagactt tcaagaaccg gaactggaac aacctcgtgg   5760
gactggtatt tggcaatggt ctgcaaggtt tttccgtgac atggtggaag gacagacaca   5820
atgcacatca ttcggcaacc aatgttcaag ggcacgaccc tgatattgac aacctccccc   5880
tcttagcctg gtctgaggat gacgtcacac gggcgtcacc gatttcccgc aagctcattc   5940
agttccagca gtactatttc ttggtcatct gtatcttgtt gcggttcatt tggtgtttcc   6000
agagcgtgtt gaccgtgcgc agtttgaagg acagagataa ccaattctat cgctctcagt   6060
ataagaagga ggccattggc ctcgccctgc actggacctt gaagaccctg ttccacttat   6120
tctttatgcc cagcatcctc acatcgctgt tggtgttttt cgtttcggag ctggttggcg   6180
gcttcggcat tgcgatcgtg gtgttcatga accactaccc actggagaag atcggggact   6240
```

```
cagtctggga tggccatgga ttctcggttg gccagatcca tgagaccatg aacattcggc   6300

gagggattat cacagattgg tttttcggag gcttgaatta ccagattgag caccatttgt   6360

ggccgaccct ccctcgccac aacctgacag cggttagcta ccaggtggaa cagctgtgcc   6420

agaagcacaa cctgccgtat cggaacccgc tgccccatga agggttggtc atcctgctgc   6480

gctatctggc ggtgttcgcc cggatggcgg agaagcaacc cgcggggaag gctctataag   6540

gaatcactag tgaattcgc                                                6559


<210> SEQ ID NO 35
<211> LENGTH: 9014
<212> TYPE: DNA
<213> ORGANISM: Artificial Sequence
<220> FEATURE:
<223> OTHER INFORMATION: plasmid pKR913
<220> FEATURE:
<221> NAME/KEY: misc_feature
<222> LOCATION: (7839)..(7839)
<223> OTHER INFORMATION: n is a, c, g, or t

<400> SEQUENCE: 35

gtacgagatc cggccggcca gatcctgcag gagatccaag cttttgatcc atgcccttca     60

tttgccgctt attaattaat ttggtaacag tccgtactaa tcagttactt atccttcccc    120

catcataatt aatcttggta gtctcgaatg ccacaacact gactagtctc ttggatcata    180

agaaaaagcc aaggaacaaa agaagacaaa acacaatgag agtatccttt gcatagcaat    240

gtctaagttc ataaaattca aacaaaaacg caatcacaca cagtggacat cacttatcca    300

ctagctgatc aggatcgccg cgtcaagaaa aaaaaactgg accccaaaag ccatgcacaa    360

caacacgtac tcacaaaggt gtcaatcgag cagcccaaaa cattcaccaa ctcaacccat    420

catgagccct cacatttgtt gtttctaacc caacctcaaa ctcgtattct cttccgccac    480

ctcatttttg tttatttcaa cacccgtcaa actgcatgcc accccgtggc caaatgtcca    540

tgcatgttaa caagacctat gactataaat agctgcaatc tcggcccagg ttttcatcat    600

caagaaccag ttcaatatcc tagtacaccg tattaaagaa tttaagatat actgcggccg    660

caccatggag gtggtgaatg aaatagtctc aattgggcag gaagttttac ccaaagttga    720

ttatgcccaa ctctggagtg atgccagtca ctgtgaggtg ctttacttgt ccatcgcatt    780

tgtcatcttg aagttcactc ttggccccct tggtccaaaa ggtcagtctc gtatgaagtt    840

tgttttcacc aattacaacc ttctcatgtc catttattcg ttgggatcat tcctctcaat    900

ggcatatgcc atgtacacca tcggtgttat gtctgacaac tgcgagaagg cttttgacaa    960

caacgtcttc aggatcacca cgcagttgtt ctatttgagc aagttcctgg agtatattga   1020

ctccttctat ttgccactga tgggcaagcc tctgacctgg ttgcaattct tccatcattt   1080

gggggcaccg atggatatgt ggctgttcta taattaccga aatgaagctg tttggatttt   1140

tgtgctgttg aatggtttca tccactggat catgtacggt tattattgga ccagattgat   1200

caagctgaag ttccccatgc caaaatccct gattacatca atgcagatca ttcaattcaa   1260

tgttggtttc tacattgtct ggaagtacag gaacattccc tgttatcgcc aagatgggat   1320

gaggatgttt ggctggttct tcaattactt ttatgttggc acagtcttgt gtttgttctt   1380

gaatttctat gtgcaaacgt atatcgtcag gaagcacaag ggagccaaaa agattcagtg   1440

agcggccgca agtatgaact aaaatgcatg taggtgtaag agctcatgga gagcatggaa   1500

tattgtatcc gaccatgtaa cagtataata actgagctcc atctcacttc ttctatgaat   1560

aaacaaagga tgttatgata tattaacact ctatctatgc accttattgt tctatgataa   1620
```

```
atttcctctt attattataa atcatctgaa tcgtgacggc ttatggaatg cttcaaatag   1680
tacaaaaaca aatgtgtact ataagacttt ctaaacaatt ctaaccttag cattgtgaac   1740
gagacataag tgttaagaag acataacaat tataatggaa gaagtttgtc tccatttata   1800
tattatatat tacccactta tgtattatat taggatgtta aggagacata acaattataa   1860
agagagaagt ttgtatccat ttatatatta tatactaccc atttatatat tatacttatc   1920
cacttattta atgtctttat aaggtttgat ccatgatatt tctaatattt tagttgatat   1980
gtatatgaaa gggtactatt tgaactctct tactctgtat aaaggttgga tcatccttaa   2040
agtgggtcta tttaatttta ttgcttctta cagataaaaa aaaaattatg agttggtttg   2100
ataaaatatt gaaggattta aaataataat aaataacata taatatatgt atataaattt   2160
attataatat aacatttatc tataaaaaag taaatattgt cataaatcta tacaatcgtt   2220
tagccttgct ggacgaatct caattattta aacgagagta aacatatttg actttttggt   2280
tatttaacaa attattattt aacactatat gaaatttttt tttttatcag caaagaataa   2340
aattaaatta agaaggacaa tggtgtccca atccttatac aaccaacttc cacaagaaag   2400
tcaagtcaga gacaacaaaa aaacaagcaa aggaaatttt ttaatttgag ttgtcttgtt   2460
tgctgcataa tttatgcagt aaaacactac acataaccct tttagcagta gagcaatggt   2520
tgaccgtgtg cttagcttct tttattttat ttttttatca gcaaagaata aataaaataa   2580
aatgagacac ttcagggatg tttcaacaag cttggcgcgc cgttctatag tgtcacctaa   2640
atcgtatgtg tatgatacat aaggttatgt attaattgta gccgcgttct aacgacaata   2700
tgtccatatg gtgcactctc agtacaatct gctctgatgc cgcatagtta agccagcccc   2760
gacacccgcc aacacccgct gacgcgccct gacgggcttg tctgctcccg gcatccgctt   2820
acagacaagc tgtgaccgtc tccgggagct gcatgtgtca gaggttttca ccgtcatcac   2880
cgaaacgcgc gagacgaaag ggcctcgtga tacgcctatt tttataggtt aatgtcatga   2940
ccaaaatccc ttaacgtgag ttttcgttcc actgagcgtc agaccccgta gaaaagatca   3000
aaggatcttc ttgagatcct ttttttctgc gcgtaatctg ctgcttgcaa acaaaaaaac   3060
caccgctacc agcggtggtt tgtttgccgg atcaagagct accaactctt tttccgaagg   3120
taactggctt cagcagagcg cagataccaa atactgtcct tctagtgtag ccgtagttag   3180
gccaccactt caagaactct gtagcaccgc ctacatacct cgctctgcta atcctgttac   3240
cagtggctgc tgccagtggc gataagtcgt gtcttaccgg gttggactca agacgatagt   3300
taccggataa ggcgcagcgg tcgggctgaa cggggggttc gtgcacacag cccagcttgg   3360
agcgaacgac ctacaccgaa ctgagatacc tacagcgtga gcattgagaa agcgccacgc   3420
ttcccgaagg gagaaaggcg gacaggtatc cggtaagcgg cagggtcgga acaggagagc   3480
gcacgaggga gcttccaggg ggaaacgcct ggtatcttta tagtcctgtc gggtttcgcc   3540
acctctgact tgagcgtcga tttttgtgat gctcgtcagg ggggcggagc ctatggaaaa   3600
acgccagcaa cgcggccttt ttacggttcc tggccttttg ctggcctttt gctcacatgt   3660
tctttcctgc gttatcccct gattctgtgg ataaccgtat taccgccttt gagtgagctg   3720
ataccgctcg ccgcagccga acgaccgagc gcagcgagtc agtgagcgag gaagcggaag   3780
agcgcccaat acgcaaaccg cctctccccg cgcgttggcc gattcattaa tgcaggttga   3840
tcagatctcg atcccgcgaa attaatacga ctcactatag ggagaccaca acggtttccc   3900
tctagaaata attttgttta actttaagaa ggagatatac ccatggaaaa gcctgaactc   3960
```

```
accgcgacgt ctgtcgagaa gtttctgatc gaaaagttcg acagcgtctc cgacctgatg   4020
cagctctcgg agggcgaaga atctcgtgct ttcagcttcg atgtaggagg gcgtggatat   4080
gtcctgcggg taaatagctg cgccgatggt ttctacaaag atcgttatgt ttatcggcac   4140
tttgcatcgg ccgcgctccc gattccggaa gtgcttgaca ttggggaatt cagcgagagc   4200
ctgacctatt gcatctcccg ccgtgcacag ggtgtcacgt tgcaagacct gcctgaaacc   4260
gaactgcccg ctgttctgca gccggtcgcg gaggctatgg atgcgatcgc tgcggccgat   4320
cttagccaga cgagcgggtt cggcccattc ggaccgcaag gaatcggtca atacactaca   4380
tggcgtgatt tcatatgcgc gattgctgat ccccatgtgt atcactggca aactgtgatg   4440
gacgacaccg tcagtgcgtc cgtcgcgcag gctctcgatg agctgatgct ttgggccgag   4500
gactgccccg aagtccggca cctcgtgcac gcggatttcg gctccaacaa tgtcctgacg   4560
gacaatggcc gcataacagc ggtcattgac tggagcgagg cgatgttcgg ggattcccaa   4620
tacgaggtcg ccaacatctt cttctggagg ccgtggttgg cttgtatgga gcagcagacg   4680
cgctacttcg agcggaggca tccggagctt gcaggatcgc cgcggctccg ggcgtatatg   4740
ctccgcattg gtcttgacca actctatcag agcttggttg acggcaattt cgatgatgca   4800
gcttgggcgc agggtcgatg cgacgcaatc gtccgatccg gagccgggac tgtcgggcgt   4860
acacaaatcg cccgcagaag cgcggccgtc tggaccgatg gctgtgtaga agtactcgcc   4920
gatagtggaa accgacgccc cagcactcgt ccgagggcaa aggaatagtg aggtacagct   4980
tggatcgatc cggctgctaa caaagcccga aaggaagctg agttggctgc tgccaccgct   5040
gagcaataac tagcataacc ccttggggcc tctaaacggg tcttgagggg ttttttgctg   5100
aaaggaggaa ctatatccgg atgatcgggc gcgccgtcga cggatccgta cgcaaaggca   5160
aagatttaaa ctcgaaaaca ttacaaaagt ctcaaaacag aggcaaggcc atgcacaaag   5220
cacactctaa gtgcttccat tgcctactaa gtagggtacg tacacgatca ccattcacca   5280
gtgatgatct ttattaatat acaacacact cagagacagc ttatgttata gctagctagc   5340
ataaactatc acatcatgtg ttagtacgac aagtgacaac attgctttta acttcgcggc   5400
cttggatcct ctagaccgga tataatgagc cgtaaacaaa gatgattaag tagtaattaa   5460
tacgtactag taaaagtggc aaaagataac gagaaagaac caatttcttt gcattcggcc   5520
ttagcggaag gcatatataa gctttgatta ttttatttag tgtaatgatt tcgtacaacc   5580
aaagcattta tttagtactc tcacacttgt gtcgcggccg cgaattcact agtgattcct   5640
tatagagcct tccccgcggg ttgcttctcc gccatccggg cgaacaccgc cagatagcgc   5700
agcaggatga ccaacccttc atggggcagc gggttccgat acggcaggtt gtgcttctgg   5760
cacagctgtt ccacctggta gctaaccgct gtcaggttgt ggcgagggag ggtcggccac   5820
aaatggtgct caatctggta attcaagcct ccgaaaaacc aatctgtgat aatccctcgc   5880
cgaatgttca tggtctcatg gatctggcca accgagaatc catggccatc ccagactgag   5940
tccccgatct tctccagtgg gtagtggttc atgaacacca cgatcgcaat gccgaagccg   6000
ccaaccagct ccgaaacgaa aaacaccaac agcgatgtga ggatgctggg cataaagaat   6060
aagtggaaca gggtcttcaa ggtccagtgc agggcgaggc caatggcctc cttcttatac   6120
tgagagcgat agaattggtt atctctgtcc ttcaaactgc gcacggtcaa cacgctctgg   6180
aaacaccaaa tgaaccgcaa caagatacag atgaccaaga aatagtactg ctggaactga   6240
atgagcttgc gggaaatcgg tgacgcccgt gtgacgtcat cctcagacca ggctaagagg   6300
gggaggttgt caatatcagg gtcgtgccct tgaacattgg ttgccgaatg atgtgcattg   6360
```

```
tgtctgtcct tccaccatgt cacggaaaaa ccttgcagac cattgccaaa taccagtccc   6420
acgaggttgt tccagttccg gttcttgaaa gtctggtggt ggcaaatgtc atgagaaagc   6480
cagcccatct gttgatagtg catcccaagc aacactgccc caatgaaata catctgatac   6540
tgaaccatca ggaaataacc cagcactcca aggcccagtg tggtgctgat tttgtatgag   6600
taccagaggg gggaggcatc aaacatgcca gttgcgatca actcttctcg gagcttccgg   6660
aaatcctctt gagcttcatt cactgcagcc tggggtggca actcagaact gggattgatt   6720
ttgggcatgc gcttgagctt gtcgaaggct tcttgagagt gcataaccat gaaggcatca   6780
gtggcatccc ttccttggta attctctata atttccgcac caccagggtg gaaattgacc   6840
caggcagaca catcatatgt tgttccatca attgtaaggg gaagcgcttg gcgctttgac   6900
ttcatttcaa tcgaattccc gcggccgctt ggggggctat ggaagacttt cttagttagt   6960
tgtgtgaata agcaatgttg ggagaatcgg gactacttat aggataggaa taaaacagaa   7020
aagtattaag tgctaatgaa atatttagac tgataattaa aatcttcacg tatgtccact   7080
tgatataaaa acgtcaggaa taaaggaagt acagtagaat ttaaaggtac tctttttata   7140
tatacccgtg ttctcttttt ggctagctag ttgcataaaa aataatctat atttttatca   7200
ttatttaaa tatcttatga gatggtaaat atttatcata attttttta ctattattta   7260
ttatttgtgt gtgtaataca tatagaagtt aattacaaat tttatttact ttttcattat   7320
tttgatatga ttcaccatta atttagtgtt attatttata atagttcatt ttaatctttt   7380
tgtatatatt atgcgtgcag tacttttttc ctacatataa ctactattac attttattta   7440
tataatattt ttattaatga attttcgtga taatatgtaa tattgttcat tattatttca   7500
gattttttaa aaatatttgt gttattattt atgaaatatg taattttttt agtatttgat   7560
tttatgatga taaagtgttc taaattcaaa agaaggggga aagcgtaaac attaaaaaac   7620
gtcatcaaac aaaaacaaaa tcttgttaat aaagataaaa ctgtttgttt tgatcactgt   7680
tatttcgtaa tataaaaaca ttatttatat ttatattgtt gacaaccaaa tttgcctatc   7740
aaatctaacc aatataatgc atgcgtggca ggtaatgtac taccatgaac ttaagtcatg   7800
acataataaa ccgtgaatct gaccaatgca tgtacctanc taaattgtat ttgtgacacg   7860
aagcaaatga ttcaattcac aatggagatg ggaaacaaat aatgaagaac ccagaactaa   7920
gaaagctttt ctgaaaaata aaataaaggc aatgtcaaaa gtatactgca tcatcagtcc   7980
agaaagcaca tgatattttt ttatcagtat caatgcagct agttttattt tacaatatcg   8040
atatagctag tttaaatata ttgcagctag atttataaat atttgtgtta ttatttatca   8100
tttgtgtaat cctgttttta gtattttagt ttatatatga tgataatgta ttccaaattt   8160
aaaagaaggg aaataaattt aaacaagaaa aaaagtcatc aaacaaaaaa caaatgaaag   8220
ggtggaaaga tgttaccatg taatgtgaat gttacagtat ttcttttatt atagagttaa   8280
caaattaact aatatgattt tgttaataat gataaaatat ttttttttatt attatttcat   8340
aatataaaaa tagtttactt aatataaaaa aaattctatc gttcacaaca aagttggcca   8400
cctaatttaa ccatgcatgt acccatggac catattaggt aaccatcaaa cctgatgaag   8460
agataaagag atgaagactt aagtcataac acaaaaccat aaaaaacaaa aatacaatca   8520
accgtcaatc tgaccaatgc atgaaaaagc tgcaatagtg agtggcgaca caaagcacat   8580
gattttctta caacggagat aaaaccaaaa aaatatttca tgaacaacct agaacaaata   8640
aagcttttat ataataaata tataaataaa taaaggctat ggaataatat acttcaatat   8700
```

atttggatta aataaattgt tggcggggtt gatatattta tacacaccta aagtcacttc 8760
aatctcattt tcacttaact tttatttttt ttttcttttt atttatcata aagagaatat 8820
tgataatata ctttttaaca tatttttatg acatttttta ttggtgaaaa cttattaaaa 8880
atcataaatt ttgtaagtta gatttattta aagagttcct cttcttattt taaatttttt 8940
aataaatttt taaataacta aaatttgtgt taaaaatgtt aaaaaatgtg ttattaaccc 9000
ttctcttcga ggac 9014

<210> SEQ ID NO 36
<211> LENGTH: 30
<212> TYPE: DNA
<213> ORGANISM: Artificial Sequence
<220> FEATURE:
<223> OTHER INFORMATION: oligonucleotide oEAd5-1-1

<400> SEQUENCE: 36
agcggccgca ccatggccac catctctttg 30

<210> SEQ ID NO 37
<211> LENGTH: 30
<212> TYPE: DNA
<213> ORGANISM: Artificial Sequence
<220> FEATURE:
<223> OTHER INFORMATION: olignonucleotide oEAd5-1-2

<400> SEQUENCE: 37
tgcggccgct cagaattcct gggcatcctg 30

<210> SEQ ID NO 38
<211> LENGTH: 4899
<212> TYPE: DNA
<213> ORGANISM: Artificial Sequence
<220> FEATURE:
<223> OTHER INFORMATION: plasmid pKR1136

<400> SEQUENCE: 38
aattccagca cactggcggc cgttactagt ggatccgagc tcggtaccaa gcttgatgca 60
tagcttgagt attctaacgc gtcacctaaa tagcttggcg taatcatggt catagctgtt 120
tcctgtgtga aattgttatc cgctcacaat tccacacaac atacgagccg gaagcataaa 180
gtgtaaagcc tggggtgcct aatgagtgag ctaactcaca ttaattgcgt tgcgctcact 240
gcccgctttc cagtcgggaa acctgtcgtg ccagctgcat taatgaatcg gccaacgcgc 300
ggggagaggc ggtttgcgta ttgggcgctc ttccgcttcc tcgctcactg actcgctgcg 360
ctcggtcgtt cggctgcggc gagcggtatc agctcactca aaggcggtaa tacggttatc 420
cacagaatca ggggataacg caggaaagaa catgtgagca aaaggccagc aaaagcccag 480
gaaccgtaaa aaggccgcgt tgctggcgtt tttccatagg ctccgccccc ctgacgagca 540
tcacaaaaat cgacgctcaa gtcagaggtg gcgaaacccg acaggactat aaagatacca 600
ggcgtttccc cctggaagct ccctcgtgcg ctctcctgtt ccgaccctgc cgcttaccgg 660
atacctgtcc gcctttctcc cttcgggaag cgtggcgctt tctcatagct cacgctgtag 720
gtatctcagt tcggtgtagg tcgttcgctc caagctgggc tgtgtgcacg aaccccccgt 780
tcagcccgac cgctgcgcct tatccggtaa ctatcgtctt gagtccaacc cggtaagaca 840
cgacttatcg ccactggcag cagccactgg taacaggatt agcagagcga ggtatgtagg 900
cggtgctaca gagttcttga agtggtggcc taactacggc tacactagaa ggacagtatt 960
tggtatctgc gctctgctga agccagttac cttcggaaaa agagttggta gctcttgatc 1020

```
cggcaaacaa accaccgctg gtagcggtgg tttttttgtt tgcaagcagc agattacgcg   1080
cagaaaaaaa ggatctcaag aagatccttt gatcttttct acggggtctg acgctcagtg   1140
gaacgaaaac tcacgttaag ggattttggt catgagatta tcaaaaagga tcttcaccta   1200
gatcctttta aattaaaaat gaagttttag cacgtgtcag tcctgctcct cggccacgaa   1260
gtgcacgcag ttgccggccg ggtcgcgcag ggcgaactcc cgcccccacg gctgctcgcc   1320
gatctcggtc atggccggcc cggaggcgtc ccggaagttc gtggacacga cctccgacca   1380
ctcggcgtac agctcgtcca ggccgcgcac ccacacccag gccagggtgt tgtccggcac   1440
cacctggtcc tggaccgcgc tgatgaacag ggtcacgtcg tcccggacca caccggcgaa   1500
gtcgtcctcc acgaagtccc gggagaaccc gagccggtcg gtccagaact cgaccgctcc   1560
ggcgacgtcg cgcgcggtga gcaccggaac ggcactggtc aacttggcca tggtggccct   1620
cctcacgtgc tattattgaa gcatttatca gggttattgt ctcatgagcg gatacatatt   1680
tgaatgtatt tagaaaaata aacaaatagg ggttccgcgc acatttcccc gaaaagtgcc   1740
acctgtatgc ggtgtgaaat accgcacaga tgcgtaagga gaaaataccg catcaggaaa   1800
ttgtaagcgt taataattca gaagaactcg tcaagaaggc gatagaaggc gatgcgctgc   1860
gaatcgggag cggcgatacc gtaaagcacg aggaagcggt cagcccattc gccgccaagc   1920
tcttcagcaa tatcacgggt agccaacgct atgtcctgat agcggtccgc cacacccagc   1980
cggccacagt cgatgaatcc agaaaagcgg ccattttcca ccatgatatt cggcaagcag   2040
gcatcgccat gggtcacgac gagatcctcg ccgtcgggca tgctcgcctt gagcctggcg   2100
aacagttcgg ctggcgcgag cccctgatgc tcttcgtcca gatcatcctg atcgacaaga   2160
ccggcttcca tccgagtacg tgctcgctcg atgcgatgtt tcgcttggtg gtcgaatggg   2220
caggtagccg gatcaagcgt atgcagccgc cgcattgcat cagccatgat ggatactttc   2280
tcggcaggag caaggtgaga tgacaggaga tcctgccccg gcacttcgcc caatagcagc   2340
cagtcccttc ccgcttcagt gacaacgtcg agcacagctg cgcaaggaac gcccgtcgtg   2400
gccagccacg atagccgcgc tgcctcgtct tgcagttcat tcagggcacc ggacaggtcg   2460
gtcttgacaa aaagaaccgg gcgcccctgc gctgacagcc ggaacacggc ggcatcagag   2520
cagccgattg tctgttgtgc ccagtcatag ccgaatagcc tctccaccca agcggccgga   2580
gaacctgcgt gcaatccatc ttgttcaatc atgcgaaacg atcctcatcc tgtctcttga   2640
tcagagcttg atcccctgcg ccatcagatc cttggcggcg agaaagccat ccagtttact   2700
ttgcagggct tcccaacctt accagagggc gccccagctg gcaattccgg ttcgcttgct   2760
gtccataaaa ccgcccagtc tagctatcgc catgtaagcc cactgcaagc tacctgcttt   2820
ctctttgcgc ttgcgttttc ccttgtccag atagcccagt agctgacatt catccggggt   2880
cagcaccgtt tctgcggact ggctttctac gtgaaaagga tctaggtgaa gatccttttt   2940
gataatctca tgcctgacat ttatattccc cagaacatca ggttaatggc gtttttgatg   3000
tcattttcgc ggtggctgag atcagccact tcttccccga taacggagac cggcacactg   3060
gccatatcgg tggtcatcat gcgccagctt tcatccccga tatgcaccac cgggtaaagt   3120
tcacgggaga ctttatctga cagcagacgt gcactggcca gggggatcac catccgtcgc   3180
cccggcgtgt caataatatc actctgtaca tccacaaaca gacgataacg gctctctctt   3240
ttataggtgt aaaccttaaa ctgccgtacg tataggctgc gcaactgttg ggaagggcga   3300
tcggtgcggg cctcttcgct attacgccag ctggcgaaag ggggatgtgc tgcaaggcga   3360
```

```
ttaagttggg taacgccagg gttttcccag tcacgacgtt gtaaaacgac ggccagtgaa   3420

ttgtaatacg actcactata gggcgaattg ggccctctag atgcatgctc gagcggccgc   3480

cagtgtgatg gatatctgca gaattcagga gcggccgcac catggccacc atctctttga   3540

ctactgagca acttttagaa cacccagaac tggttgcaat tgatggggtg ttgtacgatc   3600

tcttcggact ggcgaaagtg catccaggtg gcaacctcat tgaagccgcc ggtgcctccg   3660

acggaaccgc cctgttctac tccatgcacc ctggagtgaa gccagagaat tcgaagctgc   3720

tgcagcaatt tgcccgaggc aaacacgaac gaagctcgaa ggacccagtg tacacctttg   3780

acagtccctt cgcccaggat gtcaagcaga gcgttcggga ggtcatgaag gggcgcaact   3840

ggtacgccac gcccggcttt tggctgcgga ccgcgctgat catcgcgtgc actgccatag   3900

gcgaatggta ttggatcact accggggcag tgatgtgggg catcttcacc gggtacttcc   3960

acagccagat tgggttggcg attcaacacg atgcctctca cggagccatc agcaaaaagc   4020

cctgggtgaa cgcctttttc gcctacggca tcgacgccat tggatcctcc cgctggatct   4080

ggctgcagtc ccacattatg cgccaccaca cctacaccaa ccagcatggc ctggacctgg   4140

acgctgcctc ggcggagccg ttcattttgt tccactccta cccggcaaca aatgcgtcac   4200

gaaagtggta ccatcggttc caggcgtggt acatgtacat cgttttgggg atgtatggtg   4260

tgtcgatggt gtacaatccg atgtacttgt tcacgatgca gcacaacgac acaatcccag   4320

aggccacctc tcttagacca ggcagctttt tcaaccggca gcgcgccttc gccgtttccc   4380

tccgcctact gttcatcttc cgcaacgcct tcctcccctg gtacatcgcg ggcgcctctc   4440

cgctgctcac catcctgctg gtgccaacgg tcacaggcat cttcttgaca tttgtttttg   4500

tgctgtccca taactttgaa ggcgctgagc ggacccccga aaagaactgc aaggccaaaa   4560

gggccaagga ggggaaggag gtccgcgatg tagaggagga ccgggtggac tggtaccggg   4620

cgcaggccga gaccgcggcg acctacgggg gcagcgtcgg gatgatgctg accggcggtt   4680

tgaacctgca gatcgagcac cacttgttcc cccgcatgtc ctcttggcac taccccttca   4740

tccaagatac ggtgcgggaa tgttgcaagc gccatggcgt gcgctacaca tactacccga   4800

ccatcctgga gaatataatg tccacgctcc gctacatgca gaaggtgggc gtggcccaca   4860

caattcagga tgcccaggaa ttctgagcgg ccgcacctg                          4899
```

<210> SEQ ID NO 39
<211> LENGTH: 5561
<212> TYPE: DNA
<213> ORGANISM: Artificial Sequence
<220> FEATURE:
<223> OTHER INFORMATION: plasmid pKR767

<400> SEQUENCE: 39

```
catggtcaat caatgagacg ccaacttctt aatctattga gacctgcagg tctagaaggg     60

cggatccccg ggtaccgagc tcgaattcac tggccgtcgt tttacaacgt cgtgactggg    120

aaaaccctgg cgttacccaa cttaatcgcc ttgcagcaca tccccctttc gccagctggc    180

gtaatagcga agaggcccgc accgatcgcc cttcccaaca gttgcgcagc ctgaatggcg    240

aatggcgcct gatgcggtat tttctcctta cgcatctgtg cggtatttca caccgcatat    300

ggtgcactct cagtacaatc tgctctgatg ccgcatagtt aagccagccc cgacacccgc    360

caacacccgc tgacgcgccc tgacgggctt gtctgctccc ggcatccgct tacagacaag    420

ctgtgaccgt ctccgggagc tgcatgtgtc agaggttttc accgtcatca ccgaaacgcg    480

cgagacgaaa gggcctcgtg atacgcctat ttttataggt taatgtcatg ataataatgg    540
```

```
tttcttagac gtcaggtggc acttttcggg gaaatgtgcg cggaacccct atttgtttat    600
ttttctaaat acattcaaat atgtatccgc tcatgagaca ataaccctga taaatgcttc    660
aataatattg aaaaaggaag agtatgagta ttcaacattt ccgtgtcgcc cttattccct    720
tttttgcggc attttgcctt cctgtttttg ctcacccaga aacgctggtg aaagtaaaag    780
atgctgaaga tcagttgggt gcacgagtgg gttacatcga actggatctc aacagcggta    840
agatccttga gagttttcgc cccgaagaac gttttccaat gatgagcact tttaaagttc    900
tgctatgtgg cgcggtatta tcccgtattg acgccgggca agagcaactc ggtcgccgca    960
tacactattc tcagaatgac ttggttgagt actcaccagt cacagaaaag catcttacgg   1020
atggcatgac agtaagagaa ttatgcagtg ctgccataac catgagtgat aacactgcgg   1080
ccaacttact tctgacaacg atcggaggac cgaaggagct aaccgctttt ttgcacaaca   1140
tgggggatca tgtaactcgc cttgatcgtt gggaaccgga gctgaatgaa gccataccaa   1200
acgacgagcg tgacaccacg atgcctgtag caatggcaac aacgttgcgc aaactattaa   1260
ctggcgaact acttactcta gcttcccggc aacaattaat agactggatg gaggcggata   1320
aagttgcagg accacttctg cgctcggccc ttccggctgg ctggtttatt gctgataaat   1380
ctggagccgg tgagcgtggg tctcgcggta tcattgcagc actggggcca gatggtaagc   1440
cctcccgtat cgtagttatc tacacgacgg ggagtcaggc aactatggat gaacgaaata   1500
gacagatcgc tgagataggt gcctcactga ttaagcattg gtaactgtca gaccaagttt   1560
actcatatat actttagatt gatttaaaac ttcattttta atttaaaagg atctaggtga   1620
agatcctttt tgataatctc atgaccaaaa tcccttaacg tgagttttcg ttccactgag   1680
cgtcagaccc cgtagaaaag atcaaaggat cttcttgaga tccttttttt ctgcgcgtaa   1740
tctgctgctt gcaaacaaaa aaaccaccgc taccagcggt ggtttgtttg ccggatcaag   1800
agctaccaac tctttttccg aaggtaactg gcttcagcag agcgcagata ccaaatactg   1860
tccttctagt gtagccgtag ttaggccacc acttcaagaa ctctgtagca ccgcctacat   1920
acctcgctct gctaatcctg ttaccagtgg ctgctgccag tggcgataag tcgtgtctta   1980
ccgggttgga ctcaagacga tagttaccgg ataaggcgca gcggtcgggc tgaacggggg   2040
gttcgtgcac acagcccagc ttggagcgaa cgacctacac cgaactgaga tacctacagc   2100
gtgagctatg agaaagcgcc acgcttcccg aagggagaaa ggcggacagg tatccggtaa   2160
gcggcagggt cggaacagga gagcgcacga gggagcttcc agggggaaac gcctggtatc   2220
tttatagtcc tgtcgggttt cgccacctct gacttgagcg tcgatttttg tgatgctcgt   2280
caggggggcg gagcctatgg aaaaacgcca gcaacgcggc ctttttacgg ttcctggcct   2340
tttgctggcc ttttgctcac atgttctttc ctgcgttatc ccctgattct gtggataacc   2400
gtattaccgc ctttgagtga gctgataccg ctcgccgcag ccgaacgacc gagcgcagcg   2460
agtcagtgag cgaggaagcg gaagagcgcc caatacgcaa accgcctctc cccgcgcgtt   2520
ggccgattca ttaatgcagc tggcacgaca ggtttcccga ctggaaagcg ggcagtgagc   2580
gcaacgcaat taatgtgagt tagctcactc attaggcacc ccaggcttta cactttatgc   2640
ttccggctcg tatgttgtgt ggaattgtga gcggataaca atttcacaca ggaaacagct   2700
atgaccatga ttacgccaag cttgcatgcc tgcaggctag cctaagtacg tactcaaaat   2760
gccaacaaat aaaaaaaaag ttgctttaat aatgccaaaa caaattaata aaacacttac   2820
aacaccggat tttttttaat taaaatgtgc catttaggat aaatagttaa tatttttaat   2880
```

-continued

```
aattatttaa aaagccgtat ctactaaaat gatttttatt tggttgaaaa tattaatatg   2940
tttaaatcaa cacaatctat caaaattaaa ctaaaaaaaa aataagtgta cgtggttaac   3000
attagtacag taatataaga ggaaaatgag aaattaagaa attgaaagcg agtctaattt   3060
ttaaattatg aacctgcata tataaaagga aagaaagaat ccaggaagaa aagaaatgaa   3120
accatgcatg gtcccctcgt catcacgagt ttctgccatt tgcaatagaa acactgaaac   3180
acctttctct ttgtcactta attgagatgc cgaagccacc tcacaccatg aacttcatga   3240
ggtgtagcac ccaaggcttc catagccatg catactgaag aatgtctcaa gctcagcacc   3300
ctacttctgt gacgtgtccc tcattcacct tcctctcttc cctataaata accacgcctc   3360
aggttctccg cttcacaact caaacattct ctccattggt ccttaaacac tcatcagtca   3420
tcaccgcggc cgcatgggaa cggaccaagg aaaaaccttc acctgggaag agctggcggc   3480
ccataacacc aaggacgacc tactcttggc catccgcggc agggtgtacg atgtcacaaa   3540
gttcttgagc cgccatcctg gtggagtgga cactctcctg ctcggagctg gccgagatgt   3600
tactccggtc tttgagatgt atcacgcgtt tggggctgca gatgccatta tgaagaagta   3660
ctatgtcggt acactggtct cgaatgagct gcccatcttc ccggagccaa cggtgttcca   3720
caaaaccatc aagacgagag tcgagggcta ctttacggat cggaacattg atcccaagaa   3780
tagaccagag atctggggac gatacgctct tatctttgga tccttgatcg cttcctacta   3840
cgcgcagctc tttgtgcctt tcgttgtcga acgcacatgg cttcaggtgg tgtttgcaat   3900
catcatggga tttgcgtgcg cacaagtcgg actcaaccct cttcatgatg cgtctcactt   3960
ttcagtgacc cacaacccca ctgtctggaa gattctggga gccacgcacg actttttcaa   4020
cggagcatcg tacctggtgt ggatgtacca acatatgctc ggccatcacc cctacaccaa   4080
cattgctgga gcagatcccg acgtgtcgac gtctgagccc gatgttcgtc gtatcaagcc   4140
caaccaaaag tggtttgtca accacatcaa ccagcacatg tttgttcctt tcctgtacgg   4200
actgctggcg ttcaaggtgc gcattcagga catcaacatt ttgtactttg tcaagaccaa   4260
tgacgctatt cgtgtcaatc ccatctcgac atggcacact gtgatgttct ggggcggcaa   4320
ggctttcttt gtctggtatc gcctgattgt tcccctgcag tatctgcccc tgggcaaggt   4380
gctgctcttg ttcacggtcg cggacatggt gtcgtcttac tggctggcgc tgaccttcca   4440
ggcgaaccac gttgttgagg aagttcagtg gccgttgcct gacgagaacg ggatcatcca   4500
aaaggactgg gcagctatgc aggtcgagac tacgcaggat tacgcacacg attcgcacct   4560
ctggaccagc atcactggca gcttgaacta ccaggctgtg caccatctgt tccccaacgt   4620
gtcgcagcac cattatcccg atattctggc catcatcaag aacacctgca gcgagtacaa   4680
ggttccatac cttgtcaagg atacgttttg gcaagcattt gcttcacatt tggagcactt   4740
gcgtgttctt ggactccgtc ccaaggaaga gtaggcggcc gcatttcgca ccaaatcaat   4800
gaaagtaata atgaaaagtc tgaataagaa tacttaggct tagatgcctt tgttacttgt   4860
gtaaaataac ttgagtcatg tacctttggc ggaaacagaa taaataaaag gtgaaattcc   4920
aatgctctat gtataagtta gtaatactta atgtgttcta cggttgtttc aatatcatca   4980
aactctaatt gaaactttag aaccacaaat ctcaatcttt tcttaatgaa atgaaaaatc   5040
ttaattgtac catgtttatg ttaaacacct tacaattggt tggagaggag gaccaaccga   5100
tgggacaaca ttgggagaaa gagattcaat ggagatttgg ataggagaac aacattcttt   5160
ttcacttcaa tacaagatga gtgcaacact aaggatatgt atgagacttt cagaagctac   5220
gacaacatag atgagtgagg tggtgattcc tagcaagaaa gacattagag gaagccaaaa   5280
```

```
tcgaacaagg aagacatcaa gggcaagaga caggaccatc catctcagga aaaggagctt   5340

tgggatagtc cgagaagttg tacaagaaat tttttggagg gtgagtgatg cattgctggt   5400

gactttaact caatcaaaat tgagaaagaa agaaaaggga gggggctcac atgtgaatag   5460

aagggaaacg ggagaatttt acagttttga tctaatgggc atcccagcta gtggtaacat   5520

attcaccatg tttaaccttc acgtacgtct agaggatccc c                       5561
```

<210> SEQ ID NO 40
<211> LENGTH: 1338
<212> TYPE: DNA
<213> ORGANISM: Mortierella alpina

<400> SEQUENCE: 40

```
atgggaacgg accaaggaaa aaccttcacc tgggaagagc tggcggccca taacaccaag     60

gacgacctac tcttggccat ccgcggcagg gtgtacgatg tcacaaagtt cttgagccgc    120

catcctggtg gagtggacac tctcctgctc ggagctggcc gagatgttac tccggtcttt    180

gagatgtatc acgcgtttgg ggctgcagat gccattatga agaagtacta tgtcggtaca    240

ctggtctcga atgagctgcc catcttcccg gagccaacgg tgttccacaa aaccatcaag    300

acgagagtcg agggctactt tacggatcgg aacattgatc ccaagaatag accagagatc    360

tggggacgat acgctcttat ctttggatcc ttgatcgctt cctactacgc gcagctcttt    420

gtgcctttcg ttgtcgaacg cacatggctt caggtggtgt ttgcaatcat catgggattt    480

gcgtgcgcac aagtcggact caaccctctt catgatgcgt ctcacttttc agtgacccac    540

aaccccactg tctggaagat tctgggagcc acgcacgact tttcaacgg agcatcgtac     600

ctggtgtgga tgtaccaaca tatgctcggc catcacccct acaccaacat tgctggagca    660

gatcccgacg tgtcgacgtc tgagcccgat gttcgtcgta tcaagcccaa ccaaaagtgg    720

tttgtcaacc acatcaacca gcacatgttt gttcctttcc tgtacggact gctggcgttc    780

aaggtgcgca ttcaggacat caacattttg tactttgtca agaccaatga cgctattcgt    840

gtcaatccca tctcgacatg gcacactgtg atgttctggg gcggcaaggc tttctttgtc    900

tggtatcgcc tgattgttcc cctgcagtat ctgcccctgg gcaaggtgct gctcttgttc    960

acggtcgcgg acatggtgtc gtcttactgg ctggcgctga ccttccaggc gaaccacgtt   1020

gttgaggaag ttcagtggcc gttgcctgac gagaacggga tcatccaaaa ggactgggca   1080

gctatgcagg tcgagactac gcaggattac gcacacgatt cgcacctctg gaccagcatc   1140

actggcagct tgaactacca ggctgtgcac catctgttcc ccaacgtgtc gcagcaccat   1200

tatcccgata ttctggccat catcaagaac acctgcagcg agtacaaggt tccatacctt   1260

gtcaaggata cgttttggca agcatttgct tcacatttgg agcacttgcg tgttcttgga   1320

ctccgtccca aggaagag                                                 1338
```

<210> SEQ ID NO 41
<211> LENGTH: 5661
<212> TYPE: DNA
<213> ORGANISM: Artificial Sequence
<220> FEATURE:
<223> OTHER INFORMATION: plasmid pKR974

<400> SEQUENCE: 41

```
gtacgtctag aggatccccc atggtcaatc aatgagacgc caacttctta atctattgag     60

acctgcaggt ctagaagggc ggatccccgg gtaccgagct cgaattcact ggccgtcgtt    120
```

-continued

```
ttacaacgtc gtgactggga aaaccctggc gttacccaac ttaatcgcct tgcagcacat    180
ccccctttcg ccagctggcg taatagcgaa gaggcccgca ccgatcgccc ttcccaacag    240
ttgcgcagcc tgaatggcga atggcgcctg atgcggtatt ttctccttac gcatctgtgc    300
ggtatttcac accgcatatg gtgcactctc agtacaatct gctctgatgc cgcatagtta    360
agccagcccc gacacccgcc aacacccgct gacgcgccct gacgggcttg tctgctcccg    420
gcatccgctt acagacaagc tgtgaccgtc tccgggagct gcatgtgtca gaggttttca    480
ccgtcatcac cgaaacgcgc gagacgaaag ggcctcgtga tacgcctatt tttataggtt    540
aatgtcatga taataatggt ttcttagacg tcaggtggca cttttcgggg aaatgtgcgc    600
ggaaccccta tttgtttatt tttctaaata cattcaaata tgtatccgct catgagacaa    660
taaccctgat aaatgcttca ataatattga aaaaggaaga gtatgagtat tcaacatttc    720
cgtgtcgccc ttattccctt ttttgcggca ttttgccttc ctgtttttgc tcacccagaa    780
acgctggtga aagtaaaaga tgctgaagat cagttgggtg cacgagtggg ttacatcgaa    840
ctggatctca acagcggtaa gatccttgag agttttcgcc ccgaagaacg ttttccaatg    900
atgagcactt ttaaagttct gctatgtggc gcggtattat cccgtattga cgccgggcaa    960
gagcaactcg gtcgccgcat acactattct cagaatgact tggttgagta ctcaccagtc   1020
acagaaaagc atcttacgga tggcatgaca gtaagagaat tatgcagtgc tgccataacc   1080
atgagtgata acactgcggc caacttactt ctgacaacga tcggaggacc gaaggagcta   1140
accgcttttt tgcacaacat gggggatcat gtaactcgcc ttgatcgttg ggaaccggag   1200
ctgaatgaag ccataccaaa cgacgagcgt gacaccacga tgcctgtagc aatggcaaca   1260
acgttgcgca aactattaac tggcgaacta cttactctag cttcccggca acaattaata   1320
gactggatgg aggcggataa agttgcagga ccacttctgc gctcggccct tccggctggc   1380
tggtttattg ctgataaatc tggagccggt gagcgtgggt ctcgcggtat cattgcagca   1440
ctggggccag atggtaagcc ctcccgtatc gtagttatct acacgacggg gagtcaggca   1500
actatggatg aacgaaatag acagatcgct gagataggtg cctcactgat taagcattgg   1560
taactgtcag accaagttta ctcatatata ctttagattg atttaaaact tcatttttaa   1620
tttaaaagga tctaggtgaa gatccttttt gataatctca tgaccaaaat cccttaacgt   1680
gagttttcgt tccactgagc gtcagacccc gtagaaaaga tcaaaggatc ttcttgagat   1740
cctttttttc tgcgcgtaat ctgctgcttg caaacaaaaa aaccaccgct accagcggtg   1800
gtttgtttgc cggatcaaga gctaccaact ctttttccga aggtaactgg cttcagcaga   1860
gcgcagatac caaatactgt ccttctagtg tagccgtagt taggccacca cttcaagaac   1920
tctgtagcac cgcctacata cctcgctctg ctaatcctgt taccagtggc tgctgccagt   1980
ggcgataagt cgtgtcttac cgggttggac tcaagacgat agttaccgga taaggcgcag   2040
cggtcgggct gaacgggggg ttcgtgcaca cagcccagct tggagcgaac gacctacacc   2100
gaactgagat acctacagcg tgagctatga gaaagcgcca cgcttcccga agggagaaag   2160
gcggacaggt atccggtaag cggcagggtc ggaacaggag agcgcacgag ggagcttcca   2220
gggggaaacg cctggtatct ttatagtcct gtcgggtttc gccacctctg acttgagcgt   2280
cgatttttgt gatgctcgtc aggggggcgg agcctatgga aaaacgccag caacgcggcc   2340
tttttacggt tcctggcctt ttgctggcct tttgctcaca tgttctttcc tgcgttatcc   2400
cctgattctg tggataaccg tattaccgcc tttgagtgag ctgataccgc tcgccgcagc   2460
cgaacgaccg agcgcagcga gtcagtgagc gaggaagcgg aagagcgccc aatacgcaaa   2520
```

```
ccgcctctcc ccgcgcgttg gccgattcat taatgcagct ggcacgacag gtttcccgac   2580
tggaaagcgg gcagtgagcg caacgcaatt aatgtgagtt agctcactca ttaggcaccc   2640
caggctttac actttatgct tccggctcgt atgttgtgtg gaattgtgag cggataacaa   2700
tttcacacag gaaacagcta tgaccatgat tacgccaagc ttgcatgcct gcaggctagc   2760
ctaagtacgt actcaaaatg ccaacaaata aaaaaaaagt tgctttaata atgccaaaac   2820
aaattaataa aacacttaca acaccggatt ttttttaatt aaaatgtgcc atttaggata   2880
aatagttaat atttttaata attatttaaa aagccgtatc tactaaaatg atttttattt   2940
ggttgaaaat attaatatgt ttaaatcaac acaatctatc aaaattaaac taaaaaaaaa   3000
ataagtgtac gtggttaaca ttagtacagt aatataagag gaaaatgaga aattaagaaa   3060
ttgaaagcga gtctaatttt taaattatga acctgcatat ataaaaggaa agaaagaatc   3120
caggaagaaa agaaatgaaa ccatgcatgg tcccctcgtc atcacgagtt tctgccattt   3180
gcaatagaaa cactgaaaca cctttctctt tgtcacttaa ttgagatgcc gaagccacct   3240
cacaccatga acttcatgag gtgtagcacc caaggcttcc atagccatgc atactgaaga   3300
atgtctcaag ctcagcaccc tacttctgtg acgtgtccct cattcacctt cctctcttcc   3360
ctataaataa ccacgcctca ggttctccgc ttcacaactc aaacattctc tccattggtc   3420
cttaaacact catcagtcat caccgcggcc gccaattcat ggccccgcag acggagctcc   3480
gccagcgcca cgccgccgtc gccgagacgc cggtggccgg caagaaggcc tttacatggc   3540
aggaggtcgc gcagcacaac acggcggcct cggcctggat cattatccgc ggcaaggtct   3600
acgacgtgac cgagtgggcc aacaagcacc ccggcggccg cgagatggtg ctgctgcacg   3660
ccggtcgcga ggccaccgac acgttcgact cgtaccaccc gttcagcgac aaggccgagt   3720
cgatcttgaa caagtatgag attggcacgt tcacgggccc gtccgagttt ccgaccttca   3780
agccggacac gggcttctac aaggagtgcc gcaagcgcgt tggcgagtac ttcaagaaga   3840
acaacctcca tccgcaggac ggcttcccgg gcctctggcg catgatggtc gtgtttgcgg   3900
tcgccggcct cgccttgtac ggcatgcact tttcgactat ctttgcgctg cagctcgcgg   3960
ccgcggcgct ctttggcgtc tgccaggcgc tgccgctgct ccacgtcatg cacgactcgt   4020
cgcacgcgtc gtacaccaac atgccgttct tccattacgt cgtcggccgc tttgccatgg   4080
actggtttgc cggcggctcg atggtgtcat ggctcaacca gcacgtcgtg ggccaccaca   4140
tctacacgaa cgtcgcgggc tcggacccgg atcttccggt caacatggac ggcgacatcc   4200
gccgcatcgt gaaccgccag gtgttccagc ccatgtacgc attccagcac atctaccttc   4260
cgccgctcta tggcgtgctt ggcctcaagt tccgcatcca ggacttcacc gacacgttcg   4320
gctcgcacac gaacggcccg atccgcgtca acccgcacgc gctctcgacg tggatggcca   4380
tgatcagctc caagtcgttc tgggccttct accgcgtgta ccttccgctt gccgtgctcc   4440
agatgcccat caagacgtac cttgcgatct tcttcctcgc cgagtttgtc acgggctggt   4500
acctcgcgtt caacttccaa gtaagccatg tctcgaccga gtgcggctac ccatgcggcg   4560
acgaggccaa gatggcgctc caggacgagt gggcagtctc gcaggtcaag acgtcggtcg   4620
actacgccca tggctcgtgg atgacgacgt tccttgccgg cgcgctcaac taccaggtcg   4680
tgcaccactt gttccccagc gtgtcgcagt accactaccc ggcgatcgcg cccatcatcg   4740
tcgacgtctg caaggagtac aacatcaagt acgccatctt gccggacttt acggcggcgt   4800
tcgttgccca cttgaagcac ctccgcaaca tgggccagca gggcatcgcc gccacgatcc   4860
```

-continued

```
acatgggcta actcgagctc agctagatcg cggccgcatt tcgcaccaaa tcaatgaaag   4920

taataatgaa aagtctgaat aagaatactt aggcttagat gcctttgtta cttgtgtaaa   4980

ataacttgag tcatgtacct ttggcggaaa cagaataaat aaaaggtgaa attccaatgc   5040

tctatgtata agttagtaat acttaatgtg ttctacggtt gtttcaatat catcaaactc   5100

taattgaaac tttagaacca caaatctcaa tcttttctta atgaaatgaa aaatcttaat   5160

tgtaccatgt ttatgttaaa caccttacaa ttaattggtt ggagaggagg accaaccgat   5220

gggacaacat tgggagaaag agattcaatg gagatttgga taggagaaca acattctttt   5280

tcacttcaat acaagatgag tgcaacacta aggatatgta tgagactttc agaagctacg   5340

acaacataga tgagtgaggt ggtgattcct agcaagaaag acattagagg aagccaaaat   5400

cgaacaagga agacatcaag ggcaagagac aggaccatcc atctcaggaa aaggagcttt   5460

gggatagtcc gagaagttgt acaagaaatt ttttggaggg tgagtgatgc attgctggtg   5520

actttaactc aatcaaaatt gagaaagaaa gaaaagggag ggggctcaca tgtgaataga   5580

agggaaacgg gagaatttta cagttttgat ctaatgggca tcccagctag tggtaacata   5640

ttcaccatgt ttaaccttca c                                              5661
```

<210> SEQ ID NO 42
<211> LENGTH: 1413
<212> TYPE: DNA
<213> ORGANISM: Saprolegnia diclina

<400> SEQUENCE: 42

```
atggccccgc agacggagct ccgccagcgc cacgccgccg tcgccgagac gccggtggcc     60

ggcaagaagg cctttacatg gcaggaggtc gcgcagcaca acacggcggc ctcggcctgg    120

atcattatcc gcggcaaggt ctacgacgtg accgagtggg ccaacaagca ccccggcggc    180

cgcgagatgg tgctgctgca cgccggtcgc gaggccaccg acacgttcga ctcgtaccac    240

ccgttcagcg acaaggccga gtcgatcttg aacaagtatg agattggcac gttcacgggc    300

ccgtccgagt ttccgacctt caagccggac acgggcttct acaaggagtg ccgcaagcgc    360

gttggcgagt acttcaagaa gaacaacctc catccgcagg acggcttccc gggcctctgg    420

cgcatgatgg tcgtgtttgc ggtcgccggc ctcgccttgt acggcatgca cttttcgact    480

atctttgcgc tgcagctcgc ggccgcggcg ctctttggcg tctgccaggc gctgccgctg    540

ctccacgtca tgcacgactc gtcgcacgcg tcgtacacca acatgccgtt cttccattac    600

gtcgtcggcc gctttgccat ggactggttt gccggcggct cgatggtgtc atggctcaac    660

cagcacgtcg tgggccacca catctacacg aacgtcgcgg gctcggaccc ggatcttccg    720

gtcaacatgg acggcgacat ccgccgcatc gtgaaccgcc aggtgttcca gcccatgtac    780

gcattccagc acatctacct tccgccgctc tatggcgtgc ttggcctcaa gttccgcatc    840

caggacttca ccgacacgtt cggctcgcac acgaacggcc cgatccgcgt caacccgcac    900

gcgctctcga cgtggatggc catgatcagc tccaagtcgt tctgggcctt ctaccgcgtg    960

taccttccgc ttgccgtgct ccagatgccc atcaagacgt accttgcgat cttcttcctc   1020

gccgagtttg tcacgggctg gtacctcgcg ttcaacttcc aagtaagcca tgtctcgacc   1080

gagtgcggct acccatgcgg cgacgaggcc aagatggcgc tccaggacga gtgggcagtc   1140

tcgcaggtca agacgtcggt cgactacgcc catggctcgt ggatgacgac gttccttgcc   1200

ggcgcgctca actaccaggt cgtgcaccac ttgttcccca gcgtgtcgca gtaccactac   1260

ccggcgatcg cgcccatcat cgtcgacgtc tgcaaggagt acaacatcaa gtacgccatc   1320
```

```
ttgccggact ttacggcggc gttcgttgcc cacttgaagc acctccgcaa catgggccag   1380

cagggcatcg ccgccacgat ccacatgggc taa                                1413
```

<210> SEQ ID NO 43
<211> LENGTH: 5592
<212> TYPE: DNA
<213> ORGANISM: Artificial Sequence
<220> FEATURE:
<223> OTHER INFORMATION: plasmid pKR1139

<400> SEQUENCE: 43

```
ggccgcattt cgcaccaaat caatgaaagt aataatgaaa agtctgaata agaatactta     60

ggcttagatg cctttgttac ttgtgtaaaa taacttgagt catgtacctt tggcggaaac    120

agaataaata aaaggtgaaa ttccaatgct ctatgtataa gttagtaata cttaatgtgt    180

tctacggttg tttcaatatc atcaaactct aattgaaact ttagaaccac aaatctcaat    240

cttttcttaa tgaaatgaaa aatcttaatt gtaccatgtt tatgttaaac accttacaat    300

taattggttg gagaggagga ccaaccgatg ggacaacatt gggagaaaga gattcaatgg    360

agatttggat aggagaacaa cattcttttt cacttcaata caagatgagt gcaacactaa    420

ggatatgtat gagactttca gaagctacga caacatagat gagtgaggtg gtgattccta    480

gcaagaaaga cattagagga agccaaaatc gaacaaggaa gacatcaagg gcaagagaca    540

ggaccatcca tctcaggaaa aggagctttg ggatagtccg agaagttgta caagaaattt    600

tttggagggt gagtgatgca ttgctggtga ctttaactca atcaaaattg agaaagaaag    660

aaaagggagg gggctcacat gtgaatagaa gggaaacggg agaattttac agttttgatc    720

taatgggcat cccagctagt ggtaacatat tcaccatgtt taaccttcac gtacgtctag    780

aggatccccc atggtcaatc aatgagacgc caacttctta atctattgag acctgcaggt    840

ctagaagggc ggatccccgg gtaccgagct cgaattcact ggccgtcgtt ttacaacgtc    900

gtgactggga aaaccctggc gttacccaac ttaatcgcct tgcagcacat ccccctttcg    960

ccagctggcg taatagcgaa gaggcccgca ccgatcgccc ttcccaacag ttgcgcagcc   1020

tgaatggcga atggcgcctg atgcggtatt ttctccttac gcatctgtgc ggtatttcac   1080

accgcatatg gtgcactctc agtacaatct gctctgatgc cgcatagtta agccagcccc   1140

gacacccgcc aacacccgct gacgcgccct gacgggcttg tctgctcccg gcatccgctt   1200

acagacaagc tgtgaccgtc tccgggagct gcatgtgtca gaggttttca ccgtcatcac   1260

cgaaacgcgc gagacgaaag ggcctcgtga tacgcctatt tttataggtt aatgtcatga   1320

taataatggt ttcttagacg tcaggtggca cttttcgggg aaatgtgcgc ggaaccccta   1380

tttgtttatt tttctaaata cattcaaata tgtatccgct catgagacaa taaccctgat   1440

aaatgcttca ataatattga aaaaggaaga gtatgagtat tcaacatttc cgtgtcgccc   1500

ttattccctt ttttgcggca ttttgccttc ctgtttttgc tcacccagaa acgctggtga   1560

aagtaaaaga tgctgaagat cagttgggtg cacgagtggg ttacatcgaa ctggatctca   1620

acagcggtaa gatccttgag agttttcgcc ccgaagaacg ttttccaatg atgagcactt   1680

ttaaagttct gctatgtggc gcggtattat cccgtattga cgccgggcaa gagcaactcg   1740

gtcgccgcat acactattct cagaatgact tggttgagta ctcaccagtc acagaaaagc   1800

atcttacgga tggcatgaca gtaagagaat tatgcagtgc tgccataacc atgagtgata   1860

acactgcggc caacttactt ctgacaacga tcggaggacc gaaggagcta accgcttttt   1920
```

```
tgcacaacat gggggatcat gtaactcgcc ttgatcgttg ggaaccggag ctgaatgaag   1980
ccataccaaa cgacgagcgt gacaccacga tgcctgtagc aatggcaaca acgttgcgca   2040
aactattaac tggcgaacta cttactctag cttcccggca acaattaata gactggatgg   2100
aggcggataa agttgcagga ccacttctgc gctcggccct tccggctggc tggtttattg   2160
ctgataaatc tggagccggt gagcgtgggt ctcgcggtat cattgcagca ctggggccag   2220
atggtaagcc ctcccgtatc gtagttatct acacgacggg gagtcaggca actatggatg   2280
aacgaaatag acagatcgct gagataggtg cctcactgat taagcattgg taactgtcag   2340
accaagttta ctcatatata ctttagattg atttaaaact tcatttttaa tttaaaagga   2400
tctaggtgaa gatccttttt gataatctca tgaccaaaat cccttaacgt gagttttcgt   2460
tccactgagc gtcagacccc gtagaaaaga tcaaaggatc ttcttgagat cctttttttc   2520
tgcgcgtaat ctgctgcttg caaacaaaaa aaccaccgct accagcggtg gtttgtttgc   2580
cggatcaaga gctaccaact ctttttccga aggtaactgg cttcagcaga gcgcagatac   2640
caaatactgt ccttctagtg tagccgtagt taggccacca cttcaagaac tctgtagcac   2700
cgcctacata cctcgctctg ctaatcctgt taccagtggc tgctgccagt ggcgataagt   2760
cgtgtcttac cgggttggac tcaagacgat agttaccgga taaggcgcag cggtcgggct   2820
gaacgggggg ttcgtgcaca cagcccagct tggagcgaac gacctacacc gaactgagat   2880
acctacagcg tgagctatga gaaagcgcca cgcttcccga agggagaaag gcggacaggt   2940
atccggtaag cggcagggtc ggaacaggag agcgcacgag ggagcttcca gggggaaacg   3000
cctggtatct ttatagtcct gtcgggtttc gccacctctg acttgagcgt cgatttttgt   3060
gatgctcgtc aggggggcgg agcctatgga aaaacgccag caacgcggcc tttttacggt   3120
tcctggcctt ttgctggcct tttgctcaca tgttctttcc tgcgttatcc cctgattctg   3180
tggataaccg tattaccgcc tttgagtgag ctgataccgc tcgccgcagc cgaacgaccg   3240
agcgcagcga gtcagtgagc gaggaagcgg aagagcgccc aatacgcaaa ccgcctctcc   3300
ccgcgcgttg gccgattcat taatgcagct ggcacgacag gtttcccgac tggaaagcgg   3360
gcagtgagcg caacgcaatt aatgtgagtt agctcactca ttaggcaccc caggctttac   3420
actttatgct tccggctcgt atgttgtgtg gaattgtgag cggataacaa tttcacacag   3480
gaaacagcta tgaccatgat tacgccaagc ttgcatgcct gcaggctagc ctaagtacgt   3540
actcaaaatg ccaacaaata aaaaaaaagt tgctttaata atgccaaaac aaattaataa   3600
aacacttaca acaccggatt ttttttaatt aaaatgtgcc atttaggata aatagttaat   3660
atttttaata attatttaaa aagccgtatc tactaaaatg atttttattt ggttgaaaat   3720
attaatatgt ttaaatcaac acaatctatc aaaattaaac taaaaaaaaa ataagtgtac   3780
gtggttaaca ttagtacagt aatataagag gaaaatgaga aattaagaaa ttgaaagcga   3840
gtctaatttt taaattatga acctgcatat ataaaaggaa agaaagaatc caggaagaaa   3900
agaaatgaaa ccatgcatgg tcccctcgtc atcacgagtt tctgccattt gcaatagaaa   3960
cactgaaaca cctttctctt tgtcacttaa ttgagatgcc gaagccacct cacaccatga   4020
acttcatgag gtgtagcacc caaggcttcc atagccatgc atactgaaga atgtctcaag   4080
ctcagcaccc tacttctgtg acgtgtccct cattcacctt cctctcttcc ctataaataa   4140
ccacgcctca ggttctccgc ttcacaactc aaacattctc tccattggtc cttaaacact   4200
catcagtcat caccgcggcc gcaccatggc caccatctct ttgactactg agcaactttt   4260
agaacaccca gaactggttg caattgatgg ggtgttgtac gatctcttcg gactggcgaa   4320
```

```
agtgcatcca ggtggcaacc tcattgaagc cgccggtgcc tccgacggaa ccgccctgtt   4380

ctactccatg caccctggag tgaagccaga gaattcgaag ctgctgcagc aatttgcccg   4440

aggcaaacac gaacgaagct cgaaggaccc agtgtacacc tttgacagtc ccttcgccca   4500

ggatgtcaag cagagcgttc gggaggtcat gaaggggcgc aactggtacg ccacgcccgg   4560

cttttggctg cggaccgcgc tgatcatcgc gtgcactgcc ataggcgaat ggtattggat   4620

cactaccggg gcagtgatgt ggggcatctt caccgggtac ttccacagcc agattgggtt   4680

ggcgattcaa cacgatgcct ctcacggagc catcagcaaa aagccctggg tgaacgcctt   4740

tttcgcctac ggcatcgacg ccattggatc ctcccgctgg atctggctgc agtcccacat   4800

tatgcgccac cacacctaca ccaaccagca tggcctggac ctggacgctg cctcggcgga   4860

gccgttcatt ttgttccact cctacccggc aacaaatgcg tcacgaaagt ggtaccatcg   4920

gttccaggcg tggtacatgt acatcgtttt ggggatgtat ggtgtgtcga tggtgtacaa   4980

tccgatgtac ttgttcacga tgcagcacaa cgacacaatc ccagaggcca cctctcttag   5040

accaggcagc tttttcaacc ggcagcgcgc cttcgccgtt tccctccgcc tactgttcat   5100

cttccgcaac gccttcctcc cctggtacat cgcgggcgcc tctccgctgc tcaccatcct   5160

gctggtgcca acggtcacag gcatcttctt gacatttgtt tttgtgctgt cccataactt   5220

tgaaggcgct gagcggaccc ccgaaaagaa ctgcaaggcc aaaagggcca aggaggggaa   5280

ggaggtccgc gatgtagagg aggaccgggt ggactggtac cgggcgcagg ccgagaccgc   5340

ggcgacctac gggggcagcg tcgggatgat gctgaccggc ggtttgaacc tgcagatcga   5400

gcaccacttg ttcccccgca tgtcctcttg gcactacccc ttcatccaag atacggtgcg   5460

ggaatgttgc aagcgccatg gcgtgcgcta cacatactac ccgaccatcc tggagaatat   5520

aatgtccacg ctccgctaca tgcagaaggt gggcgtggcc cacacaattc aggatgccca   5580

ggaattctga gc                                                       5592
```

<210> SEQ ID NO 44
<211> LENGTH: 11920
<212> TYPE: DNA
<213> ORGANISM: Artificial Sequence
<220> FEATURE:
<223> OTHER INFORMATION: plasmid pKR1153
<220> FEATURE:
<221> NAME/KEY: misc_feature
<222> LOCATION: (7810)..(7810)
<223> OTHER INFORMATION: n is a, c, g, or t

<400> SEQUENCE: 44

```
ggagatccaa gcttttgatc catgcccttc atttgccgct tattaattaa tttggtaaca     60

gtccgtacta atcagttact tatccttccc ccatcataat taatcttggt agtctcgaat    120

gccacaacac tgactagtct cttggatcat aagaaaaagc caaggaacaa aagaagacaa    180

aacacaatga gagtatcctt tgcatagcaa tgtctaagtt cataaaattc aaacaaaaac    240

gcaatcacac acagtggaca tcacttatcc actagctgat caggatcgcc gcgtcaagaa    300

aaaaaaactg gaccccaaaa gccatgcaca acaacacgta ctcacaaagg tgtcaatcga    360

gcagcccaaa acattcacca actcaaccca tcatgagccc tcacatttgt tgtttctaac    420

ccaacctcaa actcgtattc tcttccgcca cctcattttt gtttatttca acacccgtca    480

aactgcatgc caccccgtgg ccaaatgtcc atgcatgtta acaagaccta tgactataaa    540

tagctgcaat ctcggcccag gttttcatca tcaagaacca gttcaatatc ctagtacacc    600
```

-continued

```
gtattaaaga atttaagata tactgcggcc gcaccatgga ggtggtgaat gaaatagtct    660
caattgggca ggaagtttta cccaaagttg attatgccca actctggagt gatgccagtc    720
actgtgaggt gctttacttg tccatcgcat ttgtcatctt gaagttcact cttggccccc    780
ttggtccaaa aggtcagtct cgtatgaagt ttgttttcac caattacaac cttctcatgt    840
ccatttattc gttgggatca ttcctctcaa tggcatatgc catgtacacc atcggtgtta    900
tgtctgacaa ctgcgagaag gcttttgaca acaacgtctt caggatcacc acgcagttgt    960
tctatttgag caagttcctg gagtatattg actccttcta tttgccactg atgggcaagc   1020
ctctgacctg gttgcaattc ttccatcatt tgggggcacc gatggatatg tggctgttct   1080
ataattaccg aaatgaagct gtttggattt ttgtgctgtt gaatggtttc atccactgga   1140
tcatgtacgg ttattattgg accagattga tcaagctgaa gttccccatg ccaaaatccc   1200
tgattacatc aatgcagatc attcaattca atgttggttt ctacattgtc tggaagtaca   1260
ggaacattcc ctgttatcgc caagatggga tgaggatgtt tggctggttc ttcaattact   1320
tttatgttgg cacagtcttg tgtttgttct tgaatttcta tgtgcaaacg tatatcgtca   1380
ggaagcacaa gggagccaaa aagattcagt gagcggccgc aagtatgaac taaaatgcat   1440
gtaggtgtaa gagctcatgg agagcatgga atattgtatc cgaccatgta acagtataat   1500
aactgagctc catctcactt cttctatgaa taaacaaagg atgttatgat atattaacac   1560
tctatctatg caccttattg ttctatgata aatttcctct tattattata aatcatctga   1620
atcgtgacgg cttatggaat gcttcaaata gtacaaaaac aaatgtgtac tataagactt   1680
tctaaacaat tctaacctta gcattgtgaa cgagacataa gtgttaagaa gacataacaa   1740
ttataatgga agaagtttgt ctccatttat atattatata ttacccactt atgtattata   1800
ttaggatgtt aaggagacat aacaattata aagagagaag tttgtatcca tttatatatt   1860
atatactacc catttatata ttatacttat ccacttattt aatgtcttta taaggtttga   1920
tccatgatat ttctaatatt ttagttgata tgtatatgaa agggtactat ttgaactctc   1980
ttactctgta taaaggttgg atcatcctta aagtgggtct atttaatttt attgcttctt   2040
acagataaaa aaaaaattat gagttggttt gataaaatat tgaaggattt aaaataataa   2100
taaataacat ataatatatg tatataaatt tattataata taacatttat ctataaaaaa   2160
gtaaatattg tcataaatct atacaatcgt ttagccttgc tggacgaatc tcaattattt   2220
aaacgagagt aaacatattt gactttttgg ttatttaaca aattattatt taacactata   2280
tgaaattttt tttttatca gcaaagaata aaattaaatt aagaaggaca atggtgtccc   2340
aatccttata caaccaactt ccacaagaaa gtcaagtcag agacaacaaa aaaacaagca   2400
aaggaaattt tttaatttga gttgtcttgt ttgctgcata atttatgcag taaaacacta   2460
cacataaccc ttttagcagt agagcaatgg ttgaccgtgt gcttagcttc ttttatttta   2520
ttttttatc agcaaagaat aaataaaata aaatgagaca cttcagggat gtttcaacaa   2580
gcttggcgcg ccgttctata gtgtcaccta aatcgtatgt gtatgataca taaggttatg   2640
tattaattgt agccgcgttc taacgacaat atgtccatat ggtgcactct cagtacaatc   2700
tgctctgatg ccgcatagtt aagccagccc cgacacccgc caacacccgc tgacgcgccc   2760
tgacgggctt gtctgctccc ggcatccgct tacagacaag ctgtgaccgt ctccgggagc   2820
tgcatgtgtc agaggttttc accgtcatca ccgaaacgcg cgagacgaaa gggcctcgtg   2880
atacgcctat ttttataggt taatgtcatg accaaaatcc cttaacgtga gttttcgttc   2940
cactgagcgt cagaccccgt agaaaagatc aaaggatctt cttgagatcc tttttttctg   3000
```

-continued

```
cgcgtaatct gctgcttgca aacaaaaaaa ccaccgctac cagcggtggt ttgtttgccg   3060
gatcaagagc taccaactct ttttccgaag gtaactggct tcagcagagc gcagatacca   3120
aatactgtcc ttctagtgta gccgtagtta ggccaccact tcaagaactc tgtagcaccg   3180
cctacatacc tcgctctgct aatcctgtta ccagtggctg ctgccagtgg cgataagtcg   3240
tgtcttaccg ggttggactc aagacgatag ttaccggata aggcgcagcg gtcgggctga   3300
acggggggtt cgtgcacaca gcccagcttg gagcgaacga cctacaccga actgagatac   3360
ctacagcgtg agcattgaga aagcgccacg cttcccgaag ggagaaaggc ggacaggtat   3420
ccggtaagcg gcagggtcgg aacaggagag cgcacgaggg agcttccagg gggaaacgcc   3480
tggtatcttt atagtcctgt cgggtttcgc cacctctgac ttgagcgtcg atttttgtga   3540
tgctcgtcag gggggcggag cctatggaaa aacgccagca acgcggcctt tttacggttc   3600
ctggcctttt gctggccttt tgctcacatg ttctttcctg cgttatcccc tgattctgtg   3660
gataaccgta ttaccgcctt tgagtgagct gataccgctc gccgcagccg aacgaccgag   3720
cgcagcgagt cagtgagcga ggaagcggaa gagcgcccaa tacgcaaacc gcctctcccc   3780
gcgcgttggc cgattcatta atgcaggttg atcagatctc gatcccgcga aattaatacg   3840
actcactata gggagaccac aacggtttcc ctctagaaat aattttgttt aactttaaga   3900
aggagatata cccatggaaa agcctgaact caccgcgacg tctgtcgaga agtttctgat   3960
cgaaaagttc gacagcgtct ccgacctgat gcagctctcg gagggcgaag aatctcgtgc   4020
tttcagcttc gatgtaggag ggcgtggata tgtcctgcgg gtaaatagct gcgccgatgg   4080
tttctacaaa gatcgttatg tttatcggca ctttgcatcg gccgcgctcc cgattccgga   4140
agtgcttgac attggggaat tcagcgagag cctgacctat tgcatctccc gccgtgcaca   4200
gggtgtcacg ttgcaagacc tgcctgaaac cgaactgccc gctgttctgc agccggtcgc   4260
ggaggctatg gatgcgatcg ctgcggccga tcttagccag acgagcgggt tcggcccatt   4320
cggaccgcaa ggaatcggtc aatacactac atggcgtgat ttcatatgcg cgattgctga   4380
tccccatgtg tatcactggc aaactgtgat ggacgacacc gtcagtgcgt ccgtcgcgca   4440
ggctctcgat gagctgatgc tttgggccga ggactgcccc gaagtccggc acctcgtgca   4500
cgcggatttc ggctccaaca atgtcctgac ggacaatggc cgcataacag cggtcattga   4560
ctggagcgag gcgatgttcg gggattccca atacgaggtc gccaacatct tcttctggag   4620
gccgtggttg gcttgtatgg agcagcagac gcgctacttc gagcggaggc atccggagct   4680
tgcaggatcg ccgcggctcc gggcgtatat gctccgcatt ggtcttgacc aactctatca   4740
gagcttggtt gacggcaatt tcgatgatgc agcttgggcg cagggtcgat gcgacgcaat   4800
cgtccgatcc ggagccggga ctgtcgggcg tacacaaatc gcccgcagaa gcgcggccgt   4860
ctggaccgat ggctgtgtag aagtactcgc cgatagtgga aaccgacgcc ccagcactcg   4920
tccgagggca aaggaatagt gaggtacagc ttggatcgat ccggctgcta acaaagcccg   4980
aaaggaagct gagttggctg ctgccaccgc tgagcaataa ctagcataac cccttggggc   5040
ctctaaacgg gtcttgaggg gttttttgct gaaaggagga actatatccg gatgatcggg   5100
cgcgccgtcg acggatccgt acgcaaaggc aaagatttaa actcgaaaac attacaaaag   5160
tctcaaaaca gaggcaaggc catgcacaaa gcacactcta agtgcttcca ttgcctacta   5220
agtagggtac gtacacgatc accattcacc agtgatgatc tttattaata tacaacacac   5280
tcagagacag cttatgttat agctagctag cataaactat cacatcatgt gttagtacga   5340
```

```
caagtgacaa cattgctttt aacttcgcgg ccttggatcc tctagaccgg atataatgag   5400
ccgtaaacaa agatgattaa gtagtaatta atacgtacta gtaaaagtgg caaaagataa   5460
cgagaaagaa ccaatttctt tgcattcggc cttagcggaa ggcatatata agctttgatt   5520
attttattta gtgtaatgat ttcgtacaac caaagcattt atttagtact ctcacacttg   5580
tgtcgcggcc gcgaattcac tagtgattcc ttatagagcc ttccccgcgg gttgcttctc   5640
cgccatccgg gcgaacaccg ccagatagcg cagcaggatg accaaccctt catggggcag   5700
cgggttccga tacggcaggt tgtgcttctg gcacagctgt tccacctggt agctaaccgc   5760
tgtcaggttg tggcgaggga gggtcggcca caaatggtgc tcaatctggt aattcaagcc   5820
tccgaaaaac caatctgtga taatccctcg ccgaatgttc atggtctcat ggatctggcc   5880
aaccgagaat ccatggccat cccagactga gtccccgatc ttctccagtg ggtagtggtt   5940
catgaacacc acgatcgcaa tgccgaagcc gccaaccagc tccgaaacga aaaacaccaa   6000
cagcgatgtg aggatgctgg gcataaagaa taagtggaac agggtcttca aggtccagtg   6060
cagggcgagg ccaatggcct ccttcttata ctgagagcga tagaattggt tatctctgtc   6120
cttcaaactg cgcacggtca acacgctctg gaaacaccaa atgaaccgca acaagataca   6180
gatgaccaag aaatagtact gctggaactg aatgagcttg cgggaaatcg gtgacgcccg   6240
tgtgacgtca tcctcagacc aggctaagag gggagaggttg tcaatatcag ggtcgtgccc   6300
ttgaacattg gttgccgaat gatgtgcatt gtgtctgtcc ttccaccatg tcacggaaaa   6360
accttgcaga ccattgccaa ataccagtcc cacgaggttg ttccagttcc ggttcttgaa   6420
agtctggtgg tggcaaatgt catgagaaag ccagcccatc tgttgatagt gcatcccaag   6480
caacactgcc ccaatgaaat acatctgata ctgaaccatc aggaaataac ccagcactcc   6540
aaggcccagt gtggtgctga ttttgtatga gtaccagagg ggggaggcat caaacatgcc   6600
agttgcgatc aactcttctc ggagcttccg gaaatcctct tgagcttcat tcactgcagc   6660
ctggggtggc aactcagaac tgggattgat tttgggcatg cgcttgagct tgtcgaaggc   6720
ttcttgagag tgcataacca tgaaggcatc agtggcatcc cttccttggt aattctctat   6780
aatttccgca ccaccagggt ggaaattgac ccaggcagac acatcatatg ttgttccatc   6840
aattgtaagg ggaagcgctt ggcgctttga cttcatttca atcgaattcc cgcggccgct   6900
tggggggcta tggaagactt tcttagttag ttgtgtgaat aagcaatgtt gggagaatcg   6960
ggactactta taggatagga ataaaacaga aaagtattaa gtgctaatga aatatttaga   7020
ctgataatta aaatcttcac gtatgtccac ttgatataaa aacgtcagga ataaaggaag   7080
tacagtagaa tttaaaggta ctctttttat atatacccgt gttctctttt tggctagcta   7140
gttgcataaa aaataatcta tatttttatc attattttaa atatcttatg agatggtaaa   7200
tatttatcat aatttttttt actattattt attatttgtg tgtgtaatac atatagaagt   7260
taattacaaa ttttatttac tttttcatta ttttgatatg attcaccatt aatttagtgt   7320
tattatttat aatagttcat tttaatcttt ttgtatatat tatgcgtgca gtactttttt   7380
cctacatata actactatta cattttattt atataatatt tttattaatg aattttcgtg   7440
ataatatgta atattgttca ttattatttc agatttttta aaaatatttg tgttattatt   7500
tatgaaatat gtaatttttt tagtatttga ttttatgatg ataaagtgtt ctaaattcaa   7560
aagaaggggg aaagcgtaaa cattaaaaaa cgtcatcaaa caaaaacaaa atcttgttaa   7620
taaagataaa actgtttgtt ttgatcactg ttatttcgta atataaaaac attatttata   7680
tttatattgt tgacaaccaa atttgcctat caaatctaac caatataatg catgcgtggc   7740
```

```
aggtaatgta ctaccatgaa cttaagtcat gacataataa accgtgaatc tgaccaatgc   7800
atgtacctan ctaaattgta tttgtgacac gaagcaaatg attcaattca caatggagat   7860
gggaaacaaa taatgaagaa cccagaacta agaaagcttt tctgaaaaat aaaataaagg   7920
caatgtcaaa agtatactgc atcatcagtc cagaaagcac atgatatttt tttatcagta   7980
tcaatgcagc tagttttatt ttacaatatc gatatagcta gtttaaatat attgcagcta   8040
gatttataaa tatttgtgtt attatttatc atttgtgtaa tcctgttttt agtattttag   8100
tttatatatg atgataatgt attccaaatt taaaagaagg gaaataaatt taaacaagaa   8160
aaaaagtcat caaacaaaaa acaaatgaaa gggtggaaag atgttaccat gtaatgtgaa   8220
tgttacagta tttcttttat tatagagtta acaaattaac taatatgatt ttgttaataa   8280
tgataaaata tttttttat tattatttca taatataaaa atagtttact taatataaaa   8340
aaaattctat cgttcacaac aaagttggcc acctaattta accatgcatg tacccatgga   8400
ccatattagg taaccatcaa acctgatgaa gagataaaga gatgaagact taagtcataa   8460
cacaaaacca taaaaaacaa aaatacaatc aaccgtcaat ctgaccaatg catgaaaaag   8520
ctgcaatagt gagtggcgac acaaagcaca tgattttctt acaacggaga taaaaccaaa   8580
aaaatatttc atgaacaacc tagaacaaat aaagctttta tataataaat atataaataa   8640
ataaaggcta tggaataata tacttcaata tatttggatt aaataaattg ttggcggggt   8700
tgatatattt atacacacct aaagtcactt caatctcatt ttcacttaac ttttattttt   8760
tttttctttt tatttatcat aaagagaata ttgataatat actttttaac atatttttat   8820
gacatttttt attggtgaaa acttattaaa aatcataaat tttgtaagtt agatttattt   8880
aaagagttcc tcttcttatt ttaaattttt taataaattt ttaaataact aaaatttgtg   8940
ttaaaaatgt taaaaaatgt gttattaacc cttctcttcg aggacgtacg agatccggcc   9000
ggccagatcc tgcaggtctc aatagattaa gaagttggcg tctcattgat tgaccatggg   9060
ggatcctcta gacgtacgtg aaggttaaac atggtgaata tgttaccact agctgggatg   9120
cccattagat caaaactgta aaattctccc gtttcccttc tattcacatg tgagcccccct   9180
cccttttctt tctttctcaa ttttgattga gttaaagtca ccagcaatgc atcactcacc   9240
ctccaaaaaa tttcttgtac aacttctcgg actatcccaa agctcctttt cctgagatgg   9300
atggtcctgt ctcttgccct tgatgtcttc cttgttcgat tttggcttcc tctaatgtct   9360
ttcttgctag gaatcaccac ctcactcatc tatgttgtcg tagcttctga aagtctcata   9420
catatcctta gtgttgcact catcttgtat tgaagtgaaa aagaatgttg ttctcctatc   9480
caaatctcca ttgaatctct ttctcccaat gttgtcccat cggttggtcc tcctctccaa   9540
ccaattaatt gtaaggtgtt taacataaac atggtacaat taagattttt catttcatta   9600
agaaaagatt gagatttgtg gttctaaagt ttcaattaga gtttgatgat attgaaacaa   9660
ccgtagaaca cattaagtat tactaactta tacatagagc attggaattt caccttttat   9720
ttattctgtt tccgccaaag gtacatgact caagttattt tacacaagta acaaaggcat   9780
ctaagcctaa gtattcttat tcagactttt cattattact ttcattgatt tggtgcgaaa   9840
tgcggccgct cagaattcct gggcatcctg aattgtgtgg gccacgccca ccttctgcat   9900
gtagcggagc gtggacatta tattctccag gatggtcggg tagtatgtgt agcgcacgcc   9960
atggcgcttg caacattccc gcaccgtatc ttggatgaag ggtagtgcc aagaggacat  10020
gcgggggaac aagtggtgct cgatctgcag gttcaaaccg ccggtcagca tcatcccgac  10080
```

```
gctgcccccg taggtcgccg cggtctcggc ctgcgcccgg taccagtcca cccggtcctc  10140
ctctacatcg cggacctcct tcccctcctt ggccctttttg gccttgcagt tcttttcggg  10200
ggtccgctca gcgccttcaa agttatggga cagcacaaaa acaaatgtca agaagatgcc  10260
tgtgaccgtt ggcaccagca ggatggtgag cagcggagag gcgcccgcga tgtaccaggg  10320
gaggaaggcg ttgcggaaga tgaacagtag gcggagggaa acggcgaagg cgcgctgccg  10380
gttgaaaaag ctgcctggtc taagagaggt ggcctctggg attgtgtcgt tgtgctgcat  10440
cgtgaacaag tacatcggat tgtacaccat cgacacacca tacatcccca aaacgatgta  10500
catgtaccac gcctggaacc gatggtacca ctttcgtgac gcatttgttg ccgggtagga  10560
gtggaacaaa atgaacggct ccgccgaggc agcgtccagg tccaggccat gctggttggt  10620
gtaggtgtgg tggcgcataa tgtgggactg cagccagatc cagcgggagg atccaatggc  10680
gtcgatgccg taggcgaaaa aggcgttcac ccagggcttt ttgctgatgg ctccgtgaga  10740
ggcatcgtgt tgaatcgcca acccaatctg gctgtggaag tacccggtga agatgcccca  10800
catcactgcc ccggtagtga tccaatacca ttcgcctatg gcagtgcacg cgatgatcag  10860
cgcggtccgc agccaaaagc cgggcgtggc gtaccagttg cgccccttca tgacctcccg  10920
aacgctctgc ttgacatcct gggcgaaggg actgtcaaag gtgtacactg ggtccttcga  10980
gcttcgttcg tgtttgcctc gggcaaattg ctgcagcagc ttcgaattct ctggcttcac  11040
tccagggtgc atggagtaga acagggcggt tccgtcggag gcaccggcgg cttcaatgag  11100
gttgccacct ggatgcactt tcgccagtcc gaagagatcg tacaacaccc catcaattgc  11160
aaccagttct gggtgttcta aaagttgctc agtagtcaaa gagatggtgg ccatggtgcg  11220
gccgcggtga tgactgatga gtgtttaagg accaatggag agaatgtttg agttgtgaag  11280
cggagaacct gaggcgtggt tatttatagg gaagagagga aggtgaatga gggacacgtc  11340
acagaagtag ggtgctgagc ttgagacatt cttcagtatg catggctatg gaagccttgg  11400
gtgctacacc tcatgaagtt catggtgtga ggtggcttcg gcatctcaat taagtgacaa  11460
agagaaaggt gtttcagtgt ttctattgca aatggcagaa actcgtgatg acgaggggac  11520
catgcatggt ttcatttctt ttcttcctgg attctttctt tccttttata tatgcaggtt  11580
cataatttaa aaattagact cgctttcaat ttcttaattt ctcattttcc tcttatatta  11640
ctgtactaat gttaaccacg tacacttatt ttttttttag tttaattttg atagattgtg  11700
ttgatttaaa catattaata ttttcaacca aataaaaatc attttagtag atacggcttt  11760
ttaaataatt attaaaaata ttaactattt atcctaaatg gcacatttta attaaaaaaa  11820
atccggtgtt gtaagtgttt tattaatttg ttttggcatt attaaagcaa cttttttttt  11880
atttgttggc attttgagta cgtacttagg ctagcctgca                       11920
```

<210> SEQ ID NO 45
<211> LENGTH: 1362
<212> TYPE: DNA
<213> ORGANISM: Artificial Sequence
<220> FEATURE:
<223> OTHER INFORMATION: codon-optimized Euglena anabaena delta-5 desaturase

<400> SEQUENCE: 45

```
atggccacca tctccctgac taccgagcag ctcctggaac accccgagct cgttgccatc     60
gacggagtcc tgtacgatct cttcggtctg gccaaggtgc atccaggagg caacctcatc    120
gaagctgccg gtgcatccga cggaaccgct ctgttctact ccatgcatcc tggagtcaag    180
```

```
ccagagaact cgaagcttct gcagcaattt gcccgaggca agcacgaacg aagctccaag    240

gatcccgtgt acaccttcga ctctcccttt gctcaggacg tcaagcagtc cgttcgagag    300

gtcatgaagg gtcgaaactg gtacgccact cctggcttct ggctgagaac cgcactcatc    360

atcgcttgta ctgccattgg cgagtggtac tggatcacaa ccggagcagt gatgtggggt    420

atctttactg gatacttcca ctcgcagatt ggcttggcca ttcaacacga tgcttctcac    480

ggagccatca gcaaaaagcc ctgggtcaac gcctttttcg cttatggcat cgacgccatt    540

ggttcctctc gttggatctg gctgcagtcc cacattatgc gacatcacac ttacaccaac    600

cagcatggcc tcgacctgga tgctgcctcg gcagagccgt tcatcttgtt ccactcctat    660

cctgctacca acgcctctcg aaagtggtac caccgatttc aggcgtggta catgtacatc    720

gttctgggaa tgtatggtgt ctcgatggtg tacaatccca tgtacctctt cacaatgcag    780

cacaacgaca ccattcccga ggccacttct ctcagaccag gcagcttttt caatcggcag    840

cgagctttcg ccgtttccct tcgactgctc ttcatcttcc gaaacgcctt tcttccctgg    900

tacattgctg gtgcctctcc tctgctcacc attcttctgg tgcccacggt cacaggcatc    960

ttcctcacct ttgtgttcgt tctgtcccat aacttcgagg gagccgaacg gaccccagag   1020

aagaactgca aggccaaacg agctaaggaa ggcaaggagg tcagagacgt ggaagaggat   1080

cgagtcgact ggtaccgagc acaggccgag actgctgcca cctacggtgg cagcgtggga   1140

atgatgctta caggcggtct caacctgcag atcgagcatc acttgtttcc ccgaatgtcc   1200

tcttggcact atcccttcat tcaagacacc gttcgggagt gttgcaagcg acatggcgtc   1260

cgttacacat actatcctac cattctcgag aacatcatgt ccactcttcg atacatgcag   1320

aaggtgggtg ttgctcacac cattcaggat gcccaggagt tc                      1362
```

```
<210> SEQ ID NO 46
<211> LENGTH: 3983
<212> TYPE: DNA
<213> ORGANISM: Artificial Sequence
<220> FEATURE:
<223> OTHER INFORMATION: plasmid pEaD5S

<400> SEQUENCE: 46

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cgagctcggt acctcgcgaa    420

tgcatctaga tccatggtca agcgacccgc tctgcctctc accgtggacg gtgtcaccta    480

cgacgtttct gcctggctca accaccatcc cggaggtgcc gacattatcg agaactaccg    540

aggtcgggat gctaccgacg tcttcatggt tatgcactcc gagaacgccg tgtccaaact    600

cagacgaatg cccatcatgg aaccttcctc tcccctgact ccaacacctc ccaagccaaa    660

ctccgacgaa cctcaggagg atttccgaaa gctgcgagac gagctcattg ctgcaggcat    720

gttcgatgcc tctcccatgt ggtacgctta caagaccctg tcgactctcg gactgggtgt    780

ccttgccgtg ctgttgatga cccagtggca ctggtacctg gttggtgcta tcgtcctcgg    840

cattcacttt caacagatgg gatggctctc gcacgacatt tgccatcacc agctgttcaa    900
```

```
ggaccgatcc atcaacaatg ccattggcct gctcttcgga aacgtgcttc agggcttttc    960
tgtcacttgg tggaaggacc gacacaacgc tcatcactcc gccaccaacg tgcagggtca   1020
cgatcccgac atcgacaacc tgcctctcct ggcgtggtcc aaggaggacg tcgagcgagc   1080
tggcccgttt tctcgacgga tgatcaagta ccaacagtat tacttctttt tcatctgtgc   1140
ccttctgcga ttcatctggt gctttcagtc cattcatact gccacgggtc tcaaggatcg   1200
aagcaatcag tactatcgaa gacagtacga gaaggagtcc gtcggtctgg cactccactg   1260
gggtctcaag gccttgttct actatttcta catgccctcg tttctcaccg gactcatggt   1320
gttctttgtc tccgagctgc ttggtggctt cggaattgcc atcgttgtct tcatgaacca   1380
ctaccctctg gagaagattc aggactccgt gtgggatggt catggcttct gtgctggaca   1440
gattcacgag accatgaacg ttcagcgagg cctcgtcaca gactggtttt tcggtggcct   1500
caactaccag atcgaacatc acctgtggcc tactcttccc agacacaacc tcaccgctgc   1560
ctccatcaaa gtggagcagc tgtgcaagaa gcacaacctg ccctaccgat ctcctcccat   1620
gctcgaaggt gtcggcattc ttatctccta cctgggcacc ttcgctcgaa tggttgccaa   1680
ggcagacaag gcctaagcgg ccgcatcgga tcccgggccc gtcgactgca gaggcctgca   1740
tgcaagcttg gcgtaatcat ggtcatagct gtttcctgtg tgaaattgtt atccgctcac   1800
aattccacac aacatacgag ccggaagcat aaagtgtaaa gcctggggtg cctaatgagt   1860
gagctaactc acattaattg cgttgcgctc actgcccgct ttccagtcgg gaaacctgtc   1920
gtgccagctg cattaatgaa tcggccaacg cgcggggaga ggcggtttgc gtattgggcg   1980
ctcttccgct tcctcgctca ctgactcgct gcgctcggtc gttcggctgc ggcgagcggt   2040
atcagctcac tcaaaggcgg taatacggtt atccacagaa tcaggggata acgcaggaaa   2100
gaacatgtga gcaaaaggcc agcaaaaggc caggaaccgt aaaaaggccg cgttgctggc   2160
gtttttccat aggctccgcc cccctgacga gcatcacaaa aatcgacgct caagtcagag   2220
gtggcgaaac ccgacaggac tataaagata ccaggcgttt ccccctggaa gctccctcgt   2280
gcgctctcct gttccgaccc tgccgcttac cggatacctg tccgcctttc tcccttcggg   2340
aagcgtggcg ctttctcata gctcacgctg taggtatctc agttcggtgt aggtcgttcg   2400
ctccaagctg ggctgtgtgc acgaaccccc cgttcagccc gaccgctgcg ccttatccgg   2460
taactatcgt cttgagtcca acccggtaag acacgactta tcgccactgg cagcagccac   2520
tggtaacagg attagcagag cgaggtatgt aggcggtgct acagagttct tgaagtggtg   2580
gcctaactac ggctacacta gaagaacagt atttggtatc tgcgctctgc tgaagccagt   2640
taccttcgga aaaagagttg gtagctcttg atccggcaaa caaaccaccg ctggtagcgg   2700
tggttttttt gtttgcaagc agcagattac gcgcagaaaa aaaggatctc aagaagatcc   2760
tttgatcttt tctacggggt ctgacgctca gtggaacgaa aactcacgtt aagggatttt   2820
ggtcatgaga ttatcaaaaa ggatcttcac ctagatcctt ttaaattaaa aatgaagttt   2880
taaatcaatc taaagtatat atgagtaaac ttggtctgac agttaccaat gcttaatcag   2940
tgaggcacct atctcagcga tctgtctatt tcgttcatcc atagttgcct gactccccgt   3000
cgtgtagata actacgatac gggagggctt accatctggc cccagtgctg caatgatacc   3060
gcgagaccca cgctcaccgg ctccagattt atcagcaata aaccagccag ccggaagggc   3120
cgagcgcaga agtggtcctg caactttatc cgcctccatc cagtctatta attgttgccg   3180
ggaagctaga gtaagtagtt cgccagttaa tagtttgcgc aacgttgttg ccattgctac   3240
```

-continued

```
aggcatcgtg gtgtcacgct cgtcgtttgg tatggcttca ttcagctccg gttcccaacg   3300

atcaaggcga gttacatgat cccccatgtt gtgcaaaaaa gcggttagct ccttcggtcc   3360

tccgatcgtt gtcagaagta agttggccgc agtgttatca ctcatggtta tggcagcact   3420

gcataattct cttactgtca tgccatccgt aagatgcttt tctgtgactg gtgagtactc   3480

aaccaagtca ttctgagaat agtgtatgcg gcgaccgagt tgctcttgcc cggcgtcaat   3540

acgggataat accgcgccac atagcagaac tttaaaagtg ctcatcattg gaaaacgttc   3600

ttcggggcga aaactctcaa ggatcttacc gctgttgaga tccagttcga tgtaacccac   3660

tcgtgcaccc aactgatctt cagcatcttt tactttcacc agcgtttctg ggtgagcaaa   3720

aacaggaagg caaaatgccg caaaaaaggg aataagggcg acacggaaat gttgaatact   3780

catactcttc ctttttcaat attattgaag catttatcag ggttattgtc tcatgagcgg   3840

atacatattt gaatgtattt agaaaaataa acaaataggg gttccgcgca catttccccg   3900

aaaagtgcca cctgacgtct aagaaaccat tattatcatg acattaacct ataaaaatag   3960

gcgtatcacg aggccctttc gtc                                           3983
```